(12) United States Patent
Boss et al.

(10) Patent No.: US 11,267,824 B2
(45) Date of Patent: Mar. 8, 2022

(54) INHIBITORS OF INDOLEAMINE 2,3-DIOXYGENASE AND/OR TRYPTOPHAN 2,3-DIOXYGENASE

(71) Applicant: IDORSIA PHARMACEUTICALS LTD, Allschwil (CH)

(72) Inventors: Christoph Boss, Allschwil (CH); Daniel Bur, Therwil (CH); Sylvaine Cren, Allschwil (CH); Thierry Kimmerlin, Allschwil (CH); Carina Lotz-Jenne, Allschwil (CH); Julien Pothier, Allschwil (CH); Naomi Tidten-Luksch, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 116 days.

(21) Appl. No.: 16/638,051

(22) PCT Filed: Aug. 16, 2018

(86) PCT No.: PCT/EP2018/072187
§ 371 (c)(1),
(2) Date: Feb. 10, 2020

(87) PCT Pub. No.: WO2019/034725
PCT Pub. Date: Feb. 21, 2019

(65) Prior Publication Data
US 2020/0216467 A1    Jul. 9, 2020

(30) Foreign Application Priority Data
Aug. 17, 2017 (WO) ............... PCT/EP2017/070861

(51) Int. Cl.
C07D 513/04 (2006.01)
A61P 35/00 (2006.01)
A61K 45/06 (2006.01)

(52) U.S. Cl.
CPC ............ C07D 513/04 (2013.01); A61P 35/00 (2018.01); A61K 45/06 (2013.01)

(58) Field of Classification Search
None
See application file for complete search history.

(56) References Cited

U.S. PATENT DOCUMENTS 5,990,101 A * 11/1999 Aihara ................ C07D 477/14
514/210.09

FOREIGN PATENT DOCUMENTS

| CN | 107556244 | 1/2018 |
|---|---|---|
| WO | WO 2010/005958 | 1/2010 |
| WO | WO 2011/037780 | 3/2011 |
| WO | WO 2012/142237 | 10/2012 |
| WO | WO 2015/033299 | 3/2015 |
| WO | WO 2015/034820 | 3/2015 |
| WO | WO 2015/044900 | 4/2015 |
| WO | WO 2015/173764 | 11/2015 |
| WO | WO 2016/073770 | 5/2016 |
| WO | WO 2016/161960 | 10/2016 |
| WO | WO 2017/007700 | 1/2017 |
| WO | WO 2017/133258 | 8/2017 |
| WO | WO 2017/134555 | 8/2017 |
| WO | WO 2017/189386 | 11/2017 |
| WO | WO 2018/036414 | 3/2018 |
| WO | WO 2018/054365 | 3/2018 |
| WO | WO 2018/057973 | 3/2018 |
| WO | WO 2018/136887 | 7/2018 |
| WO | WO 2019/138107 | 7/2019 |

OTHER PUBLICATIONS

"3rd Immunotherapy of Cancer Conference," ITOC3 Abstract Book, *European Journal of Cancer*, 55S2, S1-S30; 44 pages (2016).
"A Phase 3 Study of Pembrolizumab + Epacadostat or Placebo in Subjects With Unresectable or Metastatic Melanoma (Keynote-252 / ECHO-301)," *ClinicalTrials.gov*, Search Results Mar. 16, 2020, 1 page.
"A Study of Atezolizumab (MPDL3280A) in Combination With Epacadostat (INCB024360) in Subjects With Previously Treated Stage IIIB or Stage IV Non-Small Cell Lung Cancer and Previously Treated Stage IV Urothelial Carcinoma (ECHO-110)," *ClinicalTrials.gov*, Search Results Mar. 16, 2020, 1 page.
"A Study of GDC-0919 and Atezolizumab Combination Treatment in Participants With Locally Advanced or Metastatic Solid Tumors," *ClinicalTrials.gov*, Search Results Mar. 16, 2020, 1 page.
"A Study of Epacadostat (INCB024360) in Combination With Durvalumab (MEDI4736) in Subjects With Selected Advanced Solid Tumors (ECHO-203)," *ClinicalTrials.gov*, Search Results Mar. 16, 2020, 1 page.
"A Study of the Safety, Tolerability, and Efficacy of Epacadostat Administered in Combination With Nivolumab in Select Advanced Cancers (ECHO-204)," *ClinicalTrials.gov*, Search Results Mar. 16, 2020, 1 page.
"An Investigational Immuno-therapy Study of BMS-986205 Given in Combination With Nivolumab and in Combination With Both Nivolumab and Ipilimumab in Cancers That Are Advanced or Have Spread," *ClinicalTrials.gov*, Search Results Mar. 16, 2020, 1 page.
"Itacitinib Combined With INCB024360 and/or Itacitinib Combined With INCB050465 in Advanced Solid Tumors," *ClinicalTrials.gov*, Search Results Mar. 16, 2020, 1 page.

(Continued)

*Primary Examiner* — Po-Chih Chen
(74) *Attorney, Agent, or Firm* — Hoxie & Associates LLC

(57) ABSTRACT

The present invention relates to compounds of Formula (I) inhibiting indoleamine 2,3-dioxygenase (IDO) and/or tryptophan 2,3-dioxygenase (TDO) enzymes. Further, their synthesis and their use as medicaments in inter alia cancer is disclosed.

Formula (I)

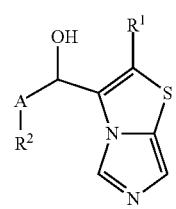

14 Claims, No Drawings

(56) References Cited

OTHER PUBLICATIONS

"Study to Explore the Safety, Tolerability and Efficacy of MK-3475 in Combination With INCB024360 in Participants With Selected Cancers," *ClinicalTrials.gov*, Search Results Mar. 16, 2020, 1 page.
Aghajanova et al., "Molecular Evidence for Differences in Endometrium in Severe Versus Mild Endometriosis," *Reproductive Sciences*, 18(3):229-251 (2011).
Amirkhani et al., "Interferon-β affects the tryptophan metabolism in multiple sclerosis patients," *European Journal of Neurology*, 12:625-631 (2005).
Balachandran et al., "Imatinib potentiates anti-tumor T cell responses in gastrointestinal stromal tumor through the inhibition of Ido," *Nat Med*, 17(9): 1094-1100 (2012); 23 pages.
Barry et al., "Kynurenine pathway in psychosis: evidence of increased tryptophan degradation," *Journal of Psychopharmacology*, 23(3):287-294 (2009).
Barth et al., "Persistent infectious diseases say—IDO. Role of indoleamine-2,3-dioxygenase in disease pathogenesis and implications for therapy," *Critical Reviews in Microbiology*, 40(4):360-368 (2014).
Block et al., "Microglia-mediated neurotoxicity: uncovering the molecular mechanisms," *Nature Reviews | Neuroscience*, 8:57-69 (2007).
Braidy et al., "Mechanism for Quinolinic Acid Cytotoxicity in Human Astrocytes and Neurons," *Neurotox Res*, 16:77-86 (2009).
Breda et al., "Tryptophan-2,3-dioxygenase (TDO) inhibition ameliorates neurodegeneration by modulation of kynurenine pathway metabolites," *PNAS*, 113(19):5435-5440 (2016).
Burney et al., "Gene Expression Analysis of Endometrium Reveals Progesterone Resistance and Candidate Susceptibility Genes in Women with Endometriosis," *Endocrinology*, 148(8):3814-3826 (2007).
Cammer, "Oligodendrocyte killing by quinolinic acid in vitro," *Brain Research*, 896:157-160 (2001).
Campesan et al., "The Kynurenine Pathway Modulates Neurodegeneration in a *Drosophila* Model of Huntington's Disease," *Curr Biol.*, 21(11):961-966 (2011); 14 pages.
Carpenedo et al., "Presynaptic kynurenate-sensitive receptors inhibit glutamate release," *European Journal of Neuroscience*, 13:2141-2147 (2001).
CAS Registry, Registry-Eintrag RN: 2169203-74-9, 1 page.
Chen et al., "The Kynurenine Pathway and Inflammation in Amyotrophic Lateral Sclerosis," *Neurotox Res*, 18:132-142 (2010).
Cuartero et al., "The Kynurenine Pathway in the Acute and Chronic Phases of Cerebral Ischemia," *Current Pharmaceutical Design*, 22:1060-1073 (2016).
D'Amato et al., "A TDO2-AhR Signaling Axis Facilitates Anoikis Resistance and Metastasis in Triple-Negative Breast Cancer," *Cancer Res*, 75(21):4651-4664 (2015).
Dantzer et al., "From inflammation to sickness and depression: when the immune system subjugates the brain," *Nature Reviews | Neuroscience*, 9:46-57 (2008).
Dürr et al., "Implication of indolamine 2,3 dioxygenase in the tolerance toward fetuses, tumors, and allografts," *J. Leukoc. Biol.*, 93:681-687 (2013).
Emsley et al., "Features and development of Coot," *Biological Crystallography, Acta Crystallographica*, D66:486-501 (2010).
Feig et al., "Targeting CXCL12 from FAP-expressing carcinoma-associated fibroblasts synergizes with anti-PD-L1 immunotherapy in pancreatic cancer," *PNAS*, 110(50): 20212-20217 (2013).
Ferns et al., "Indoleamine-2,3-dioxygenase (IDO) metabolic activity is detrimental for cervical cancer patient survival," *OncoImmunology*, 4(2): e981457-7 (2015).
Flanagan et al., "Neurotoxin Quinolinic Acid Is Selectively Elevated in Spinal Cords of Rats with Experimental Allergic Encephalomyelitis," *Journal of Neurochemistry*, 64(3):1192-1196 (1995).
Forrest et al., "Blood levels of kynurenines, interleukin-23 and soluble human leucocyte antigen-G at different stages of Huntington's disease," *Journal of Neurochemistry*, 112:112-122 (2010).

Forrest et al., "Kynurenine metabolism predicts cognitive function in patients following cardias bypass and thoracic surgery," *Journal of Neurochemistry*, vol. 119:136-152 (2011).
Foster et al., "Kynurenic Acid Blocks Neurotoxicity and Seizures Induced in Rats by The Related Brain Metabolite Quinolinic Acid," *Neuroscience Letters*, 48:273-278 (1984).
Gao et al., "Why neurodegenerative diseases are progressive: uncontrolled inflammation drives disease progression," *Trends Immunol.*, 29(8):357-365 (2008); pp. 1-18.
Goda et al., "Radical Scavenging Properties of Tryptophan Metabolites, Estimation of Their Radical Reactivity," *Adv. Exp. Biol.*, 397-402 (1999).
Graves et al., "Inflammation in amyotrophic lateral sclerosis spinal cord and brain is mediated by activated macrophages, mast cells and T cells," *ALS and other motor neuron disorders*, 5:213-219 (2004).
Greene et al., "Protective Groups in Organic Synthesis, Third Edition," John Wiley & Sons, Inc., 52 pages (1999).
Guillemin et al., "Characterisation of kynurenine pathway metabolism in human astrocytes and implications in neuropathogenesis," *Redox Report*, 5(2-3):108-111 (2000).
Guillemin et al, "IFN-β1b Induces Kynurenine Pathway Metabolism in Human Macrophages: Potential Implications for Multiple Sclerosis Treatment," *Journal of Interferon and Cytokine Research*, 21:1097-1101 (2001); 9 pages.
Guillemin et al., "Implications of the kynurenine pathway and quinolinic acid in Alzheimer's disease," *Redox Report*, 7(4):199-206 (2002).
Guillemin et al., "Indoleamine 2,3 dioxygenase and quinolinic acid Immunoreactivity in Alzheimer's disease hippocampus," *Neuropathology and Applied Neurobiology*, 31:395-404 (2005).
Hanihara et al., "Synergistic antitumor effect with indoleamine 2,3-dioxygenase inhibition and temozolomide in a murine glioma model," *J Neurosurg*, 124:1594-1601 (2016).
Harrington et al., "Deficiency of Indoleamine 2,3-Dioxygenase Enhances Commensal-Induced Antibody Responses and Protects against Citrobacter rodentium-Induced Colitis," *Infection and Immunity*, 76(7):3045-3053 (2008).
Henkel et al., "Presence of Dendritic Cells, MCP-1, and Activated Microglia/Macrophages in Amyotrophic Lateral Sclerosis Spinal Cord Tissue," *Ann Neurol*, 55:221-235 (2004).
Heyes et al., Quinolinic Acid and Kynurenine Pathway Metabolism in Inflammatory and Non-Inflammatory Neurological Disease, *Brain*, 115:1249-1273 (1992).
Hiraku et al., "Metal-mediated oxidative damage to cellular and isolated DNA by certain tryptophan metabolites," *Carcinogenesis*, 16(2):349-356 (1995).
Holmgaard et al., "Indoleamine 2,3-dioxygenase is a critical resistance mechanism in antitumor T cell immunotherapy targeting CTLA-4," *J. Exp. Med.*, 210(7):1389-1402 (2013).
Holmgaard et al., "Targeting myeloid-derived suppressor cells with colony stimulating factor-1 receptor blockade can reverse immune resistance to immunotherapy in indoleamine 2,3-dioxygenase-expressing tumors," *EBioMedicine*, 6:50-58 (2016).
Holmgaard et al., "Tumor-Expressed IDO Recruits and Activates MDSCs in a Treg-Dependent Manner," *Cell Reports*, 13:412-424 (2015).
Holtze et al., "Kynurenine 3-monooxygenase polymorphisms: relevance for kynurenic acid synthesis in patients with schizophrenia and healthy controls," *J Psychiatry Neurosci*, 37(1):53-57 (2012).
Hoshi et al., "The Absence of IDO Upregulates Type I IFN Replication in the Retrovirus-Infected Mouse Production, Resulting in Suppression of Viral," *J Immunol*, 185:3305-3312(2010).
Hou et al., "Inhibition of Indoleamine 2,3-Dioxygenase in Dendritic Cells by Stereoisomers of 1-Methyl-Tryptophan Correlates with Antitumor Responses," *Cancer Res*, 67(2):792-801 (2007).
Ishii et al., "Formation of Hydroxanthommatin-Derived Radical in the Oxidation of 3-Hydroxykyurenine," *Archives of Biochemistry and Biophysics*, 294(2):616-622 (1992).
Jhamandas et al., "Quinolinate-induced cortical cholinergic damage: modulation by tryptophan metabolites," *Brain Research*, 529:185-191(1990).
Kabsch, "XDS," Biological Crystallography, *Acta Crystallographica*, D66:125-132 (2010).

(56) References Cited

OTHER PUBLICATIONS

Kandanearatchi et al., "The kynurenine pathway and quinolinic acid: pivotal roles in HIV associated neurocognitive disorders," *FEBS Journal*, 279:1366-1374 (2012).

Kim et al., "Brain indoleamine 2,3-dioxygenase contributes to the comorbidity of pain and depression," *The Journal of Clinical Investigation*, 122(8):2940-2954 (2012).

Koblish et al., "Abstract 2618: Agonist antibodies targeting OX40 and GITR enhance the activity of the IDO1-selective inhibitor epacadostat in preclinical models," AACR Annual Meeting—Washington, DC, 1 page (2017).

Koblish et al., "Hydroxyamidine Inhibitors of Indoleamine-2,3-dioxygenase Potently Suppress Systemic Tryptophan Catabolism and the Growth of IDO-Expressing Tumors," *Mol Cancer Ther*, 9(2):489-498 (2010).

Larrea et al., "Upregulation of Indoleamine 2,3-Dioxygenase in Hepatitis C Virus Infection," *Journal of Virology*, 81(7):3662-3666 (2007).

Laurans et al., "Genetic deficiency of indoleamine 2,3-dioxygenase promotes gut microbiotamediated metabolic health," *Nature Medicine*, 24:1113-1120 (2018); Life Sciences Reporting Summary, 3 pages; Flow Cytometry Reporting Summary, 1 page.

Lemos et al., "Sting Promotes the Growth of Tumors Characterized by Low Antigenicity via IDO Activation," *Cancer Res*, 76(8):2076-2081 (2016).

Leonhardt et al., "Quinolinic acid: an endogenous metabolite that produces axon-sparing lesions in rat brain," *Science*, 219(4582):316-318 (1983).

Li et al., "The indoleamine 2,3-dioxygenase pathway controls complement-dependent enhancement of chemo-radiation therapy against murine glioblastoma," *Journal for Immuno Therapy of Cancer*, 2(21):1-13 (2014).

Lim et al., "Characterization of the kynurenine pathway in human oligodendrocytes," *International Congress Series*, 1304:213-217 (2007).

Lin et al., "Phenyl Benzenesulfonylhydrazides Exhibit Selective Indoleamine 2,3-Dioxygenase Inhibition with Potent in Vivo Pharmacodynamic Activity and Antitumor Efficacy," *J. Med. Chem.*, vol. 59:419-430 (2016).

Liu et al., "Discovery of novel and potent inhibitors of indoleamine-2,3-dioxygenase (IDO1) for cancer immunotherapy," *AACR Abstract #4877*, 1 page (2016).

Liu et al., "Selective inhibition of IDO1 effectively regulates mediators of antitumor Immunity," *Blood*, 115(17):3520-3530 (2010).

Mailankot, et al., "Indoleamine 2,3-dioxygenase overexpression causes kynurenine-modification of proteins, fiber cell apoptosis and cataract formation in the mouse lens," *Laboratory Investigation*, 89:498-512 (2009).

Maranon et al., "Benznidazole treatment reduces the induction of indoleamine 2,3-dioxygenase (IDO) enzymatic activity in Chagas disease symptomatic patients," *Parasite Immunology*, 35:180-187 (2013).

Mautino et al., Abstract 5023: Synergistic antitumor effects of combinatorial immune checkpoint inhibition with anti-PD-1/PD-L antibodies and the IDO pathway inhibitors NLG-919 and indoximod in the context of active immunotherapy, AACR Annual Meeting—San Diego, CA, 1 page (2014).

Mccoy et al., "Phaser crystallographic software," *Journal of Applied Crystallography*, 40:658-674 (2007).

Mcgeer et al., "Inflammatory Processes in Amyotrophic Lateral Sclerosis," *Muscle Nerve*, 26: 459-470 (2002).

Mei et al., "Indoleamine 2,3-dioxygenase-1 (IDO1) enhances survival and invasiveness of endometrial stromal cells via the activation of JNK signaling pathway," *Int J Clin Exp Pathol*, 6(3):431-444 (2013).

Meininger, et al., "Purification and kinetic characterization of human indoleamine 2,3-dioxygenases 1 and 2 (IDO1 and IDO2) and discovery of selective IDO1 inhibitors," *Biochimica et Biophysica Acta*, 1814:1947-1954 (2011).

Miller et al., "Alterations in kynurenine precursor and product levels in schizophrenia and bipolar disorder," *Neurochemistry International*, 52:1297-1303 (2008).

Miller et al., "Expression of the kynurenine pathway enzyme tryptophan 2,3-dioxygenase is increased in the frontal cortex of individuals with schizophrenia," *Neurobiology of Disease*, 15:618-629 (2004).

Miller et al., "Upregulation of the initiating step of the kynurenine pathway in postmortem anterior cingulate cortex from individuals with schizophrenia and bipolar disorder," *Brain Research*, 1073-1074:25-37 (2006).

Muller et al., "Chronic inflammation that facilitates tumor progression creates local immune suppression by inducing indoleamine 2,3 dioxygenase," *PNAS*, 105(44):17073-17078 (2008).

Munn et al., "IDO in the Tumor Microenvironment: Inflammation, Counter-Regulation, and Tolerance," *Trends in Immunology*, 37(3):193-207 (2016).

Munn et al., "Prevention of Allogeneic Fetal Rejection by Tryptophan Catabolism," *Science*, 281:1191-1193 (1998).

Murry, "Tryptophan depletion and HIV infection: a metabolic link to pathogenesis," *The Lancet Infectious Diseases*, 3:644-652 (2003).

Natividad et al., "Impaired Aryl Hydrocarbon Receptor Ligand Production by the Gut Microbiota Is a Key Factor in Metabolic Syndrome," *Cell Metabolism*, 28:1-13 (2018); Star Methods, Key Resources Table, e1-e4.

Ninomiya et al., "Tumor indoleamine 2,3-dioxygenase (IDO) inhibits CD19-CAR T cells and is downregulated by lymphodepleting drugs," *Blood*, 125(25):3905-3916 (2015).

Okuda et al., "3-Hydroxykynurenine, an Endogenous Oxidative Stress Generator, Causes Neuronal Cell Death with Apoptotic Features and Region Selectivity," *Journal of Neurochemistry*, 70(1): 299-307 (1998).

Opitz et al., "An endogenous tumour-promoting ligand of the human aryl hydrocarbon receptor," *Nature*, vol. 478:197-203 (2011).

Owens et al., "The enigma of multiple sclerosis: inflammation and neurodegeneration cause heterogeneous dysfunction and damage," *Curr Opin Neurol*, 16:259-265 (2003).

Pilotte et al., "Reversal of tumoral immune resistance by inhibition of tryptophan 2,3-dioxygenase," *PNAS*, 109(7):2497-2502 (2012).

Rahman et al., "The Excitotoxin Quinolinic Acid Induces Tau Phosphorylation in Human Neurons," *PLoS One*, 4(7): e6344; pp. 1-15 (2009).

Reardon et al., Inhibition of IDO1 with epacadostat enhances anti-tumor efficacy of PD-1 blockade in a syngeneic glioblastoma (GBM) model, *AACR—Abstract #572*, 1 page (2017).

Remington, "Part 5—Pharmaceutical Manufacturing," The Science and Practice of Pharmacy, 21$^{st}$ Edition, 5 pages (2005).

Sala et al., "Human α-1-Microglobulin Is Covalently Bound to Kynurenine-derived Chromophores," *The Journal of Biological Chemistry*, 279(49)(3):51033-51041 (2004).

Salter et al., "The role of tryptophan 2,3-dioxygenase in the hormonal control of tryptophan metabolism in isolated rat liver cells, Effects of glucocorticoids and experimental diabetes," *Biochem. J.*, 229:499-504 (1985).

Sapko et al., "Endogenous kynurenate controls the vulnerability of striatal neurons to quinolinate: Implications for Huntington's disease," *Experimental Neurology*, 197:31-40 (2006).

Seegers et al., "High-Throughput Fluorescence-Based Screening Assays for Tryptophan-Catabolizing Enzymes," *Journal of Biomolecular Screening*, 19(9):1266-1274 (2014).

Spahn et al., "Improved anti-tumor immunity and efficacy upon combination of the IDO1 inhibitor GDC-0919 with anti-PD-11 blockade versus anti-PD-11 alone in preclinical tumor models," *30th Annual Meeting and Associated Programs of the Society for Immunotherapy of Cancer (SITC)*, 1 page (2015).

Spranger et al., "Mechanism of tumor rejection with doublets of CTLA-4, PD-1/PD-L1, or IDO blockade involves restored IL-2 production and proliferation of CD8+ T cells directly within the tumor microenvironment," *Journal for Immuno Therapy of Cancer*, 2(3): 1-14 (2014).

Stahl, Handbook of Pharmaceutical Salts, Properties, Selection, and Use, Wiley-VCH, 24 pages (2008).

(56) References Cited

OTHER PUBLICATIONS

Stone et al., "An expanding range of targets for kynurenine metabolites of tryptophan," *Trends in Pharmacological Sciences*, 34(2):136-143 (2013).
Stone et al., "Quinolinic Acid: A Potent Endogenous Excitant at Amino Acid Receptors in CNS," *European Journal of Pharmacology*, 72:411-412 (1981).
Sullivan et al., "The treatment of depression in chronic low back pain: review and recommendations," *Pain*, 50:5-13 (1992).
Suzuki et al., "Serum activity of indoleamine 2,3-dioxygenase predicts prognosis of community-acquired pneumonia," *Journal of Infection*, 63:215-222 (2011).
Suzuki et al., "Serum Indoleamine 2,3-Dioxygenase Activity Predicts Prognosis of Pulmonary Tuberculosis," *Clinical and Vaccine Immunology*, 19(3):436-442 (2012).
Takikawa et al., "Regulation of Indoleamine 2,3-Dioxygenase, The First Enzyme in UV Filter Biosynthesis In The Human Lens, Relevance for Senile Nuclear Cataract," *Adv Exp Med Biol*, 467:241-245 (1999).
Tankiewicz et al., "Kidney and Liver Kynurenine Pathway Enzymes in Chronic Renal Failure," *Adv. Exp. Med. Biol.*, 527:409-414 (2003).
Taylor et al., "UV Filter Instability: Consequences for the Human Lens," *Exp. Eye Res.*, 75:165-175 (2002).
Thèate et al., "Extensive Profiling of the Expression of the Indoleamine 2,3-Dioxygenase 1 Protein in Normal and Tumoral Human Tissues," *Cancer Immunol Res*, 3(2):161-172 (2015).
Thevandavakkam et al., "Targeting Kynurenine 3-Monooxygenase (KMO): Implications for Therapy in Huntington's Disease," *CNS & Neurological Disorders—Drug Targets*, 9:791-800 (2010).
Trapp et al., "Axonal pathology in multiple sclerosis: relationship to neurologic disability," *Current Opinion in Neurology*, 12(3):295-302 (1999); Abstract, 1 page.
Tumang et al., "Abstract 4863: PF-06840003: a highly selective IDO-1 inhibitor that shows good in vivo efficacy in combination with immune checkpoint inhibitors," AACR 107th Annual Meeting—New Orleans, LA, 1 page (2016).
Uyttenhove et al., "Evidence for a tumoral immune resistance mechanism based on tryptophan degradation by indoleamine 2,3-dioxygenase," *Nature Medicine*, 9(10):1269-1274 (2003).
Vagin et al., "REFMAC5 dictionary: organization of prior chemical knowledge and guidelines for its use," Biological Crystallography, *Acta Crystallographica*, D60:2184-2195 (2004).
Van Der Sluijs et al., "Influenza-Induced Expression of Indoleamine 2,3-Dioxygenase Enhances Interleukin-10 Production and Bacterial Outgrowth during Secondary Pneumococcal Pneumonia," *The Journal of Infectious Diseases*, 193:214-222 (2006).
Vécsei et al., "Intracerebroventricular Injection of Kynurenic Acid, But Not Kynurenine, Induces Ataxia and Stereotyped Behavior in Rats," *Brain Research Bulletin*, 25:623-627 (1990).

Von Geldern et al., "Azole Endothelin Antagonists. 1. A Receptor Model Explains an Unusual Structure-Activity Profile," *J. Med. Chem.*, 39:957-967 (1996).
Wainwright et al., "Durable Therapeutic Efficacy Utilizing Combinatorial Blockade against IDO, CTLA-4, and PD-L1 in Mice with Brain Tumors," *Clin Cancer Res*, 20(20):5290-5301 (2014); Correction, 1 page.
Walker et al., "Gene expression changes by amyloid β peptide-stimulated human postmortem brain microglia identify activation of multiple inflammatory processes," *Journal of Leukocyte Biology*, 79:596-610 (2006).
Wang et al., "Abstract 3847: Creating the tumor microenvironment for effective immunotherapy: Antitumor activity of intratumoral IMO-2125, a TLR9 agonist is further enhanced by inhibition of indoleamine-pyrrole 2,3-dioxygenase (IDO)," AACR 107th Annual Meeting 2016—New Orleans, LA, 1 page (2016).
Wang et al., "Pharmacological inactivation of PI3Kδ in the tumor microenvironment enhances efficacy of other immunotherapeutic agents," *Journal for Immuno Therapy of Cancer*, 3(Suppl 2):P377; 1 page (2015).
Widner et al., "Tryptophan degradation and immune activation in Alzheimer's disease," *J Neural Transm*, 107:343-353 (2000).
Wirleitner et al., "Immune activation and degradation of tryptophan in coronary heart disease," *European Journal of Clinical Investigation*, 33(7):550-554 (2003).
Wise et al., "Abstract 5115: Pre-clinical development of next generation inhibitors of the enzymes indoleamine 2,3-dioxygenase 1 and tryptophan 2,3-dioxygenase as cancer immunotherapies," AACR 107th Annual Meeting—New Orleans, LA, 1 page (2016).
Wouters et al., Pharmaceutical Salts and Co-crystals, RSC Drug Discovery, 10 pages (2012).
Wu et al., "Expression of Tryptophan 2,3-Dioxygenase and Production of Kynurenine Pathway Metabolites in Triple Transgenic Mice and Human Alzheimer's Disease Brain," *PLoS One*, 8(4): e59749; pp. 1-11 (2013).
Yan et al., "Activation of the kynurenine pathway and increased production of the excitotoxin quinolinic acid following traumatic brain injury in humans," *Journal of Neuroinflammation*, 12:110:1-17 (2015).
Yang et al., "Discovery of Tryptanthrin Derivatives as Potent Inhibitors of Indoleamine 2,3-Dioxygenase with Therapeutic Activity in Lewis Lung Cancer (LLC) Tumor-Bearing Mice," *J. Med. Chem.*, vol. 56:8321-8331 (2013).
Yue et al., "Discovery of Potent Competitive Inhibitors of Indoleamine 2,3-Dioxygenase with in Vivo Pharmacodynamic Activity and Efficacy in a Mouse Melanoma Model," *J. Med. Chem.*, 52(23):7364-7367 (2009).
Zhai et al., "Molecular Pathways: Targeting IDO1 and Other Tryptophan Dioxygenases for Cancer Immunotherapy," *Clin Cancer Res*, 21(24):5427-5433 (2015).
Asghar et al., "Indoleamine 2,3-dioxygenase expression and activity in patients with hepatitis C virus-induced liver cirrhosis," *Experimental and Therapeutic Medicine*, 9:901-904 (2015).

\* cited by examiner

INHIBITORS OF INDOLEAMINE 2,3-DIOXYGENASE AND/OR TRYPTOPHAN 2,3-DIOXYGENASE

This application is a United States Application under 35 U.S.C. 371 claiming benefit of PCT Application No. PCT/EP2018/072187, filed on Aug. 16, 2018, which claims the benefit of PCT Application No. PCT/EP2017/070861, filed on Aug. 17, 2017.

The present invention relates to compounds represented by Formula (I), or pharmaceutically acceptable salts thereof, and their use as active ingredients in medicine. The invention further concerns a process for the preparation of said compounds, pharmaceutical compositions containing one or more of said compounds, and their use, either alone or in combination with other active compounds or therapies as modulators of the activity of indoleamine 2,3-dioxygenase (IDO) and/or tryptophan 2,3-dioxygenase (TDO) enzymes.

The enzymes IDO and TDO catalyze the first and rate limiting step in the kynurenine pathway which is responsible for more than 95% of the degradation of the essential amino acid tryptophan (TRP). The catabolism of TRP is a central pathway maintaining the immunosuppressive microenvironment in many types of cancers. The kynurenine pathway is also involved in physiological functions such as behavior, sleep, thermo-regulation and pregnancy.

The classic concept proposes that tumor cells or myeloid cells in the tumor microenvironment or draining lymph nodes express high levels of IDO resulting in the depletion of TRP and accumulation of TRP metabolites in the local microenvironment and subsequent inhibition of T cell responses. This IDO-centered concept is supported by numerous preclinical studies in models of tumor immunity, autoimmunity, infection, and allergy. More recent preclinical studies propose an alternative route of TRP degradation in tumors via the enzyme TDO. It has been suggested that targeting TDO may complement IDO inhibition. Thus, inhibition of IDO and/or TDO enzymes may be utilized in preventing and/or treating cancers. Moreover, a wide spectrum of further diseases and/or disorders notably neurological conditions, infectious and other diseases may be prevented and/or treated by targeting IDO and/or TDO.

Several IDO and/or TDO inhibitors are described in WO2010005958, WO2012142237, WO2015173764, WO2016073770 and some have been clinically tested as anticancer agents either alone or in combination with other compounds/therapies. WO2016161960, WO2017134555, WO2018036414, WO2017007700, WO2017189386, WO2017133258, CN107556244, WO2018057973, WO2018136887 and WO2018054365 disclose certain heterocyclic derivatives which may be used for inhibiting IDO and/or TDO enzymes. The chemical structure of cyclopentyl-(2-methyl-imidazo[5,1-b]thiazol-3-yl)-methanol appears to have been mentioned in CAS REGISTRY database (RN: 2169203-74-9).

Studying human tumor samples for expression of TDO2 gene revealed significant expression in 41% of bladder carcinomas, 50% of melanomas and 100% of hepatocarcinomas (Pilotte et al.; Proc Natl Acad Sci. 2012, 109(7): 2497-502). Moreover, TDO is expressed constitutively in human glioblastomas. Besides the suppression of anti-tumor immune responses, TDO-derived kynurenine (KYN) has been shown to have a tumor cell autonomous effect in glioblastoma, promoting tumor-cell survival and motility through the aryl hydrocarbon receptor (AHR) in an autocrine fashion. The TDO-AHR pathway in human brain tumors was found to be associated with malignant progression and poor survival. Elevated expression of TDO has also been observed in clinical specimens of Triple Negative Breast Cancer (TNBC) and was associated with increased disease grade, estrogen receptor negative status and shorter overall survival. KYN production mediated by TDO in TNBC cells was sufficiently to activate the AhR promoting anoikis resistance, migration, and invasion (D'Amato et al.; Cancer Res. 2015, 75(21):4651-64).

TDO expression has been detected in other cancer indications, such as for example renal cell carcinoma, mesothelioma, neuroblastoma, leukemia, lung carcinoma (NSCLC), head&neck carcinoma, colorectal carcinoma, sarcoma, astrocytoma, myeloma, and pancreatic carcinoma (Pilotte et al.; Proc Natl Acad Sci. 2012, 109(7):2497-502).

IDO expression levels in patient tumor samples varied slightly with the use of different antibodies reflecting the potential for alternative splice variants and/or post-translational modifications. Overall, IDO expression was found in a large fraction (>50%) of human tumors comprising tumor cells, endothelial cells, and stromal cells in proportions that varied depending on the tumor type (Uyttenhove et al.; Nat Med. 2003, 9(10):1269-74). Tumors showing the highest proportions of IDO-immunolabeled samples were carcinomas of the endometrium and cervix, followed by kidney, lung, and colon. This hierarchy of IDO expression was confirmed by gene expression data mined from The Cancer Genome Atlas database (Theate et al.; Cancer Immunol Res. 2015, 3(2):161-72). In most studies, high expression of IDO in the tumor or draining lymph nodes has been an adverse prognostic factor. Tumor in this category include melanoma, colon cancer, brain tumors, ovarian cancer, acute myelogenous leukemia, endometrial cancer, high-grade osteosarcoma and a number of others (Munn and Mellor; Trends in Immunol. 2016, 37(3): 193-207). In a smaller number of tumor types, IDO expression appears to be induced or 'reactive'—that is associated with increased T cell infiltration and inflammation. In this situation, upregulation of IDO may be a proxy for a stronger spontaneous anti-tumor immune response, and thus associated with more favorable prognosis. However, even in these immune-responsive patients, the IDO itself is not beneficial, and the patient might do even better if IDO were blocked.

Because of the differences observed for IDO expression levels in patient samples using different antibodies, measuring IDO activity by determining concentrations of KYN and TRP in the serum might be more meaningful. Indeed, increased KYN/TRP ratios have been detected in sera from cancer patients compared to normal volunteers (Liu et al.; Blood. 2010, 115(17):3520-30). The KYN/TRP ratio was recently validated as a prognostic tool in cervical cancer patients whereby low TRP levels indicated a tumor size greater than 4 cm and metastatic spread to the lymph node (Ferns et al.; Oncoimmunology. 2015, 4(2):e981457). Accordingly, high KYN/TRP ratios in patient sera were associated with lymph node metastasis, FIGO stage, tumor size, parametrial invasion and poor disease-specific survival, further suggesting the relevance of IDO targeting based on a TRP catabolic signature. Moreover, serum KYN/TRP ratio was a significantly independent detrimental prognostic factor in patients with adult T-cell leukemia/lymphoma (Zhai et al.; Clin Cancer Res. 2015, 21(24):5427-33).

In preclinical models transfection of immunogenic tumor cells with recombinant IDO prevented their rejection in mice (Uyttenhove et al.; Nat Med. 2003, 9(10):1269-74). While ablation of IDO expression led to a decrease in the incidence and growth of 7,12-dimethylbenz[a]anthracene-induced premalignant skin papillomas (Muller et al.; Proc Natl Acad Sci USA. 2008, 105(44):17073-8).

In preclinical models of B16 melanoma overexpressing IDO and 4T1 breast cancer, IDO expression by tumor cells promoted tumor growth through the recruitment and activation of myeloid-derived suppressor cells (MDSC) and resistance to checkpoint blockade using anti-CTLA-4 and anti-PD-1. In the same study, it was also noted that IDO expression in human melanoma tumors is strongly associated with MDSC infiltration (Holmgaard et al.; Cell Rep. 2015, 13(2):412-24).

Imatinib, a small-molecule receptor tyrosine kinase inhibitor targeting KIT (CD117), used for treatment of gastrointestinal stromal tumor (GIST), has been shown to modulate the KYN pathway. In a mouse model of GIST, imatinib therapy produced a number of immunological responses by reducing tumor cell expression of IDO. To test the hypothesis that the immune effects of imatinib are partially mediated by its reduction of IDO expression, GIST mice were treated with a cocktail of KYN pathway metabolites-KYN, 3-hydroxyanthranilic acid (3-HAA), and 3-hydroxykynurenine (3-HK), designed to simulate a system with competent IDO activity. The antitumor effects of imatinib were diminished by coadministration of the TRP metabolite cocktail. However, the antitumor effects of imatinib were not increased by co-administration of the IDO inhibitor 1-methyl-tryptophan (1-MT), consistent with the hypothesis that both agents are impacting the same pathway (Balachandran et al.; Nat Med. 2011, 17(9): 1094-100).

It has been shown that TDO expression by tumors prevented their rejection by immunized mice and systemic treatment with a TDO inhibitor restored the ability of mice to reject the TDO-expressing tumors (Pilotte et al.; Proc Natl Acad Sci. 2012, 109(7):2497-502). In a transplantable model of glioma, TDO expression in tumor cells promoted tumor growth while TDO knockdown decreased tumor incidence (Opitz et al.; Nature 2011, 478(7368):197-203).

IDO inhibitors have been found to suppress TRP metabolism in vivo in tumors and blood which was accompanied by a slowdown of tumor outgrowth in experimental models of colorectal cancer (Lin et al.; J Med Chem. 2016, 59(1):419-30; Koblish et al.; Mol Cancer Ther. 2010, 9(2):489-98; Kraus et al.; AACR 2016: abstract #4863; Wise et al.; AACR 2016: abstract #5115; Liu et al.; AACR 2016:abstract #4877), pancreatic cancer (Koblish et al.; Mol Cancer Ther. 2010, 9(2):489-98), melanoma (Yue et al.; J Med Chem. 2009, 52(23):7364-7), lung (Yang et al.; J Med Chem. 2013, 56(21):8321-31), breast cancer (Holmgaard et al.; Cell Rep. 2015, 13(2):412-24), glioma (Hanihara et al.; J Neurosurg. 2016, 124(6):1594-601).

1-Methyl-Tryptophan (1-MT) augmented the effect of chemotherapy in mouse models of transplantable melanoma (B16) and transplantable and autochthonous breast cancer (4T1) (Hou et al.; Cancer Res. 2007, 67(2):792-801). Furthermore, 1-MT enhanced chemo-radiation therapy to prolong survival in mice bearing intracranial glioblastoma tumors (GL-261). In this context inhibition of IDO allowed chemo-radiation to trigger widespread complement deposition at sites of tumor growth. IDO-blockade led to upregulation of VCAM-1 on vascular endothelium within the tumor microenvironment. Mice genetically deficient in complement component C3 lost all of the synergistic effects of IDO-blockade on chemo-radiation-induced survival (Li et al.; Journal Immunother Cancer. 2014, 2:21). IDO expression is induced in the tumor epithelium of a significant number of patients with pancreatic cancer after GVAX (irradiated, GM-CSF-secreting, allogeneic PDAC) vaccination. GVAX vaccination combined with IDO inhibition increases survival in a preclinical model of pancreatic cancer and with the combination of cyclophosphamide, GVAX vaccine, IDO inhibition and PD-L1 blockade all mice survived (Zheng, John Hopkins School of Medicine; ITOC3 2016). In this context, vaccination combined with increasing doses of anti-OX40 has also been shown to induce IDO in the TC1 tumor model and inhibition of IDO by 1-MT showed synergistic effects with anti-OX40 and vaccination in the same model (Khleif, Georgia Cancer Center; ITOC3 2016). Moreover, IDO inhibitor epacadostat has been shown to enhance the effect of anti-OX40 and anti-GITR in preclinical models (Koblish et al.; AACR 2017: abstract #2618).

The IDO/TDO dual inhibitor NLG919 enhanced the antitumor responses of naïve, resting adoptively transferred pmel-1 cells to vaccination with cognate human gp100 peptide in the B16F10 tumor model. The effect was additive with chemotherapy and even more pronounced once chemotherapy was combined with indoximod/anti-PD-1 (Mautino et al.; AACR 2014: abstract 5023). Along these lines, improved depth and duration of tumor growth inhibition was detected when NLG-919 was combined with anti-PD-L1 in the EMT-6 mouse model (Spahn et al.; SITC 2015).

IDO-selective inhibitors have been shown to enhance chemotherapy in the CT26 and Pan02 tumor mouse models: Epacadostat enhances chemotherapy (doxorubicin) in the CT26 tumor mouse model (Koblish; SITC 2015). An IDO-selective inhibitor from IOMet Pharma enhances chemotherapy (gemcitabine and abraxane) in the PAN02 model (Wise et al.; AACR 2016: abstract #5115).

In plasma and tumor tissue, anti-PD-L1 and anti-CTLA4 checkpoint blockade induce IDO activity, while the combination of an IDO-selective inhibitor (PF-06840003) and anti-PD-L1 treatment resulted in significant tumor growth inhibition in the CT-26 syngeneic mouse colon tumor model (Kraus et al.; AACR 2016: abstract #4863).

In another study, doublet therapies using either anti-CTLA-4, anti-PD-L1 and/or an IDO inhibitor showed synergistic retardation of tumor outgrowth in the B16(SIY) melanoma mouse model (Spranger et al.; J Immunother Cancer. 2014, 2:3). The major biologic correlate to this improved efficacy was restored IL-2 production and proliferation of tumor-infiltrating CD8 T cells. Functional restoration did not require new T cell migration to the tumor. In yet another study, inhibition of IDO by 1-MT in combination with therapies targeting immune checkpoints such as CTL-4, PD-1/PD-L1, and GITR synergize to control tumor outgrowth and enhance overall survival in the B16-F10 and 4T1 tumor mouse models (Holmgaard et al.; J Exp Med. 2013, 210(7):1389-402). In an orthotopic glioma model triple treatment with anti-CTLA-4, anti-PD-L1 and 1-MT as well as the combination of Epacadostat and anti-PD-1 resulted in a highly effective durable survival advantage (Wainwright et al.; Clin Cancer Res. 2014, 20(20):5290-301; Reardon et al.; AACR 2017: abstract 572). The concept of targeting IDO in combination with checkpoint blockade is currently investigated in several clinical trials (NCT02752074, NCT02658890, NCT02327078, NCT02318277, NCT02178722, NCT02471846, NCT02298153).

Intra-tumoral treatment with a TLR9 agonist was shown to induce IDO expression in treated and distant tumors and the combination of an IDO inhibitor with the same TLR9 agonist showed additive anti tumor effects in the CT-26 syngeneic mouse colon tumor model (Wang et al.; AACR 2016: abstract #3847).

High IDO expression induces recruitment of immunosuppressive MDSC to tumors in several mouse models. CSF-1R was found to be expressed on MDSCs and CSF-1R blockade to inhibit intratumoral MDSCs. Accordingly, inhibiting IDO with D-1-MT was shown to synergize with CSF-1R blockade in the B16 model overexpressing IDO (Holmgaard et al.; EBioMedicine 2016, 6:50-8).

There is experimental evidence that IDO inhibition also improves the therapeutic response to chimeric antigen receptor (CAR) T cell therapy in B cell lymphoma. In a mouse model of B cell lymphoma IDO expression in tumor cells suppress CD19 CAR T cell therapy through the action of TRP metabolites. The treatment with the IDO inhibitor 1-MT restored tumor control by CAR T cells in this model (Ninomiya et al.; Blood, 2015, 125(25):3905-16).

DNA nanoparticles can induce IDO via a pathway dependent on the stimulator of interferon genes (STING) sensor of cytosolic DNA. Accordingly STING agonists can induce IDO and promote tolerogenic responses. This scenario has been studied in preclinical models using tumors with low and high antigenicity. In tumors exhibiting low antigenicity IDO activation by STING is predominant and overcomes STING/IFN immunogenic responses while in tumors with high antigenicity the STING/IFN signaling rather potentiates immunogenic responses and fails to induce IDO. Overall these data suggest that IDO inhibition can enhance the anti-tumor response to STING agonists particularly in tumors with low antigenicity (Lemos et al.; Cancer Res. 2016, 76(8):2076-81).

Given the role of the JAK-STAT (signal transducer and activator of transcription) signalling system in mediating interferon-γ-induced IDO expression, it is obvious to combine IDO inhibitors with JAK/STAT inhibitors. A clinical trial on this treatment concept is currently under investigation (NCT02559492).

In the central nervous system both fates of TRP which act as a precursor to KYN and serotonin are pathways of interest and importance. Metabolites produced by the KYN pathway have been implicated to play a role in the pathomechanism of neuroinflammatory and neurodegenerative disorder such as Huntington's disease. The first stable intermediate from the KYN pathway is KYN. Subsequently, several neuroactive intermediates are generated. They include Kynurenic acid (KYNA), 3-Hydroxykynurenine (3-HK), and Quinolinic acid (QUIN). 3-HK and QUIN are neurotoxic by distinct mechanisms; 3-HK is a potent free-radical generator (Thevandavakkam et al.; CNS Neurol Disord. Drug Targets. 2010, 9(6):791-800; Ishii et al.; Arch Biochem Biophys. 1992, 294(2):616-622; Hiraku et al.; Carcinogenesis. 1995, 16(2):349-56), whereas QUIN is an excitotoxic N-methyl-D-aspartate (NMDA) receptor agonist (Stone and Perkins; Eur J Pharmacol. 1981, 72(4):411-2; Schwarcz et al; Science. 1983, 219(4582):316-8). KYNA, on the other hand, is neuroprotective through its antioxidant properties and antagonism of both the a7 nicotinic acetylcholine receptor and the glycine coagonist site of the NMDA receptor (Vecsei and Beal; Brain Res Bull. 1990, 25(4):623-7; Foster et al.; Neurosci Lett. 1984, 48(3):273-8; Carpenedo et al.; Eur J Neurosci. 2001, 13(11):2141-7; Goda et al.; Adv. Exp. Med. Biol. 1999, 467:397-402). Changes in the concentration levels of TRP catabolites can shift the balance to pathological conditions. The ability to influence the metabolism towards the neuroprotective branch of the KYN pathway, i.e. towards KYNA synthesis, may be used in preventing neurodegenerative diseases.

In the CNS, the KYN pathway is present to varying extents in most cell types, infiltrating macrophages, activated microglia and neurons have the complete repertoire of KYN pathway enzymes. On the other hand, neuroprotective astrocytes and oligodendrocytes lack the enzyme, KYN 3-monooxygenase (KMO) and IDO-1 respectively, and are incapable of synthesizing the excitotoxin QUIN (Guillemin et al.; Redox Rep 2000, 5(2-3): 108-11; Lim et al.; International Congress Series. 2007, 1304: 213-7). TDO is expressed in low quantities in the brain, and is induced by TRP or corticosteroids (Salter and Pogson; Biochem J. 1985, 229(2): 499-504; Miller et al.; Neurobiol Dis. 2004, 15(3): 618-29). Given the role of TDO and IDO in the pathogenesis of several CNS disorders such as schizophrenia as well as the role of TDO in controlling systemic TRP levels, IDO and/or TDO inhibitors could be used to improve the outcomes of patients with a wide variety of CNS diseases and neurodegeneration.

IDO and/or TDO inhibitors may in addition be useful for the treatment of Amyotrophic lateral sclerosis (ALS) (or Lou Gehrig's disease). ALS results in the selective attacking and destruction of motor neurons in the motor cortex, brainstem and spinal cord. Although multiple mechanisms are likely to contribute to ALS, the KYN pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic KYN metabolites that further destroy motor neurons. In the brain and spinal cord of ALS patients large numbers of activated microglia, reactive astrocytes, T cells and infiltrating macrophages have been observed (Graves et al.; Amyotroph Lateral Scler Other Motor Neuron Disord. 2004, 5(4):213-9; Henkel et al.; Ann Neurol. 2004, 55(2):221-35). These cells release inflammatory and neurotoxic mediators, among others IFN-γ, the most potent inducer of IDO (McGeer and McGeer; Muscle Nerve. 2002; 26(4):459-70). The neuronal and microglial expression of IDO is increased in ALS motor cortex and spinal cord (Chen et al.; Neurotox Res. 2010, 18(2):132-42). It has been proposed that the release of immune activating agents activates the rate-limiting enzyme of the KYN pathway, IDO, which generates metabolites such as the neurotoxin QUIN. Therefore, inhibition of IDO may reduce the synthesis of neurotoxic QUIN, which has been clearly implicated in the pathogenesis of ALS.

IDO and/or TDO inhibitors may in addition be useful for the treatment of Huntington's disease (HD). HD is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites within the KYN pathway provide one of the few biomarkers that correlates with the number of CAG repeats and hence the severity of the disorder (Forrest et al.; J Neurochem 2010, 112(1):112-22). Indeed, in patients with HD and HD model mice, 3-HK and QUIN levels are increased in the neostriatum and cortex. Moreover, KYNA levels are reduced in the striatum of patients with HD. Intrastriatal injection of QUIN in rodents reproduces behavioural and pathological features of HD (Sapko et al.; Exp Neurol. 2006 197(1):31-40). Importantly, TDO ablation in a *Drosophila* model of HD ameliorated neurodegeneration (Campesan et al.; Curr Biol. 2011; 21(11):961-6).

IDO and/or TDO inhibitors may in addition be useful for the treatment of Alzheimer's disease (AD). AD is an age-related neurodegenerative disorder characterised by neuronal loss and dementia. The histopathology of the disease is manifested by the accumulation of intracellular β-amyloid (AP) and subsequent formation of neuritic plaques as well as the presence of neurofibrillary tangles in specific brain regions associated with learning and memory. The pathological mechanisms underlying this disease are still controversial, however, there is growing evidence implicating KYN pathway metabolites in the development and progression of AD. It has been shown that A3 (1-42) can activate primary cultured microglia and induce IDO expression (Guillemin et al.; Redox Rep. 2002, 7(4):199-206; Walker et al.; J Leukoc Biol. 2006, 79:596-610). Furthermore, IDO overexpression and increased production of QUIN have been observed in microglia associated with the amyloid plaques in the brain of AD patients (Guillemin et al.; Neuropathol Appl Neurobiol. 2005, 31(4):395-404). QUIN has been shown to lead to tau hyperphosphorylation in human cortical neurons (Rahman et al.; PLOS One. 2009, 4(7):e6344). Thus, overexpression of IDO and over-activation of the KYN pathway in microglia are implicated in the pathogenesis of AD. There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al.; PLOS One. 2013, 8(4):e59749). Preclinical evidence supports the use of KMO, TDO, IDO, and 3HAO inhibitors to offset the effects of neuroinflammation in AD. Moreover, other observations have demonstrated that the ratio of KYN/TRP is increased in the serum of AD patients (Widner et al.; J Neural Transm (Vienna). 2000, 107(3):343-53). In fly models of AD both genetic and pharmacological inhibition of TDO provides robust neuroprotection (Breda et al.; Proc Natl Acad Sci. 2016, 113(19): 5435-40). Therefore, the KYN pathway is over-activated in AD by both TDO and IDO and may be involved in neurofibrillary tangle formation and associated with senile plaque formation.

IDO and/or TDO inhibitors may in addition be useful for the treatment of Parkinson's disease (PD). PD is a common neurodegenerative disorder characterised by loss of dopaminergic neurons and localized neuroinflammation. Parkinson's disease is associated with chronic activation of microglia (Gao and Hong; Trends Immunol. 2008, 29(8): 357-65). Microglia activation release neurotoxic substances including reactive oxygen species (ROS) and proinflammatory cytokines such as INF-γ (Block et al.; Nat Rev Neurosci. 2007; 8(1):57-69), a potent activator of KYN pathway via induction of IDO expression. KYN pathway in activated microglia leads to upregulation of 3HK and QUIN. 3HK is toxic primarily as a result of conversion to ROS (Okuda et al.; J Neurochem. 1998; 70(1):299-307). The combined effects of ROS and NMDA receptor-mediated excitotoxicity by QUIN contribute to the dysfunction of neurons and their death (Stone and Perkins; Eur J Pharmacol. 1981, 72(4): 411-2; Braidy et al.; Neurotox Res. 2009, 16(1):77-86). However, picolinic acid (PIC) produced through KYN pathway activation in neurons, has the ability to protect neurons against QUIN-induced neurotoxicity, being a NMDA agonist (Jhamandas et al.; Brain Res. 1990, 529(1-2):185-91). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. Therefore, PD is associated with an imbalance between the two main branches of the KYN pathway within the brain. KYNA synthesis by astrocytes is decreased and concomitantly, QUIN production by microglia is increased. Importantly, both genetic and pharmacological inhibition of TDO provided robust neuroprotection in a fly model of PD (Breda et al.; Proc Natl Acad Sci. 2016, 113(19):5435-40).

IDO and/or TDO inhibitors may in addition be useful for the treatment of Multiple sclerosis (MS). MS is an autoimmune disease characterized by inflammatory lesions in the white matter of the nervous system, consisting of a specific immune response to the myelin sheet resulting in inflammation and axonal loss (Trapp et al.; Curr Opin Neurol. 1999, 12: 295-302; Owens; Curr Opin Neurol. 2003, 16:259-265). Accumulation of neurotoxic KYN metabolites caused by the activation of the immune system is implicated in the pathogenesis of MS. QUIN was found to be selectively elevated in the spinal cords of rats with EAE, an autoimmune animal model of MS (Flanagan et al.; J Neurochem. 1995, 64: 1192-6). The origin of the increased QUIN in EAE was suggested to be the macrophages. QUIN is an initiator of lipid peroxidation and high local levels of QUIN near myelin may contribute to the demyelination in EAE and possibly MS. Interferon-β Ib (IFN-pib) induces KYN pathway metabolism in macrophages at concentrations comparable to those found in the sera of IFN-β treated patients, which may be a limiting factor in its efficacy in the treatment of MS (Guillemin et al.; J Interferon Cytokine Res. 2001, 21:1097-1101). After IFN-β administration, increased KYN levels and KYN/TRP ratio were found in the plasma of MS patients receiving IFN-β injection compared to healthy subjects indicating an induction of IDO by IFN-β (Amirkhani et al.; Eur. J. Neurol. 2005, 12, 625-31). IFN-pib, leads to production of QUIN at concentrations sufficient to disturb the ability of neuronal dendrites to integrate incoming signals and kill oligodendrocytes (Cammer et al.; Brain Res. 2001, 896: 157-160). In IFN-pib-treated patients concomitant blockade of the KYN pathway with an IDO/TDO inhibitor may improve its efficacy of IFN-pib.

Most TRP is processed through the KYN pathway. A small proportion of TRP is processed to 5-HT and hence to melatonin, both of which are also substrates for IDO. It has long been known that amongst other effects acute TRP depletion can trigger a depressive episode and produces a profound change in mood even in healthy individuals. These observations link well with the clinical benefits of serotonergic drugs both to enhance mood and stimulate neurogenesis.

In recent years, the general view of the pathophysiology of schizophrenia (i.e., disturbances in dopamine [DA]transmission) has been expanded to also involve a glutamatergic dysfunction of the brain. Thus, clinical observations show that systemic administration of N-methyl-D-aspartate (NMDA) receptor antagonists (e.g., phencyclidine [PCP] and ketamine) evokes schizophrenia-like symptoms in healthy individuals and provokes symptoms in patients with schizophrenia (Holtze et al.; J Psychiatry Neurosci. 2012, 37(1):53-7). Furthermore, the glutamate deficiency theory has gained some support from genetic findings. A hypoglutamatergic state of the brain can also be achieved by elevation of the endogenous NMDA receptor antagonist KYNA. Indeed, altered brain level of KYNA and of KYNA-producing enzymes are found in the post-mortem brains of schizophrenic patients (Barry et al.; J Psychopharmacol. 2009, 23(3):287-94). In particular, elevated KYN and KYNA levels are found in the frontal cortex and an upregulation of the first step of the KYN pathway is observed in the anterior cingulate cortex of individuals with schizophrenia (Miller et al.; Brain Res. 2006, 1073-1074:25-37). However, other researchers have found that KYNA is decreased and 3-HAA is increased in schizophrenia (Miller et al.; Neurochem Int. 2008, 52(6):1297-303). The mechanism of elevation of KYN metabolites in schizophrenia has not been fully elucidated. Mechanisms include KMO polymorphisms and TDO upregulation (Miller et al.; Neurobiol Dis. 2004, 15(3):618-29). Therefore, IDO and/or TDO inhibitors may be useful for the treatment of schizophrenia.

IDO and/or TDO inhibitors may in addition be useful for the treatment of pain and depression. Pain and depression are frequently comorbid disorders. It has been shown that IDO plays a key role in this comorbidity. Recent studies have shown that IDO activity is linked to (a) decreased serotonin content and depression (Dantzer et al.; Nat Rev Neurosci. 2008, 9(1):46-56; Sullivan et al; Pain. 1992, 50(1):5-13) and (b) increased KYN content and neuroplastic changes through the effect of its derivatives such as quinolinic acid on glutamate receptors (Heyes et al.; Brain. 1992, 115(Pt5):1249-73).

In rats chronic pain induced depressive behaviour and IDO upregulation in the bilateral hippocampus. Upregulation of IDO resulted in the increased KYN/TRP ratio and decreased serotonin/TRP ratio in the bilateral hippocampus. Furthermore, IDO gene knockout or pharmacological inhibition of hippocampal IDO activity attenuated both nociceptive and depressive behaviour (Kim et al.; J Clin Invest. 2012, 122(8):2940-54).

Since proinflammatory cytokines have been implicated in the pathophysiology of both pain and depression, the regulation of brain IDO by proinflammatory cytokines serves as a critical mechanistic link in the comorbid relationship between pain and depression through the regulation of TRP metabolism.

Moreover, the KYN pathway has been associated with traumatic brain injury (TBI). TBI has been shown to induce a striking activation of the KYN pathway with sustained increase of QUIN (Yan et al.; Journal of Neuroinflammation 2015, 12 (110): 1-17). The exceeding production of QUIN together with increased IDO1 activation and mRNA expression in brain-injured areas suggests that TBI selectively induces a robust stimulation of the neurotoxic branch of the KYN pathway. QUIN's detrimental roles are supported by its association to adverse outcome potentially becoming an early prognostic factor post-TBI. Hence, IDO and/or TDO inhibitors may in addition be useful for the prevention/treatment of TBI.

Infection by bacteria, parasites, or viruses induces a strong IFN-γ-dependent inflammatory response. IDO can dampen protective host immunity, thus indirectly leading to increased pathogen burdens. For example, in mice infected with murine leukaemia virus (MuLV), IDO was found to be highly expressed, and ablation of IDO enhanced control of viral replication and increased survival (Hoshi et al.; J Immunol. 2010, 185(6):3305-3312).

In a model of influenza infection, the immunosuppressive effects of IDO could predispose lungs to secondary bacterial infection (van der Sluijs et al.; J Infect Dis. 2006, 193(2): 214-22). Hence, IDO activity was increased in community-acquired pneumonia (CAP), and this activity was associated with the severity and outcome of this disease. These results suggest that IDO activity can predict prognosis of CAP (Suzuki et al.; J Infect. 2011 September; 63(3):215-22).

In Chagas Disease, which is caused by the *Trypanosoma cruzi* parasite, KYN is increased in patients and correlates with disease severity (Maranon et al.; Parasite Immunol. 2013, 35 (5-6):180-7). Infection with *Chlamydia trachomatis* induces the production of a large amount of IFN-γ which in turn causes IDO induction. A study has shown that IDO mediated depletion of the TRP pool causes *Chlamydia* to convert into a persistent form which is highly adapted to survive in hostile environments (Barth and Raghuraman; Crit Rev Microbiol. 2014, 40(4):360-8). In patients with chronic cutaneous leishmaniasis, high levels of IDO mRNA expression has been detected in infectious lesions and was associated with the accumulation of intralesional Treg cells. *Leishmania major* infection in mice induces IDO expression in local cutaneous lesions and draining lymph nodes. Genetic and pharmacological ablation of IDO resulted in improved control of *L. major*. Cerebral malaria can be a fatal manifestation of *Plasmodium falciparum* infection in humans. IDO activity is increased in the mouse brain during cerebral malaria and inhibition of IDO in a mouse model of malaria enhanced the function of anti-malarial T cells and slightly reduce the parasite load (Barth and Raghuraman; Crit Rev Microbiol. 2014, 40(4):360-8).

Measuring serum concentrations of KYN and TRP and assessed IDO activity in patients with pulmonary tuberculosis showed significant increases in Kyn concentrations and IDO activity and significant decreases in Trp concentrations compared to control subjects. Interestingly, among the pulmonary tuberculosis patients, nonsurvivors had significantly higher Kyn concentrations and significantly lower Trp concentrations, resulting in a significant increase in IDO activity over that in survivors. Most importantly, multivariate analysis showed that the IDO activity was a significant independent predictor of death in pulmonary tuberculosis (Suzuki et al.; Clin Vaccine Immunol. 2012, 19(3): 436-442).

Therefore, IDO inhibitors could be used to improve the outcomes of patients with a wide variety of infectious diseases and inflammatory conditions. Given the role of TDO in controlling systemic TRP levels, TDO inhibitors could also be used to improve the outcomes of patients with a wide variety of infectious diseases and inflammatory conditions.

Patients infected with HIV have chronically reduced levels of plasma TRP and increased levels of KYN, and increased IDO expression (Murray; Lancet Infect Dis. 2003, 3(10):644-52). In HIV patients the upregulation of IDO acts to suppress immune responses to HIV antigens contributing to the immune evasion of the virus. A characteristic feature during advanced HIV infection is the preferential depletion of Th17 cells from both the gastrointestinal tract and blood. Interestingly, the loss of Th17 cells in HIV infection is accompanied by a concomitant rise in the frequency of induced Treg cells and directly correlated with IDO activity. Treg cells may dampen efficient HIV specific cellular immune responses while the progressive depletion of Th17 cells may increase susceptibility to mucosal infections. Thus sustained IDO activation may establish a favourable environment for HIV persistence and contribute to the immunodeficiency seen in HIV-infected individuals with progressive disease (Barth and Raghuraman; Crit Rev Microbiol. 2014, 40(4):360-8). HIV patients, particularly those with HIV-linked dementia (Kandanearatchi & Brew; FEBS J. 2012, 279(8):1366-74), often have significantly elevated KYN levels in CSF. These levels are directly related to the development of neurocognitive decline (HIV-associated neurocognitive disorder (HAND)) and often the presence of severe psychotic symptoms (Stone & Darlington; Trends Pharmacol Sci. 2013, 34(2):136-43). Therefore, IDO and/or TDO inhibitors may in addition be useful for the treatment of HIV (AIDS including its manifestations such as cachexia, dementia and diarrhea).

As with HIV infection, patients chronically infected with HCV present increased KYN to TRP ratios in blood compared to patients with resolved HCV infections and healthy individuals (Larrea et al.; J Virol. 2007, 81(7):3662-6). Furthermore, it has been suggested that expression of IDO correlated with the pathogenesis of the disease and the high expression of IDO in progressively cirrhotic livers of HCV-infected patients might contribute to the development of hepatocellular carcinoma (Asghar et al.; Exp Ther Med. 2015, 9(3):901-4). Hence, IDO and/or TDO inhibitors may be useful for the treatment of patients chronically infected with HCV.

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al.; Infect Immunol. 2008, 76(7):3045-53).

Therefore, pharmacological targeting of IDO/TDO activity may represent a new approach to manipulating intestinal immunity and controlling the pathology caused by enteric pathogens including colitis (Harrington et al.; Infect Immunol. 2008, 76(7):3045-53).

Recent literature highlights a role for IDO in metabolic disorders (Laurans et al.; Nature Medicine https://doi.org/10.1038/s41591-018-0060-4 (2018); Natividad et al.; Cell Metabolism 2018, 28: 1-13). It was found that Idol knockout mice that were fed a high-fat diet gained less weight, had a lower fat mass, better glucose and insulin tolerance and less macrophage infiltration into fat tissue than wild-type mice did. Treatment with an IDO inhibitor, L-1-MT, concurrent with a high-fat diet had a similar effect on insulin and glucose tolerance to that in the knockout. The fact that antibiotic treatment prevented Idol knockout mice from gaining weight on a high-fat diet and co-housing of Idol knockout and wt mice had metabolic measurements similar to those of Idol knockout mice suggested that the microbiota from Idol knock-out mice is protective. Consistent with these hypotheses, Ido-1 knock-out mice had different intestinal microbiota composition. TRP can be metabolized either by IDO to produce KYN or by the gut microbiota to produce indole derivatives such as indole-3-acetic acid, a ligand for the AhR. Depletion of IDO increased the lecels of indole-3-acetic acid in the faeces. Indole-3-acetic acid induced activation of the AhR in intestinal immune cells increases the production of IL-17 and IL-22. Reduced levels of IL-22 were accompanied with dysfunction of the gut barrier. These data support the importance of IDO in controlling KYN and indole-3-acetic acid-activating AhR balance. Consistent with the observations in mice, people with obesity or type 2 diabetes had higher levels of KYN in their plasma and faeces and lower levels of indole-3-acetic acid in their faeces (Laurans et al.; Nature Medicine https://doi.org/10.1038/s41591-018-0060-4 (2018). Increased KYN levels were also found in fecal samples of individuals with metabolic syndrome compared to healthy subjects in another study (Natividad et al.; Cell Metabolism 2018, 28: 1-13). Thus far it is unknown whether the alterations of AhR agonist production by the gut microbiota is the primary event in metabolic syndrome pathogenesis. However, the therapeutic effects of the correction of this defect by applying an AhR agonist shows its involvement in the pathogenesis (Natividad et al.; Cell Metabolism 2018, 28: 1-13). Hence IDO inhibitors through altering the balance of TRP derived AhR agonist balance may be useful in regulating metabolic disorders such as obesity, type 2 diabetes and/or fatty acid liver disease.

A cataract is a clouding of the lens inside the eye that leads to a decrease in vision. Recent studies suggest that KYNs might chemically alter protein structure in the human lens leading to cataract formation. In the human lens IDO activity is present mainly in the anterior epithelium (Takikawa et al.; Adv Exp Med Biol. 1999, 467: 241-5). Several KYNs, such as KYN, 3-HK, and 3-hydroxykynurenine glucoside (3-HK-G) have been detected in the lens; where they were thought to protect the retina by absorbing UV light and therefore are commonly referred to as UV filters. However, several recent studies show that KYNs are prone to deamination and oxidation to form $\alpha,\beta$-unsaturated ketones that chemically react and modify lens proteins (Taylor et al.; Exp Eye Res. 2002; 75(2): 165-75). KYN mediated modification could contribute to the lens protein modifications during aging and cataractogenesis. They may also reduce the chaperone function of a-crystallin, which is necessary for maintaining lens transparency.

Transgenic mouse lines that overexpress human IDO in the lens developed bilateral cataracts within 3 months of birth. It was demonstrated that IDO-mediated production of KYNs results in defects in fibre cell differentiation and their apoptosis (Mailankot et al.; Lab Invest. 2009; 89(5):498-512). Therefore, inhibition of IDO/TDO may slow the progression of cataract formation.

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al.; Endocrinology. 2007; 148(8): 3814-26; Aghajanova et al.; Reprod Sci. 2011, 18(3):229-251). Furthermore, IDO was shown to enhance the survival and invasiveness of endometrial stromal cells (Mei et al.; Int J Clin Exp Pathol. 2013; 6(3): 431-44). Therefore, an IDO/TDO inhibitor may be used as a treatment for endometriosis.

The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal-maternal interface is necessary to prevent rejection of the foetal allograft (Munn et al.; Science 1998, 281(5380): 1191-3:). Accumulating evidence indicates that IDO production and normal function at the foetal-maternal interface may play a prominent role in pregnancy tolerance (Durr and Kindler; J Leukoc Biol. 2013, 93(5): 681-700). Therefore, an IDO/TDO inhibitor could be used as a contraceptive or abortive agent.

In experimental chronic renal failure, activation of IDO leads to increased blood levels of KYNs (Tankiewicz et al.; Adv Exp Med Biol. 2003, 527:409-14), and in uremic patients KYN-modified proteins are present in urine (Sala et al.; J Biol Chem. 2004, 279(49):51033-41). Further, renal IDO expression may be deleterious during inflammation, because it enhances tubular cell injury.

In coronary heart disease, inflammation and immune activation are associated with increased blood levels of KYN (Wirleitner et al.; Eur J Clin Invest. 2003, 33(7):550-4) possibly via interferon-γ-mediated activation of IDO.

Cardiac surgery involving extra-corporeal circulation can lead to cognitive dysfunction. As such surgery is associated with signs of inflammation and pro-inflammatory mediators activate tryptophan oxidation to neuroactive kynurenines which modulate NMDA receptor function and oxidative stress. Post anaesthesia cognitive dysfunction has often been correlated with these sequelae. Recently these deficits have been shown to be correlated with changes in KYN pathway markers, but not cytokines, following cardiac surgery and in recovering stroke patients (Forrest et al.; J. Neurochem. 201, 119(1):136-52).

In general, TRP catabolism has been reported to be altered in stroke. The activation of the KYN pathway in the acute phase of stroke may participate in the ischemic damage by direct mechanisms which include excitotoxicity and oxidative stress among others, since inhibition of the KYN pathway decreases brain injury in animal models of stroke. Probably, an interplay between the immune system and the KYN pathway could exist after stroke, but also different inflammatory-independent mechanisms could mediate a role in the regulation of this pathway, modulating the rate-limiting enzymes of TRP catabolism. Interestingly, the KYN pathway after cerebral ischemia could also play a role during the chronic phase of this pathology in which stroke survivors present a high incidence of disabilities such as dementia and depression or even being a risk factor for stroke outcome and mortality. All together the KYN and TRP catabolism could have a significant role in after cerebral ischemia and IDO/TDO inhibitors may provide new pharmacological tools in both acute and chronic phases of stroke (Cuartero et al.; Curr Pharm Des. 2016; 22(8): 1060-1073).

The present invention provides novel compounds of Formula (I) which inhibit the activity of IDO and/or TDO enzymes.

1) A first embodiment of the present invention relates to compounds of Formula (I)

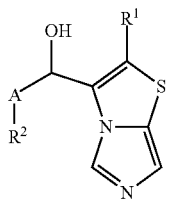

Formula (I)

wherein
A represents a direct bond (i.e. $R^2$ is directly attached to the carbon atom bearing the OH group), $C_{1-3}$-alkylene, $C_{2-3}$-alkenylene or $C_{2-3}$-alkynylene;
$R^1$ represents:
  $C_{2-3}$-alkenyl;
  $C_{1-4}$-alkyl;
  $C_{1-3}$-fluoroalkyl;
  halogen;
  $C_{3-6}$-cycloalkyl which independently is unsubstituted, or mono-, or di-substituted, wherein the substituents are independently selected from $C_{1-4}$-alkyl and fluorine;
  phenyl which independently is unsubstituted, or mono-, or di-substituted, wherein the substituents are independently selected from $C_{1-4}$-alkyl, halogen, $C_{1-3}$-alkoxy, $C_{1-3}$-fluoroalkyl and $C_{1-3}$-fluoroalkoxy;
  5- to 6-membered heteroaryl which contains one or two ring heteroatoms independently selected from nitrogen, oxygen and sulphur, wherein said 5- to 6-membered heteroaryl independently is unsubstituted or mono-substituted with $C_{1-4}$-alkyl;
  $C_{1-3}$-alkoxy-methyl; or
  benzyl;
$R^2$ represents:
  aryl or 5- to 6-membered heteroaryl, wherein said aryl or 5- to 6-membered heteroaryl independently is unsubstituted, or mono-, di- or tri-substituted, wherein the substituents are independently selected from $C_{1-4}$-alkyl, $C_{3-6}$-cycloalkyl, halogen, $C_{1-3}$-fluoroalkyl, $C_{1-3}$-alkoxy, $C_{1-3}$-fluoroalkoxy, and —$NR^{N1}R^{N2}$, wherein $R^{N1}$ and $R^{N2}$ independently represent hydrogen or $C_{1-4}$-alkyl;
  5- to 6-membered heterocycloalkyl which independently is unsubstituted, or mono-substituted with phenyl;
  $C_{3-7}$-cycloalkyl, wherein said $C_{3-7}$-cycloalkyl independently is unsubstituted, or mono-, di- or tri-substituted, wherein the substituents are independently selected from $C_{1-4}$-alkyl; hydroxy; halogen; $C_{1-3}$-alkoxy; $C_{1-3}$-fluoroalkoxy; $C_{1-3}$-fluoroalkyl; $C_{3-6}$-cycloalkyl; $NR^{N3}R^{N4}$, wherein $R^{N3}$ and $R^{N4}$ independently represent hydrogen or $C_1a4$-alkyl; and phenyl-$(CH_2)_{0-1}$—, wherein the phenyl is independently unsubstituted, or mono- or di-substituted, wherein the substituents are independently selected from $C_{1-4}$-alkyl, halogen, $C_{1-3}$-fluoroalkyl, $C_{1-3}$-alkoxy and $C_{1-3}$-fluoroalkoxy;
  a saturated 5- to 11-membered bridged, fused, or spirobicyclic hydrocarbon ring system; wherein said ring system independently is unsubstituted or mono-substituted with phenyl; wherein said ring system optionally contains one carbon-carbon double bond; or wherein in said ring system optionally one ring carbon atom is replaced by a ring oxygen atom;
  $C_{5-6}$-cycloalkyl which is fused to a phenyl ring, wherein said $C_{5-6}$-cycloalkyl is independently unsubstituted, or mono-, or di-substituted, wherein the substituents are independently selected from $C_{1-4}$-alkyl; and wherein said fused phenyl ring is independently unsubstituted, or mono- or di-substituted, wherein the substituents are independently selected from $C_{1-4}$-alkyl, halogen, $C_{1-3}$-fluoroalkyl, $C_{1-3}$-alkoxy and $C_{1-3}$-fluoroalkoxy; or
  branched $C_{3-6}$-alkyl.

2) Another embodiment of the present invention relates to compounds of embodiment 1), wherein
A represents a direct bond (i.e. $R^2$ is directly attached to the carbon atom bearing the OH group) or $C_{1-3}$-alkylene;
$R^1$ represents $C_{1-4}$-alkyl, $C_{2-3}$-alkenyl, halogen, $C_{1-3}$-fluoroalkyl or $C_{3-6}$-cycloalkyl; and
$R^2$ represents:
  aryl or 5- to 6-membered heteroaryl; wherein said aryl or 5- to 6-membered heteroaryl independently is unsubstituted, or mono-, di- or tri-substituted, wherein the substituents are independently selected from $C_{1-4}$-alkyl, halogen, $C_{1-3}$-fluoroalkyl, $C_{1-3}$-alkoxy, $C_{1-3}$-fluoroalkoxy, and —$NR^{N1}R^{N2}$, wherein $R^{N1}$ and $R^{N2}$ independently represent hydrogen or $C_{1-4}$-alkyl;
  $C_{3-7}$-cycloalkyl, wherein said $C_{3-7}$-cycloalkyl independently is unsubstituted, or mono-, di- or tri-substituted, wherein the substituents are independently selected from $C_{1-4}$-alkyl, halogen, $C_{1-3}$-alkoxy, $C_{1-3}$-fluoroalkoxy, $C_{1-3}$-fluoroalkyl; $C_{3-6}$-cycloalkyl; and phenyl-$(CH_2)_{0-1}$—, wherein the phenyl is independently unsubstituted, or mono- or di-substituted, wherein the substituents are independently selected from $C_{1-4}$-alkyl, halogen, $C_{1-3}$-fluoroalkyl, $C_{1-3}$-alkoxy and $C_{1-3}$-fluoroalkoxy;

a saturated 7- to 11-membered bridged, fused, or spiro-bicyclic hydrocarbon ring system; wherein said ring system optionally contains one carbon-carbon double bond, or wherein in said ring system optionally one ring carbon atom is replaced by a ring oxygen atom;

$C_{5-6}$-cycloalkyl which is fused to a phenyl ring; wherein said $C_{5-6}$-cycloalkyl is independently unsubstituted, or mono-, or di-substituted, wherein the substituents are independently selected from $C_{1-4}$-alkyl; and wherein said fused phenyl ring is independently unsubstituted, or mono- or di-substituted, wherein the substituents are independently selected from $C_{1-4}$-alkyl, halogen, $C_{1-3}$-fluoroalkyl, $C_{1-3}$-alkoxy and $C_{1-3}$-fluoroalkoxy; or branched $C_{3-6}$-alkyl.

3) Another embodiment of the present invention relates to compounds according to embodiment 1), wherein
A represents a direct bond (i.e. $R^2$ is directly attached to the carbon atom bearing the OH group), —$CH_2$—, —CH($CH_2CH_3$)—, —$CH_2CH(CH_3)$— or —C≡C—;
$R^1$ represents:
vinyl;
$C_{1-4}$-alkyl;
trifluoromethyl;
chlorine or bromine;
$C_{3-6}$-cycloalkyl (especially cyclopropyl, cyclobutyl or cyclopentyl), wherein said $C_{3-6}$-cycloalkyl independently is unsubstituted, or mono-, or di-substituted, wherein the substituents independently are selected from methyl, ethyl or fluorine;
phenyl which independently is unsubstituted or mono-substituted, wherein the substituents independently are selected from methyl, fluorine or methoxy;
5- to 6-membered heteroaryl which contains one or two ring nitrogen atoms (especially pyridinyl or pyrazolyl), wherein said 5- to 6-membered heteroaryl independently is unsubstituted or mono-substituted with methyl; or
thiophenyl which is unsubstituted or mono-substituted with methyl;
$R^2$ represents:
phenyl, which is unsubstituted, or mono-substituted, wherein the substituents are independently selected from $C_{1-4}$-alkyl, halogen, methoxy, dimethylamino and trifluoromethyl;
naphthyl;
thiophenyl;
5-membered heteroaryl which contains two or three ring nitrogen atoms (especially pyrazolyl or triazolyl), wherein said 5-membered heteroaryl is unsubstituted, or mono-substituted, wherein the substituents are independently selected from $C_{1-4}$-alkyl (especially methyl, ethyl or iso-propyl) and $C_{3-7}$-cycloalkyl (especially cyclobutyl, cyclopentyl and cyclohexyl);
piperidinyl, which is mono-substituted with phenyl;
$C_{3-7}$-cycloalkyl, wherein said $C_{3-7}$-cycloalkyl independently is unsubstituted, or mono-, or di-substituted, wherein the substituents are independently selected from $C_{1-4}$-alkyl, hydroxy, fluorine, methoxy, trifluoromethyl, difluoromethyl, $C_{3-6}$-cycloalkyl (especially cyclobutyl or cyclopentyl), ethylamino, phenyl and benzyl;
bicyclo[1.1.1]pentyl, bicyclo[2.1.1]hexyl, bicyclo[2.2.1]heptyl, bicyclo[2.2.1]hept-5-en-2-yl and 7-oxa-bicyclo[2.2.1]hept-2-yl, 4-phenyl-bicyclo[2.1.1]hex-1-yl or 3-phenyl-bicyclo[1.1.1]pent-1-yl;
bicyclo[3.3.0]octyl or bicyclo[4.4.0]decyl;
spiro[4.5]decyl; or
1,2,3,4-tetrahydronaphthalenyl.

4) Another embodiment of the present invention relates to compounds according to any one of embodiments 1) to 2), wherein $R^2$ represents:
aryl or 5-membered heteroaryl (especially thiophenyl, pyrazolyl or triazolyl), wherein said aryl or 5-membered heteroaryl independently is unsubstituted, or mono-, di- or tri-substituted (especially unsubstituted or mono-substituted), wherein the substituents are independently selected from $C_{1-4}$-alkyl, $C_{3-6}$-cycloalkyl, halogen, $C_{1-3}$-fluoroalkyl, $C_{1-3}$-alkoxy, $C_{1-3}$-fluoroalkoxy, and —$NR^{N1}R^{N2}$, wherein $R^{N1}$ and $R^{N2}$ independently represent hydrogen or $C_{1-4}$-alkyl;
6-membered heterocycloalkyl, wherein one carbon atom is replaced by a ring heteroatom selected from nitrogen and oxygen (especially piperidinyl) which independently is unsubstituted, or mono-substituted with phenyl;
$C_{3-7}$-cycloalkyl, wherein said $C_{3-7}$-cycloalkyl independently is unsubstituted, or mono-, di- or tri-substituted (especially unsubstituted, or mono-, or di-substituted), wherein the substituents are independently selected from $C_{1-4}$-alkyl; hydroxy; halogen; $C_{1-3}$-alkoxy; $C_{1-3}$-fluoroalkoxy; $C_{1-3}$-fluoroalkyl; $C_{3-6}$-cycloalkyl; $NR^{N3}R^{N4}$, wherein $R^{N3}$ and $R^{N4}$ independently represent hydrogen or $C_{1-4}$-alkyl (especially hydrogen, methyl or ethyl); and phenyl-$(CH_2)_{0-1}$—, wherein the phenyl is independently unsubstituted, or mono-, di- or tri-substituted (especially unsubstituted phenyl-$(CH_2)_{0-1}$—), wherein the substituents are independently selected from $C_{1-4}$-alkyl, halogen, $C_{1-3}$-fluoroalkyl, $C_{1-3}$-alkoxy and $C_{1-3}$-fluoroalkoxy;
bicyclo[x.y.z]alkyl, wherein the total number of carbon atoms is an integer from 5 to 8, and each one of the integers "x", "y" and "z" is larger than 0; wherein said bicyclo[x.y.z]alkyl is unsubstituted or mono-substituted with phenyl; wherein said bicyclo[x.y.z]alkyl optionally contains one carbon-carbon double bond, or wherein in said bicyclo[x.y.z]alkyl optionally one ring carbon atom is replaced by a ring oxygen atom (especially bicyclo[1.1.1]pentyl, bicyclo[2.1.1]hexyl, bicyclo[2.2.1]heptyl, bicyclo[2.2.1]hept-5-en-2-yl and 7-oxa-bicyclo[2.2.1]hept-2-yl);
bicyclo[x.y.0]alkyl, wherein the total number of carbon atoms is an integer from 7 to 11 (especially bicyclo[3.3.0]octyl and bicyclo[4.4.0]decyl);
spiro[x.y]alkyl, wherein the total number of carbon atoms is an integer from 7 to 11 (especially spiro[4.5]decyl; or
$C_{5-6}$-cycloalkyl which is fused to a phenyl ring; wherein said $C_{5-6}$-cycloalkyl is unsubstituted, or mono-, or di-substituted, wherein the substituents are independently selected from $C_{1-4}$-alkyl; and wherein said fused phenyl ring is unsubstituted (especially unsubstituted 1,2,3,4-tetrahydronaphthalenyl).

5) A further embodiment of the present invention relates to compounds according to any one of embodiments 1) to 2), wherein $R^2$ represents:
aryl or 5-membered heteroaryl (especially thiophenyl); wherein said aryl or 5-membered heteroaryl independently is unsubstituted, or mono-, di- or tri-substituted, wherein the substituents are independently selected from $C_{1-4}$-alkyl, halogen, $C_{1-3}$-fluoroalkyl, $C_{1-3}$- alkoxy, $C_{1-3}$-fluoroalkoxy, and —$NR^{N1}R^{N2}$, wherein $R^{N1}$ and $R^{N2}$ independently represent hydrogen or $C_{1-4}$-alkyl;

$C_{4-7}$-cycloalkyl; wherein said $C_{4-7}$-cycloalkyl independently is unsubstituted, or mono-, or di-substituted, wherein the substituents are independently selected from $C_{1-4}$-alkyl, halogen, $C_{1-3}$-fluoroalkyl, and phenyl;

bicyclo[x.y.z]alkyl, wherein the total number of carbon atoms is an integer from 7 to 11, and each one of the integers "x", "y" and "z" is larger than 0; wherein said bicyclo[x.y.z]alkyl optionally contains one carbon-carbon double bond, or wherein in said bicyclo[x.y.z]alkyl optionally one ring carbon atom is replaced by a ring oxygen atom;

bicyclo[x.y.0]alkyl, wherein the total number of carbon atoms is an integer from 7 to 11;

spiro[x.y]alkyl, wherein the total number of carbon atoms is an integer from 7 to 11;

$C_{5-6}$-cycloalkyl which is fused to a phenyl ring; wherein said $C_{5-6}$-cycloalkyl is unsubstituted, or mono-, or di-substituted, wherein the substituents are independently selected from $C_{1-4}$-alkyl; and wherein said fused phenyl ring is unsubstituted; or branched $C_{3-6}$-alkyl.

6) Another embodiment of the present invention relates to compounds according to any one of embodiments 1) to 2), wherein $R^2$ represents:

phenyl, thiophenyl, triazolyl or pyrazolyl (especially phenyl, thiophen-2-yl, thiophen-3-yl, 1,2,3-triazol-4-yl or pyrazol-4-yl), wherein said groups independently are unsubstituted, or mono-, or di-substituted, wherein the substituents are independently selected from $C_{1-4}$-alkyl (especially methyl, ethyl or iso-propyl), cyclopentyl, trifluoromethyl, halogen, methoxy and dimethylamino;

$C_{3-7}$-cycloalkyl, wherein said $C_{3-7}$-cycloalkyl independently is unsubstituted, or mono-, di- or tri-substituted, wherein the substituents are independently selected from $C_{1-4}$-alkyl, $C_{3-6}$-cycloalkyl (especially cyclobutyl or cyclopentyl), hydroxy, fluorine, difluoromethyl, trifluoromethyl, methoxy, ethylamino, phenyl and benzyl;

bicyclo[1.1.1]pent-1-yl, bicyclo[2.1.1]hex-1-yl, bicyclo[2.2.1]hept-2-yl, bicyclo[2.2.1]hept-1-yl, 4-phenyl-bicyclo[2.1.1]hex-1-yl, 3-phenyl-bicyclo[1.1.1]pent-1-yl, bicyclo[2.2.1]hept-5-en-2-yl, or 7-oxa-bicyclo[2.2.1]hept-2-yl;

bicyclo[3.3.0]oct-3-yl or bicyclo[4.4.0]dec-3-yl;

1,2,3,4-tetrahydronaphthalen-2-yl; or spiro[4.5]dec-8-yl.

7) Another embodiment of the present invention relates to compounds according to any one of embodiments 1) to 2), wherein $R^2$ represents:

phenyl, naphthyl or thiophenyl, wherein said groups are independently unsubstituted, or mono-, or di-substituted (especially mono- or di-substituted), wherein the substituents are independently selected from methyl, ethyl, chloro, methoxy and dimethylamino;

$C_{4-7}$-cycloalkyl; wherein said $C_{4-7}$-cycloalkyl independently is unsubstituted, or mono-, or di-substituted, wherein the substituents are independently selected from methyl, ethyl, trifluoromethyl and fluorine; or bicyclo[2.2.1]hept-2-yl, bicyclo[2.2.1]hept-5-en-2-yl, 7-oxa-bicyclo[2.2.1]hept-2-yl.

8) Another embodiment of the present invention relates to compounds according to any one of embodiments 1) to 2), wherein $R^2$ represents $C_{3-7}$-cycloalkyl, wherein said $C_{3-7}$-cycloalkyl independently is unsubstituted, or mono-, di- or tri-substituted, wherein the substituents are independently selected from $C_{1-4}$-alkyl, halogen, $C_{1-3}$-alkoxy, $C_{1-3}$-fluoroalkyl, $C_{3-6}$-cycloalkyl, hydroxy and phenyl.

9) Another embodiment of the present invention relates to compounds according to any one of embodiments 1) to 2), wherein $R^2$ represents $C_{3-7}$-cycloalkyl, wherein said $C_{3-7}$-cycloalkyl independently is unsubstituted, or mono-, or di-substituted, wherein the substituents are independently selected from methyl, methoxy and phenyl.

10) Another embodiment of the present invention relates to compounds according to any one of embodiments 1) to 2), wherein $R^2$ represents:

bicyclo[x.y.0]alkyl, wherein the total number of carbon atoms is an integer from 7 to 11;

spiro[x.y]alkyl, wherein the total number of carbon atoms is an integer from 7 to 11; or $C_{5-6}$-cycloalkyl which is fused to a phenyl ring; wherein said $C_{5-6}$-cycloalkyl is unsubstituted, or mono-, or di-substituted, wherein the substituents are independently selected from $C_{1-4}$-alkyl; and wherein said fused phenyl ring is unsubstituted.

11) Another embodiment of the present invention relates to compounds according to any one of embodiments 1) to 2), wherein $R^2$ represents bicyclo[1.1.1]pentyl, bicyclo[2.1.1]hexyl, bicyclo[2.2.1]heptyl, bicyclo[2.2.1]hept-5-en-2-yl and 7-oxa-bicyclo[2.2.1]hept-2-yl, 4-phenyl-bicyclo[2.1.1]hex-1-yl, 3-phenyl-bicyclo[1.1.1]pent-1-yl, bicyclo[3.3.0]octyl, bicyclo[4.4.0]decyl, spiro[4.5]decyl or 1,2,3,4-tetrahydronaphthalenyl.

12) Another embodiment of the present invention relates to compounds according to any one of embodiments 1) to 2), wherein $R^2$ represents any one chemical group selected from group I) or group II):

I)

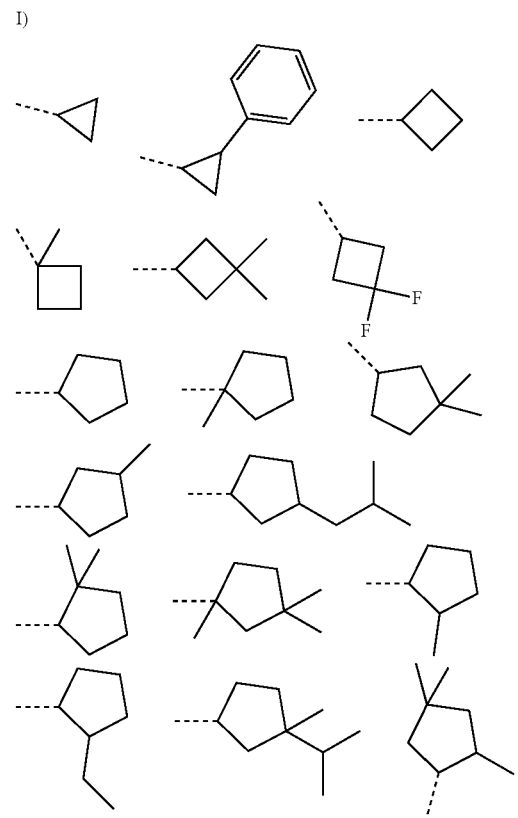

-continued
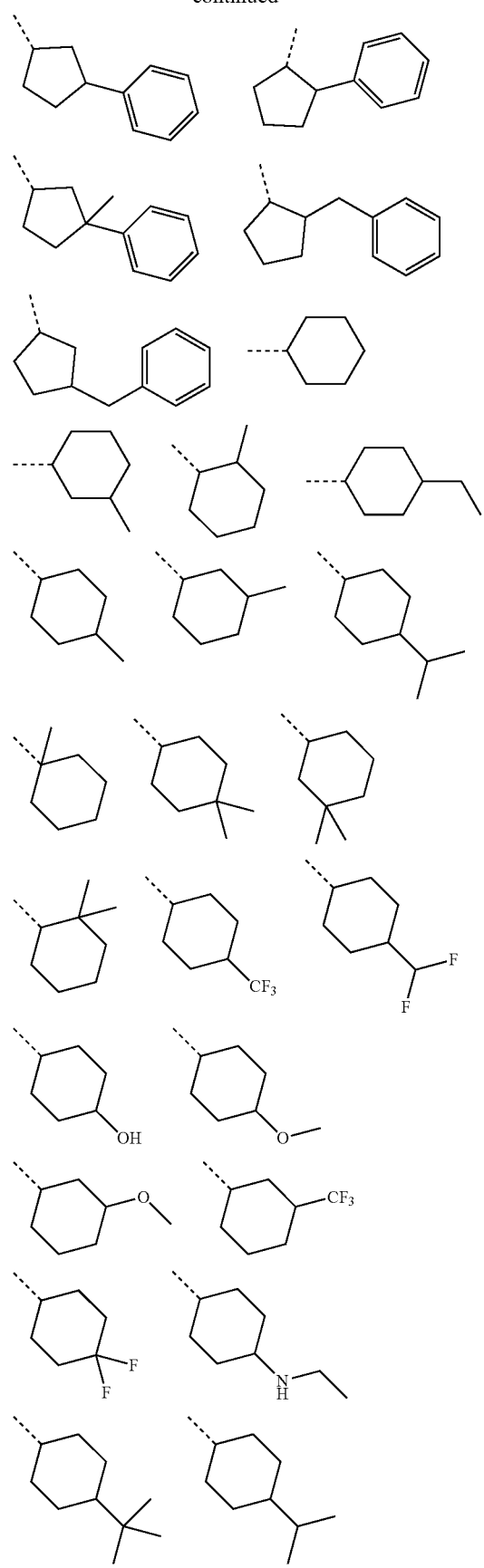
-continued
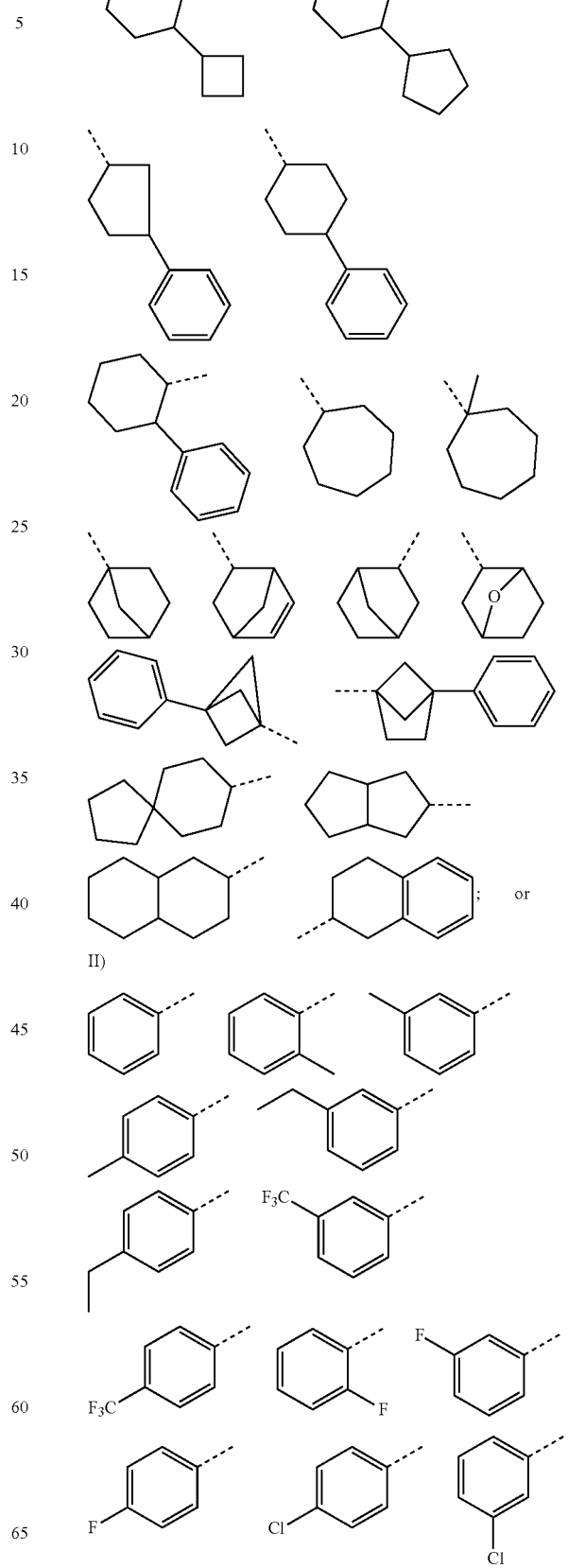
II)

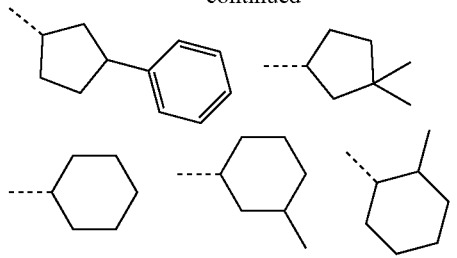
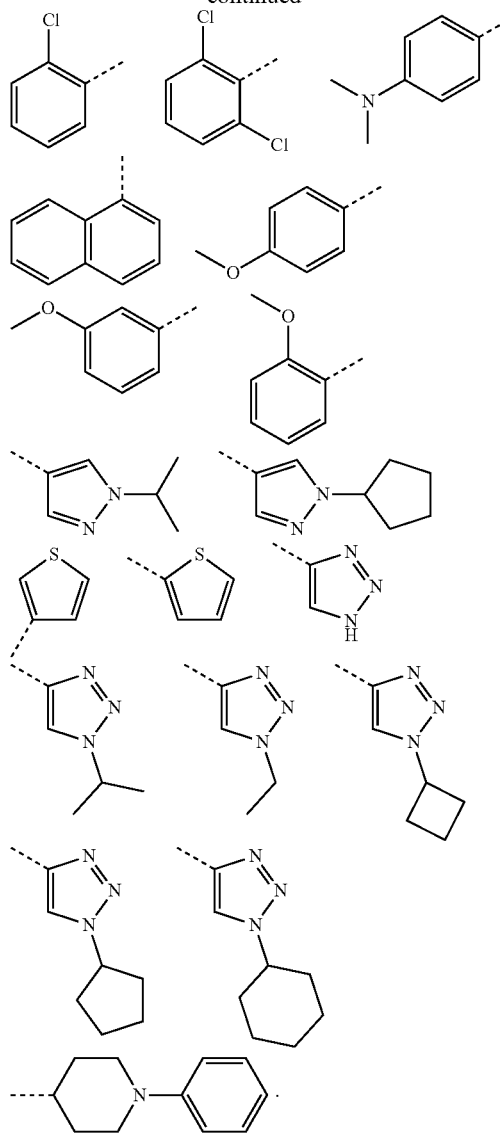
13) Another embodiment of the present invention relates to compounds according to any one of embodiments 1) to 2), wherein $R^2$ represents any one chemical group selected from group III) or group IV):
III)
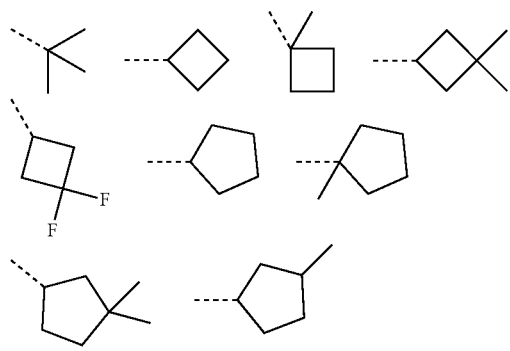
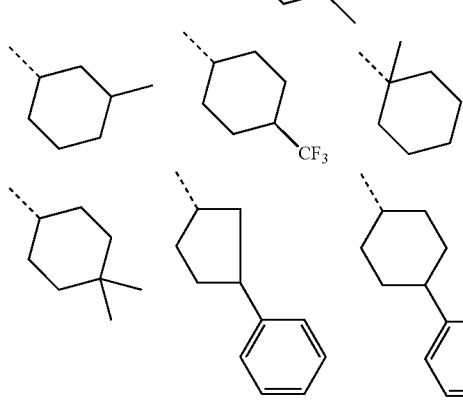
IV)
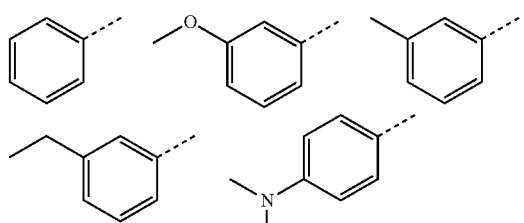
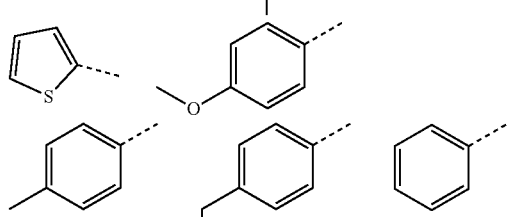
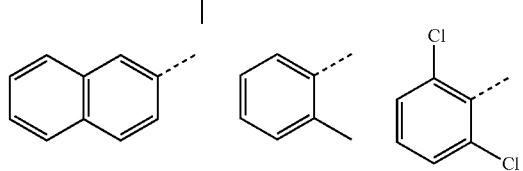
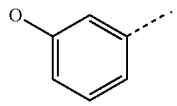; or
14) Another embodiment of the present invention relates to compounds according to any one of embodiments 1) to 2), wherein the fragment R²-A- represents any one chemical group selected from group V) or group VI):
V)
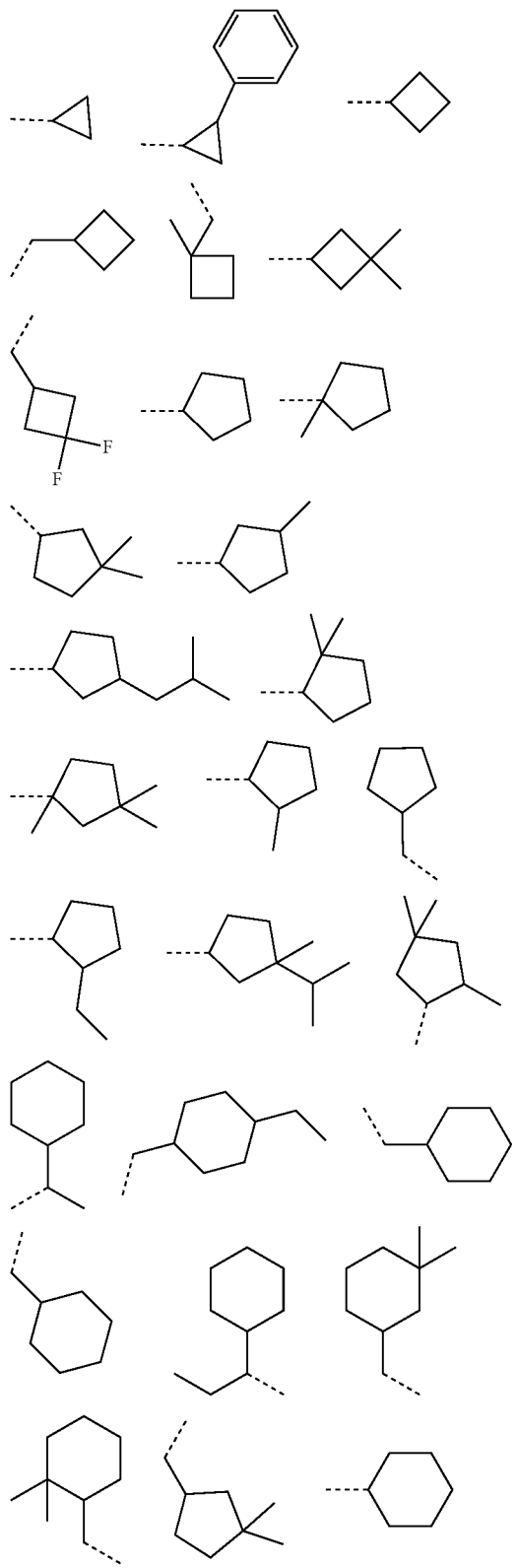
-continued
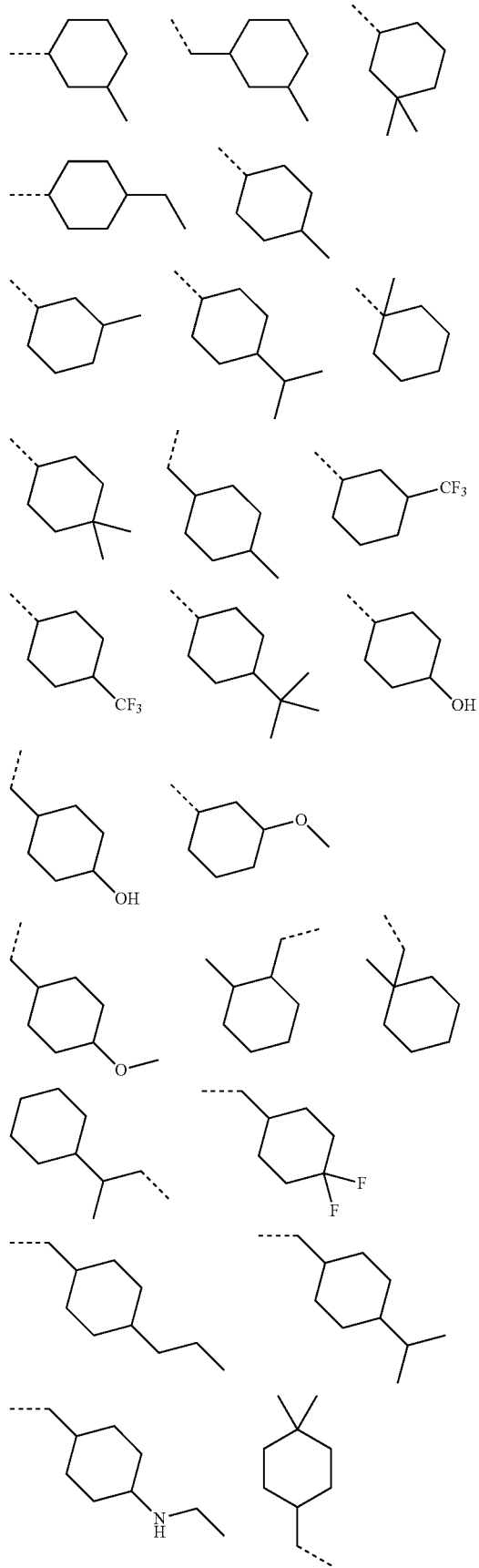

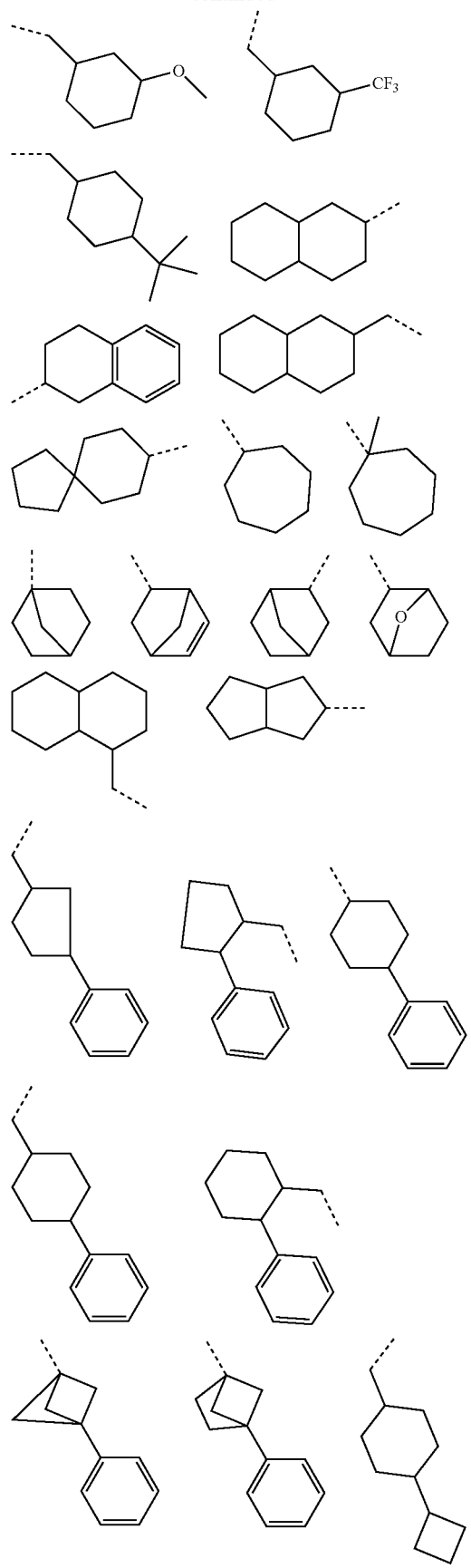
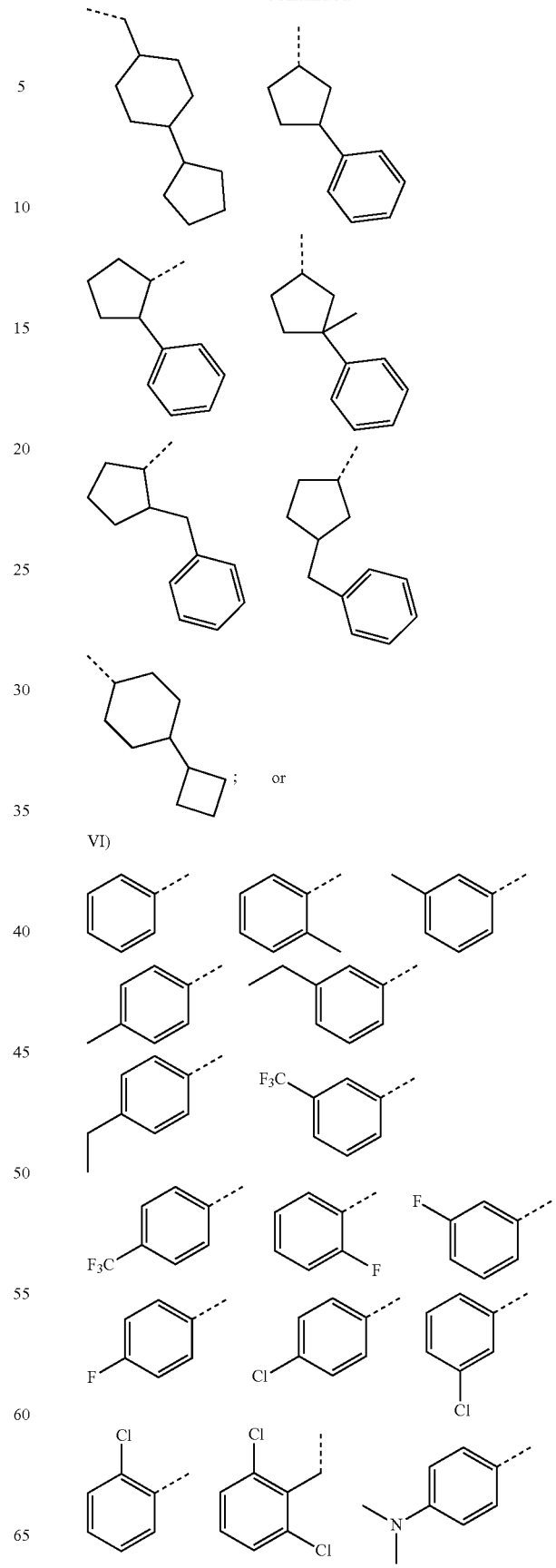
; or
VI)

-continued
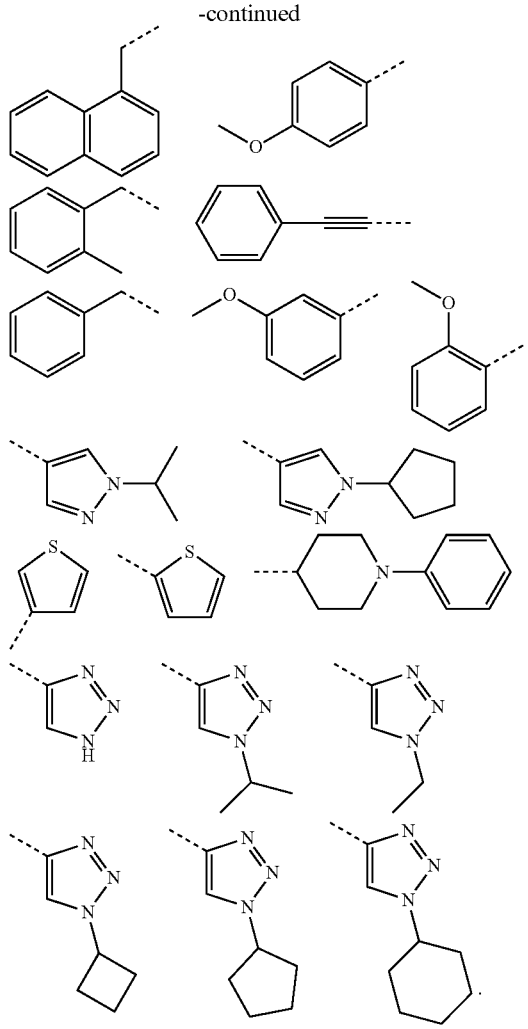
15) Another embodiment of the present invention relates to compounds according to any one of embodiments 1) to 2), wherein the fragment $R^2$-A- represents any one chemical group selected from group VII) or group VIII):
VII)
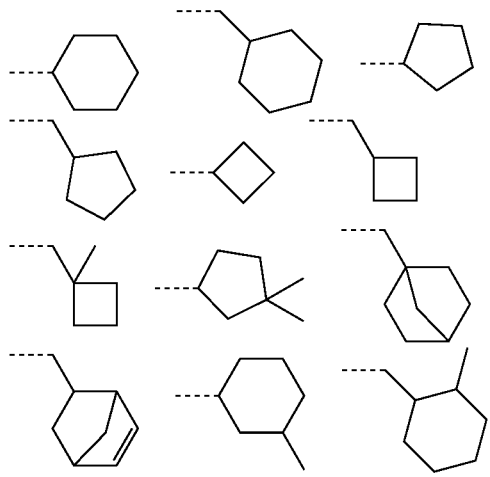
-continued
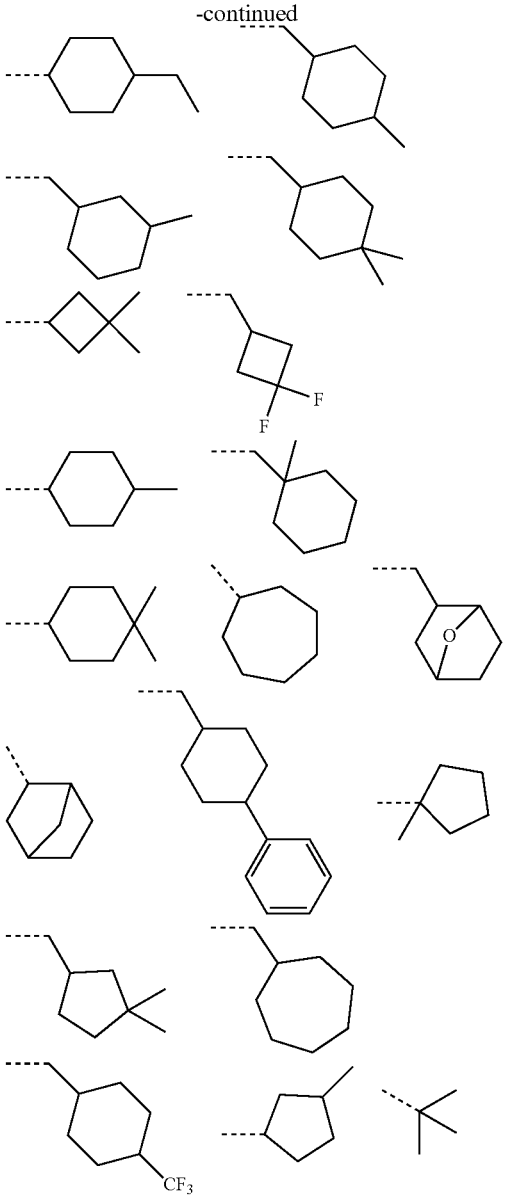
; or
VIII)

-continued

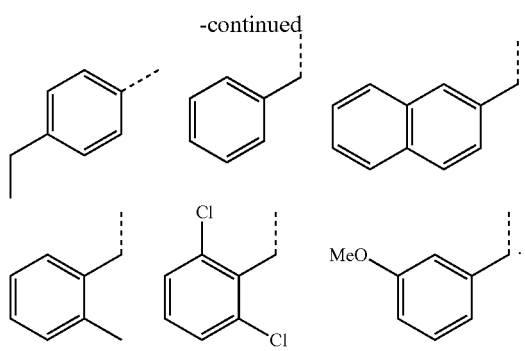

16) Another embodiment of the present invention relates to compounds according to any one of embodiments 1) to 13), wherein A represents a direct bond (i.e. $R^2$ is directly attached to the carbon atom bearing the OH group).
17) Another embodiment of the present invention relates to compounds according to any one of embodiments 1) to 13), wherein A represents $C_{1-3}$-alkylene (especially —$CH_2$—, —$CH(CH_2CH_3)$— or —$CH_2CH(CH_3)$—).
18) Another embodiment of the present invention relates to compounds according to any one of embodiments 1) to 13), wherein A represents —$CH_2$—.
19) Another embodiment of the present invention relates to compounds according to any one of embodiments 1) to 18), wherein
$R^1$ represents:
- $C_{2-3}$-alkenyl (especially vinyl);
- $C_{1-4}$-alkyl (especially methyl, ethyl, n-propyl, iso-propyl, iso-butyl, sec-butyl, tert-butyl);
- $C_{1-3}$-fluoroalkyl (especially trifluoromethyl);
- halogen (especially chlorine or bromine);
- $C_{3-6}$-cycloalkyl (especially cyclopropyl, cyclobutyl or cyclopentyl) which independently is unsubstituted, or mono-, or di-substituted, wherein the substituents independently are selected from $C_{1-4}$-alkyl (especially methyl) or fluorine;
- phenyl which independently is unsubstituted or mono-substituted, wherein the substituents independently are selected from $C_{1-4}$-alkyl, halogen or $C_{1-3}$-alkoxy (especially methyl, fluoro or methoxy);
- 5- to 6-membered heteroaryl which contains one or two ring nitrogen atoms (especially pyridinyl or pyrazolyl), wherein said 5- to 6-membered heteroaryl independently is unsubstituted or mono-substituted with $C_{1-4}$-alkyl (especially methyl); or
- thiophenyl which is unsubstituted or mono-substituted with $C_{1-4}$-alkyl (especially methyl).
20) Another embodiment of the present invention relates to compounds according to any one of embodiments 1) to 18), wherein $R^1$ represents $C_{1-4}$-alkyl (especially methyl, ethyl, n-propyl, iso-propyl, iso-butyl, sec-butyl, and tert-butyl), chloro, bromo, C-fluoroalkyl (especially trifluoromethyl), $C_{3-6}$-cycloalkyl (especially cyclopropyl, cyclobutyl or cyclopentyl) or $C_{2-3}$-alkenyl (especially vinyl).
21) Another embodiment of the present invention relates to compounds according to any one of embodiments 1) to 18), wherein $R^1$ represents $C_{1-4}$-alkyl (especially methyl, ethyl, iso-propyl and tert-butyl), chloro, bromo, $C_1$-fluoroalkyl (especially trifluoromethyl), $C_{3-5}$-cycloalkyl (especially cyclopropyl, cyclobutyl or cyclopentyl) or $C_{2-3}$-alkenyl (especially vinyl).
22) Another embodiment of the present invention relates to compounds according to any one of embodiments 1) to 18), wherein $R^1$ represents $C_{1-4}$-alkyl (especially methyl, ethyl, n-propyl, iso-propyl, iso-butyl, sec-butyl, tert-butyl; and notably methyl, ethyl, iso-propyl or tert-butyl).
23) Another embodiment of the present invention relates to compounds according to any one of embodiments 1) to 18), wherein $R^1$ represents chlorine or bromine.
24) Another embodiment of the present invention relates to compounds according to any one of embodiments 1) to 18), wherein $R^1$ represents methyl, ethyl, iso-propyl or cyclopropyl (especially cyclopropyl).
25) Another embodiment of the present invention relates to compounds according to any one of embodiments 1) to 18), wherein $R^1$ represents $C_1$-fluoroalkyl (especially trifluoromethyl) or $C_{3-5}$-cycloalkyl (especially cyclopropyl, cyclobutyl or cyclopentyl).
26) Another embodiment of the present invention relates to compounds according to any one of embodiments 1) to 18), wherein $R^1$ represents chloro, bromo, $C_1$-fluoroalkyl (especially trifluoromethyl), $C_{3-6}$-cycloalkyl (especially cyclopropyl, cyclobutyl, cyclopentyl) or $C_{2-3}$-alkenyl (especially vinyl).
27) Another embodiment of the present invention relates to compounds according to any one of embodiments 1) to 26), wherein the asymmetric carbon atom to which the fragment $R^2$-A- is attached has the absolute configuration depicted in Formula (II):

Formula (II)

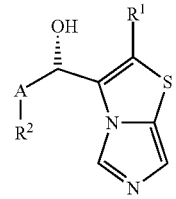

28) Another embodiment of the present invention relates to compounds according to any one of embodiments 1) or 27), wherein A represents a bond or methylene (especially a bond); $R^1$ represents vinyl, methyl, ethyl, cyclopropyl or cyclobutyl (especially methyl, ethyl or cyclopropyl); and $R^2$ represents $C_{3-7}$-cycloalkyl (especially cyclopentyl or cyclohexyl), wherein said $C_{3-7}$-cycloalkyl independently is unsubstituted, mono-, or di-substituted (especially unsubstituted or mono-substituted), wherein the substituents are independently selected from $C_{1-4}$-alkyl, $C_{3-6}$-cycloalkyl (especially cyclobutyl or cyclopentyl), hydroxy, fluorine, difluoromethyl, trifluoromethyl, methoxy and phenyl.
29) Another embodiment of the present invention relates to compounds according to any one of embodiments 1) or 27), wherein A represents a bond or methylene; $R^1$ represents methyl; and $R^2$ represents cyclohexyl.
30) Another embodiment of the present invention relates to compounds according to any one of embodiments 1) or 27), wherein A represents a bond; $R^1$ represents cyclopropyl; and $R^2$ represents 3,3-dimethyl-cyclobutyl, cyclopentyl, 1-methyl-cyclopentyl or cyclohexyl.
31) Another embodiment of the present invention relates to compounds according to any one of embodiments 1) or 27), wherein A represents a bond; $R^1$ represents ethyl, vinyl or cyclopropyl (especially cyclopropyl); and $R^2$ represents 3,3-dimethyl-cyclobutyl, cyclopentyl, 1-methyl-cyclopentyl, 3,3-dimethyl-cyclopentyl or cyclohexyl.
32) Another embodiment of the present invention relates to compounds according to any one of embodiments 1) or 27), wherein A represents bond or methylene; $R^1$ represent vinyl, methyl, ethyl, iso-propyl, cyclopropyl, trifluoromethyl or cyclopropyl, wherein said cyclopropyl is unsubstituted or mono-substituted with fluorine; and $R^2$ represents $C_{3-7}$-cycloalkyl (especially cyclobutyl, cyclopentyl or cyclohexyl), wherein said $C_{3-7}$-cycloalkyl independently is unsubstituted, mono-, or di-substituted (especially unsubstituted or mono-substituted), wherein the substituents are independently selected from methyl, hydroxy, methoxy and phenyl (especially methyl or phenyl).

33) Another embodiment of the present invention relates to compounds according to embodiment 27), wherein A represents methylene; $R^1$ represent cyclopropyl; and $R^2$ represents cyclopentyl, cyclohexyl, cycloheptyl.

34) Another embodiment of the present invention relates to compounds according to embodiment 27), wherein A represents a bond or methylene; $R^1$ represent iso-propyl; and $R^2$ represents cyclohexyl.

35) Another embodiment of the present invention relates to compounds according to embodiment 1) or 27), wherein A represents a bond or methylene; $R^1$ represent cyclopropyl; $R^2$ represents phenyl, optionally mono-substituted with $C_{1-4}$-alkyl or $C_{1-3}$-alkoxy.

36) Another embodiment of the present invention relates to compounds according to embodiments 1) or 27), wherein A represents a bond or methylene; $R^1$ represents trifluoromethyl; and $R^2$ represents cyclohexyl.

37) Another embodiment of the present invention relates to compounds according to any one of embodiments 1) to 36) with the exception of cyclopentyl-(2-methyl-imidazo[5,1-b]thiazol-3-yl)-methanol.

38) Another embodiment of the present invention relates to a compound of embodiment 1) selected from a group consisting of:
(S)-cyclohexyl(2-cyclopropylimidazo[5,1-b]thiazol-3-yl) methanol;
(S)-2-cyclohexyl-1-(2-cyclopropylimidazo[5,1-b]thiazol-3-yl)ethan-1-ol;
(S)-cyclohexyl-(2-isopropyl-imidazo[5,1-b]thiazol-3-yl)-methanol;
(S)-2-cyclohexyl-1-(2-isopropyl-imidazo[5,1-b]thiazol-3-yl)-ethanol;
(S)-2-cyclohexyl-1-(2-methyl-imidazo[5,1-b]thiazol-3-yl)-ethanol;
(S)-cyclohexyl-(2-methyl-imidazo[5,1-b]thiazol-3-yl)-methanol;
(S)-(2-cyclobutylimidazo[5,1-b]thiazol-3-yl)(cyclohexyl) methanol;
(S)-1-(2-cyclobutylimidazo[5,1-b]thiazol-3-yl)-2-cyclohexylethan-1-ol;
(S)-cyclohexyl(2-cyclopentylimidazo[5,1-b]thiazol-3-yl) methanol;
(S)-2-cyclohexyl-1-(2-cyclopentylimidazo[5,1-b]thiazol-3-yl)ethan-1-ol;
(2-(tert-butyl)imidazo[5,1-b]thiazol-3-yl)(cyclohexyl) methanol;
1-(2-(tert-butyl)imidazo[5,1-b]thiazol-3-yl)-2-cyclohexylethan-1-ol;
(S)-(2-chloroimidazo[5,1-b]thiazol-3-yl)(cyclohexyl) methanol;
(2-bromoimidazo[5,1-b]thiazol-3-yl)(cyclohexyl)methanol;
(2-chloro-imidazo[5,1-b]thiazol-3-yl)-thiophen-2-yl-methanol;
(S)-1-(2-chloro-imidazo[5,1-b]thiazol-3-yl)-2-cyclohexyl-ethanol;
(2-chloro-imidazo[5,1-b]thiazol-3-yl)-cycloheptyl-methanol;
(2-chloro-imidazo[5,1-b]thiazol-3-yl)-cyclopentyl-methanol;
(2-chloro-imidazo[5,1-b]thiazol-3-yl)-cyclopropyl-methanol;
(1R*,2R*,4S*)-bicyclo[2.2.1]hept-2-yl-(2-cyclopropyl-imidazo[5,1-b]thiazol-3-yl)-methanol;
1-(2-cyclopropyl-imidazo[5,1-b]thiazol-3-yl)-2-(3,3-difluoro-cyclobutyl)-ethanol;
2-bicyclo[2.2.1]hept-1-yl-1-(2-cyclopropyl-imidazo[5,1-b]thiazol-3-yl)-ethanol;
1-(2-cyclopropyl-imidazo[5,1-b]thiazol-3-yl)-2-(1-methyl-cyclohexyl)-ethanol;
(S)-2-cyclopentyl-1-(2-cyclopropyl-imidazo[5,1-b]thiazol-3-yl)-ethanol;
1-(2-cyclopropyl-imidazo[5,1-b]thiazol-3-yl)-2-(4,4-dimethyl-cyclohexyl)-ethanol;
(2-cyclopropyl-imidazo[5,1-b]thiazol-3-yl)-(4,4-dimethyl-cyclohexyl)-methanol;
(2-cyclopropyl-imidazo[5,1-b]thiazol-3-yl)-(3-methyl-cyclohexyl)-methanol;
(S)-2-cycloheptyl-1-(2-cyclopropyl-imidazo[5,1-b]thiazol-3-yl)-ethanol;
1-(2-cyclopropyl-imidazo[5,1-b]thiazol-3-yl)-2-(3-methyl-cyclohexyl)-ethanol;
(2-cyclopropyl-imidazo[5,1-b]thiazol-3-yl)-(3-methyl-cyclopentyl)-methanol;
1-(2-cyclopropyl-imidazo[5,1-b]thiazol-3-yl)-2-(2-methyl-cyclohexyl)-ethanol;
(2-bromo-imidazo[5,1-b]thiazol-3-yl)-thiophen-2-yl-methanol;
1-(2-bromo-imidazo[5,1-b]thiazol-3-yl)-2-cyclohexyl-ethanol;
(S)-1-(2-cyclopropyl-imidazo[5,1-b]thiazol-3-yl)-2-(3,3-dimethyl-cyclopentyl)-ethanol;
1-(2-cyclopropyl-imidazo[5,1-b]thiazol-3-yl)-2-(3-phenyl-cyclopentyl)-ethanol;
(S)-(2-cyclopropyl-imidazo[5,1-b]thiazol-3-yl)-(3,3-dimethyl-cyclobutyl)-methanol;
1-(2-cyclopropyl-imidazo[5,1-b]thiazol-3-yl)-2-(4-phenyl-cyclohexyl)-ethanol;
2-bicyclo[2.2.1]hept-5-en-2-yl-1-(2-cyclopropyl-imidazo[5,1-b]thiazol-3-yl)-ethanol;
1-(2-cyclopropyl-imidazo[5,1-b]thiazol-3-yl)-2-(1-methyl-cyclobutyl)-ethanol;
2-cyclobutyl-1-(2-cyclopropyl-imidazo[5,1-b]thiazol-3-yl)-ethanol;
1-(2-cyclopropyl-imidazo[5,1-b]thiazol-3-yl)-2-(7-oxa-bicyclo[2.2.1]hept-2-yl)-ethanol;
1-(2-cyclopropyl-imidazo[5,1-b]thiazol-3-yl)-2-(4-trifluoromethyl-cyclohexyl)-ethanol;
cyclobutyl-(2-cyclopropyl-imidazo[5,1-b]thiazol-3-yl)-methanol;
(2-cyclopropyl-imidazo[5,1-b]thiazol-3-yl)-(4-methyl-cyclohexyl)-methanol;
(2-cyclopropyl-imidazo[5,1-b]thiazol-3-yl)-(4-ethyl-cyclohexyl)-methanol;
cyclopentyl-(2-cyclopropyl-imidazo[5,1-b]thiazol-3-yl)-methanol;
(2-cyclopropyl-imidazo[5,1-b]thiazol-3-yl)-(3,3-dimethyl-cyclopentyl)-methanol;
(S)-(2-cyclopropyl-imidazo[5,1-b]thiazol-3-yl)-((R)-3,3-dimethyl-cyclopentyl)-methanol;
(S)-(2-cyclopropyl-imidazo[5,1-b]thiazol-3-yl)-((S)-3,3-dimethyl-cyclopentyl)-methanol;
(S)-(2-cyclopropyl-imidazo[5,1-b]thiazol-3-yl)-(1-methyl-cyclopentyl)-methanol;

1-(2-cyclopropyl-imidazo[5,1-b]thiazol-3-yl)-2-(4-methyl-cyclohexyl)-ethanol;
(S)-(2-cyclopropyl-imidazo[5,1-b]thiazol-3-yl)-phenyl-methanol;
(2-cyclopropyl-imidazo[5,1-b]thiazol-3-yl)-p-tolyl-methanol;
(2-cyclopropyl-imidazo[5,1-b]thiazol-3-yl)-m-tolyl-methanol;
2-cyclopropyl-imidazo[5,1-b]thiazol-3-yl)-(4-ethyl-phenyl)-methanol;
(2-cyclopropyl-imidazo[5,1-b]thiazol-3-yl)-(3-ethyl-phenyl)-methanol;
2-cyclopropyl-imidazo[5,1-b]thiazol-3-yl)-(4-methoxy-phenyl)-methanol;
(2-cyclopropyl-imidazo[5,1-b]thiazol-3-yl)-(3-methoxy-phenyl)-methanol;
(2-methyl-imidazo[5,1-b]thiazol-3-yl)-thiophen-2-yl-methanol;
(4-dimethylamino-phenyl)-(2-methyl-imidazo[5,1-b]thiazol-3-yl)-methanol;
1-(2-cyclopropyl-imidazo[5,1-b]thiazol-3-yl)-2-phenyl-ethanol;
1-(2-cyclopropyl-imidazo[5,1-b]thiazol-3-yl)-2-(2,6-dichloro-phenyl)-ethanol;
1-(2-cyclopropyl-imidazo[5,1-b]thiazol-3-yl)-2-o-tolyl-ethanol;
2-(3-methoxy-phenyl)-1-(2-methyl-imidazo[5,1-b]thiazol-3-yl)-ethanol;
(S)-cyclohexyl-(2-trifluoromethyl-imidazo[5,1-b]thiazol-3-yl)-methanol;
2-cyclohexyl-1-(2-trifluoromethyl-imidazo[5,1-b]thiazol-3-yl)-ethanol;
3-cyclohexyl-1-(2-cyclopropyl-imidazo[5,1-b]thiazol-3-yl)-butan-1-ol;
2-cyclohexyl-1-(2-cyclopropyl-imidazo[5,1-b]thiazol-3-yl)-butan-1-ol;
1-(2-cyclopropyl-imidazo[5,1-b]thiazol-3-yl)-2-naphthalen-1-yl-ethanol;
(S)-cyclohexyl-(2-vinyl-imidazo[5,1-b]thiazol-3-yl)-methanol;
(2-cyclopropyl-imidazo[5,1-b]thiazol-3-yl)-(3,3-dimethyl-cyclohexyl)-methanol;
(2-cyclopropyl-imidazo[5,1-b]thiazol-3-yl)-spiro[4.5]dec-8-yl-methanol;
1-(2-cyclopropyl-imidazo[5,1-b]thiazol-3-yl)-2-(4,4-difluoro-cyclohexyl)-ethanol;
(2-cyclopropyl-imidazo[5,1-b]thiazol-3-yl)-(4-isopropyl-cyclohexyl)-methanol;
(2-cyclopropyl-imidazo[5,1-b]thiazol-3-yl)-(4-phenyl-cyclohexyl)-methanol;
(S)-(2-cyclopropyl-imidazo[5,1-b]thiazol-3-yl)-(trans-4-phenyl-cyclohexyl)-methanol; trans
2-(4-tert-butyl-cyclohexyl)-1-(2-cyclopropyl-imidazo[5,1-b]thiazol-3-yl)-ethanol;
1-(2-cyclopropyl-imidazo[5,1-b]thiazol-3-yl)-2-(2-phenyl-cyclohexyl)-ethanol;
1-(2-cyclopropyl-imidazo[5,1-b]thiazol-3-yl)-2-(2,2-dimethyl-cyclohexyl)-ethanol;
(3-benzyl-cyclopentyl)-(2-cyclopropyl-imidazo[5,1-b]thiazol-3-yl)-methanol;
(2-cyclopropyl-imidazo[5,1-b]thiazol-3-yl)-(3-isobutyl-cyclopentyl)-methanol;
(2-cyclopropyl-imidazo[5,1-b]thiazol-3-yl)-(3-methoxy-cyclohexyl)-methanol;
(2-cyclopropyl-imidazo[5,1-b]thiazol-3-yl)-(1,2,3,4-tetrahydro-naphthalen-2-yl)-methanol;
(2-cyclopropyl-imidazo[5,1-b]thiazol-3-yl)-(4-trifluoromethyl-cyclohexyl)-methanol;
2-cyclohexyl-1-(2-cyclopropyl-imidazo[5,1-b]thiazol-3-yl)-propan-1-ol;
(2-cyclopropyl-imidazo[5,1-b]thiazol-3-yl)-(2-phenyl-cyclopentyl)-methanol;
(2-cyclopropyl-imidazo[5,1-b]thiazol-3-yl)-(2,2-dimethyl-cyclopentyl)-methanol;
1-(2-cyclopropyl-imidazo[5,1-b]thiazol-3-yl)-2-(4-isopropyl-cyclohexyl)-ethanol;
(4-tert-butyl-cyclohexyl)-(2-cyclopropyl-imidazo[5,1-b]thiazol-3-yl)-methanol;
2-(4-cyclobutyl-cyclohexyl)-1-(2-cyclopropyl-imidazo[5,1-b]thiazol-3-yl)-ethanol;
(2-cyclopropyl-imidazo[5,1-b]thiazol-3-yl)-(3-methyl-3-phenyl-cyclopentyl)-methanol;
1-(2-cyclopropyl-imidazo[5,1-b]thiazol-3-yl)-2-(decahydro-naphthalen-1-yl)-ethanol;
(2-cyclopropyl-imidazo[5,1-b]thiazol-3-yl)-(decahydro-naphthalen-2-yl)-methanol;
(2-benzyl-cyclopentyl)-(2-cyclopropyl-imidazo[5,1-b]thiazol-3-yl)-methanol;
(S)-cyclohexyl-(2-phenyl-imidazo[5,1-b]thiazol-3-yl)-methanol;
2-cyclohexyl-1-(2-phenyl-imidazo[5,1-b]thiazol-3-yl)-ethanol;
cyclohexyl-(2-thiophen-3-yl-imidazo[5,1-b]thiazol-3-yl)-methanol;
2-cyclohexyl-1-(2-thiophen-3-yl-imidazo[5,1-b]thiazol-3-yl)-ethanol;
(S)-cyclohexyl-(2-ethyl-imidazo[5,1-b]thiazol-3-yl)-methanol;
2-cyclohexyl-1-(2-vinyl-imidazo[5,1-b]thiazol-3-yl)-ethanol;
cyclohexyl-(2-isobutyl-imidazo[5,1-b]thiazol-3-yl)-methanol;
2-cyclohexyl-1-(2-isobutyl-imidazo[5,1-b]thiazol-3-yl)-ethanol;
(S)-2-cyclohexyl-1-(2-ethyl-imidazo[5,1-b]thiazol-3-yl)-ethanol;
1-(2-cyclopropyl-imidazo[5,1-b]thiazol-3-yl)-2-(decahydro-naphthalen-2-yl)-ethanol;
1-(2-cyclopropyl-imidazo[5,1-b]thiazol-3-yl)-2-(3-trifluoromethyl-cyclohexyl)-ethanol;
(4-cyclobutyl-cyclohexyl)-(2-cyclopropyl-imidazo[5,1-b]thiazol-3-yl)-methanol;
(2-cyclopropyl-imidazo[5,1-b]thiazol-3-yl)-(3-trifluoromethyl-cyclohexyl)-methanol;
(2-cyclopropyl-imidazo[5,1-b]thiazol-3-yl)-(1-methyl-cyclohexyl)-methanol;
1-(2-cyclopropyl-imidazo[5,1-b]thiazol-3-yl)-2-(3,3-dimethyl-cyclohexyl)-ethanol;
1-(2-Methyl-imidazo[5,1-b]thiazol-3-yl)-2-(3-phenyl-cyclopentyl)-ethanol;
(3,3-Dimethyl-cyclopentyl)-(2-trifluoromethyl-imidazo[5,1-b]thiazol-3-yl)-methanol;
(3,3-Dimethyl-cyclobutyl)-(2-methyl-imidazo[5,1-b]thiazol-3-yl)-methanol;
(3,3-Dimethyl-cyclobutyl)-(2-trifluoromethyl-imidazo[5,1-b]thiazol-3-yl)-methanol;
2-cyclopentyl-1-(2-trifluoromethyl-imidazo[5,1-b]thiazol-3-yl)-ethanol;
2-(3-Phenyl-cyclopentyl)-1-(2-trifluoromethyl-imidazo[5,1-b]thiazol-3-yl)-ethanol;
1-(2-cyclopropyl-imidazo[5,1-b]thiazol-3-yl)-2-(3-methoxy-cyclohexyl)-ethanol;

(4-Methyl-cyclohexyl)-(2-trifluoromethyl-imidazo[5,1-b]thiazol-3-yl)-methanol;
(3-Methyl-cyclopentyl)-(2-trifluoromethyl-imidazo[5,1-b]thiazol-3-yl)-methanol;
2-(2-M ethyl-cyclohexyl)-1-(2-trifluoromethyl-imidazo[5,1-b]thiazol-3-yl)-ethanol;
2-(4,4-Dimethyl-cyclohexyl)-1-(2-trifluoromethyl-imidazo[5,1-b]thiazol-3-yl)-ethanol;
(2-Methyl-cyclopentyl)-(2-trifluoromethyl-imidazo[5,1-b]thiazol-3-yl)-methanol;
(2-cyclopropyl-imidazo[5,1-b]thiazol-3-yl)-(2,4,4-trimethyl-cyclopentyl)-methanol;
2-(3,3-Dimethyl-cyclopentyl)-1-(2-trifluoromethyl-imidazo[5,1-b]thiazol-3-yl)-ethanol;
2-(3-M ethyl-cyclohexyl)-1-(2-trifluoromethyl-imidazo[5,1-b]thiazol-3-yl)-ethanol;
(2-cyclopropyl-imidazo[5,1-b]thiazol-3-yl)-(2-ethyl-cyclopentyl)-methanol;
cyclohexyl-(2-pyridin-3-yl-imidazo[5,1-b]thiazol-3-yl)-methanol;
cyclohexyl-[2-(1-methyl-1H-pyrazol-4-yl)-imidazo[5,1-b]thiazol-3-yl]-methanol;
cyclohexyl-(2-p-tolyl-imidazo[5,1-b]thiazol-3-yl)-methanol;
cyclohexyl-[2-(4-methoxy-phenyl)-imidazo[5,1-b]thiazol-3-yl]-methanol;
cyclohexyl-[2-(4-methyl-thiophen-3-yl)-imidazo[5,1-b]thiazol-3-yl]-methanol;
2-cyclohexyl-1-(2-propyl-imidazo[5,1-b]thiazol-3-yl)-ethanol;
cyclohexyl-(2-propyl-imidazo[5,1-b]thiazol-3-yl)-methanol;
1-(2-cyclopropyl-imidazo[5,1-b]thiazol-3-yl)-2-(4-methoxy-cyclohexyl)-ethanol;
cyclopentyl-(2-trifluoromethyl-imidazo[5,1-b]thiazol-3-yl)-methanol;
(2-cyclopropyl-imidazo[5,1-b]thiazol-3-yl)-(octahydro-pentalen-2-yl)-methanol;
2-(4-cyclopentyl-cyclohexyl)-1-(2-cyclopropyl-imidazo[5,1-b]thiazol-3-yl)-ethanol;
1-(2-cyclopropyl-imidazo[5,1-b]thiazol-3-yl)-2-(2-phenyl-cyclopentyl)-ethanol;
(2-cyclopropyl-imidazo[5,1-b]thiazol-3-yl)-(3-isopropyl-3-methyl-cyclopentyl)-methanol;
(1-Methyl-cyclopentyl)-(2-trifluoromethyl-imidazo[5,1-b]thiazol-3-yl)-methanol;
1-(2-cyclopropyl-imidazo[5,1-b]thiazol-3-yl)-2-(4-difluoromethyl-cyclohexyl)-ethanol;
(2-cyclopropyl-imidazo[5,1-b]thiazol-3-yl)-(1,3,3-trimethyl-cyclopentyl)-methanol;
(S)-(1-Methyl-cyclopentyl)-(2-methyl-imidazo[5,1-b]thiazol-3-yl)-methanol;
(3,3-Dimethyl-cyclopentyl)-(2-methyl-imidazo[5,1-b]thiazol-3-yl)-methanol;
1-(2-cyclopropyl-imidazo[5,1-b]thiazol-3-yl)-2-(4-ethyl-cyclohexyl)-ethanol;
(2-cyclopropyl-imidazo[5,1-b]thiazol-3-yl)-(3-trifluoromethyl-phenyl)-methanol;
(2-cyclopropyl-imidazo[5,1-b]thiazol-3-yl)-(4-fluoro-phenyl)-methanol;
(2-cyclopropyl-imidazo[5,1-b]thiazol-3-yl)-(3-fluoro-phenyl)-methanol;
(4-chloro-phenyl)-(2-cyclopropyl-imidazo[5,1-b]thiazol-3-yl)-methanol;
(2-cyclopropyl-imidazo[5,1-b]thiazol-3-yl)-(2-methoxy-phenyl)-methanol;
(2-cyclopropyl-imidazo[5,1-b]thiazol-3-yl)-o-tolyl-methanol;
(3-chloro-phenyl)-(2-cyclopropyl-imidazo[5,1-b]thiazol-3-yl)-methanol;
1-(2-cyclopropyl-imidazo[5,1-b]thiazol-3-yl)-2-(4-propyl-cyclohexyl)-ethanol;
4-[(2-cyclopropyl-imidazo[5,1-b]thiazol-3-yl)-hydroxy-methyl]-cyclohexanol;
4-[2-(2-cyclopropyl-imidazo[5,1-b]thiazol-3-yl)-2-hydroxy-ethyl]-cyclohexanol;
cyclohexyl-[2-(5-methyl-thiophen-3-yl)-imidazo[5,1-b]thiazol-3-yl]-methanol;
(2-Benzyl-imidazo[5,1-b]thiazol-3-yl)-cyclohexyl-methanol;
2-cyclohexyl-1-[2-(3,3-difluoro-cyclobutyl)-imidazo[5,1-b]thiazol-3-yl]-ethanol;
cyclohexyl-[2-(3,3-difluoro-cyclobutyl)-imidazo[5,1-b]thiazol-3-yl]-methanol;
cyclohexyl-(2-methoxymethyl-imidazo[5,1-b]thiazol-3-yl)-methanol;
1-(2-Methyl-imidazo[5,1-b]thiazol-3-yl)-3-phenyl-prop-2-yn-1-ol;
(2-cyclopropyl-imidazo[5,1-b]thiazol-3-yl)-(4-trifluoromethyl-phenyl)-methanol;
1-(2-cyclopropyl-imidazo[5,1-b]thiazol-3-yl)-2-(4-ethyl-amino-cyclohexyl)-ethanol;
(4,4-Dimethyl-cyclohexyl)-(2-trifluoromethyl-imidazo[5,1-b]thiazol-3-yl)-methanol;
(2-Methyl-imidazo[5,1-b]thiazol-3-yl)-phenyl-methanol;
(2-cyclopropyl-imidazo[5,1-b]thiazol-3-yl)-(2-fluoro-phenyl)-methanol;
(2-chloro-phenyl)-(2-cyclopropyl-imidazo[5,1-b]thiazol-3-yl)-methanol;
cycloheptyl-(2-cyclopropyl-imidazo[5,1-b]thiazol-3-yl)-methanol;
(2-cyclopropyl-imidazo[5,1-b]thiazol-3-yl)-(1-methyl-cycloheptyl)-methanol;
(S*)-(2-Methyl-imidazo[5,1-b]thiazol-3-yl)-((1 S*,2S*)-2-phenyl-cyclopropyl)-methanol;
(R*)-(2-Methyl-imidazo[5,1-b]thiazol-3-yl)-((1 S*,2S*)-2-phenyl-cyclopropyl)-methanol;
(2-Methyl-imidazo[5,1-b]thiazol-3-yl)-(1-phenyl-piperidin-4-yl)-methanol;
cyclohexyl-[2-(1-methyl-cyclopropyl)-imidazo[5,1-b]thiazol-3-yl]-methanol;
(2-cyclopropyl-imidazo[5,1-b]thiazol-3-yl)-thiophen-2-yl-methanol;
(2-Ethyl-imidazo[5,1-b]thiazol-3-yl)-(1-methyl-cyclopentyl)-methanol;
(2-cyclopropyl-imidazo[5,1-b]thiazol-3-yl)-thiophen-3-yl-methanol;
(1-Methyl-cyclohexyl)-(2-methyl-imidazo[5,1-b]thiazol-3-yl)-methanol;
(2-Ethyl-imidazo[5,1-b]thiazol-3-yl)-(1-methyl-cyclohexyl)-methanol;
(2-Ethyl-imidazo[5,1-b]thiazol-3-yl)-phenyl-methanol;
2-(4,4-Dimethyl-cyclohexyl)-1-(2-methyl-imidazo[5,1-b]thiazol-3-yl)-ethanol;
2-(4,4-Dimethyl-cyclohexyl)-1-(2-ethyl-imidazo[5,1-b]thiazol-3-yl)-ethanol;
2-cyclopentyl-1-(2-ethyl-imidazo[5,1-b]thiazol-3-yl)-ethanol;
(3,3-Dimethyl-cyclobutyl)-(2-ethyl-imidazo[5,1-b]thiazol-3-yl)-methanol;
cyclohexyl-[2-(3-fluoro-phenyl)-imidazo[5,1-b]thiazol-3-yl]-methanol;

cyclohexyl-[2-(2-fluoro-phenyl)-imidazo[5,1-b]thiazol-3-yl]-methanol;
2-cyclopentyl-1-(2-methyl-imidazo[5,1-b]thiazol-3-yl)-ethanol;
cyclohexyl-[2-(1-fluoro-cyclopropyl)-imidazo[5,1-b]thiazol-3-yl]-methanol;
[2-((S)-sec-Butyl)-imidazo[5,1-b]thiazol-3-yl]-cyclohexyl-methanol;
cyclohexyl-[2-(cis-2-fluoro-cyclopropyl)-imidazo[5,1-b]thiazol-3-yl]-methanol;
cyclohexyl-[2-(trans-2-fluoro-cyclopropyl)-imidazo[5,1-b]thiazol-3-yl]-methanol;
(2-cyclopropyl-imidazo[5,1-b]thiazol-3-yl)-(1-isopropyl-1H-pyrazol-4-yl)-methanol;
(1-cyclopentyl-1H-pyrazol-4-yl)-(2-cyclopropyl-imidazo[5,1-b]thiazol-3-yl)-methanol;
(2-cyclopropyl-imidazo[5,1-b]thiazol-3-yl)-(4-phenyl-bicyclo[2.1.1]hex-1-yl)-methanol;
(2-cyclopropyl-imidazo[5,1-b]thiazol-3-yl)-(3-phenyl-bicyclo[1.1.1]pent-1-yl)-methanol;
(2-cyclopropyl-imidazo[5,1-b]thiazol-3-yl)-(1-methyl-1H-[1,2,3]triazol-4-yl)-methanol;
(2-cyclopropyl-imidazo[5,1-b]thiazol-3-yl)-(1-ethyl-1H-[1,2,3]triazol-4-yl)-methanol;
(2-cyclopropyl-imidazo[5,1-b]thiazol-3-yl)-(1-isopropyl-1H-[1,2,3]triazol-4-yl)-methanol;
(1-cyclopentyl-1H-[1,2,3]triazol-4-yl)-(2-cyclopropyl-imidazo[5,1-b]thiazol-3-yl)-methanol;
(1-cyclobutyl-1H-[1,2,3]triazol-4-yl)-(2-cyclopropyl-imidazo[5,1-b]thiazol-3-yl)-methanol;
(1-cyclohexyl-1H-[1,2,3]triazol-4-yl)-(2-cyclopropyl-imidazo[5,1-b]thiazol-3-yl)-methanol;
(1-cyclopentyl-1H-[1,2,3]triazol-4-yl)-(2-ethyl-imidazo[5,1-b]thiazol-3-yl)-methanol;
cyclopentyl-(2-methyl-imidazo[5,1-b]thiazol-3-yl)-methanol;
(1-cyclopentyl-1H-[1,2,3]triazol-4-yl)-(2-methyl-imidazo[5,1-b]thiazol-3-yl)-methanol; and
(2-cyclopropyl-imidazo[5,1-b]thiazol-3-yl)-(1H-[1,2,3]triazol-4-yl)-methanol.

39) Another embodiment of the present invention relates to a compound of embodiment 1) selected from a group consisting of:
(S)-cyclohexyl-(2-cyclopropyl-imidazo[5,1-b]thiazol-3-yl)-methanol;
(S)-2-cyclohexyl-1-(2-cyclopropyl-imidazo[5,1-b]thiazol-3-yl)-ethanol;
(S)-cyclohexyl-(2-isopropyl-imidazo[5,1-b]thiazol-3-yl)-methanol;
(S)-2-cycloheptyl-1-(2-cyclopropyl-imidazo[5,1-b]thiazol-3-yl)-ethanol;
(S)-1-(2-cyclopropyl-imidazo[5,1-b]thiazol-3-yl)-2-(3,3-dimethyl-cyclopentyl)-ethanol;
(S)-2-cyclopentyl-1-(2-cyclopropyl-imidazo[5,1-b]thiazol-3-yl)-ethanol;
(S)-(2-cyclopropyl-imidazo[5,1-b]thiazol-3-yl)-(3,3-dimethyl-cyclobutyl)-methanol;
(S)-2-cyclohexyl-1-(2-isopropyl-imidazo[5,1-b]thiazol-3-yl)-ethanol;
(S)-2-cyclohexyl-1-(2-methyl-imidazo[5,1-b]thiazol-3-yl)-ethanol;
(S)-(2-cyclopropyl-imidazo[5,1-b]thiazol-3-yl)-((R)-3,3-dimethyl-cyclopentyl)-methanol;
(S)-(2-cyclopropyl-imidazo[5,1-b]thiazol-3-yl)-((S)-3,3-dimethyl-cyclopentyl)-methanol;
(S)-(2-cyclopropyl-imidazo[5,1-b]thiazol-3-yl)-(1-methyl-cyclopentyl)-methanol;
(S)-(2-cyclopropyl-imidazo[5,1-b]thiazol-3-yl)-phenyl-methanol;
(S)-cyclohexyl-(2-trifluoromethyl-imidazo[5,1-b]thiazol-3-yl)-methanol;
(S)-(2-cyclopropyl-imidazo[5,1-b]thiazol-3-yl)-(trans-4-phenyl-cyclohexyl)-methanol;
(S)-cyclohexyl-(2-ethyl-imidazo[5,1-b]thiazol-3-yl)-methanol;
(S)-2-cyclohexyl-1-(2-ethyl-imidazo[5,1-b]thiazol-3-yl)-ethanol;
(S)-(1-Methyl-cyclopentyl)-(2-methyl-imidazo[5,1-b]thiazol-3-yl)-methanol; and
(S)-cyclohexyl-(2-vinyl-imidazo[5,1-b]thiazol-3-yl)-methanol.

40) Another embodiment of the present invention relates to a compound of embodiment 1) selected from a group consisting of:
(S)-cyclohexyl(2-cyclopropylimidazo[5,1-b]thiazol-3-yl)methanol;
(S)-2-cyclohexyl-1-(2-cyclopropylimidazo[5,1-b]thiazol-3-yl)ethan-1-ol;
(S)-cyclohexyl-(2-isopropyl-imidazo[5,1-b]thiazol-3-yl)-methanol;
(S)-2-cyclohexyl-1-(2-isopropyl-imidazo[5,1-b]thiazol-3-yl)-ethanol;
(S)-2-cyclohexyl-1-(2-methyl-imidazo[5,1-b]thiazol-3-yl)-ethanol;
(S)-(2-cyclobutylimidazo[5,1-b]thiazol-3-yl)(cyclohexyl)methanol;
(S)-1-(2-cyclobutylimidazo[5,1-b]thiazol-3-yl)-2-cyclohexylethan-1-ol;
(S)-cyclohexyl(2-cyclopentylimidazo[5,1-b]thiazol-3-yl)methanol;
(S)-2-cyclohexyl-1-(2-cyclopentylimidazo[5,1-b]thiazol-3-yl)ethan-1-ol;
(S)-(2-(tert-butyl)imidazo[5,1-b]thiazol-3-yl)(cyclohexyl)methanol;
(S)-1-(2-(tert-butyl)imidazo[5,1-b]thiazol-3-yl)-2-cyclohexylethan-1-ol;
(S)-(2-chloroimidazo[5,1-b]thiazol-3-yl)(cyclohexyl)methanol;
(2-bromoimidazo[5,1-b]thiazol-3-yl)(cyclohexyl)methanol;
(2-chloro-imidazo[5,1-b]thiazol-3-yl)-thiophen-2-yl-methanol;
1-(2-chloro-imidazo[5,1-b]thiazol-3-yl)-2-cyclohexyl-ethanol;
(2-chloro-imidazo[5,1-b]thiazol-3-yl)-cycloheptyl-methanol;
(2-chloro-imidazo[5,1-b]thiazol-3-yl)-cyclopentyl-methanol;
(2-chloro-imidazo[5,1-b]thiazol-3-yl)-cyclopropyl-methanol;
(1R*,2R*,4S*)-bicyclo[2.2.1]hept-2-yl-(2-cyclopropyl-imidazo[5,1-b]thiazol-3-yl)-methanol;
1-(2-cyclopropyl-imidazo[5,1-b]thiazol-3-yl)-2-(3,3-difluoro-cyclobutyl)-ethanol;
2-bicyclo[2.2.1]hept-1-yl-1-(2-cyclopropyl-imidazo[5,1-b]thiazol-3-yl)-ethanol;
1-(2-cyclopropyl-imidazo[5,1-b]thiazol-3-yl)-2-(1-methyl-cyclohexyl)-ethanol;
2-cyclopentyl-1-(2-cyclopropyl-imidazo[5,1-b]thiazol-3-yl)-ethanol;
1-(2-cyclopropyl-imidazo[5,1-b]thiazol-3-yl)-2-(4,4-dimethyl-cyclohexyl)-ethanol;
(2-cyclopropyl-imidazo[5,1-b]thiazol-3-yl)-(4,4-dimethyl-cyclohexyl)-methanol;

(2-cyclopropyl-imidazo[5,1-b]thiazol-3-yl)-(3-methyl-cyclohexyl)-methanol;
2-cycloheptyl-1-(2-cyclopropyl-imidazo[5,1-b]thiazol-3-yl)-ethanol;
1-(2-cyclopropyl-imidazo[5,1-b]thiazol-3-yl)-2-(3-methyl-cyclohexyl)-ethanol;
(2-cyclopropyl-imidazo[5,1-b]thiazol-3-yl)-(3-methyl-cyclopentyl)-methanol;
1-(2-cyclopropyl-imidazo[5,1-b]thiazol-3-yl)-2-(2-methyl-cyclohexyl)-ethanol;
(2-bromo-imidazo[5,1-b]thiazol-3-yl)-thiophen-2-yl-methanol;
1-(2-bromo-imidazo[5,1-b]thiazol-3-yl)-2-cyclohexyl-ethanol;
1-(2-cyclopropyl-imidazo[5,1-b]thiazol-3-yl)-2-(3,3-dimethyl-cyclopentyl)-ethanol;
1-(2-cyclopropyl-imidazo[5,1-b]thiazol-3-yl)-2-(3-phenyl-cyclopentyl)-ethanol;
(2-cyclopropyl-imidazo[5,1-b]thiazol-3-yl)-(3,3-dimethyl-cyclobutyl)-methanol;
1-(2-cyclopropyl-imidazo[5,1-b]thiazol-3-yl)-2-(4-phenyl-cyclohexyl)-ethanol;
2-bicyclo[2.2.1]hept-5-en-2-yl-1-(2-cyclopropyl-imidazo[5,1-b]thiazol-3-yl)-ethanol;
1-(2-cyclopropyl-imidazo[5,1-b]thiazol-3-yl)-2-(1-methyl-cyclobutyl)-ethanol;
2-cyclobutyl-1-(2-cyclopropyl-imidazo[5,1-b]thiazol-3-yl)-ethanol;
1-(2-cyclopropyl-imidazo[5,1-b]thiazol-3-yl)-2-(7-oxa-bicyclo[2.2.1]hept-2-yl)-ethanol;
1-(2-cyclopropyl-imidazo[5,1-b]thiazol-3-yl)-2-(4-trifluoromethyl-cyclohexyl)-ethanol;
cyclobutyl-(2-cyclopropyl-imidazo[5,1-b]thiazol-3-yl)-methanol;
(2-cyclopropyl-imidazo[5,1-b]thiazol-3-yl)-(4-methyl-cyclohexyl)-methanol;
(2-cyclopropyl-imidazo[5,1-b]thiazol-3-yl)-(4-ethyl-cyclohexyl)-methanol;
cyclopentyl-(2-cyclopropyl-imidazo[5,1-b]thiazol-3-yl)-methanol;
(2-cyclopropyl-imidazo[5,1-b]thiazol-3-yl)-(3,3-dimethyl-cyclopentyl)-methanol;
(2-cyclopropyl-imidazo[5,1-b]thiazol-3-yl)-(2-methyl-cyclopentyl)-methanol; and
1-(2-cyclopropyl-imidazo[5,1-b]thiazol-3-yl)-2-(4-methyl-cyclohexyl)-ethanol.

Based on the dependencies of the different embodiments 1) to 37) as disclosed hereinabove, the following embodiments are thus possible and intended and herewith specifically disclosed in individualized form:
1, 2+1, 3+1, 4+1, 4+2+1, 5+1, 5+2+1, 6+1, 6+2+1, 7+1, 7+2+1, 8+1, 8+2+1, 9+1, 9+2+1, 10+1, 10+2+1, 11+1, 11+2+1, 12+1, 12+2+1, 13+1, 13+2+1, 14+1, 14+2+1, 15+1, 15+2+1, 16+1, 16+2+1, 16+3+1, 16+4+1, 16+4+2+1, 16+5+1, 16+5+2+1, 16+6+1, 16+6+2+1, 16+7+1, 16+7+2+1, 16+8+1, 16+8+2+1, 16+9+1, 16+9+2+1, 16+10+1, 16+10+2+1, 16+11+1, 16+11+2+1, 16+12+1, 16+12+2+1, 16+13+1, 16+13+2+1, 17+1, 17+2+1, 17+3+1, 17+4+1, 17+4+2+1, 17+5+1, 17+5+2+1, 17+6+1, 17+6+2+1, 17+7+1, 17+7+2+1, 17+8+1, 17+8+2+1, 17+9+1, 17+9+2+1, 17+10+1, 17+10+2+1, 17+11+1, 17+11+2+1, 17+12+1, 17+12+2+1, 17+13+1, 17+13+2+1, 18+1, 18+2+1, 18+3+1, 18+4+1, 18+4+2+1, 18+5+1, 18+5+2+1, 18+6+1, 18+6+2+1, 18+7+1, 18+7+2+1, 18+8+1, 18+8+2+1, 18+9+1, 18+9+2+1, 18+10+1, 18+10+2+1, 18+11+1, 18+11+2+1, 18+12+1, 18+12+2+1, 18+13+1, 18+13+2+1, 19+1, 19+2+1, 19+3+1, 19+4+1, 19+4+2+1, 19+5+1, 19+5+2+1, 19+6+1, 19+6+2+1, 19+7+1, 19+7+2+1, 19+8+1, 19+8+2+1, 19+9+1, 19+9+2+1, 19+10+1, 19+10+2+1, 19+11+1, 19+11+2+1, 19+12+1, 19+12+2+1, 19+13+1, 19+13+2+1, 19+14+1, 19+14+2+1, 19+15+1, 19+15+2+1, 19+16+1, 19+16+2+1, 19+16+3+1, 19+16+4+1, 19+16+4+2+1, 19+16+5+1, 19+16+5+2+1, 19+16+6+1, 19+16+6+2+1, 19+16+7+1, 19+16+7+2+1, 19+16+8+1, 19+16+8+2+1, 19+16+9+1, 19+16+9+2+1, 19+16+10+1, 19+16+10+2+1, 19+16+11+1, 19+16+11+2+1, 19+16+12+1, 19+16+12+2+1, 19+16+13+1, 19+16+13+2+1, 19+17+1, 19+17+2+1, 19+17+3+1, 19+17+4+1, 19+17+4+2+1, 19+17+5+1, 19+17+5+2+1, 19+17+6+1, 19+17+6+2+1, 19+17+7+1, 19+17+7+2+1, 19+17+8+1, 19+17+8+2+1, 19+17+9+1, 19+17+9+2+1, 19+17+10+1, 19+17+10+2+1, 19+17+11+1, 19+17+11+2+1, 19+17+12+1, 19+17+12+2+1, 19+17+13+1, 19+17+13+2+1, 19+18+1, 19+18+2+1, 19+18+3+1, 19+18+4+1, 19+18+4+2+1, 19+18+5+1, 19+18+5+2+1, 19+18+6+1, 19+18+6+2+1, 19+18+7+1, 19+18+7+2+1, 19+18+8+1, 19+18+8+2+1, 19+18+9+1, 19+18+9+2+1, 19+18+10+1, 19+18+10+2+1, 19+18+11+1, 19+18+11+2+1, 19+18+12+1, 19+18+12+2+1, 19+18+13+1, 19+18+13+2+1, 20+1, 20+2+1, 20+3+1, 20+4+1, 20+4+2+1, 20+5+1, 20+5+2+1, 20+6+1, 20+6+2+1, 20+7+1, 20+7+2+1, 20+8+1, 20+8+2+1, 20+9+1, 20+9+2+1, 20+10+1, 20+10+2+1, 20+11+1, 20+11+2+1, 20+12+1, 20+12+2+1, 20+13+1, 20+13+2+1, 20+14+1, 20+14+2+1, 20+15+1, 20+15+2+1, 20+16+1, 20+16+2+1, 20+16+3+1, 20+16+4+1, 20+16+4+2+1, 20+16+5+1, 20+16+5+2+1, 20+16+6+1, 20+16+6+2+1, 20+16+7+1, 20+16+7+2+1, 20+16+8+1, 20+16+8+2+1, 20+16+9+1, 20+16+9+2+1, 20+16+10+1, 20+16+10+2+1, 20+16+11+1, 20+16+11+2+1, 20+16+12+1, 20+16+12+2+1, 20+16+13+1, 20+16+13+2+1, 20+17+1, 20+17+2+1, 20+17+3+1, 20+17+4+1, 20+17+4+2+1, 20+17+5+1, 20+17+5+2+1, 20+17+6+1, 20+17+6+2+1, 20+17+7+1, 20+17+7+2+1, 20+17+8+1, 20+17+8+2+1, 20+17+9+1, 20+17+9+2+1, 20+17+10+1, 20+17+10+2+1, 20+17+11+1, 20+17+11+2+1, 20+17+12+1, 20+17+12+2+1, 20+17+13+1, 20+17+13+2+1, 20+18+1, 20+18+2+1, 20+18+3+1, 20+18+4+1, 20+18+4+2+1, 20+18+5+1, 20+18+5+2+1, 20+18+6+1, 20+18+6+2+1, 20+18+7+1, 20+18+7+2+1, 20+18+8+1, 20+18+8+2+1, 20+18+9+1, 20+18+9+2+1, 20+18+10+1, 20+18+10+2+1, 20+18+11+1, 20+18+11+2+1, 20+18+12+1, 20+18+12+2+1, 20+18+13+1, 20+18+13+2+1, 21+1, 21+2+1, 21+3+1, 21+4+1, 21+4+2+1, 21+5+1, 21+5+2+1, 21+6+1, 21+6+2+1, 21+7+1, 21+7+2+1, 21+8+1, 21+8+2+1, 21+9+1, 21+9+2+1, 21+10+1, 21+10+2+1, 21+11+1, 21+11+2+1, 21+12+1, 21+12+2+1, 21+13+1, 21+13+2+1, 21+14+1, 21+14+2+1, 21+15+1, 21+15+2+1, 21+16+1, 21+16+2+1, 21+16+3+1, 21+16+4+1, 21+16+4+2+1, 21+16+5+1, 21+16+5+2+1, 21+16+6+1, 21+16+6+2+1, 21+16+7+1, 21+16+7+2+1, 21+16+8+1, 21+16+8+2+1, 21+16+9+1, 21+16+9+2+1, 21+16+10+1, 21+16+10+2+1, 21+16+11+1, 21+16+11+2+1, 21+16+12+1, 21+16+12+2+1, 21+16+13+1, 21+16+13+2+1, 21+17+1, 21+17+2+1, 21+17+3+1, 21+17+4+1, 21+17+4+2+1, 21+17+5+1, 21+17+5+2+1, 21+17+6+1, 21+17+6+2+1, 21+17+7+1, 21+17+7+2+1, 21+17+8+1, 21+17+8+2+1, 21+17+9+1, 21+17+9+2+1, 21+17+10+1, 21+17+10+2+1, 21+17+11+1, 21+17+11+2+1, 21+17+12+1, 21+17+12+2+1, 21+17+13+1, 21+17+13+2+1, 21+18+1, 21+18+2+1, 21+18+3+1, 21+18+4+1, 21+18+4+2+1, 21+18+5+1, 21+18+5+2+1, 21+18+6+1, 21+18+6+2+1, 21+18+7+1, 21+18+7+2+1, 21+18+8+1, 21+18+8+2+1, 21+18+9+1, 21+18+9+2+1, 21+18+10+1, 21+18+10+2+1, 21+18+11+1, 21+18+11+2+1, 21+18+12+1, 21+18+12+2+1, 21+18+13+1, 21+18+13+2+1, 22+1, 22+2+1, 22+3+1, 22+4+1, 22+4+2+1, 22+5+1, 22+5+2+1, 22+6+1, 22+6+2+1, 22+7+1, 22+7+2+1, 22+8+1, 22+8+2+1, 22+9+1, 22+9+

2+1, 22+10+1, 22+10+2+1, 22+11+1, 22+11+2+1, 22+12+1, 22+12+2+1, 22+13+1, 22+13+2+1, 22+14+1, 22+14+2+1, 22+15+1, 22+15+2+1, 22+16+1, 22+16+2+1, 22+16+3+1, 22+16+4+1, 22+16+4+2+1, 22+16+5+1, 22+16+5+2+1, 22+16+6+1, 22+16+6+2+1, 22+16+7+1, 22+16+7+2+1, 22+16+8+1, 22+16+8+2+1, 22+16+9+1, 22+16+9+2+1, 22+16+10+1, 22+16+10+2+1, 22+16+11+1, 22+16+11+2+1, 22+16+12+1, 22+16+12+2+1, 22+16+13+1, 22+16+13+2+1, 22+17+1, 22+17+2+1, 22+17+3+1, 22+17+4+1, 22+17+4+2+1, 22+17+5+1, 22+17+5+2+1, 22+17+6+1, 22+17+6+2+1, 22+17+7+1, 22+17+7+2+1, 22+17+8+1, 22+17+8+2+1, 22+17+9+1, 22+17+9+2+1, 22+17+10+1, 22+17+10+2+1, 22+17+11+1, 22+17+11+2+1, 22+17+12+1, 22+17+12+2+1, 22+17+13+1, 22+17+13+2+1, 22+18+1, 22+18+2+1, 22+18+3+1, 22+18+4+1, 22+18+4+2+1, 22+18+5+1, 22+18+5+2+1, 22+18+6+1, 22+18+6+2+1, 22+18+7+1, 22+18+7+2+1, 22+18+8+1, 22+18+8+2+1, 22+18+9+1, 22+18+9+2+1, 22+18+10+1, 22+18+10+2+1, 22+18+11+1, 22+18+11+2+1, 22+18+12+1, 22+18+12+2+1, 22+18+13+1, 22+18+13+2+1, 23+1, 23+2+1, 23+3+1, 23+4+1, 23+4+2+1, 23+5+1, 23+5+2+1, 23+6+1, 23+6+2+1, 23+7+1, 23+7+2+1, 23+8+1, 23+8+2+1, 23+9+1, 23+9+2+1, 23+10+1, 23+10+2+1, 23+11+1, 23+11+2+1, 23+12+1, 23+12+2+1, 23+13+1, 23+13+2+1, 23+14+1, 23+14+2+1, 23+15+1, 23+15+2+1, 23+16+1, 23+16+2+1, 23+16+3+1, 23+16+4+1, 23+16+4+2+1, 23+16+5+1, 23+16+5+2+1, 23+16+6+1, 23+16+6+2+1, 23+16+7+1, 23+16+7+2+1, 23+16+8+1, 23+16+8+2+1, 23+16+9+1, 23+16+9+2+1, 23+16+10+1, 23+16+10+2+1, 23+16+11+1, 23+16+11+2+1, 23+16+12+1, 23+16+12+2+1, 23+16+13+1, 23+16+13+2+1, 23+17+1, 23+17+2+1, 23+17+3+1, 23+17+4+1, 23+17+4+2+1, 23+17+5+1, 23+17+5+2+1, 23+17+6+1, 23+17+6+2+1, 23+17+7+1, 23+17+7+2+1, 23+17+8+1, 23+17+8+2+1, 23+17+9+1, 23+17+9+2+1, 23+17+10+1, 23+17+10+2+1, 23+17+11+1, 23+17+11+2+1, 23+17+12+1, 23+17+12+2+1, 23+17+13+1, 23+17+13+2+1, 23+18+1, 23+18+2+1, 23+18+3+1, 23+18+4+1, 23+18+4+2+1, 23+18+5+1, 23+18+5+2+1, 23+18+6+1, 23+18+6+2+1, 23+18+7+1, 23+18+7+2+1, 23+18+8+1, 23+18+8+2+1, 23+18+9+1, 23+18+9+2+1, 23+18+10+1, 23+18+10+2+1, 23+18+11+1, 23+18+11+2+1, 23+18+12+1, 23+18+12+2+1, 23+18+13+1, 23+18+13+2+1, 24+1, 24+2+1, 24+3+1, 24+4+1, 24+4+2+1, 24+5+1, 24+5+2+1, 24+6+1, 24+6+2+1, 24+7+1, 24+7+2+1, 24+8+1, 24+8+2+1, 24+9+1, 24+9+2+1, 24+10+1, 24+10+2+1, 24+11+1, 24+11+2+1, 24+12+1, 24+12+2+1, 24+13+1, 24+13+2+1, 24+14+1, 24+14+2+1, 24+15+1, 24+15+2+1, 24+16+1, 24+16+2+1, 24+16+3+1, 24+16+4+1, 24+16+4+2+1, 24+16+5+1, 24+16+5+2+1, 24+16+6+1, 24+16+6+2+1, 24+16+7+1, 24+16+7+2+1, 24+16+8+1, 24+16+8+2+1, 24+16+9+1, 24+16+9+2+1, 24+16+10+1, 24+16+10+2+1, 24+16+11+1, 24+16+11+2+1, 24+16+12+1, 24+16+12+2+1, 24+16+13+1, 24+16+13+2+1, 24+17+1, 24+17+2+1, 24+17+3+1, 24+17+4+1, 24+17+4+2+1, 24+17+5+1, 24+17+5+2+1, 24+17+6+1, 24+17+6+2+1, 24+17+7+1, 24+17+7+2+1, 24+17+8+1, 24+17+8+2+1, 24+17+9+1, 24+17+9+2+1, 24+17+10+1, 24+17+10+2+1, 24+17+11+1, 24+17+11+2+1, 24+17+12+1, 24+17+12+2+1, 24+17+13+1, 24+17+13+2+1, 24+18+1, 24+18+2+1, 24+18+3+1, 24+18+4+1, 24+18+4+2+1, 24+18+5+1, 24+18+5+2+1, 24+18+6+1, 24+18+6+2+1, 24+18+7+1, 24+18+7+2+1, 24+18+8+1, 24+18+8+2+1, 24+18+9+1, 24+18+9+2+1, 24+18+10+1, 24+18+10+2+1, 24+18+11+1, 24+18+11+2+1, 24+18+12+1, 24+18+12+2+1, 24+18+13+1, 24+18+13+2+1, 25+1, 25+2+1, 25+3+1, 25+4+1, 25+4+2+1, 25+5+1, 25+5+2+1, 25+6+1, 25+6+2+1, 25+7+1, 25+7+2+1, 25+8+1, 25+8+2+1, 25+9+1, 25+9+2+1, 25+10+1, 25+10+2+1, 25+11+1, 25+11+2+1, 25+12+1, 25+12+2+1, 25+13+1, 25+13+2+1, 25+14+1, 25+14+2+1, 25+15+1, 25+15+2+1, 25+16+1, 25+16+2+1, 25+16+3+1, 25+16+4+1, 25+16+4+2+1, 25+16+5+1, 25+16+5+2+1, 25+16+6+1, 25+16+6+2+1, 25+16+7+1, 25+16+7+2+1, 25+16+8+1, 25+16+8+2+1, 25+16+9+1, 25+16+9+2+1, 25+16+10+1, 25+16+10+2+1, 25+16+11+1, 25+16+11+2+1, 25+16+12+1, 25+16+12+2+1, 25+16+13+1, 25+16+13+2+1, 25+17+1, 25+17+2+1, 25+17+3+1, 25+17+4+1, 25+17+4+2+1, 25+17+5+1, 25+17+5+2+1, 25+17+6+1, 25+17+6+2+1, 25+17+7+1, 25+17+7+2+1, 25+17+8+1, 25+17+8+2+1, 25+17+9+1, 25+17+9+2+1, 25+17+10+1, 25+17+10+2+1, 25+17+11+1, 25+17+11+2+1, 25+17+12+1, 25+17+12+2+1, 25+17+13+1, 25+17+13+2+1, 25+18+1, 25+18+2+1, 25+18+3+1, 25+18+4+1, 25+18+4+2+1, 25+18+5+1, 25+18+5+2+1, 25+18+6+1, 25+18+6+2+1, 25+18+7+1, 25+18+7+2+1, 25+18+8+1, 25+18+8+2+1, 25+18+9+1, 25+18+9+2+1, 25+18+10+1, 25+18+10+2+1, 25+18+11+1, 25+18+11+2+1, 25+18+12+1, 25+18+12+2+1, 25+18+13+1, 25+18+13+2+1, 26+1, 26+2+1, 26+3+1, 26+4+1, 26+4+2+1, 26+5+1, 26+5+2+1, 26+6+1, 26+6+2+1, 26+7+1, 26+7+2+1, 26+8+1, 26+8+2+1, 26+9+1, 26+9+2+1, 26+10+1, 26+10+2+1, 26+11+1, 26+11+2+1, 26+12+1, 26+12+2+1, 26+13+1, 26+13+2+1, 26+14+1, 26+14+2+1, 26+15+1, 26+15+2+1, 26+16+1, 26+16+2+1, 26+16+3+1, 26+16+4+1, 26+16+4+2+1, 26+16+5+1, 26+16+5+2+1, 26+16+6+1, 26+16+6+2+1, 26+16+7+1, 26+16+7+2+1, 26+16+8+1, 26+16+8+2+1, 26+16+9+1, 26+16+9+2+1, 26+16+10+1, 26+16+10+2+1, 26+16+11+1, 26+16+11+2+1, 26+16+12+1, 26+16+12+2+1, 26+16+13+1, 26+16+13+2+1, 26+17+1, 26+17+2+1, 26+17+3+1, 26+17+4+1, 26+17+4+2+1, 26+17+5+1, 26+17+5+2+1, 26+17+6+1, 26+17+6+2+1, 26+17+7+1, 26+17+7+2+1, 26+17+8+1, 26+17+8+2+1, 26+17+9+1, 26+17+9+2+1, 26+17+10+1, 26+17+10+2+1, 26+17+11+1, 26+17+11+2+1, 26+17+12+1, 26+17+12+2+1, 26+17+13+1, 26+17+13+2+1, 26+18+1, 26+18+2+1, 26+18+3+1, 26+18+4+1, 26+18+4+2+1, 26+18+5+1, 26+18+5+2+1, 26+18+6+1, 26+18+6+2+1, 26+18+7+1, 26+18+7+2+1, 26+18+8+1, 26+18+8+2+1, 26+18+9+1, 26+18+9+2+1, 26+18+10+1, 26+18+10+2+1, 26+18+11+1, 26+18+11+2+1, 26+18+12+1, 26+18+12+2+1, 26+18+13+1, 26+18+13+2+1, 27+1, 27+2+1, 27+3+1, 27+4+1, 27+4+2+1, 27+5+1, 27+5+2+1, 27+6+1, 27+6+2+1, 27+7+1, 27+7+2+1, 27+8+1, 27+8+2+1, 27+9+1, 27+9+2+1, 27+10+1, 27+10+2+1, 27+11+1, 27+11+2+1, 27+12+1, 27+12+2+1, 27+13+1, 27+13+2+1, 27+14+1, 27+14+2+1, 27+15+1, 27+15+2+1, 27+16+1, 27+16+2+1, 27+16+3+1, 27+16+4+1, 27+16+4+2+1, 27+16+5+1, 27+16+5+2+1, 27+16+6+1, 27+16+6+2+1, 27+16+7+1, 27+16+7+2+1, 27+16+8+1, 27+16+8+2+1, 27+16+9+1, 27+16+9+2+1, 27+16+10+1, 27+16+10+2+1, 27+16+11+1, 27+16+11+2+1, 27+16+12+1, 27+16+12+2+1, 27+16+13+1, 27+16+13+2+1, 27+18+1, 27+18+2+1, 27+18+3+1, 27+18+4+1, 27+18+4+2+1, 27+18+5+1, 27+18+5+2+1, 27+18+6+1, 27+18+6+2+1, 27+18+7+1, 27+18+7+2+1, 27+18+8+1, 27+18+8+2+1, 27+18+9+1, 27+18+9+2+1, 27+18+10+1, 27+18+10+2+1, 27+18+11+1, 27+18+11+2+1, 27+18+12+1, 27+18+12+2+1, 27+18+13+1, 27+18+13+2+1, 27+19+1, 27+19+2+1, 27+19+3+1, 27+19+4+1, 27+19+4+2+1, 27+19+5+1, 27+19+5+2+1, 27+19+6+1, 27+19+6+2+1, 27+19+7+1, 27+19+7+2+1, 27+19+8+1, 27+19+8+2+1, 27+19+9+1, 27+19+9+2+1, 27+19+10+1, 27+19+10+2+1, 27+19+11+1, 27+19+11+2+1, 27+19+12+1, 27+19+12+2+1, 27+19+13+1, 27+19+13+2+1, 27+19+14+1, 27+19+14+2+1, 27+19+15+1, 27+19+15+2+1, 27+19+16+1, 27+19+16+2+1, 27+19+16+3+1, 27+19+16+4+1, 27+19+16+4+2+1, 27+19+16+5+1, 27+19+16+5+2+1, 27+19+16+6+1, 27+19+16+6+2+1, 27+19+16+7+1, 27+19+16+7+2+1,

27+19+16+8+1, 27+19+16+8+2+1, 27+19+16+9+1, 27+19+16+9+2+1, 27+19+16+10+1, 27+19+16+10+2+1, 27+19+16+11+1, 27+19+16+11+2+1, 27+19+16+12+1, 27+19+16+12+2+1, 27+19+16+13+1, 27+19+16+13+2+1, 27+19+17+1, 27+19+17+2+1, 27+19+17+3+1, 27+19+17+4+1, 27+19+17+4+2+1, 27+19+17+5+1, 27+19+17+5+2+1, 27+19+17+6+1, 27+19+17+6+2+1, 27+19+17+7+1, 27+19+17+7+2+1, 27+19+17+8+1, 27+19+17+8+2+1, 27+19+17+9+1, 27+19+17+9+2+1, 27+19+17+10+1, 27+19+17+10+2+1, 27+19+17+11+1, 27+19+17+11+2+1, 27+19+17+12+1, 27+19+17+12+2+1, 27+19+17+13+1, 27+19+17+13+2+1, 27+19+18+1, 27+19+18+2+1, 27+19+18+3+1, 27+19+18+4+1, 27+19+18+4+2+1, 27+19+18+5+1, 27+19+18+5+2+1, 27+19+18+6+1, 27+19+18+6+2+1, 27+19+18+7+1, 27+19+18+7+2+1, 27+19+18+8+1, 27+19+18+8+2+1, 27+19+18+9+1, 27+19+18+9+2+1, 27+19+18+10+1, 27+19+18+10+2+1, 27+19+18+11+1, 27+19+18+11+2+1, 27+19+18+12+1, 27+19+18+12+2+1, 27+19+18+13+1, 27+19+18+13+2+1, 27+24+1, 27+24+2+1, 27+24+3+1, 27+24+4+1, 27+24+4+2+1, 27+24+5+1, 27+24+5+2+1, 27+24+6+1, 27+24+6+2+1, 27+24+7+1, 27+24+7+2+1, 27+24+8+1, 27+24+8+2+1, 27+24+9+1, 27+24+9+2+1, 27+24+10+1, 27+24+10+2+1, 27+24+11+1, 27+24+11+2+1, 27+24+12+1, 27+24+12+2+1, 27+24+13+1, 27+24+13+2+1, 27+24+14+1, 27+24+14+2+1, 27+24+15+1, 27+24+15+2+1, 27+24+16+1, 27+24+16+2+1, 27+24+16+3+1, 27+24+16+4+1, 27+24+16+4+2+1, 27+24+16+5+1, 27+24+16+5+2+1, 27+24+16+6+1, 27+24+16+6+2+1, 27+24+16+7+1, 27+24+16+7+2+1, 27+24+16+8+1, 27+24+16+8+2+1, 27+24+16+9+1, 27+24+16+9+2+1, 27+24+16+10+1, 27+24+16+10+2+1, 27+24+16+11+1, 27+24+16+11+2+1, 27+24+16+12+1, 27+24+16+12+2+1, 27+24+16+13+1, 27+24+16+13+2+1, 27+24+17+1, 27+24+17+2+1, 27+24+17+3+1, 27+24+17+4+1, 27+24+17+4+2+1, 27+24+17+5+1, 27+24+17+5+2+1, 27+24+17+6+1, 27+24+17+6+2+1, 27+24+17+7+1, 27+24+17+7+2+1, 27+24+17+8+1, 27+24+17+8+2+1, 27+24+17+9+1, 27+24+17+9+2+1, 27+24+17+10+1, 27+24+17+10+2+1, 27+24+17+11+1, 27+24+17+11+2+1, 27+24+17+12+1, 27+24+17+12+2+1, 27+24+17+13+1, 27+24+17+13+2+1, 27+24+18+1, 27+24+18+2+1, 27+24+18+3+1, 27+24+18+4+1, 27+24+18+4+2+1, 27+24+18+5+1, 27+24+18+5+2+1, 27+24+18+6+1, 27+24+18+6+2+1, 27+24+18+7+1, 27+24+18+7+2+1, 27+24+18+8+1, 27+24+18+8+2+1, 27+24+18+9+1, 27+24+18+9+2+1, 27+24+18+10+1, 27+24+18+10+2+1, 27+24+18+11+1, 27+24+18+11+2+1, 27+24+18+12+1, 27+24+18+12+2+1, 27+24+18+13+1, 27+24+18+13+2+1, 28+1, 28+27+1, 29+1, 29+27+1, 30+1, 30+27+1, 31+1, 31+27+1, 32+1, 32+27+1, 33+1, 33+27+1, 34+1, 34+27+1, 35+1, 35+27+1, 36+1, 36+27+1, 37+1, 37+2+1, 37+3+1, 37+4+1, 37+4+2+1, 37+5+1, 37+5+2+1, 37+6+1, 37+6+2+1, 37+7+1, 37+7+2+1, 37+8+1, 37+8+2+1, 37+9+1, 37+9+2+1, 37+10+1, 37+10+2+1, 37+11+1, 37+11+2+1, 37+12+1, 37+12+2+1, 37+13+1, 37+13+2+1, 37+14+1, 37+14+2+1, 37+15+1, 37+15+2+1, 37+16+1, 37+16+2+1, 37+16+3+1, 37+16+4+1, 37+16+4+2+1, 37+16+5+1, 37+16+5+2+1, 37+16+6+1, 37+16+6+2+1, 37+16+7+1, 37+16+7+2+1, 37+16+8+1, 37+16+8+2+1, 37+16+9+1, 37+16+9+2+1, 37+16+10+1, 37+16+10+2+1, 37+16+11+1, 37+16+11+2+1, 37+16+12+1, 37+16+12+2+1, 37+16+13+1, 37+16+13+2+1, 37+17+1, 37+17+2+1, 37+17+3+1, 37+17+4+1, 37+17+4+2+1, 37+17+5+1, 37+17+5+2+1, 37+17+6+1, 37+17+6+2+1, 37+17+7+1, 37+17+7+2+1, 37+17+8+1, 37+17+8+2+1, 37+17+9+1, 37+17+9+2+1, 37+17+10+1, 37+17+10+2+1, 37+17+11+1, 37+17+11+2+1, 37+17+12+1, 37+17+12+2+1, 37+17+13+1, 37+17+13+2+1, 37+18+1, 37+18+2+1, 37+18+3+1, 37+18+4+1, 37+18+4+2+1, 37+18+5+1, 37+18+5+2+1, 37+18+6+1, 37+18+6+2+1, 37+18+7+1, 37+18+7+2+1, 37+18+8+1, 37+18+8+2+1, 37+18+9+1, 37+18+9+2+1, 37+18+10+1, 37+18+10+2+1, 37+18+11+1, 37+18+11+2+1, 37+18+12+1, 37+18+12+2+1, 37+18+13+1, 37+18+13+2+1, 37+19+1, 37+19+2+1, 37+19+3+1, 37+19+4+1, 37+19+4+2+1, 37+19+5+1, 37+19+5+2+1, 37+19+6+1, 37+19+6+2+1, 37+19+7+1, 37+19+7+2+1, 37+19+8+1, 37+19+8+2+1, 37+19+9+1, 37+19+9+2+1, 37+19+10+1, 37+19+10+2+1, 37+19+11+1, 37+19+11+2+1, 37+19+12+1, 37+19+12+2+1, 37+19+13+1, 37+19+13+2+1, 37+19+14+1, 37+19+14+2+1, 37+19+15+1, 37+19+15+2+1, 37+19+16+1, 37+19+16+2+1, 37+19+16+3+1, 37+19+16+4+1, 37+19+16+4+2+1, 37+19+16+5+1, 37+19+16+5+2+1, 37+19+16+6+1, 37+19+16+6+2+1, 37+19+16+7+1, 37+19+16+7+2+1, 37+19+16+8+1, 37+19+16+8+2+1, 37+19+16+9+1, 37+19+16+9+2+1, 37+19+16+10+1, 37+19+16+10+2+1, 37+19+16+11+1, 37+19+16+11+2+1, 37+19+16+12+1, 37+19+16+12+2+1, 37+19+16+13+1, 37+19+16+13+2+1, 37+19+17+1, 37+19+17+2+1, 37+19+17+3+1, 37+19+17+4+1, 37+19+17+4+2+1, 37+19+17+5+1, 37+19+17+5+2+1, 37+19+17+6+1, 37+19+17+6+2+1, 37+19+17+7+1, 37+19+17+7+2+1, 37+19+17+8+1, 37+19+17+8+2+1, 37+19+17+9+1, 37+19+17+9+2+1, 37+19+17+10+1, 37+19+17+10+2+1, 37+19+17+11+1, 37+19+17+11+2+1, 37+19+17+12+1, 37+19+17+12+2+1, 37+19+17+13+1, 37+19+17+13+2+1, 37+19+18+1, 37+19+18+2+1, 37+19+18+3+1, 37+19+18+4+1, 37+19+18+4+2+1, 37+19+18+5+1, 37+19+18+5+2+1, 37+19+18+6+1, 37+19+18+6+2+1, 37+19+18+7+1, 37+19+18+7+2+1, 37+19+18+8+1, 37+19+18+8+2+1, 37+19+18+9+1, 37+19+18+9+2+1, 37+19+18+10+1, 37+19+18+10+2+1, 37+19+18+11+1, 37+19+18+11+2+1, 37+19+18+12+1, 37+19+18+12+2+1, 37+19+18+13+1, 37+19+18+13+2+1, 37+20+1, 37+20+2+1, 37+20+3+1, 37+20+4+1, 37+20+4+2+1, 37+20+5+1, 37+20+5+2+1, 37+20+6+1, 37+20+6+2+1, 37+20+7+1, 37+20+7+2+1, 37+20+8+1, 37+20+8+2+1, 37+20+9+1, 37+20+9+2+1, 37+20+10+1, 37+20+10+2+1, 37+20+11+1, 37+20+11+2+1, 37+20+12+1, 37+20+12+2+1, 37+20+13+1, 37+20+13+2+1, 37+20+14+1, 37+20+14+2+1, 37+20+15+1, 37+20+15+2+1, 37+20+16+1, 37+20+16+2+1, 37+20+16+3+1, 37+20+16+4+1, 37+20+16+4+2+1, 37+20+16+5+1, 37+20+16+5+2+1, 37+20+16+6+1, 37+20+16+6+2+1, 37+20+16+7+1, 37+20+16+7+2+1, 37+20+16+8+1, 37+20+16+8+2+1, 37+20+16+9+1, 37+20+16+9+2+1, 37+20+16+10+1, 37+20+16+10+2+1, 37+20+16+11+1, 37+20+16+11+2+1, 37+20+16+12+1, 37+20+16+12+2+1, 37+20+16+13+1, 37+20+16+13+2+1, 37+20+17+1, 37+20+17+2+1, 37+20+17+3+1, 37+20+17+4+1, 37+20+17+4+2+1, 37+20+17+5+1, 37+20+17+5+2+1, 37+20+17+6+1, 37+20+17+6+2+1, 37+20+17+7+1, 37+20+17+7+2+1, 37+20+17+8+1, 37+20+17+8+2+1, 37+20+17+9+1, 37+20+17+9+2+1, 37+20+17+10+1, 37+20+17+10+2+1, 37+20+17+11+1, 37+20+17+11+2+1, 37+20+17+12+1, 37+20+17+12+2+1, 37+20+17+13+1, 37+20+17+13+2+1, 37+20+18+1, 37+20+18+2+1, 37+20+18+3+1, 37+20+18+4+1, 37+20+18+4+2+1, 37+20+18+5+1, 37+20+18+5+2+1, 37+20+18+6+1, 37+20+18+6+2+1, 37+20+18+7+1, 37+20+18+7+2+1, 37+20+18+8+1, 37+20+18+8+2+1, 37+20+18+9+1, 37+20+18+9+2+1, 37+20+18+10+1, 37+20+18+10+2+1, 37+20+18+11+1, 37+20+18+11+2+1, 37+20+18+12+1, 37+20+18+12+2+1, 37+20+18+13+1, 37+20+18+13+2+1, 37+21+1, 37+21+2+1, 37+21+3+1, 37+21+4+1, 37+21+4+2+1, 37+21+5+1, 37+21+5+2+1, 37+21+6+1, 37+21+6+2+1, 37+21+7+1, 37+21+7+2+1, 37+21+8+1, 37+21+8+2+1, 37+21+9+1, 37+21+9+2+1,

37+21+10+1, 37+21+10+2+1, 37+21+11+1, 37+21+11+2+1, 37+21+12+1, 37+21+12+2+1, 37+21+13+1, 37+21+13+2+1, 37+21+14+1, 37+21+14+2+1, 37+21+15+1, 37+21+15+2+1, 37+21+16+1, 37+21+16+2+1, 37+21+16+3+1, 37+21+16+4+1, 37+21+16+4+2+1, 37+21+16+5+1, 37+21+16+5+2+1, 37+21+16+6+1, 37+21+16+6+2+1, 37+21+16+7+1, 37+21+16+7+2+1, 37+21+16+8+1, 37+21+16+8+2+1, 37+21+16+9+1, 37+21+16+9+2+1, 37+21+16+10+1, 37+21+16+10+2+1, 37+21+16+11+1, 37+21+16+11+2+1, 37+21+16+12+1, 37+21+16+12+2+1, 37+21+16+13+1, 37+21+16+13+2+1, 37+21+17+1, 37+21+17+2+1, 37+21+17+3+1, 37+21+17+4+1, 37+21+17+4+2+1, 37+21+17+5+1, 37+21+17+5+2+1, 37+21+17+6+1, 37+21+17+6+2+1, 37+21+17+7+1, 37+21+17+7+2+1, 37+21+17+8+1, 37+21+17+8+2+1, 37+21+17+9+1, 37+21+17+9+2+1, 37+21+17+10+1, 37+21+17+10+2+1, 37+21+17+11+1, 37+21+17+11+2+1, 37+21+17+12+1, 37+21+17+12+2+1, 37+21+17+13+1, 37+21+17+13+2+1, 37+21+18+1, 37+21+18+2+1, 37+21+18+3+1, 37+21+18+4+1, 37+21+18+4+2+1, 37+21+18+5+1, 37+21+18+5+2+1, 37+21+18+6+1, 37+21+18+6+2+1, 37+21+18+7+1, 37+21+18+7+2+1, 37+21+18+8+1, 37+21+18+8+2+1, 37+21+18+9+1, 37+21+18+9+2+1, 37+21+18+10+1, 37+21+18+10+2+1, 37+21+18+11+1, 37+21+18+11+2+1, 37+21+18+12+1, 37+21+18+12+2+1, 37+21+18+13+1, 37+21+18+13+2+1, 37+22+1, 37+22+2+1, 37+22+3+1, 37+22+4+1, 37+22+4+2+1, 37+22+5+1, 37+22+5+2+1, 37+22+6+1, 37+22+6+2+1, 37+22+7+1, 37+22+7+2+1, 37+22+8+1, 37+22+8+2+1, 37+22+9+1, 37+22+9+2+1, 37+22+10+1, 37+22+10+2+1, 37+22+11+1, 37+22+11+2+1, 37+22+12+1, 37+22+12+2+1, 37+22+13+1, 37+22+13+2+1, 37+22+14+1, 37+22+14+2+1, 37+22+15+1, 37+22+15+2+1, 37+22+16+1, 37+22+16+2+1, 37+22+16+3+1, 37+22+16+4+1, 37+22+16+4+2+1, 37+22+16+5+1, 37+22+16+5+2+1, 37+22+16+6+1, 37+22+16+6+2+1, 37+22+16+7+1, 37+22+16+7+2+1, 37+22+16+8+1, 37+22+16+8+2+1, 37+22+16+9+1, 37+22+16+9+2+1, 37+22+16+10+1, 37+22+16+10+2+1, 37+22+16+11+1, 37+22+16+11+2+1, 37+22+16+12+1, 37+22+16+12+2+1, 37+22+16+13+1, 37+22+16+13+2+1, 37+22+17+1, 37+22+17+2+1, 37+22+17+3+1, 37+22+17+4+1, 37+22+17+4+2+1, 37+22+17+5+1, 37+22+17+5+2+1, 37+22+17+6+1, 37+22+17+6+2+1, 37+22+17+7+1, 37+22+17+7+2+1, 37+22+17+8+1, 37+22+17+8+2+1, 37+22+17+9+1, 37+22+17+9+2+1, 37+22+17+10+1, 37+22+17+10+2+1, 37+22+17+11+1, 37+22+17+11+2+1, 37+22+17+12+1, 37+22+17+12+2+1, 37+22+17+13+1, 37+22+17+13+2+1, 37+22+18+1, 37+22+18+2+1, 37+22+18+3+1, 37+22+18+4+1, 37+22+18+4+2+1, 37+22+18+5+1, 37+22+18+5+2+1, 37+22+18+6+1, 37+22+18+6+2+1, 37+22+18+7+1, 37+22+18+7+2+1, 37+22+18+8+1, 37+22+18+8+2+1, 37+22+18+9+1, 37+22+18+9+2+1, 37+22+18+10+1, 37+22+18+10+2+1, 37+22+18+11+1, 37+22+18+11+2+1, 37+22+18+12+1, 37+22+18+12+2+1, 37+22+18+13+1, 37+22+18+13+2+1, 37+23+1, 37+23+2+1, 37+23+3+1, 37+23+4+1, 37+23+4+2+1, 37+23+5+1, 37+23+5+2+1, 37+23+6+1, 37+23+6+2+1, 37+23+7+1, 37+23+7+2+1, 37+23+8+1, 37+23+8+2+1, 37+23+9+1, 37+23+9+2+1, 37+23+10+1, 37+23+10+2+1, 37+23+11+1, 37+23+11+2+1, 37+23+12+1, 37+23+12+2+1, 37+23+13+1, 37+23+13+2+1, 37+23+14+1, 37+23+14+2+1, 37+23+15+1, 37+23+15+2+1, 37+23+16+1, 37+23+16+2+1, 37+23+16+3+1, 37+23+16+4+1, 37+23+16+4+2+1, 37+23+16+5+1, 37+23+16+5+2+1, 37+23+16+6+1, 37+23+16+6+2+1, 37+23+16+7+1, 37+23+16+7+2+1, 37+23+16+8+1, 37+23+16+8+2+1, 37+23+16+9+1, 37+23+16+9+2+1, 37+23+16+10+1, 37+23+16+10+2+1, 37+23+16+11+1, 37+23+16+11+2+1, 37+23+16+12+1, 37+23+16+12+2+1, 37+23+16+13+1, 37+23+16+13+2+1, 37+23+17+1, 37+23+17+2+1, 37+23+17+3+1, 37+23+17+4+1, 37+23+17+4+2+1, 37+23+17+5+1, 37+23+17+5+2+1, 37+23+17+6+1, 37+23+17+6+2+1, 37+23+17+7+1, 37+23+17+7+2+1, 37+23+17+8+1, 37+23+17+8+2+1, 37+23+17+9+1, 37+23+17+9+2+1, 37+23+17+10+1, 37+23+17+10+2+1, 37+23+17+11+1, 37+23+17+11+2+1, 37+23+17+12+1, 37+23+17+12+2+1, 37+23+17+13+1, 37+23+17+13+2+1, 37+23+18+1, 37+23+18+2+1, 37+23+18+3+1, 37+23+18+4+1, 37+23+18+4+2+1, 37+23+18+5+1, 37+23+18+5+2+1, 37+23+18+6+1, 37+23+18+6+2+1, 37+23+18+7+1, 37+23+18+7+2+1, 37+23+18+8+1, 37+23+18+8+2+1, 37+23+18+9+1, 37+23+18+9+2+1, 37+23+18+10+1, 37+23+18+10+2+1, 37+23+18+11+1, 37+23+18+11+2+1, 37+23+18+12+1, 37+23+18+12+2+1, 37+23+18+13+1, 37+23+18+13+2+1, 37+24+1, 37+24+2+1, 37+24+3+1, 37+24+4+1, 37+24+4+2+1, 37+24+5+1, 37+24+5+2+1, 37+24+6+1, 37+24+6+2+1, 37+24+7+1, 37+24+7+2+1, 37+24+8+1, 37+24+8+2+1, 37+24+9+1, 37+24+9+2+1, 37+24+10+1, 37+24+10+2+1, 37+24+11+1, 37+24+11+2+1, 37+24+12+1, 37+24+12+2+1, 37+24+13+1, 37+24+13+2+1, 37+24+14+1, 37+24+14+2+1, 37+24+15+1, 37+24+15+2+1, 37+24+16+1, 37+24+16+2+1, 37+24+16+3+1, 37+24+16+4+1, 37+24+16+4+2+1, 37+24+16+5+1, 37+24+16+5+2+1, 37+24+16+6+1, 37+24+16+6+2+1, 37+24+16+7+1, 37+24+16+7+2+1, 37+24+16+8+1, 37+24+16+8+2+1, 37+24+16+9+1, 37+24+16+9+2+1, 37+24+16+10+1, 37+24+16+10+2+1, 37+24+16+11+1, 37+24+16+11+2+1, 37+24+16+12+1, 37+24+16+12+2+1, 37+24+16+13+1, 37+24+16+13+2+1, 37+24+17+1, 37+24+17+2+1, 37+24+17+3+1, 37+24+17+4+1, 37+24+17+4+2+1, 37+24+17+5+1, 37+24+17+5+2+1, 37+24+17+6+1, 37+24+17+6+2+1, 37+24+17+7+1, 37+24+17+7+2+1, 37+24+17+8+1, 37+24+17+8+2+1, 37+24+17+9+1, 37+24+17+9+2+1, 37+24+17+10+1, 37+24+17+10+2+1, 37+24+17+11+1, 37+24+17+11+2+1, 37+24+17+12+1, 37+24+17+12+2+1, 37+24+17+13+1, 37+24+17+13+2+1, 37+24+18+1, 37+24+18+2+1, 37+24+18+3+1, 37+24+18+4+1, 37+24+18+4+2+1, 37+24+18+5+1, 37+24+18+5+2+1, 37+24+18+6+1, 37+24+18+6+2+1, 37+24+18+7+1, 37+24+18+7+2+1, 37+24+18+8+1, 37+24+18+8+2+1, 37+24+18+9+1, 37+24+18+9+2+1, 37+24+18+10+1, 37+24+18+10+2+1, 37+24+18+11+1, 37+24+18+11+2+1, 37+24+18+12+1, 37+24+18+12+2+1, 37+24+18+13+1, 37+24+18+13+2+1, 37+25+1, 37+25+2+1, 37+25+3+1, 37+25+4+1, 37+25+4+2+1, 37+25+5+1, 37+25+5+2+1, 37+25+6+1, 37+25+6+2+1, 37+25+7+1, 37+25+7+2+1, 37+25+8+1, 37+25+8+2+1, 37+25+9+1, 37+25+9+2+1, 37+25+10+1, 37+25+10+2+1, 37+25+11+1, 37+25+11+2+1, 37+25+12+1, 37+25+12+2+1, 37+25+13+1, 37+25+13+2+1, 37+25+14+1, 37+25+14+2+1, 37+25+15+1, 37+25+15+2+1, 37+25+16+1, 37+25+16+2+1, 37+25+16+3+1, 37+25+16+4+1, 37+25+16+4+2+1, 37+25+16+5+1, 37+25+16+5+2+1, 37+25+16+6+1, 37+25+16+6+2+1, 37+25+16+7+1, 37+25+16+7+2+1, 37+25+16+8+1, 37+25+16+8+2+1, 37+25+16+9+1, 37+25+16+9+2+1, 37+25+16+10+1, 37+25+16+10+2+1, 37+25+16+11+1, 37+25+16+11+2+1, 37+25+16+12+1, 37+25+16+12+2+1, 37+25+16+13+1, 37+25+16+13+2+1, 37+25+17+1, 37+25+17+2+1, 37+25+17+3+1, 37+25+17+4+1, 37+25+17+4+2+1, 37+25+17+5+1, 37+25+17+5+2+1, 37+25+17+6+1, 37+25+17+6+2+1, 37+25+17+7+1, 37+25+17+7+2+1, 37+25+17+8+1, 37+25+17+8+2+1, 37+25+17+9+1, 37+25+17+9+2+1, 37+25+17+10+1, 37+25+17+10+2+1, 37+25+17+11+1, 37+25+17+11+2+1, 37+25+17+12+1, 37+25+17+12+2+1, 37+25+17+13+1, 37+25+17+13+2+1,

37+25+18+1, 37+25+18+2+1, 37+25+18+3+1, 37+25+18+4+1, 37+25+18+4+2+1, 37+25+18+5+1, 37+25+18+5+2+1, 37+25+18+6+1, 37+25+18+6+2+1, 37+25+18+7+1, 37+25+18+7+2+1, 37+25+18+8+1, 37+25+18+8+2+1, 37+25+18+9+1, 37+25+18+9+2+1, 37+25+18+10+1, 37+25+18+10+2+1, 37+25+18+11+1, 37+25+18+11+2+1, 37+25+18+12+1, 37+25+18+12+2+1, 37+25+18+13+1, 37+25+18+13+2+1, 37+26+1, 37+26+2+1, 37+26+3+1, 37+26+4+1, 37+26+4+2+1, 37+26+5+1, 37+26+5+2+1, 37+26+6+1, 37+26+6+2+1, 37+26+7+1, 37+26+7+2+1, 37+26+8+1, 37+26+8+2+1, 37+26+9+1, 37+26+9+2+1, 37+26+10+1, 37+26+10+2+1, 37+26+11+1, 37+26+11+2+1, 37+26+12+1, 37+26+12+2+1, 37+26+13+1, 37+26+13+2+1, 37+26+14+1, 37+26+14+2+1, 37+26+15+1, 37+26+15+2+1, 37+26+16+1, 37+26+16+2+1, 37+26+16+3+1, 37+26+16+4+1, 37+26+16+4+2+1, 37+26+16+5+1, 37+26+16+5+2+1, 37+26+16+6+1, 37+26+16+6+2+1, 37+26+16+7+1, 37+26+16+7+2+1, 37+26+16+8+1, 37+26+16+8+2+1, 37+26+16+9+1, 37+26+16+9+2+1, 37+26+16+10+1, 37+26+16+10+2+1, 37+26+16+11+1, 37+26+16+11+2+1, 37+26+16+12+1, 37+26+16+12+2+1, 37+26+16+13+1, 37+26+16+13+2+1, 37+26+17+1, 37+26+17+2+1, 37+26+17+3+1, 37+26+17+4+1, 37+26+17+4+2+1, 37+26+17+5+1, 37+26+17+5+2+1, 37+26+17+6+1, 37+26+17+6+2+1, 37+26+17+7+1, 37+26+17+7+2+1, 37+26+17+8+1, 37+26+17+8+2+1, 37+26+17+9+1, 37+26+17+9+2+1, 37+26+17+10+1, 37+26+17+10+2+1, 37+26+17+11+1, 37+26+17+11+2+1, 37+26+17+12+1, 37+26+17+12+2+1, 37+26+17+13+1, 37+26+17+13+2+1, 37+26+18+1, 37+26+18+2+1, 37+26+18+3+1, 37+26+18+4+1, 37+26+18+4+2+1, 37+26+18+5+1, 37+26+18+5+2+1, 37+26+18+6+1, 37+26+18+6+2+1, 37+26+18+7+1, 37+26+18+7+2+1, 37+26+18+8+1, 37+26+18+8+2+1, 37+26+18+9+1, 37+26+18+9+2+1, 37+26+18+10+1, 37+26+18+10+2+1, 37+26+18+11+1, 37+26+18+11+2+1, 37+26+18+12+1, 37+26+18+12+2+1, 37+26+18+13+1, 37+26+18+13+2+1, 37+27+1, 37+27+2+1, 37+27+3+1, 37+27+4+1, 37+27+4+2+1, 37+27+5+1, 37+27+5+2+1, 37+27+6+1, 37+27+6+2+1, 37+27+7+1, 37+27+7+2+1, 37+27+8+1, 37+27+8+2+1, 37+27+9+1, 37+27+9+2+1, 37+27+10+1, 37+27+10+2+1, 37+27+11+1, 37+27+11+2+1, 37+27+12+1, 37+27+12+2+1, 37+27+13+1, 37+27+13+2+1, 37+27+14+1, 37+27+14+2+1, 37+27+15+1, 37+27+15+2+1, 37+27+16+1, 37+27+16+2+1, 37+27+16+3+1, 37+27+16+4+1, 37+27+16+4+2+1, 37+27+16+5+1, 37+27+16+5+2+1, 37+27+16+6+1, 37+27+16+6+2+1, 37+27+16+7+1, 37+27+16+7+2+1, 37+27+16+8+1, 37+27+16+8+2+1, 37+27+16+9+1, 37+27+16+9+2+1, 37+27+16+10+1, 37+27+16+10+2+1, 37+27+16+11+1, 37+27+16+11+2+1, 37+27+16+12+1, 37+27+16+12+2+1, 37+27+16+13+1, 37+27+16+13+2+1, 37+27+18+1, 37+27+18+2+1, 37+27+18+3+1, 37+27+18+4+1, 37+27+18+4+2+1, 37+27+18+5+1, 37+27+18+5+2+1, 37+27+18+6+1, 37+27+18+6+2+1, 37+27+18+7+1, 37+27+18+7+2+1, 37+27+18+8+1, 37+27+18+8+2+1, 37+27+18+9+1, 37+27+18+9+2+1, 37+27+18+10+1, 37+27+18+10+2+1, 37+27+18+11+1, 37+27+18+11+2+1, 37+27+18+12+1, 37+27+18+12+2+1, 37+27+18+13+1, 37+27+18+13+2+1, 37+27+19+1, 37+27+19+2+1, 37+27+19+3+1, 37+27+19+4+1, 37+27+19+4+2+1, 37+27+19+5+1, 37+27+19+5+2+1, 37+27+19+6+1, 37+27+19+6+2+1, 37+27+19+7+1, 37+27+19+7+2+1, 37+27+19+8+1, 37+27+19+8+2+1, 37+27+19+9+1, 37+27+19+9+2+1, 37+27+19+10+1, 37+27+19+10+2+1, 37+27+19+11+1, 37+27+19+11+2+1, 37+27+19+12+1, 37+27+19+12+2+1, 37+27+19+13+1, 37+27+19+13+2+1, 37+27+19+14+1, 37+27+19+14+2+1, 37+27+19+15+1, 37+27+19+15+2+1, 37+27+19+16+1, 37+27+19+16+2+1, 37+27+19+16+3+1, 37+27+19+16+4+1, 37+27+19+16+4+2+1, 37+27+19+16+5+1, 37+27+19+16+5+2+1, 37+27+19+16+6+1, 37+27+19+16+6+2+1, 37+27+19+16+7+1, 37+27+19+16+7+2+1, 37+27+19+16+8+1, 37+27+19+16+8+2+1, 37+27+19+16+9+1, 37+27+19+16+9+2+1, 37+27+19+16+10+1, 37+27+19+16+10+2+1, 37+27+19+16+11+1, 37+27+19+16+11+2+1, 37+27+19+16+12+1, 37+27+19+16+12+2+1, 37+27+19+16+13+1, 37+27+19+16+13+2+1, 37+27+19+17+1, 37+27+19+17+2+1, 37+27+19+17+3+1, 37+27+19+17+4+1, 37+27+19+17+4+2+1, 37+27+19+17+5+1, 37+27+19+17+5+2+1, 37+27+19+17+6+1, 37+27+19+17+6+2+1, 37+27+19+17+7+1, 37+27+19+17+7+2+1, 37+27+19+17+8+1, 37+27+19+17+8+2+1, 37+27+19+17+9+1, 37+27+19+17+9+2+1, 37+27+19+17+10+1, 37+27+19+17+10+2+1, 37+27+19+17+11+1, 37+27+19+17+11+2+1, 37+27+19+17+12+1, 37+27+19+17+12+2+1, 37+27+19+17+13+1, 37+27+19+17+13+2+1, 37+27+19+18+1, 37+27+19+18+2+1, 37+27+19+18+3+1, 37+27+19+18+4+1, 37+27+19+18+4+2+1, 37+27+19+18+5+1, 37+27+19+18+5+2+1, 37+27+19+18+6+1, 37+27+19+18+6+2+1, 37+27+19+18+7+1, 37+27+19+18+7+2+1, 37+27+19+18+8+1, 37+27+19+18+8+2+1, 37+27+19+18+9+1, 37+27+19+18+9+2+1, 37+27+19+18+10+1, 37+27+19+18+10+2+1, 37+27+19+18+11+1, 37+27+19+18+11+2+1, 37+27+19+18+12+1, 37+27+19+18+12+2+1, 37+27+19+18+13+1, 37+27+19+18+13+2+1, 37+27+24+1, 37+27+24+2+1, 37+27+24+3+1, 37+27+24+4+1, 37+27+24+4+2+1, 37+27+24+5+1, 37+27+24+5+2+1, 37+27+24+6+1, 37+27+24+6+2+1, 37+27+24+7+1, 37+27+24+7+2+1, 37+27+24+8+1, 37+27+24+8+2+1, 37+27+24+9+1, 37+27+24+9+2+1, 37+27+24+10+1, 37+27+24+10+2+1, 37+27+24+11+1, 37+27+24+11+2+1, 37+27+24+12+1, 37+27+24+12+2+1, 37+27+24+13+1, 37+27+24+13+2+1, 37+27+24+14+1, 37+27+24+14+2+1, 37+27+24+15+1, 37+27+24+15+2+1, 37+27+24+16+1, 37+27+24+16+2+1, 37+27+24+16+3+1, 37+27+24+16+4+1, 37+27+24+16+4+2+1, 37+27+24+16+5+1, 37+27+24+16+5+2+1, 37+27+24+16+6+1, 37+27+24+16+6+2+1, 37+27+24+16+7+1, 37+27+24+16+7+2+1, 37+27+24+16+8+1, 37+27+24+16+8+2+1, 37+27+24+16+9+1, 37+27+24+16+9+2+1, 37+27+24+16+10+1, 37+27+24+16+10+2+1, 37+27+24+16+11+1, 37+27+24+16+11+2+1, 37+27+24+16+12+1, 37+27+24+16+12+2+1, 37+27+24+16+13+1, 37+27+24+16+13+2+1, 37+27+24+17+1, 37+27+24+17+2+1, 37+27+24+17+3+1, 37+27+24+17+4+1, 37+27+24+17+4+2+1, 37+27+24+17+5+1, 37+27+24+17+5+2+1, 37+27+24+17+6+1, 37+27+24+17+6+2+1, 37+27+24+17+7+1, 37+27+24+17+7+2+1, 37+27+24+17+8+1, 37+27+24+17+8+2+1, 37+27+24+17+9+1, 37+27+24+17+9+2+1, 37+27+24+17+10+1, 37+27+24+17+10+2+1, 37+27+24+17+11+1, 37+27+24+17+11+2+1, 37+27+24+17+12+1, 37+27+24+17+12+2+1, 37+27+24+17+13+1, 37+27+24+17+13+2+1, 37+27+24+18+1, 37+27+24+18+2+1, 37+27+24+18+3+1, 37+27+24+18+4+1, 37+27+24+18+4+2+1, 37+27+24+18+5+1, 37+27+24+18+5+2+1, 37+27+24+18+6+1, 37+27+24+18+6+2+1, 37+27+24+18+7+1, 37+27+24+18+7+2+1, 37+27+24+18+8+1, 37+27+24+18+8+2+1, 37+27+24+18+9+1, 37+27+24+18+9+2+1, 37+27+24+18+10+1, 37+27+24+18+10+2+1, 37+27+24+18+11+1, 37+27+24+18+11+2+1, 37+27+24+18+12+1, 37+27+24+18+12+2+1, 37+27+24+18+13+1, 37+27+24+18+13+2+1, 37+28, 37+29, 37+30, 37+31, 37+32, 37+33, 37+34, 37+35 or 37+36.

In the list above the numbers refer to the embodiments according to their numbering provided hereinabove whereas "+" indicates the dependency from another embodiment. The different individualized embodiments are separated by commas. In other words, "4+2+1" for example refers to embodiment 4) depending on embodiment 2), depending on embodiment 1), i.e. embodiment "4+2+1" corresponds to embodiment 1) further characterized by the features of the embodiments 2) and 4).

The compounds of formula (I) may encompass compounds with one or more asymmetric centers, such as one or more asymmetric carbon atoms, which are allowed to be present in (R)- as well as (S)-configuration. The compounds of formula (I) may further encompass compounds with one or more double bonds which are allowed to be present in Z- as well as E-configuration and/or compounds with substituents at a ring system which are allowed to be present, relative to each other, in cis- as well as trans-configuration. The compounds of formula (I) may thus be present as mixtures of stereoisomers or preferably in stereoisomerically enriched form, especially as essentially pure stereoisomers. Mixtures of stereoisomers may be separated in a manner known to a person skilled in the art.

In case a particular compound (or generic structure) is designated as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations are to be understood as referring to the respective stereoisomer in enriched, especially essentially pure, form. Likewise, in case a particular compound (or generic structure) is designated as Z- or E-stereoisomer (or in case a specific double bond in a compound is designated as being in Z- or E-configuration), such designation is to be understood as referring to the respective compound (or generic structure) in enriched, especially essentially pure, stereoisomeric form (or to the compound that is in enriched, especially essentially pure, form with regard to the respective configuration of the double bond).

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labeled, especially $^2$H (deuterium) labeled compounds of Formula (I), which compounds are identical to the compounds of Formula (I) except that one or more atoms have each been replaced by an atom having the same atomic number but an atomic mass different from the atomic mass usually found in nature. Isotopically labeled, especially $^2$H (deuterium) labeled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to a modified metabolism, resulting e.g. in an improved safety profile. In one embodiment of the invention, the compounds of Formula (I) are not isotopically labeled, or they are labeled only with one or more deuterium atoms. In a sub-embodiment, the compounds of Formula (I) are not isotopically labeled at all. Isotopically labeled compounds of Formula (I) may be prepared in analogy to the methods described hereinafter, but using the appropriate isotopic variation of suitable reagents or starting materials.

In this patent application, a bond drawn as a dashed line shows the point of attachment of the radical drawn. For example, the radical drawn below

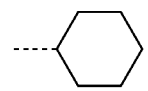

is a cyclohexyl group.

In addition to the asymmetric carbon atom shown in Formula (II), the compounds of said formula may contain further asymmetric carbon atoms. The compounds of Formula (II) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases, this is intended to mean also a single compound, salt, composition and disease.

Any reference hereinbefore or hereinafter to a compound of Formula (I) (including any reference to a compound according to any one of embodiments 1) to 40), is to be understood as referring also to salts, especially pharmaceutically acceptable salts, of a compound of Formula (I), as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008, and 'Pharmaceutical Salts and Co-crystals', Johan Wouters and Luc Quéré (Eds.), RSC Publishing, 2012.

Definitions provided herein are intended to apply uniformly to the compounds of Formula (I) as defined in any one of embodiments 1) to 37), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. If not explicitly defined otherwise in the respective embodiment or claim, groups defined herein are unsubstituted.

The term "alkyl", used alone or in combination, refers to a saturated straight or branched hydrocarbon chain containing one to six (especially one to four) carbon atoms. The term "$C_{x-y}$-alkyl" (x and y each being an integer), used alone or in combination, refers to a saturated straight or branched hydrocarbon chain with x to y carbon atoms. Thus, the term $C_{1-4}$-alkyl, alone or in combination with other groups, means saturated, branched or straight chain groups with one to four carbon atoms. Examples of $C_{1-4}$-alkyl groups are methyl, ethyl, n-propyl, iso-propyl, n-butyl, tert-butyl, sec-butyl and iso-butyl. Examples of $C_{1-3}$-alkyl groups are methyl, ethyl, n-propyl or iso-propyl. A preferred alkyl group is methyl. For the substituent $R^1$ preferred examples of $C_{1-4}$-alkyl groups are methyl, ethyl, n-propyl and iso-propyl; most preferred examples are methyl and ethyl. For the substituents borne by the group $R^1$ a preferred example of a $C_{1-4}$-alkyl group is methyl. For the substituents borne by the group $R^2$, wherein $R^2$ represents $C_{3-7}$-cycloalkyl, a preferred example of a $C_{1-4}$-alkyl group is methyl. The term "alkyl" used in the terms "spiro[x.y]alkyl" or in bicyclo[x.y.z]alkyl expresses the total number of carbon atoms, i.e. "heptyl" refers to 7 carbon atoms, "octyl" refers to 8 carbon atoms, etc. Examples of branched $C_{3-6}$-alkyl groups, used for substituent $R^2$ are iso-propyl, tert-butyl, 3-methyl-butyl, 2,2-dimethyl-propyl and 3,3-dimethyl-butyl; preferred is tert-butyl.

The term "$C_{x-y}$-alkylene" (x and y each being an integer), used alone or in combination, refers to a bivalent saturated aliphatic hydrocarbon group having x to y carbon atoms and regarded as derived from an alkane having x to y carbon atoms by removal of two hydrogen atoms. Thus, the term $C_{1-3}$-alkylene, alone or in combination with other groups, means a saturated, branched or straight, bivalent group with one to three carbon atoms. Examples of $C_{1-3}$-alkylene are the groups —CH$_2$—, —(CH$_2$)$_2$—, —CH(CH$_3$)—, —(CH$_2$)$_3$—, —CH$_2$CH(CH$_3$)—, —CH(CH$_3$)CH$_2$—, —C(CH$_3$)$_2$— or —CH(CH$_2$CH$_3$)—; especially —CH$_2$—, —CH$_2$CH(CH$_3$)— and —CH(CH$_2$CH$_3$)—. For the substituent A a preferred example is the group —CH$_2$—.

The term "$C_{x-y}$-alkenylene" (x and y each being an integer), used alone or in combination, refers to a bivalent unsaturated straight or branched hydrocarbon chain having x to y carbon atoms and comprising one carbon-carbon double bond. Thus, the term $C_{2-3}$-alkenylene, alone or in combination with other groups, means an unsaturated, branched or straight, bivalent group comprising one carbon-carbon double bond, having two to three carbon atoms. Examples of such groups are —CH=CH—, —CH=C(CH$_3$)—, —C(CH$_3$)=CH—, —CH$_2$CH=CH— and —CH=CH—CH$_2$—; especially —CH=CH—.

The term "$C_{x-y}$-alkynylene" (x and y each being an integer), used alone or in combination, refers to a bivalent unsaturated straight or branched hydrocarbon chain having x to y carbon atoms and comprising one carbon-carbon triple bond. Thus, the term $C_{2-3}$-alkynylene, alone or in combination with other groups, means an unsaturated, straight, bivalent group comprising one carbon-carbon triple bond, having two to three carbon atoms. Examples of such groups are —C≡C—, —CH$_2$—C≡C— and —C≡C—CH$_2$—; especially —C≡C—.

The term "$C_{x-y}$-alkenyl" (x and y each being an integer), used alone or in combination, refers to a straight or branched hydrocarbon chain with x to y carbon atoms, wherein said chain has one double bond. Thus, the term $C_{2-3}$-alkenyl, alone or in combination with other groups, means branched or straight chain groups having two to three carbon atoms and one double bond. Examples of $C_{2-3}$-alkenyl groups are —CH=CH$_2$, —CH=CH$_2$—CH$_3$, —CH$_2$—CH=CH$_2$, —C(CH$_3$)=CH$_2$; especially —CH=CH$_2$.

The term "halogen" means fluorine, chlorine, bromine or iodine; especially fluorine, chlorine or bromine. For the substituent $R^1$ preferred examples are bromine or chlorine. When "halogen" is a substituent to a saturated carbon atom, preferred is fluorine. For example, when $R^1$ represents a mono- or di-substituted $C_{3-6}$-cycloalkyl, preferred halogen substituent is fluorine. For the substituents borne by the group $R^2$ (e.g. $R^2$ represents a phenyl which is substituted with halogen) preferred examples are fluorine or chlorine.

The term "fluoroalkyl", used alone or in combination, refers to an alkyl group as defined before containing one to three carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $C_1$-fluoroalkyl groups such as difluoromethyl and trifluoromethyl; most preferred is trifluoromethyl.

The term "cycloalkyl", used alone or in combination, refers to a saturated monocyclic hydrocarbon ring containing three to seven carbon atoms (preferably three to six carbon atoms). The term "$C_{x-y}$-cycloalkyl" (x and y each being an integer), refers to a saturated monocyclic hydrocarbon ring containing x to y carbon atoms. For example, a $C_{3-7}$-cycloalkyl group contains from three to seven carbon atoms. Examples of $C_{3-6}$-cycloalkyl groups as used for substituent $R^1$ are cyclopropyl, cyclobutyl, cyclopentyl and cyclohexyl; preferred examples are cyclopropyl and cyclobutyl; a most preferred example is cyclopropyl. For the $C_{3-6}$-cycloalkyl substituents borne by the group $R^2$ (e.g. $R^2$ represents a phenyl which is substituted with $C_{3-6}$-cycloalkyl) preferred examples are cyclobutyl, cyclopentyl and cyclohexyl. Examples of $C_{3-7}$-cycloalkyl group as used for substituent $R^2$ are cyclopropyl, cyclobutyl, cyclopentyl, cyclohexyl and cycloheptyl; preferred examples are cyclobutyl, cyclopentyl and cyclohexyl; most preferred examples are cyclopentyl and cyclohexyl. Examples of $C_{5-6}$-cycloalkyl groups are cyclopentyl and cyclohexyl. Examples of $C_{4-7}$-cycloalkyl groups are cyclobutyl, cyclopentyl, cyclohexyl and cycloheptyl. All of the above groups are unsubstituted or substituted as explicitly defined.

The term "5- to 6-membered heterocycloalkyl", used alone or in combination, refers to a saturated monocyclic hydrocarbon ring containing five or six carbon atoms, wherein one or two carbon atoms independently from each other are replaced by a heteroatom each independently selected from nitrogen, oxygen or sulphur.

Examples of such heterocycloalkyl groups are pyrrolidinyl, pyrazolidinyl, imidazolidinyl, tetrahydrofuranyl, tetrahydrothiophenyl, 1,2-oxathiolanyl, 1,3-oxathiolanyl, piperidinyl, piperazinyl, tetrahydropyranyl, 1,4-dioxanyl, thianyl, 1,3-dithianyl, 1,4-dithianyl, morpholinyl and thiomorpholinyl. For the substituent $R^2$ a preferred example is piperidinyl; more preferably piperidin-4-yl and most preferably piperidin-4-yl which is mono-substituted at the piperidine nitrogen atom. All of the above groups are unsubstituted or substituted as explicitly defined.

The term "aryl", used alone or in combination, means phenyl or naphthyl (preferably phenyl). The aryl group may be unsubstituted or substituted as explicitly defined.

The term "5- to 6-membered heteroaryl", used alone or in combination, means a 5- to 6-membered monocyclic aromatic ring containing one to a maximum of four ring heteroatoms (preferably one to a maximum of three ring heteroatoms), each independently selected from oxygen, nitrogen and sulfur. Examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; and 6-membered heteroaryl groups such as pyridinyl, pyrimidinyl, pyridazinyl, pyrazinyl. When used to define $R^1$, the term "5-membered heteroaryl refers to 5-membered heteroaryl groups such as especially pyrazolyl or thiophenyl; in particular thiophen-2-yl, thiophen-3-yl, pyrazol-3-yl and pyrazol-4-yl (notably pyrazol-4-yl and thiophen-3-yl). When used to define $R^1$, the term "6-membered heteroaryl refers to 6-membered heteroaryl groups such as especially pyridinyl (notably pyridin-3-yl). When used to define $R^2$, one preferred embodiment of 5- to 6-membered heteroaryl is 5-membered heteroaryl. When used to define $R^2$, the term "5-membered heteroaryl refers to 5-membered heteroaryl groups such as especially pyrazolyl, triazolyl or thiophenyl; preferred groups are thiophen-2-yl, thiophen-3-yl, 1,2,3-triazolyl, 1,2,4-triazolyl and pyrazol-4-yl (notably 1,2,3-triazol-4-yl, pyrazol-4-yl, thiophen-2-yl and thiophen-3-yl). All of the above groups are unsubstituted or substituted as explicitly defined.

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. For example, a $C_{1-4}$-alkoxy group means a group of the formula $C_{1-4}$-alkyl-O— in which the term "$C_{1-4}$-alkyl" has the previously given significance. The group $C_{1-3}$-alkoxy group means a group of the formula $C_{1-3}$-alkyl-O— in which the term "$C_{1-3}$-alkyl" has the previously given significance Examples of $C_{1-4}$-alkoxy groups are methoxy, ethoxy, n-propoxy, iso-propoxy, n-butoxy, iso-butoxy, sec-butoxy and tert-butoxy. Examples of $C_{1-3}$-alkoxy groups are methoxy, ethoxy, n-propoxy and iso-propoxy; especially methoxy.

The term "$C_{1-3}$-alkoxy-methyl", used alone or in combination, refers to a $C_{1-3}$-alkoxy group as defined before, wherein said $C_{1-3}$-alkoxy group is directly attached to a methylene group. For example, $C_{1-3}$-alkoxy-methyl are the groups metoxy-methyl (—$CH_2$—O—$CH_3$), ethoxy-methyl (—$CH_2$—O—$C_2H_5$), n-propoxy-methyl (—$CH_2$—O—$C_3H_7$), iso-propoxy-methyl (—$CH_2$—O—$CH(CH_3)_2$); preferred is metoxy-methyl (—$CH_2$—O—$CH_3$).

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $C_1$-fluoroalkoxy groups such as trifluoromethoxy and difluoromethoxy, as well as the $C_2$-fluoroalkoxy group-2,2,2-trifluoroethoxy.

The term "phenyl-$(CH_2)_{0-1}$—", either used alone or in combination, refers to a phenyl ring attached either via a direct bond or via methylene group to the rest of the molecule, i.e. "phenyl-$(CH_2)_{0-1}$—" refers to a phenyl or a benzyl group. Notably, such phenyl-$(CH_2)_{0-1}$— is directly attached to the rest of the molecule, i.e. preferred is a phenyl group. The phenyl ring part of phenyl-$(CH_2)_{0-1}$— is unsubstituted or substituted as explicitly defined.

The term "saturated 7- to 11-membered bridged, fused or spiro bicyclic hydrocarbon ring system" refers to two hydrocarbon rings which have at least one carbon atom in common and wherein the total number of carbon atoms in both rings is an integer from 7 to 11. More particularly, the term saturated 7- to 11-membered bridged bicyclic hydrocarbon ring system refers to compounds described by the term "bicyclo[x.y.z]alkyl, wherein the total number of carbon atoms is an integer from 7 to 11, and each one of "x", "y" and "z" is larger than 0 [i.e. the sum of "x", "y" and "z" is from 5 to 9; and the integers "x", "y" and "z" independently indicate the number of carbon atoms in each of the three bridges linked to the two tertiary carbon atoms in descending order (x>y>z)]. Examples for such 7- to 11-membered bridged bicyclic hydrocarbon ring system are bicyclo[2.2.1]heptyl, bicyclo[2.2.2]octyl, bicyclo[3.1.1]heptyl, bicyclo[3.2.1]octyl, bicyclo[3.3.1]nonyl, bicyclo[4.2.1]nonyl, bicyclo[4.2.2]decyl, bicyclo[4.3.1]decyl, bicyclo[5.2.1]decyl bicyclo[5.2.2]undecyl, bicyclo[5.3.1]undecyl, and bicyclo[6.2.1]undecyl; especially bicyclo[2.2.1]heptyl;

the term saturated 7- to 11-membered fused bicyclic hydrocarbon ring system refers to compounds described by the term "bicyclo[x.y.0]alkyl", wherein the total number of carbon atoms is an integer from 7 to 11; [it being understood that the integers "x" and "y" independently from each other indicate the number of carbon atoms in each of the two bridges linked to the two tertiary carbon atoms in descending order (x>y>0)]. For example the following combinations [x,y,0] are possible: [3.1.0], [4.1.0], [5.1.0], [3.2.0], [4.2.0], [5.2.0], [6.2.0], [7.2.0], [3.3.0], [4.3.0], [5.3.0], [6.3.0], [4.4.0], and [5.4.0]. Examples for such 7- to 11-membered fused hydrocarbon ring system are bicyclo[3.1.0]hexyl, bicyclo[3.2.0]heptyl, bicyclo[3.3.0]octyl, bicyclo[4.1.0]heptyl, bicyclo[4.2.0]octyl bicyclo[4.3.0]nonyl, bicyclo[4.4.0]decyl, bicyclo[5.1.0]octyl, bicyclo[5.2.0]nonyl, bicyclo[5.3.0]decyl, and bicyclo[5.4.0]undecyl; and the term saturated 7- to 11-membered spiro bicyclic hydrocarbon ring system refers compounds described by the term "spiro[x.y]alkyl", wherein the total number of carbon atoms is an integer from 7 to 11; [it being understood that the integers "x" and "y" represent the number of carbon atoms in each of the two carbon cycles linked to the one quaternary carbon atom]. For example the following combinations [x.y] are possible: [3.3], [3.4], [3.5], [3.6], [3.7], [4.2], [4.4], [4.5], [4.6], [5.2] and [5.5]. Examples for such 7- to 11-membered spiro bicyclic hydrocarbon ring systems are: spiro[3.3]heptyl, spiro[3.4]octyl, spiro[3.5]nonyl, spiro[3.6]decyl, spiro[2.3]hexyl, spiro[2.4]heptyl, spiro[4.4]nonyl, and spiro[4.5]decyl.

The term "7- to 11-membered bridged, fused or spiro bicyclic hydrocarbon ring system wherein said ring system contains one carbon-carbon double bond" refers to the 7- to 11-membered bridged, fused or spiro bicyclic hydrocarbon ring systems as defined above, wherein one saturated carbon-carbon is replaced by a carbon-carbon double bond. An example of such groups is bicyclo[2.2.1]hept-5-en-2-yl-methyl.

The term "7- to 11-membered bridged, fused or spiro bicyclic hydrocarbon ring system wherein in said ring system optionally one ring carbon atom is replaced by a ring oxygen atom" refers to the 7- to 11-membered bridged, fused or spiro bicyclic hydrocarbon ring systems as defined above, wherein one ring carbon atom is replaced by an oxygen ring atom. An example of such groups is 7-oxabicyclo[2.2.1]hept-2-yl-methyl.

The term "saturated 5- to 11-membered bridged, fused or spiro bicyclic hydrocarbon ring system" refers to two hydrocarbon rings which have at least one carbon atom in common and wherein the total number of carbon atoms in both rings is an integer from 5 to 11. More particularly, the term saturated 5- to 11-membered bridged bicyclic hydrocarbon ring system refers to compounds described by the term "bicyclo[x.y.z]alkyl, wherein the total number of carbon atoms is an integer from 5 to 11, and each one of "x", "y" and "z" is larger than 0 [i.e. the sum of "x", "y" and "z" is from 3 to 9; and the integers "x", "y" and "z" independently indicate the number of carbon atoms in each of the three bridges linked to the two shared tertiary carbon atoms in descending order (x≥y≥z)]. Examples for such 5- to 11-membered bridged bicyclic hydrocarbon ring system are bicyclo[1.1.1]pentyl, bicyclo[2.1.1]hexyl, bicyclo[2.2.1]heptyl, bicyclo[2.2.2]octyl, bicyclo[3.1.1]heptyl, bicyclo[3.2.1]octyl, bicyclo[3.3.1]nonyl, bicyclo[4.2.1]nonyl, bicyclo[4.2.2]decyl, bicyclo[4.3.1]decyl, bicyclo[5.2.1]decyl bicyclo[5.2.2]undecyl, bicyclo[5.3.1]undecyl, and bicyclo[6.2.1]undecyl; especially bicyclo[1.1.1]pentyl, bicyclo[2.1.1]hexyl and bicyclo[2.2.1]heptyl;

the term saturated 5- to 11-membered fused bicyclic hydrocarbon ring system refers to compounds described by the term "bicyclo[x.y.0]alkyl", wherein the total number of carbon atoms is an integer from 5 to 11; [it being understood that the integers "x" and "y" independently from each other indicate the number of carbon atoms in each of the two bridges linked to the two shared tertiary carbon atoms in descending order (x≥y≥0)]. For example the following combinations [x,y,0] are possible: [2.1.0], [2.2.0], [3.1.0], [4.1.0], [5.1.0], [3.2.0], [4.2.0], [5.2.0], [6.2.0], [7.2.0], [3.3.0], [4.3.0], [5.3.0], [6.3.0], [4.4.0], and [5.4.0]. Examples for such 5- to 11-membered fused hydrocarbon ring system are bicyclo[2.1.0]pentyl, bicyclo[2.2.0]hexyl, bicyclo[3.1.0]hexyl, bicyclo[3.2.0]heptyl, bicyclo[3.3.0]octyl, bicyclo[4.1.0]heptyl, bicyclo[4.2.0]octyl bicyclo[4.3.0]nonyl, bicyclo[4.4.0]decyl, bicyclo[5.1.0]octyl, bicyclo[5.2.0]nonyl, bicyclo[5.3.0]decyl, and bicyclo[5.4.0]undecyl; especially bicyclo[3.3.0]octyl and bicyclo[4.4.0]decyl; and the term saturated 5- to 11-membered spiro bicyclic hydrocarbon ring system refers to compounds described by the term "spiro[x.y]alkyl", wherein the total number of carbon atoms is an integer from 5 to 11; [it being understood that the integers "x" and "y" represent the number of carbon atoms in each of the two bridges linked to the one shared quaternary carbon atom]. For example, the following combinations [x.y] are possible: [3.3], [3.4], [3.5], [3.6], [3.7], [2.4], [4.4], [4.5], [4.6], [2.5] and [5.5]. Examples for such 5- to 11-membered spiro bicyclic hydrocarbon ring systems are: spiro[3.3]heptyl, spiro[3.4]octyl, spiro[3.5]nonyl, spiro[3.6]decyl, spiro[2.3]hexyl, spiro[2.4]heptyl, spiro[4.4]nonyl, and spiro[4.5]decyl; especially spiro[4.5]decyl.

The term "5- to 11-membered bridged, fused or spiro bicyclic hydrocarbon ring system wherein said ring system contains one carbon-carbon double bond" refers to the 5- to 11-membered bridged, fused or spiro bicyclic hydrocarbon ring systems as defined above, wherein one saturated carbon-carbon bond is replaced by a carbon-carbon double bond. An example of such a group is bicyclo[2.2.1]hept-5-en-2-yl.

The term "5- to 11-membered bridged, fused or spiro bicyclic hydrocarbon ring system wherein in said ring system optionally one ring carbon atom is replaced by a ring oxygen atom" refers to the 5- to 11-membered bridged, fused or spiro bicyclic hydrocarbon ring systems as defined above, wherein one ring carbon atom (i.e. a $CH_2$-group) is replaced by an oxygen ring atom. An example of such a group is 7-oxa-bicyclo[2.2.1]hept-2-yl.

The term "$C_{5-6}$-cycloalkyl" which is fused to a phenyl ring" refers to a ring system comprising a $C_{5-6}$-cycloalkyl as defined hereinabove which has two carbon atoms in common with a phenyl ring, wherein either the $C_{5-6}$-cycloalkyl or said phenyl are attached to A; especially the $C_{5-6}$-cycloalkyl ring is attached to A. Examples of such ring systems are 1,2,3,4-tetrahydronaphthalene and 2,3-dihydro-1H-indene; especially 1,2,3,4-tetrahydronaphthalen-1-yl, 1,2,3,4-tetrahydronaphthalen-2-yl and 2,3-dihydro-1H-inden-1-yl; notably 1,2,3,4-tetrahydronaphthalen-1-yl and 1,2,3,4-tetrahydronaphthalen-2-yl.

The compounds of Formula (I) and their pharmaceutically acceptable salts can be used as medicaments, e.g. in the form of pharmaceutical compositions for enteral (such as especially oral) or parenteral (including topical application or inhalation) administration.

The compounds of Formula (I) are suitable for inhibiting IDO and/or TDO enzymes, and for the prevention and/or treatment of diseases or disorders related to the IDO and/or TDO enzymes (such as especially cancers) in mammals, such as especially humans.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The present invention also relates to a method for the prevention or treatment of a disease or disorder mentioned hereinabove and/or hereinbelow comprising administering to a subject a pharmaceutically active amount of a compound of Formula (I) either alone or in combination with other pharmacologically active compounds and/or therapies.

The meaning of the term "prevention" may also be understood as "prophylaxis".

One or more compounds of Formula (I) may be used in the prevention and/or treatment of diseases or disorders related to the IDO and/or TDO enzymes; such as especially cancers.

Cancers may be defined as including skin cancer including melanoma; metastatic melanoma; lung cancer including non-small cell lung cancer; bladder cancer including urinary bladder cancer; urothelial cell carcinoma; renal carcinomas including renal cell carcinoma; metastatic renal cell carcinoma; metastatic renal clear cell carcinoma; gastro-intestinal cancers including colorectal cancer; metastatic colorectal cancer; familial adenomatous polyposis (FAP); esophageal cancer; gastric cancer; gallbladder cancer; cholangiocarcinoma; hepatocellular carcinoma; and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas, neuroblastoma, astrocytoma; breast cancer including triple negative breast carcinoma; oral tumors; nasopharyngeal tumors; thoracic cancer; head and neck cancer; mesothelioma; leukemias including acute myeloid leukemia, adult T-cell leukemia; carcinomas; adenocarcinomas; thyroid carcinoma including papillary thyroid carcinoma; choriocarcinoma; sarcomas including Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; and virally induced tumors.

Cancers may notably be defined as including skin cancer in particular advanced melanoma and Merkel cell carcinoma; lung cancer including non-small cell lung cancer; bladder cancer; head and neck cancer; renal cell cancer; Hodgkin's lymphoma; cervical cancer; endometrial cancer; breast cancer; colon cancer; gastrointestinal stromal tumors; pancreatic cancer; prostatic cancer; leukemia including acute myeloid leukemia; lymphoma; gastric cancer; ovarian cancer; esophageal carcinomas; hepatocarcinoma; and brain tumors in particular glioblastoma, mesothelioma, neuroblastoma, sarcoma in particular high-grade osteosarcoma, astrocytoma, myeloma.

Cancers may especially be defined as including skin cancer, in particular advanced melanoma and Merkel cell carcinoma; lung cancer (especially non-small cell lung cancer (NSCLC)); bladder cancer; head and neck cancer; renal cell carcinoma; and Hodgkin's lymphoma.

One or more compounds of Formula (I) may be used in the prevention and/or treatment of any cancer, notably the cancers mentioned hereinabove, either alone, or in combination with further pharmacologically active compounds and/or therapies.

In addition to cancers, especially cancers as listed above, further diseases or disorders related to the IDO and/or TDO enzymes may be defined as including neurodegenerative disorders such as Parkinson's disease, Alzheimer's disease, Huntington's disease and Amyotrophic lateral sclerosis; Central nervous system (CNS) disorders such as Psychiatric disorders (schizophrenia, depression); pain; stroke; epilepsy; chronic infectious diseases such as HIV (AIDS including its manifestations such as cachexia, dementia and diarrhea) and HCV; infection and inflammation caused by various bacteria (such as *Chlamydia* strains and enteropathogenic strains), parasites (such as *Trypanosoma, Leishmania, plasmodium*) or viruses (such as influenza, human papilloma virus, cytomegalovirus, Epstein-Barr virus, poliovirus, varicella zoster virus and coxsackie virus); metabolic disorders such as obesity, type 2 diabetes and/or fatty acid liver disease; cataracts; endometriosis; contraception and abortion.

The terms "radiotherapy" or "radiation therapy" or "radiation oncology", refer to the medical use of ionizing radiation in the prevention (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or deliver toxic substances directly to cancer cells and kill them. An example of a targeted therapy which is in particular suitable to be combined with the compounds of the present invention is immunotherapy, especially immunotherapy targeting the programmed death 1 (PD-1) receptor or its ligand PD-L1 (Feig C et al, PNAS 2013).

When used in combination with the compounds of Formula (I), the term "targeted therapy" especially refers to agents such as: a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab); b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244)); c) Janus kinase (JAK) inhibitors (for example Ruxolitinib, Itacitinib, Momelotinib); d) Aromatase inhibitors (for example Exemestane, Letrozole, Anastrozole, Vorozole, Formestane, Fadrozole); e) Angiogenesis inhibitors, especially VEGF signalling inhibitors such as Bevacuzimab (Avastin), Ramucirumab, Sorafenib or Axitinib; f) Immune Checkpoint inhibitors (for example: anti-PD1 antibodies such as Pembrolizumab (Lambrolizumab, MK-3475), Nivolumab, Pidilizumab (CT-011), AMP-514/MED10680, PDR001, SHR-1210; REGN2810, BGBA317, PF-06801591, MGA-012, TSR042, JS-001, BCD100, IBI-308, BI-754091; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), avelumab (MSB0010718C), durvalumab (MED14736); anti-PDL2 antibodies, such as AMP224; anti-CTLA-4 antibodies, such as ipilimumab, tremelimumab; anti-Lymphocyte-activation gene 3 (LAG-3) antibodies, such as BMS-986016, IMP701, MK-4280, ImmuFact IMP321; anti T cell immunoglobulin mucin-3 (TIM-3) antibodies, such as MBG453, TSR-022; anti T cell immunoreceptor with Ig and ITIM domains (TIGIT) antibodies, such as RG6058 (anti-TIGIT, MTIG7192A); anti-Killer-cell immunoglobulin-like receptors (KIR) for example Lirilumab (IPH2102/BMS-986015); g) Vaccination approaches (for example dendritic cell vaccination, peptide or protein vaccination (for example with gp100 peptide or MAGE-A3 peptide); h) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX),or Toll like receptor enhanced GM-CSF tumor based vaccine (TEGVAX); i) T-cell based adoptive immunotherapies, including chimeric antigen receptor (CAR) engineered T-cells (for example CTL019); j) Cytokine or immunocytokine based therapy (for example Interferon alpha, interferon beta, interferon gamma, interleukin 2, interleukin 15); k) Toll-like receptor (TLR) agonists (for example resiquimod, imiquimod, motolimod, glucopyranosyl lipid A, CpG oligodesoxynucleotides); l) Thalidomide analogues (for example Lenalidomide, Pomalidomide); m) Activators of T-cell co-stimulatory receptors (for example anti-CD137/4-1BB antibodies, such as BMS-663513 (urelumab), Utomilumab (PF-05082566); anti-OX40/CD134 (Tumor necrosis factor receptor superfamily, member 4) (such as RG7888 (MOXR0916), 9B12; MED16469, GSK3174998, MED10562), anti OX40-Ligand/CD252; anti-glucocorticoid-induced TNFR family related gene (GITR) (such as TRX518, MED11873, MK-4166, BMS-986156), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab; anti-CD28 antibodies; anti-ICOS antibodies; n) Molecules binding a tumor specific antigen as well as a T-cell surface marker such as bispecific antibodies or antibody fragments, antibody mimetic proteins such as designed ankyrin repeat proteins (DARPINS), bispecific T-cell engager (BITE, for example AMG103, AMG330); o) Antibodies or small molecular weight inhibitors targeting colony-stimulating factor-1 receptor (CSF-1R) (for example Emactuzumab (RG7155), Cabiralizumab (FPA-008), PLX3397). p) Agents targeting immune cell check points on natural killer cells such as antibodies against Killer-cell immunoglobulin-like receptors (KIR) for example Lirilumab (IPH2102/BMS-986015); q) Agents targeting the Adenosine receptors or the ectonucleases CD39 and CD73 that convert ATP to Adenosine, such as MEDI9447 (anti-CD73 antibody), PBF-509; CPI-444 (Adenosine A2a receptor antagonist).

When used in combination with the compounds of Formula (I), immune checkpoint inhibitors such as those listed under f), and especially those targeting the programmed cell death receptor 1 (PD-1 receptor) or its ligand PD-L1, are preferred.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active anti-neoplastic agent inducing apoptosis or necrotic cell death. When used in combination with the compounds of formula (I), the term especially refers to conventional cytotoxic chemotherapy agents such as: 1) alkylating agents (for example mechlorethamine, chlorambucil, cyclophosphamide, ifosfamide, streptozocin, carmustine, lomustine, melphalan, busulfan, dacarbazine, temozolomide, thiotepa or altretamine; in particular temozolomide); 2) platinum drugs (for example cisplatin, carboplatin or oxaliplatin); 3) antimetabolite drugs (for example 5-fluorouracil, capecitabine, 6-mercaptopurine, methotrexate, gemcitabine, cytarabine, fludarabine or pemetrexed); 4) anti-tumor antibiotics (for example daunorubicin, doxorubicin, epirubicin, idarubicin, actinomycin-D, bleomycin, mitomycin-C or mitoxantrone); 5) mitotic inhibitors (for example paclitaxel, docetaxel, ixabepilone, vinblastine, vincristine, vinorelbine, vindesine or estramustine); or 6) topoisomerase inhibitors (for example etoposide, teniposide, topotecan, irinotecan, diflomotecan or elomotecan).

When used in combination with the compounds of Formula (I), preferred cytotoxic chemotherapy agents are the above-mentioned alkylating agents (notably fotemustine, cyclophosphamide, ifosfamide, carmustine, dacarbazine and prodrugs thereof such as especially temozolomide or pharmaceutically acceptable salts of these compounds; in particular temozolomide); mitotic inhibitors (notably paclitaxel, docetaxel, ixabepilone, or pharmaceutically acceptable salts of these compounds; in particular paclitaxel); platinum drugs (notably cisplatin, oxaliplatin and carboplatin); as well as etoposide and gemcitabine. 1) Chemotherapy may be given with a curative intent or it may aim to prolong life or to palliate symptoms. 2) Combined modality chemotherapy is the use of drugs with other cancer treatments, such as radiation therapy or surgery. 3) Induction chemotherapy is the first line treatment of cancer with a chemotherapeutic drug. This type of chemotherapy is used for curative intent. 4) Consolidation chemotherapy is given after remission in order to prolong the overall disease-free time and improve overall survival. The drug that is administered is the same as the drug that achieved remission. 5) Intensification chemotherapy is identical to consolidation chemotherapy but a different drug than the induction chemotherapy is used. 6) Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity. 7) Neoadjuvant chemotherapy is given prior to a local treatment such as surgery, and is designed to shrink the primary tumor. It is also given to cancers with a high risk of micrometastatic disease. 8) Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells. 9) Maintenance chemotherapy is a repeated low-dose treatment to prolong remission. 10) Salvage chemotherapy or palliative chemotherapy is given without curative intent, but simply to decrease tumor load and increase life expectancy. For these regimens, a better toxicity profile is generally expected.

Preparation of Compounds of Formula (I)

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimization procedures.

In the schemes below, the generic groups A, $R^1$, $R^2$ are as defined for the compounds of formula (I). In some instances, the generic groups A, $R^1$, $R^2$ may be incompatible with the assembly illustrated in the schemes, or will require the use of protecting groups (PG). The use of protecting groups is well known in the art (see for example "Protective Groups in Organic Synthesis", T.W. Greene, P.G.M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts in a manner known per se.

Compounds of the Formula (I) of the present invention can be prepared according to the general synthetic scheme (Scheme 1) as outlined below.

The synthesis starts by deprotonating ethyl N-(diphenylmethylene) glycinate (1) with a strong base such as lithium bis(trimethylsilyl) amide in a solvent like THF at low temperature as for example −78° C. This reactive intermediate is then added to a solution of a carbonyl chloride 2 in a solvent such as THF at low temperature as for example −78° C., to give, after standard aq. work up and chromatographic purification the amino-ester derivative 3. Other methods to prepare compound 3 can be used, such as opening of the corresponding oxazole (formed by standard methods) in acidic medium (Scheme 2). Compound 3 is then reacted with the Boc-protected glycine 4. In this step the acid functionality is activated at low temperature such as −20° C. in a solvent such as THF, in the presence of a base such as NMM by forming the mixed anhydride with i-butyl chloroformate. To the activated intermediate of 4, derivative 3 is added at low temperature (e.g. −20° C.). After termination of the reaction, a standard aq. work up and chromatographic purification results in the isolation of compound 5. Precursor 5 is transformed into the tri-substituted thiazole derivative 6 by reacting it with Lawesson's reagent in a polar aprotic solvent such as THF at reflux for several hours. The thiazole derivative 6 is obtained after standard aq. work up and chromatographic purification. The Boc-protecting group is cleaved off by dissolving 6 in an inert chlorinated solvent such as for example dichloromethane and trifluoroacetic acid is carefully added to the mixture. The reaction is usually fast and the unprotected amine is obtained by evaporating the solvents after about 1 hour of reaction time. Formylation to 7 can be achieved by dissolving the unprotected amine in a solvent such as for example dichloromethane and adjusting the pH with aq. carbonate base solutions to 8. To this mixture is added a mixture of formic acid and acetic anhydride (1/1 molar ratio; 3 equivalents as compared to 6) at elevated temperature such as for example 50° C. After 60 minutes compound 7 is obtained by a standard aq. work up and used in the next step without further purification. The dehydrating cyclization (condensation) of 7 to 8 is done by dissolving 7 in an inert chlorinated solvent such as dichloromethane and by addition of a dehydrating agent such as for example phosphorous(V) oxychloride followed by stirring the reaction mixture at elevated temperatures (e.g. reflux of dichloromethane) for several hours. The reaction mixture can then be quenched by carefully adding an aq. carbonate base solution and the product 8 is obtained by standard aq. work up followed by chromatographic purification. The Weinreb amide 9 is obtained from the ester 8 in a two-step procedure starting with the hydrolysis of the ethylester by dissolving 8 in a THF/water=2/1 mixture and adding an excess (for example 2-3 equivalents) of lithium hydroxide monohydrate. The reaction takes place over several hours at RT. The product is isolated by evaporating the mixture to dryness. The following amide coupling is performed by dissolving the obtained residue in a solvent mixture such as for example DMF/dichloromethane (ratio=1/1 volumes). A base such as for example DIPEA and a coupling reagent such as for example HATU and N,O-dimethylhydroxylamine hydrochloride are added to the acid. The reaction takes place over several hours (e.g. overnight) at RT. The product 9 can be isolated by a standard aq. work up followed by chromatographic purification. The Weinreb amide 9 is then reacted with commercially available Grignard reagents of the composition $R^2$-A-MgBr in a solvent such as THF at temperatures between 0° C. and RT for a few hours. The product 10 can be isolated by standard aq. work up and chromatographic purification. Reduction of the ketone 10 to the racemic alcohol 11 is achieved by dissolving 10 in a solvent such as ethanol and at RT adding a reducing agent such as $NaBH_4$ to the reaction solution. After 30 minutes to 1 hour the product can be isolated by standard aq. work up followed by preparative HPLC purification. The racemate 11 can be separated into the enantiomers 12 and 13 by preparative HPLC with chiral stationary phases or by preparative SFC with chiral stationary phases. The IDO1 inhibitory activity is usually better for one of the enantiomers and less good for the other enantiomer. The absolute chirality of the more active enantiomer can be identified by X-ray structure determinations of the inhibitor bound to the target protein. Further, said absolute chirality can be determined by other well known in the art methods such as Mosher ester analysis.

Scheme 1.

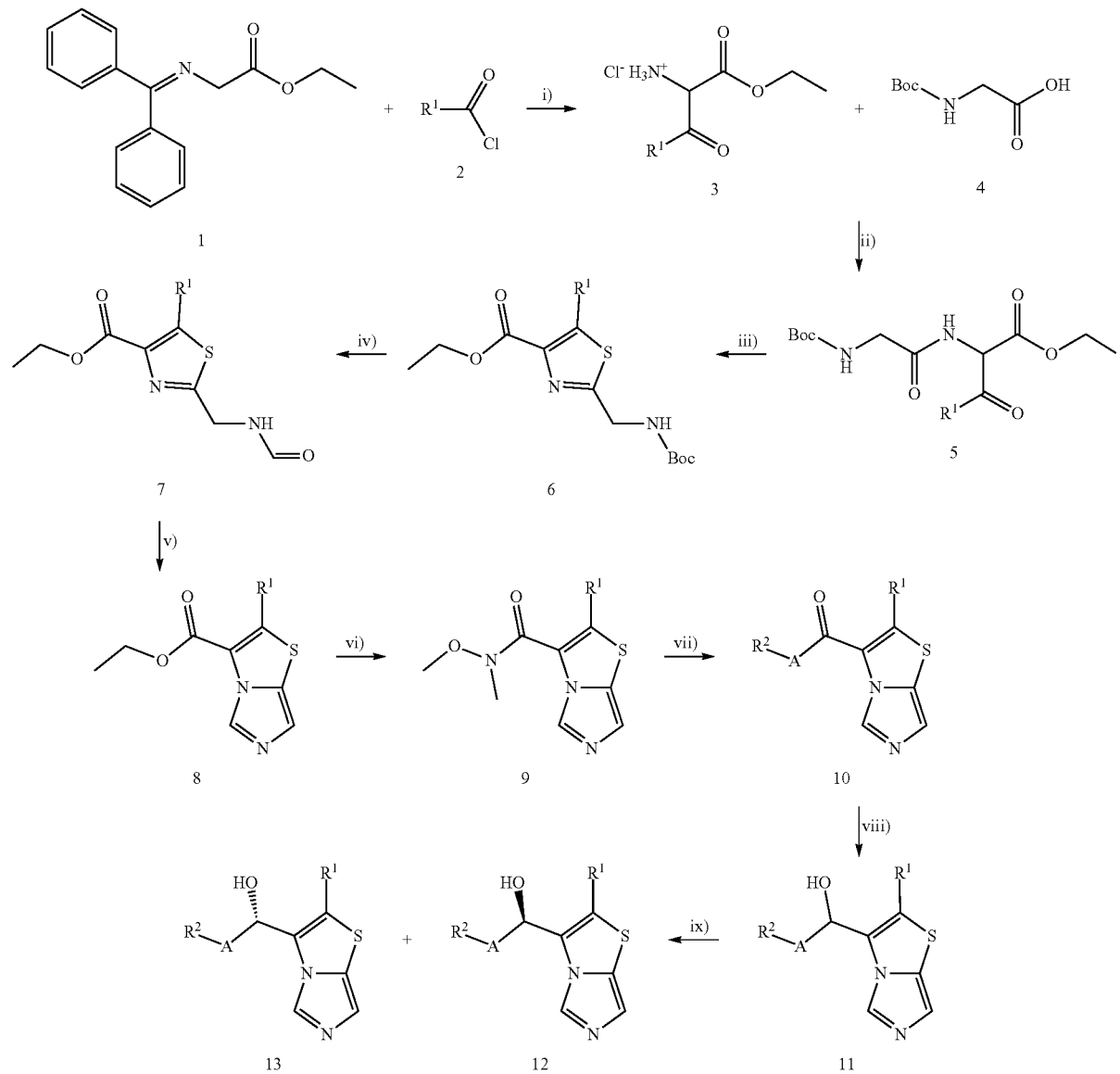

General approach for the preparation of compounds of Formula (I); i) LiHMDS, THF, −78° C.; ii) NMM, i-butyl chloroformate, −20° C., THF; iii) Lawesson's reagent, THF, rflx; iv) a) DCM, TFA, then b) DCM, pH=8 (aq NaHCO₃), formic acid/formic anhydride=1/1; v) DCM, POCl₃, 40° C.; vi) a) THF/water=2/1, LiOH then b) DMF/DCM=1/1, DIPEA, HATU, N,O-dimethylhydroxylamine x HCl; vii) THF, 0° C., R²-A-MgBr; viii) NaBH₄ in EtOH; ix) separation of the enantiomers on chiral stationary phases by HPLC.

Scheme 2

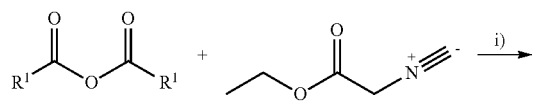

-continued

Alternative synthesis of compound 3: i) DBU, DMF, 80° C.; ii) HCl 6N, MeOH, 50° C.

Scheme 3 shows a variation of the synthesis of compounds of Formula (I). The Weinreb amide 9 is transformed into the aldehyde 14 in a solvent such as THF at 0° C. by the addition of a reducing agent such as diisobutylaluminium hydride in toluene (1M solution). The aldehyde is obtained after standard aq. work-up and used in Grignard reactions under conditions as described above (in solvents such as THF or ether at low temperatures such as 0° C. and by adding either commercially available or previously prepared Grignard reagents) to obtain racemic alcohols 11 which are then separated into the enantiomers 12 and 13 by HPLC procedures using chiral stationary phases.

THF at a temperature around RT gives the corresponding alcohol which can then be oxidized to the aldehyde using an oxidizing agent such as Dess-Martin periodinane in a solvent such as DCM at a temperature ranging from 0° C. to RT.

Scheme 3

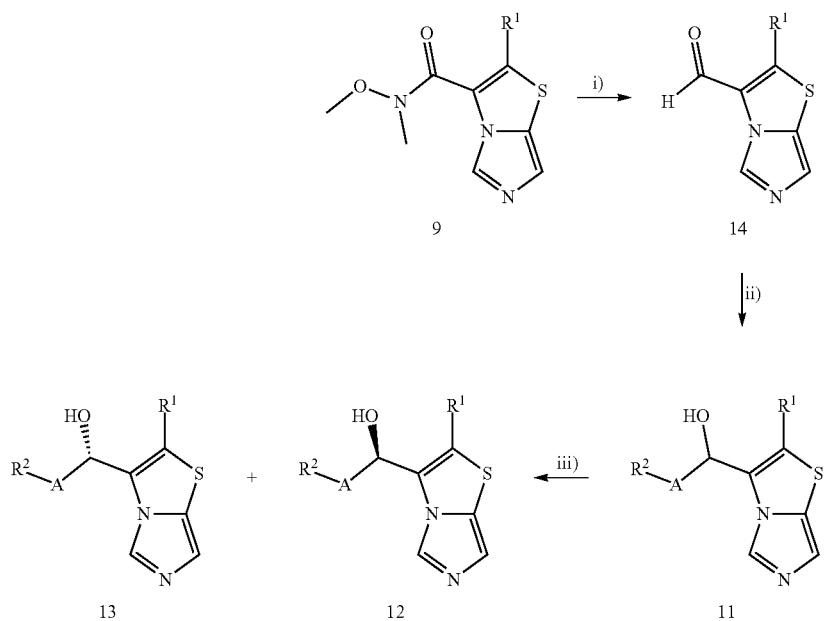

General approach for the preparation of compounds of General Formula (I); i) THF, 0° C., DIBALH in toluene; ii) THF, 0° C., $R^2$-A-MgBr or $R^2$-A-MgCl; iii) separation of the enantiomers on chiral stationary phases by HPLC.

Aldehyde 14 can be obtained via the alternative pathway depicted below (Scheme 4). Starting from methyl 5-bromo-2-methylthiazole-4-carboxylate 15, bromination using for example N-bromosuccinimide and a radical initiator such as AIBN in a solvent such as trifluorotoluene and at a temperature ranging from 85° C. to 100° C., gives dibromo compound 16. The benzylic bromide can be converted into the corresponding formamide for example by reacting it with sodium diformylamide in a solvent such as DMF and at a temperature around 20° C. Formamide 17 can then be cyclized using a dehydrating agent such as POCl₃ either neat or in a solvent such as toluene or CH₂Cl₂ at a temperature ranging from RT to 100° C. to give imidazothiazole 18. The ester function can then be transformed into the corresponding alcohol using a reducing agent such as NaBH₄ in a solvent such as EtOH at a temperature ranging from 0° C. to RT. Protection of the primary alcohol can be carried out using standard protecting group chemistry, for example with a silyl-based protecting group using tert-butyldimethylsilyl chloride in the presence of a base such as imidazole in a solvent such as DMF or DCM at a temperature such as RT. Metal-catalyzed coupling reactions allow the introduction of $R^1$ substituent using for example boronic acids or esters in the presence of a Pd-based catalyst such as Pd(PPh₃)₄ and of a base such as Na₂CO₃, in a solvent such as a mixture of dioxane and water at a temperature ranging from RT to 100° C.

Removing the silyl-based protecting group for example using a fluorine source such as TBAF in a solvent such as Scheme 4

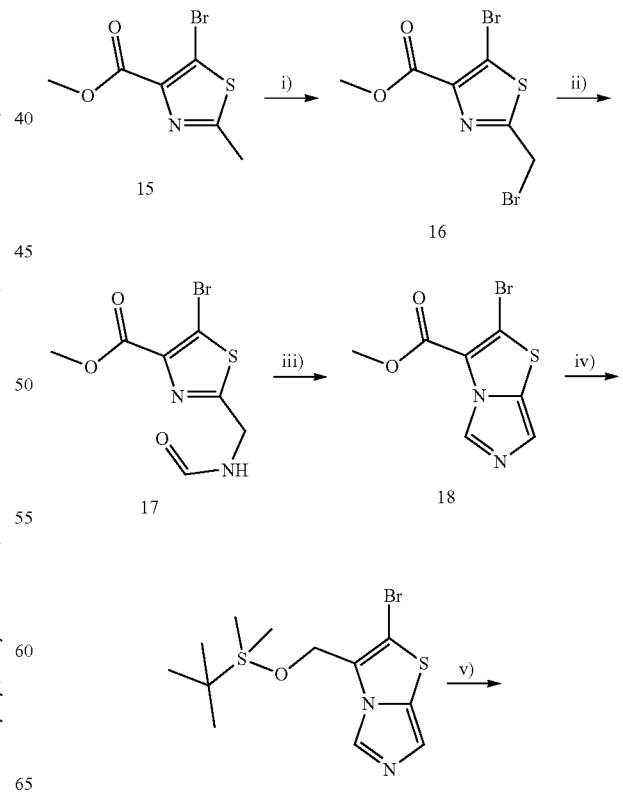

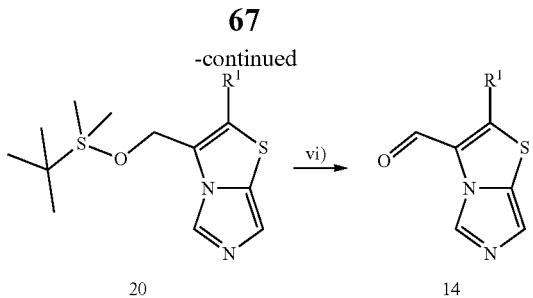

Introduction of R¹ substituents via metal-catalyzed coupling reactions; i) NBS, AIBN, trifluorotoluene, 85° C.; ii) sodium diformylamide, DMF; iii) POCl₃, RT-90° C.; iv) a) NaBH₄, EtOH, then b) t-BuMe₂SiCl, imidazole, DMF; v) R¹—B(OH)₂, Pd(PPh₃)₄, Na₂CO₃, dioxane; vi) a) TBAF, THF; b) Dess-Martin periodinane, DCM.

Alternatively, ester 18 can be converted into the corresponding Weinreb amide 21 via saponification of the ester followed by amide coupling using N,O-dimethylhydroxylamine hydrochloride and a coupling reagent such as HATU in the presence of a base such as for example DIPEA (Scheme 5). Metal-catalyzed coupling reactions allow the introduction of R¹ substituent using for example boronic acids or esters in the presence of a Pd-based catalyst such as Pd(PPh₃)₄ and of a base such as Na₂CO₃, in a solvent such as a mixture of dioxane and water at a temperature ranging from RT to 100° C. Weinreb amide 22 is then converted into aldehyde 14 via reduction using for example DIBAL-H as a reducing reagent in a solvent such as THF and at a temperature ranging from −78° C. to RT.

THF at a temperature around −78° C. and subsequent reaction of the lithiated species with an electrophile such as DMF at a temperature ranging from −78° C. to RT. Carbaldehyde 24 can then be converted into formamide 25 by standard functional group conversion methods. One way to convert the formyl functional group into the corresponding amine is to convert the aldehyde to the corresponding oxime followed by reduction of the oxime to the amine using for example zinc as a reducing agent under acidic conditions and formylation using similar conditions as described above. An alternative way is to convert the aldehyde to the formamide via the corresponding chloride. First, reduction of the aldehyde to the alcohol can be carried out using NaBH₄ as a reducing agent in a solvent such as EtOH at a temperature ranging from 0° C. to RT, then conversion of the resulting alcohol functional group into the corresponding chloride using for example thionyl chloride in a solvent such as DCM and at a temperature around 20° C., and finally substitution of the chloride by sodium diformylamide (followed by elimination of one of the 2 formyl groups). Cyclization of formylated amine 25 using a dehydrating agent such as POCl₃ either neat or in a solvent such as DCM at a temperature ranging from 0° C. to 90° C. Bromide 26 can then be reacted first with n-BuLi in a solvent such as THF at a temperature around −78° C. and then with an aldehyde R²-A-CHO (either commercially available or prepared from the corresponding carboxylic acid or ester via reduction) to give alcohol 11. The racemic compounds can then be separated using chiral preparative HPLC to give alcohols 12 and 13.

Scheme 5

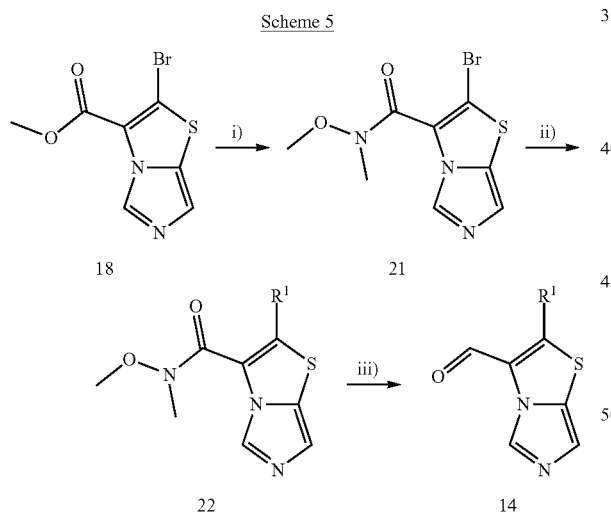

Introduction of R¹ substituents via metal-catalyzed coupling reactions; i) a) LiOH, THF/H2O; b) N,O-dimethylhydroxylamine hydrochloride, DIPEA, HATU, CH₂Cl₂/DMF; ii) R¹—B(OH)₂, Pd(PPh₃)₄, Na₂CO₃, dioxane; iii) DIBAL-H, THF.

Alternatively, compounds of formula (I) can be prepared by reacting bromide 26 with n-BuLi and subsequent addition of an aldehyde (Scheme 6). Bromide 26 can be prepared via 3 steps starting from dibromo thiazole 23 (either commercially available or prepared by bromination of the corresponding 2-bromo-thiazole). Lithium halogen exchange can be performed using for example n-BuLi in a solvent such as Scheme 6

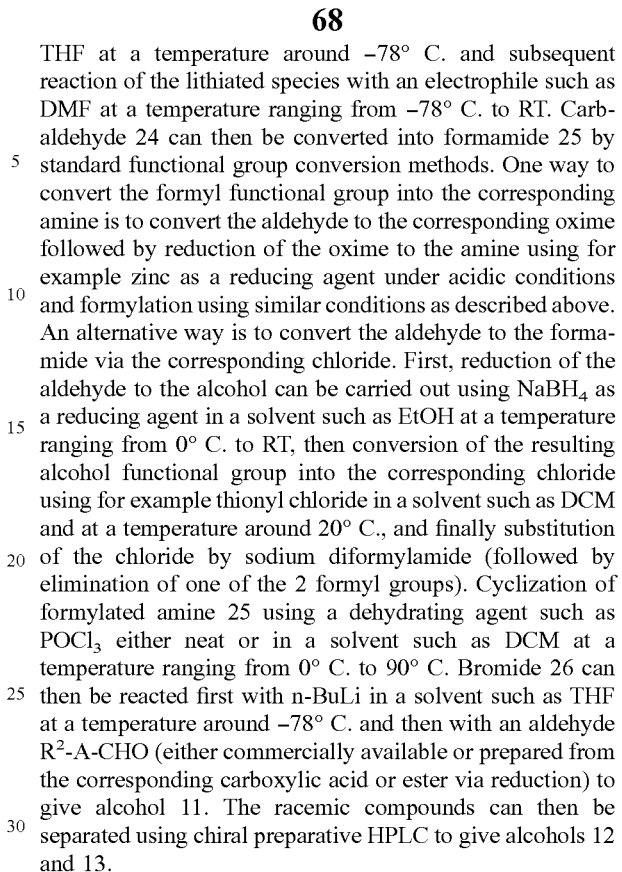

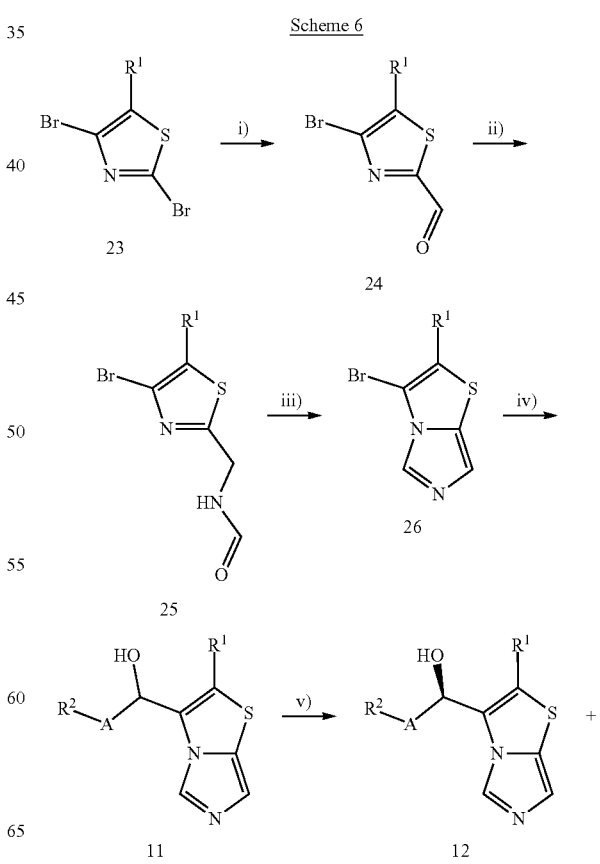

-continued

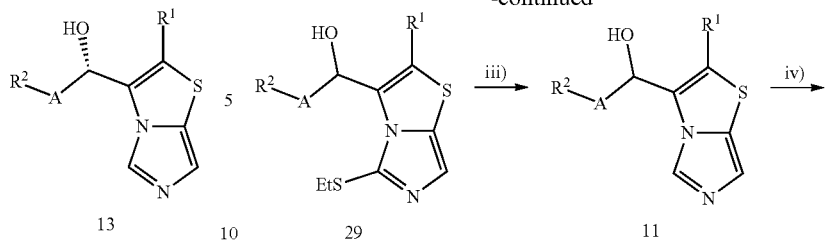

General approach for the preparation of compounds of Formula (I); i) a) n-BuLi, THF, −78° C.; then b) DMF; ii) a) NaBH₄, EtOH; b) SOCl₂, DCM; c) sodium diformylamide, DMF; iii) POCl₃, RT-90° C.; iv) a) n-BuLi, THF, −78° C.; then b) aldehyde R²-A-CHO; v) separation of the enantiomers on chiral stationary phases by HPLC.

Alternatively, a protecting/directing group strategy can be used to prepare compounds of formula (I) (Scheme 7). Primary amine 27 (either commercially available or synthesized using standard procedures) is cyclized using for example thiophosgene in the presence of a base such as K₂CO₃ and alkylated at the thiol group using for example ethyl iodide in the presence of a base such as K₂CO₃ to give imidazothiazole 28. Deprotonation using a base such as n-BuLi in a solvent such as THF at a temperature around −78° C., and subsequent addition of an aldehyde (either commercially available or prepared from the corresponding carboxylic acid or ester via reduction) give alcohol 29. Removal of the thioether function is performed using a catalyst such as Raney nickel in a solvent such as a mixture of ethanol and water, at a temperature ranging from RT to 90° C. to give compound 11. The racemic compounds can then be separated using chiral preparative HPLC to give alcohols 12 and 13.

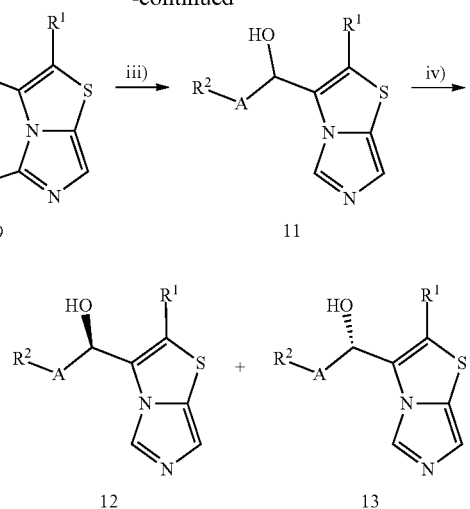

Directing group approach for the preparation of compounds of Formula (I); i) a) thiophosgene, K₂CO₃, DCM/H₂O, RT; then b) EtI, K₂CO₃, acetone; ii) a) n-BuLi, THF, −78° C.; then b) aldehyde R²-A-CHO; iii) Raney nickel, EtOH/H₂O, RT-90° C.; iv) separation of the enantiomers on chiral stationary phases by HPLC.

Alternatively, compounds of formula (I), where the group R²-A- is a 1,2,3-triazole-4-yl, substituted with R at position 1, R being e.g. hydrogen, $C_{1-4}$-alkyl or $C_{3-7}$-cycloalkyl (cf. Scheme 8), can be prepared via a click chemistry approach using propargylic alcohol 30. Racemic alcohol 30 can be prepared from aldehyde 14 by reaction with commercially available ethynylmagnesium bromide in a solvent such as THF or ether at low temperatures such as 0° C. Alcohol 30 can then be reacted with either commercially available or previously prepared azides in the presence of copper in order to obtain 1,2,3-triazole 31. Azides can be prepared using standard methods (from halides or boronic acids for example). The racemic compounds can then be separated using chiral preparative HPLC to give alcohols 32 and 33. Alternatively, propargylic alcohol 30 can be separated using chiral preparative HPLC to give alcohols 34 and 35, which can in turn be involved in a click chemistry reaction to give the corresponding enantiopure alcohol 32.

Scheme 7

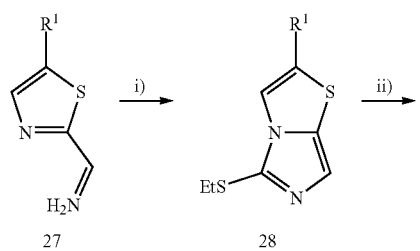

Scheme 8

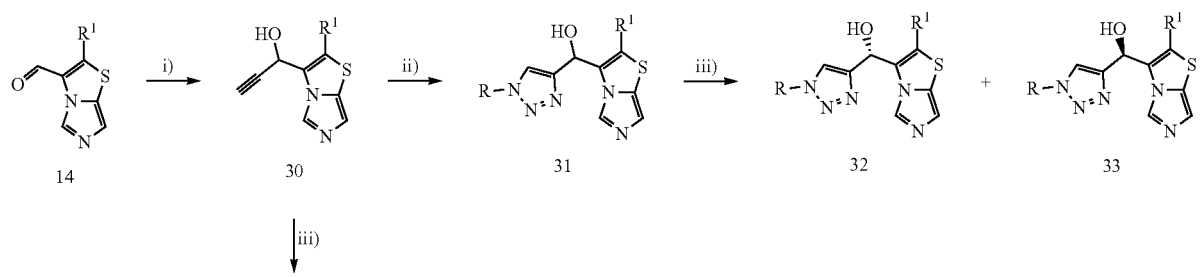

-continued

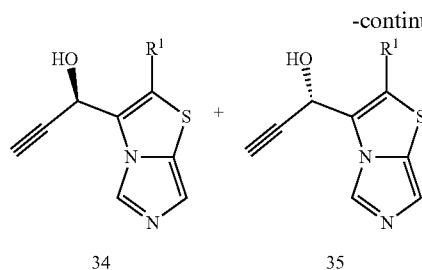 + 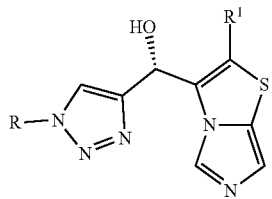 ii)→

34    35    32

Synthesis of triazoles; i) THF, 0° C., ethynyl-MgBr; ii) R—N$_3$ (or NaN$_3$, when R is hydrogen), CuSO$_4$, ascorbic acid sodium salt, DMF or DMF/H$_2$O; iii) separation of the enantiomers on chiral stationary phases by HPLC.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm), IA, IB, IC, IE, or IF (5 µm) or AD-H (5 µm) column. Typical conditions of chiral HPLC are an isocratic mixture of eluent A (EtOH, in presence or absence of an amine such as triethylamine or diethylamine) and eluent B (heptane), at a flow rate of 0.8 to 150 mL/min.

The following examples are provided to illustrate the invention. These examples are illustrative only and should not be construed as limiting the invention in any way.

Experimental Part

Chemistry

All temperatures are stated in ° C.

Preparative HPLC Conditions:

The conditions for preparative HPLC purifications were chosen among the possibilities given below depending on the properties of the compounds to be purified. More than one option per problem can lead to a successful result. Equipment: HPLC pumps: Gilson 333/334 or equivalent Autosampler: Gilson LH215 (with Gilson 845z injector) or equivalent Degasser: Dionex SRD-3200 or equivalent Make-up pump: Dionex ISO-3100A or equivalent DAD detector: Dionex DAD-3000 or equivalent MS detector: Single quadrupole mass analyzer Thermo Finnigan MSQ Plus or equivalent MRA splitter: MRA100-000 flow splitter or equivalent ELS detector: Polymer Laboratories PL-ELS1000 or equivalent. Method: Column: variable Waters Atlantis T3 30×75 mm 10 µm (acidic conditions only); Waters XBridge C18, 30×75 mm 10 µm (acidic/basic conditions); Waters XBridge C18, 50×150 mm 10 µm (acidic/basic conditions); Flow rate: variable 75 mL/min (for columns with dimension 30×75 mm), 150 ml/min (for columns with dimension 50×150 mm). Mobile phase: gradient mode A: Water+0.5% formic acid (acidic conditions) A: Water+0.5% ammonium hydroxide solution (25%) (basic conditions) B: Acetonitrile Gradient: variable, given only for 75 mL/min (too many for 150 mL/min); "extremely polar": t[min]% A % B Flow mL/min: 0.000 100 0 75; 1.000 100 0 75; 3.500 80 20 75; 4.000 5 95 75; 6.000 5 95 75; 6.200 100 0 75; 6.600 100 0 75. "very polar": t[min] % A % B Flow mL/min: 0.000 95 5 75; 0.100 95 5 75; 3.000 50 50 75; 4.000 5 95 75; 6.000 5 95 75; 6.200 95 5 75; 6.600 95 5 75; "polar": t[min] % A % B Flow mL/min: 0.000 90 10 75; 0.010 90 10 75; 4.000 5 95 75; 6.000 5 95 75; 6.200 90 10 75; 6.600 90 10 75; "normal": t[min] % A % B Flow mL/min: 0.000 80 20 75; 0.010 80 20 75; 4.000 5 95 75; 6.000 5 95 75; 6.200 80 20 75; 6.600 80 20 75; "lipophilic": t[min] % A % B Flow mL/min: 0.000 70 30 75; 0.010 70 30 75; 3.500 5 95 75; 6.000 5 95 75; 6.200 70 30 75; 6.600 70 30 75; "very lipophilic": t[min] % A % B Flow mL/min: 0.000 50 50 75; 0.010 50 50 75; 3.000 5 95 75; 6.000 5 95 75; 6.200 50 50 75; 6.600 50 50 75. Injection volume: 100-2500 µL. Collection: UV/MS/ELSD if available, and all possible combinations; Make-up flow rate: 0.50 mL/min. Make-up eluent MS: acetonitrile/water I/TFA 70:30:0.025 (V/V/V); MS ionization mode: ESI+.

LC-MS-Conditions:

Basic conditions: Column: Waters BEH C18, 3.0×50 mm, 2.5 µm/01593635616710; Temperature: 40° C.; Injection volume: 30 µl; Eluent A: water/NH3 with c(NH3)=13 mmol/l; Eluent B: Acetonitrile; Ionisation: ESI+; Gradient: at 0.0 min=5% B, at 0.01 min=5% B, at 1.20 min=95% B, at 2.00 min=5% B; Flow=1.6 ml/min.

Acidic conditions: Column: Zorbax RRHD SB-Aq, 3.0× 50 mm, 1.8 µm/USEAJ01092; Temperature: 40° C.; Injection volume: 30 µl; Eluent A: water 0.04% TFA; Eluent B: Acetonitrile; Ionisation: ESI+; Gradient: at 0.0 min=5% B, at 0.01 min=5% B, at 1.20 min=95% B, at 2.00 min=5% B; Flow=1.6 ml/min.

QC conditions: Column: Acquity UPLC CSH C18 1.7 µm 2.1×50 mm; Temperature: 60° C.; Injection volume: 0.25 µl, partial loop 2 µl; Eluent A1: H2O+0.05% v/v Fomic Acid; Eluent B1: Acetonitril+0.045% v/v Fomic Acid; Ionisation: ESI+; Gradient: at 0.0 min=2% B1, at 1.4 min=5% A1, at 1.90 min=2% A1, at 2.00 min=2% B1; Flow=1.0 ml/min.

Abbreviations (as Used Hereinbefore or Hereinafter)

aq. aqueous
AIBN azobisisobutyronitrile
BRP back pressure regulator
Boc tert-butyloxycarbonyl
DCM dichloromethane
DEA diethylamine
DIBALH diisobutylaluminium hydride
DIPEA diisopropyl ethyl amine (Huinig's base)
DMF dimethyl formamide
Et ethyl
EtOAc ethyl acetate
EtOH ethanol
FC flash chromatography
HATU (1-[Bis(dimethylamino)methylene]-1H-1,2,3-triazolo[4,5-b]pyridinium 3-oxid hexafluorophosphate)
HV high vacuum
LAH lithium aluminium hydride
LiHMDS lithium bis(trimethylsilyl)amide
MeOH methanol
NBS N-bromo succinimide NMM N-methyl-morpholine
org. organic
prepHPLC preparative HPLC
RT room temperature
rflx reflux
sat. saturated
SFC supercritical fluid chromatography
TBAF tetrabutylammonium fluoride
TFA trifluoroacetic acid
THF tetrahydrofuran
$t_R$ HPLC retention time in minutes

EXAMPLES SYNTHESIS

Example 1: rac-Cyclohexyl(2-cyclopropylimidazo[5,1-b]thiazol-3-yl)methanol

Step 1: Preparation of ethyl 2-amino-3-cyclopropyl-3-oxopropanoate hydrochloride In a first reaction vessel, ethyl N-(diphenylmethylene)glycinate (1069 mg; 4 mmol) is dissolved in THF (4 ml) and cooled to −78° C. followed by the dropwise addition of a 1M THF solution of lithium bis(trimethylsilyl) amide (4 ml; 4 mmol). Stirring is continued at −78° C. for 1 h. In a second reaction vessel, cyclopropanecarbonyl chloride (0.389 ml; 4.2 mmol) is dissolved in THF (4 ml) and cooled to −78° C. Then the reaction mixture obtained in the first vessel is slowly added to the content of the second vessel. The resulting reaction mixture is warmed to RT over 3 h followed by quenching the reaction by careful addition of 2M aq. HCl (4 ml). The THF is evaporated under reduced pressure and the remaining aq. phase is extracted twice with EtOAc. The aq. phase is concentrated under reduced pressure. The residue is treated with EtOH and filtered and the filtrate is again concentrated under reduced pressure and dried at HV overnight. 890 mg of ethyl 2-amino-3-cyclopropyl-3-oxopropanoate hydrochloride is obtained as a pale yellow solid. LC-MS (acidic): $t_R$=0.57; [M+H]$^+$=172.01.

Step 2: Preparation of ethyl 2-(2-((tert-butoxycarbonyl)amino)acetamido)-3-cyclopropyl-3-oxopropanoate In a first vessel, Boc-Gly-OH (779 mg; 4.4 mmol) is dissolved in THF (4 ml) and cooled to −20° C. followed by the addition of NMM (0.494 ml; 4.4 mmol) and isobutyl chloroformate (0.582 ml; 4.4 mmol) and stirring is continued for 30 minutes at −20° C. In a second vessel, the product from step 1, ethyl 2-amino-3-cyclopropyl-3-oxopropanoate hydrochloride (831 mg; 4 mmol) is dissolved in THF (2 ml). This solution is carefully added to the previously prepared solution of the mixed anhydride in vessel one followed by the dropwise addition of NMM (0.494 ml; 4.4 mmol). The reaction mixture is warmed to RT and stirring is continued for 60 minutes. The reaction is quenched by the addition of water. The product is extracted with EtOAc (2×25 ml). The combined organic layers are dried over MgSO$_4$, filtered and the solvents are evaporated under reduced pressure. The residue is purified by FC (Silicagel; DCM/MeOH=95/5) to give 531.2 mg of ethyl 2-(2-((tert-butoxycarbonyl)amino)acetamido)-3-cyclopropyl-3-oxopropanoate as a slightly yellow, thick oil. LC-MS (basic): $t_R$=0.84; [M+H]$^+$=329.17.

Step 3: Preparation of ethyl 2-(((tert-butoxycarbonyl)amino)methyl)-5-cyclopropylthiazole-4-carboxylate (see also *J. Med. Chem.*, 1996, 39, 957-967 for general procedure)

The product from step 2, ethyl 2-(2-((tert-butoxycarbonyl)amino)acetamido)-3-cyclopropyl-3-oxopropanoate (531 mg; 1.62 mmol) and Lawesson's reagent (1011 mg; 2.43 mmol) are suspended in THF (10 ml) and heated to reflux for 4 hours. The THF is evaporated under reduced pressure and the residue is taken up into EtOAc, washed with saturated aq. NaHCO$_3$ solution and brine, dried over Na$_2$SO$_4$, filtered and the solvent is evaporated under reduced pressure. The residue is purified by FC (Silicagel; EtOAc/heptane=1/1) to give 403 mg of ethyl 2-(((tert-butoxycarbonyl)amino)methyl)-5-cyclopropylthiazole-4-carboxylate. LC-MS (basic): $t_R$=1.01; [M+H]$^+$=327.12.

Step 4: Preparation of ethyl 5-cyclopropyl-2-(formamidomethyl)thiazole-4-carboxylate Step 4.1: Boc-cleavage: The product from step 3, ethyl 2-(((tert-butoxycarbonyl)amino)methyl)-5-cyclopropylthiazole-4-carboxylate (403 mg; 1.23 mmol) is dissolved in DCM (3 ml) followed by careful addition of TFA (3 ml) and stirring is continued for 30 minutes. Then the reaction mixture is evaporated to dryness under reduced pressure.

Step 4.2: The residue from step 4.1 is dissolved in DCM (7 ml) and saturated aq. NaHCO$_3$ solution is added until the pH is 8. Under vigorous stirring at 50° C., a mixture of formic acid (0.319 ml; 8.2 mmol) and acetic anhydride (0.319 ml; 3.34 mmol) is added and stirring is continued for 1 hour. The organic layer was separated and the aq. layer was extracted twice with DCM (2×7 ml). The combined organic layers are dried over MgSO$_4$, filtered and the solvent is evaporated under reduced pressure to give 390 mg of ethyl 5-cyclopropyl-2-(formamidomethyl)thiazole-4-carboxylate which was used without further purification in Step 5. LC-MS (basic): $t_R$=0.69; [M+H]$^+$=255.13.

Step 5: Preparation of ethyl 2-cyclopropylimidazo[5,1-b]thiazole-3-carboxylate

The product from step 4.2, ethyl 5-cyclopropyl-2-(formamidomethyl)thiazole-4-carboxylate (313 mg; 1.23 mmol) is dissolved in DCM (5 ml) and cooled to −20° C. followed by the addition of phosphorus oxychloride (0.232 ml; 2.46 mmol). The reaction mixture is slowly heated to 65° C. and kept at this temperature for 5 hours. Then the mixture is evaporated to dryness under reduced pressure, the residue is taken up in DCM followed by careful addition of saturated aq. NaHCO$_3$ solution (pH=8). The organic layer is separated, the aq. layer is washed with DCM (2×10 ml). The combined organic layers are dried over MgSO$_4$, filtered and the solvent is evaporated under reduced pressure. The residue is purified by FC (Silicagel; EtOAc/MeOH=9/1) to give 216 mg of ethyl 2-cyclopropylimidazo[5,1-b]thiazole-3-carboxylate. LC-MS (basic): $t_R$=0.91; [M+H]$^+$=237.11.

Step 6: Preparation of 2-cyclopropyl-N-methoxy-N-methylimidazo[5,1-b]thiazole-3-carboxamide Step 6.1: Ester hydrolysis: The product form step 5, ethyl 2-cyclopropylimidazo[5,1-b]thiazole-3-carboxylate (216 mg; 0.914 mmol) is dissolved in THF (2 ml) and water (1 ml) followed by the addition of LiOH monohydrate (46 mg; 1.1. mmol) and stirring at RT is continued for 1 hour. A second portion of lithium hydroxide monohydrate (46 mg; 1.1 mmol) is added and the reaction mixture is stirred for another hour. The mixture is evaporated to dryness under reduced pressure.

Step 6.2: The residue from step 6.1 is dissolved in a 1/1 mixture of DMF/DCM (6 ml in total) followed by the subsequent addition of DIPEA (0.469 ml; 2.74 mmol), HATU (417 mg; 1.1 mmol) and N,O-dimethylhydroxylamine hydrochloride (109 mg; 1.1 mmol). Stirring is continued at RT overnight. The reaction mixture is concentrated under reduced pressure and the residue is purified by FC (Silicagel; EtOAc/MeOH=9/1) to give 294 mg of 2-cyclopropyl-N-methoxy-N-methylimidazo[5,1-b]thiazole-3-carboxamide. LC-MS (basic): $t_R$=0.71; [M+H]$^+$=252.14.

Step 7: Preparation of cyclohexyl(2-cyclopropylimidazo[5,1-b]thiazol-3-yl)methanone The product from Step 6.2, 2-cyclopropyl-N-methoxy-N-methylimidazo[5,1-b]thiazole-3-carboxamide (59 mg; 0.235 mmol) is dissolved in THF (1 ml) and cooled to 0° C. followed by the addition of a solution of cyclohexylmagnesium chloride (1 M in THF; 0.704 ml; 0.704 mmol). The reaction mixture is warmed to RT and stirring is continued for 60 minutes. The reaction is quenched by careful addition of aq. ammonium chloride solution. The product is extracted with EtOAc (3×5 ml) and the combined organic layers are dried over Na$_2$SO$_4$, filtered and concentrated under reduced pressure. The residue is purified by preparative HPLC (basic conditions) to give 19 mg of cyclohexyl(2-cyclopropylimidazo[5,1-b]thiazol-3-yl)methanone. LC-MS (basic): $t_R$=1.08; [M+H]$^+$=275.22.

Step 8: Preparation of cyclohexyl(2-cyclopropylimidazo[5,1-b]thiazol-3-yl)methanol (Example 1)

The product of step 7, cyclohexyl(2-cyclopropylimidazo[5,1-b]thiazol-3-yl)methanone (19 mg; 0.0692 mmol) is dissolved in EtOH (2 ml) followed by the addition of NaBH4 (1.31 mg; 0.0346 mmol) and stirring is continued for 30 minutes. The reaction mixture is evaporated to dryness under reduced pressure. The residue is dissolved in DCM (2 ml) and washed with saturated aq. NaHCO$_3$ solution (1 ml). The aq. layer is back extracted with DCM (1 ml). The combined organic layers are dried over Na$_2$SO$_4$, filtered and concentrated under reduced pressure.

Example 1a: (S)-Cyclohexyl(2-cyclopropylimidazo[5,1-b]thiazol-3-yl)methanol

The enantiomers are separated by HPLC with chiral stationary phases to give 9.3 mg of enantiomer (S)-cyclohexyl(2-cyclopropylimidazo[5,1-b]thiazol-3-yl)methanol (Example 1a). LC-MS (basic): $t_R$=1.01; [M+H]$^+$=277.22.

Example 2: rac-2-Cyclohexyl-1-(2-cyclopropylimidazo[5,1-b]thiazol-3-yl)ethan-1-ol Step 1: Preparation of 2-cyclohexyl-1-(2-cyclopropylimidazo[5,1-b]thiazol-3-yl)ethan-1-one The product from Step 6.2 (Preparation of Example 1), 2-cyclopropyl-N-methoxy-N-methylimidazo[5,1-b]thiazole-3-carboxamide (59 mg; 0.235 mmol) is dissolved in THF (1 ml) and cooled to 0° C. followed by the addition of a 0.5 M solution of cyclohexylmethylmagnesium bromide (0.78 ml; 0.704 mmol). The reaction mixture is warmed to RT and stirring is continued for 60 minutes. The reaction is quenched by careful addition of aq. ammonium chloride solution. The product is extracted with EtOAc (3×5 ml) and the combined organic layers are dried over Na$_2$SO$_4$, filtered and concentrated under reduced pressure. The residue is purified by preparative HPLC (basic conditions) to give 24.4 mg of 2-cyclohexyl-1-(2-cyclopropylimidazo[5,1-b]thiazol-3-yl)ethan-1-one. LC-MS (basic): $t_R$=1.16; [M+H]$^+$=289.20.

Step 2: Preparation of rac-2-cyclohexyl-1-(2-cyclopropylimidazo[5,1-b]thiazol-3-yl)ethan-1-ol The product form step 1 (Preparation of Example 2), 2-cyclohexyl-1-(2-cyclopropylimidazo[5,1-b]thiazol-3-yl)ethan-1-one (24.4 mg; 0.0846 mmol) is dissolved in EtOH (2 ml) followed by the addition of NaBH4 (1.31 mg; 0.0346 mmol). Stirring is continued at RT for 30 minutes. The reaction mixture is evaporated to dryness under reduced pressure. The residue is dissolved in DCM (2 ml) and washed with saturated aq. NaHCO$_3$ solution (1 ml). The aq. layer is back extracted with DCM (1 ml). The combined organic layers are dried over Na$_2$SO$_4$, filtered and concentrated under reduced pressure.

Example 2a: (S)-2-Cyclohexyl-1-(2-cyclopropylimidazo[5,1-b]thiazol-3-yl)ethan-1-ol The enantiomers are separated by HPLC with chiral stationary phases to give 9.6 mg of (S)-2-cyclohexyl-1-(2-cyclopropylimidazo[5,1-b]thiazol-3-yl)ethan-1-ol (Example 2a). LC-MS (basic): $t_R$=1.09; [M+H]$^+$=291.23.

Example 3: rac-Cyclohexyl-(2-isopropyl-imidazo[5,1-b]thiazol-3-yl)-methanol

Step 1: Preparation of ethyl 2-amino-4-methyl-3-oxopentanoate hydrochloride

Ethyl N-(diphenylmethylene)glycinate (5000 mg; 18.3 mmol) is dissolved in THF (18 ml) and cooled to −78° C. followed by the addition of 1.0M lithium bis(trimethylsilyl) amide solution in THF (18.3 ml; 18.3 mmol). Stirring at −78° C. is continued for 60 min. The obtained mixture is added in a dropwise manner to a solution of isobutyryl chloride (2.07 ml; 19.2 mmol) in THF (9 ml) at −78° C. The resulting reaction mixture is slowly warmed to RT and stirring is continued overnight. The reaction is quenched by the addition of 2M aq HCl solution (18 ml). The THF is evaporated under reduced pressure and the remaining aq. phase is extracted with EtOAc (2×18 ml). the aq. phase is then evaporated to dryness under reduced pressure. The residue is treated with EtOH and filtered. The filtrate is concentrated under reduced pressure and the residue dried at HV overnight to give 5.9 g of ethyl 2-amino-4-methyl-3-oxopentanoate hydrochloride which was used in the next step without further purification. LC-MS (basic): $t_R$=0.65; [M+H]$^+$=174.22.

Step 2: Preparation of ethyl 2-(2-((tert-butoxycarbonyl)amino)acetamido)-4-methyl-3-oxopentanoate Boc-Gly-OH (2.59 g; 14.6 mmol) is dissolved in THF (20 ml) and cooled to −20° C. followed by the addition of 4-methylmorpholine (1.64 ml; 14.6 mmol) and isobutyl chloroformate (1.94 ml; 14.6 mmol). The reaction mixture is stirred for 30 minutes at −20° C. followed by slow addition of a solution of ethyl 2-amino-4-methyl-3-oxopentanoate hydrochloride (5.9 g obtained in step 1, example 3; theoretical 18.3 mmol) in THF (20 ml). Then a second portion of 4-methylmorpholine (1.64 ml; 14.6 mmol) is slowly added to the reaction mixture and the reaction mixture is warmed to RT and stirring is continued for 60 minutes followed by the addition of water (50 ml) and EtOAc (70 ml). The organic phase is separated and washed twice with saturated aq. NaHCO$_3$ solution and dried over MgSO$_4$, filtered and concentrated under reduced pressure. The residue is purified by FC (Silicagel; DCM) to give 4.496 g of ethyl 2-(2-((tert-butoxycarbonyl)amino)acetamido)-4-methyl-3-oxopentanoate. LC-MS (basic): t$_R$=0.91; [M+H]$^+$= 331.24.

Step 3: Preparation of ethyl 2-(((tert-butoxycarbonyl)amino)methyl)-5-isopropylthiazole-4-carboxylate Ethyl 2-(2-((tert-butoxycarbonyl)amino)acetamido)-4-methyl-3-oxopentanoate (4.496 g; 13.6 mmol) is dissolved in THF (50 ml) followed by the addition of Lawesson's reagent (8.15 g; 20.4 mmol). The mixture is heated to reflux for 2 hours. The THF is then removed under reduced pressure and the obtained residue is dissolved in EtOAc (100 ml) and washed twice with saturated aq. NaHCO$_3$ solution and with brine, dried over MgSO$_4$, filtered and the solvent is evaporated under reduced pressure. The residue is purified by FC (Silicagel; heptane to heptane/EtOAc=1/1) to give 3.416 g of ethyl 2-(((tert-butoxycarbonyl)amino)methyl)-5-isopropylthiazole-4-carboxylate. LC-MS (basic): t$_R$=1.07; [M+H]$^+$=329.20.

Step 4: Ethyl 2-(formamidomethyl)-5-isopropylthiazole-4-carboxylate

Step 4.1; Boc-cleavage: Ethyl 2-(((tert-butoxycarbonyl)amino)methyl)-5-isopropylthiazole-4-carboxylate (3.416 g; 10.4 mmol) is dissolved in trifluoroacetic acid (10 ml; 129 mmol) and stirring is continued for 1 hour followed by evaporation of the liquids under reduced pressure.

Step 4.2: The residue from step 4.1 is dissolved in saturated aq. NaHCO$_3$ solution and the pH is adjusted to 8 by the careful addition of solid NaHCO$_3$ powder. Dichloromethane (15 ml) is added and the mixture is vigorously stirred followed by the addition (under vigorous stirring) of a mixture of acetic anhydride (2.75 ml; 28.8 mmol) and formic acid (2.75 ml; 71.4 mmol). The reaction mixture is put in an oil bath of 60° C. for 30 minutes. Then the organic phase is separated from the aq. phase. The aqueous phase is extracted twice with DCM and the combined organic layers are dried over MgSO$_4$, filtered and the solvent is evaporated under reduced pressure to obtain 3.111 g of ethyl 2-(formamidomethyl)-5-isopropylthiazole-4-carboxylate, which is used in the next step without further purification. LC-MS (basic): t$_R$=0.75; [M+H]$^+$=257.18.

Step 5: Ethyl 2-isopropylimidazo[5,1-b]thiazole-3-carboxylate

Ethyl 2-(formamidomethyl)-5-isopropylthiazole-4-carboxylate (2.67 g; 10.4 mmol) is dissolved in dichloromethane (15 ml) and phosphorous(V) oxychloride (1.96 ml; 20.8 mmol) is added and the reaction mixture is stirred at 70° C. for 2 h. The solvents are evaporated and the residue is carefully taken up into water.

The pH of the aqueous phase is adjusted to 8 by the addition of solid NaHCO$_3$ powder. The resulting mixture is extracted twice with dichloromethane. The combined organic layers are dried over MgSO$_4$, filtered and concentrated in vacuo. The residue is purified by FC (Silicagel; heptane to heptane/EtOAc=1/1) to give 1.848 g of ethyl 2-isopropylimidazo[5,1-b]thiazole-3-carboxylate. LC-MS (basic): t$_R$=0.97; [M+H]$^+$=239.17.

Step 6: 2-Isopropyl-N-methoxy-N-methylimidazo[5,1-b]thiazole-3-carboxamide

Step 6.1: Hydrolysis: Ethyl 2-isopropylimidazo[5,1-b]thiazole-3-carboxylate (1.848 g; 7.75 mmol) is dissolved in a mixture of THF (15 ml) and water (7.5 ml) followed by the addition of lithium hydroxide monohydrate (394 mg; 9.31 mmol) and stirring is continued for 60 minutes. The reaction mixture is evaporated to dryness under reduced pressure.

Step 6.2; Amide coupling: The residue obtained in Step 6.1 above is suspended in a mixture of dichloromethane (20 ml) and DMF (20 ml), followed by the addition of DIPEA (3.98 ml; 23.3 mmol) and HATU (3538 mg; 9.31 mmol) and N,O-dimethylhydroxylamine hydrochloride (98%; 926 mg; 9.31 mmol) and stirring is continued at RT overnight. The reaction mixture is evaporated to dryness under reduced pressure followed by the addition of water. The product is extracted 3 times with dichloromethane, the combined organic layers are dried over MgSO$_4$, filtered and the solvent is evaporated under reduced pressure. The residue is purified by FC (Silicagel; dicholormethane to dichloromethane/MeOH=95/5) to give 1.808 g of 2-isopropyl-N-methoxy-N-methylimidazo[5,1-b]thiazole-3-carboxamide. LC-MS (basic): t$_R$=0.78; [M+H]$^+$=254.18.

Step 7: 2-Isopropylimidazo[5,1-b]thiazole-3-carbaldehyde

2-Isopropyl-N-methoxy-N-methylimidazo[5,1-b]thiazole-3-carboxamide (1.808 g; 7.14 mmol) is dissolved in THF (15 ml) and cooled to 0° C. followed by the addition of 1.0M solution of diisobutylaluminium hydride in toluene (7.14 ml; 7.14 mmol). After 30 minutes a second portion of diisobutylaluminium hydride in toluene (7.14 ml; 7.14 mmol) is added and after further 30 minutes a third portion of diisobutylaluminium hydride (7.14 ml; 7.14 mmol) is added and stirring is continued for 30 minutes followed by the addition of saturated aq. ammonium chloride solution. The product is extracted from the mixture with EtOAc (3×). The combined organic layers are dried over MgSO$_4$, filtered and the solvent is evaporated under reduced pressure to give 2.0 g of 2-isopropylimidazo[5,1-b]thiazole-3-carbaldehyde as a yellow solid which is used in the next step without further purification. LC-MS (basic): t$_R$=0.75; [M+H]$^+$= 195.20.

Step 8: rac-Cyclohexyl(2-isopropylimidazo[5,1-b]thiazol-3-yl)methanol

2-Isopropylimidazo[5,1-b]thiazole-3-carbaldehyde (97.1 mg; 0.5 mmol) is dissolved in THF (3.5 ml), cooled to 0° C. and a solution of cyclohexylmagnesium bromide in THF (18%; approx. 1M; 1.5 ml; 1.5 mmol) is slowly added and stirring is continued at 0° C. for 30 minutes. The reaction is quenched by the addition of saturated aq. ammonium chloride solution and the product is extracted from the mixture with EtOAc (3×). The combined organic layers are dried over MgSO$_4$, filtered and the solvent is evaporated under reduced pressure. The residue is purified by reversed phase preparative HPLC to give 13.3 mg of rac-cyclohexyl(2-isopropylimidazo[5,1-b]thiazol-3-yl)methanol. LC-MS (basic): t$_R$=1.07; [M+H]$^+$=279.21.

Example 3a: (S)-Cyclohexyl-(2-isopropyl-imidazo[5,1-b]thiazol-3-yl)-methanol Separation of the enantiomers on chiral stationary phase:
Method: Column: ChiralPak AS-H 30×250 mm, 5 μM; Detector Settings: UV-Vis-1; 271 nM; Eluent: 70% CO$_2$ and 30% (EtOH, 0.1% DEA); Flow: 160.00 ml/min; BPR: 100 bar; Temperature: 40° C. Injection volume: 1000 μl.
13.3 mg of the racemate were separated by the method described above to give:
6.4 mg of the S-enantiomer Example 3a and 6.2 mg of the R-enantiomer.

Example 4: rac-2-Cyclohexyl-1-(2-isopropyl-imidazo[5,1-b]thiazol-3-yl)-ethanol

Step 1: Preparation of rac-2-cyclohexyl-1-(2-isopropyl-imidazo[5,1-b]thiazol-3-yl)-ethanol According to the descriptions given for the preparation of Example 3 the precursor used to prepare Example 4, 2-Isopropylimidazo[5,1-b]thiazole-3-carbaldehyde, is prepared.
2-Isopropylimidazo[5,1-b]thiazole-3-carbaldehyde (97.1 mg; 0.5 mmol) is dissolved in THF (2.0 ml), cooled to 0° C. and a solution of cyclohexylmethylmagnesium bromide in THF (0.4-0.6M; 3.0 ml; approx. 1.5 mmol) is slowly added and stirring is continued at 0° C. for 30 minutes. The reaction is quenched by the addition of saturated aq. ammonium chloride solution and the product is extracted from the mixture with EtOAc (3×). The combined organic layers are dried over MgSO$_4$, filtered and the solvent is evaporated under reduced pressure. The residue is purified by reversed phase preparative HPLC to give 16.4 mg of rac-cyclohexyl(2-isopropylimidazo[5,1-b]thiazol-3-yl)ethanol. LC-MS (basic): t$_R$=1.13; [M+H]$^+$=293.27.

Example 4a: (S)-2-Cyclohexyl-1-(2-isopropyl-imidazo[5,1-b]thiazol-3-yl)-ethanol Separation of the enantiomers on chiral stationary phase:
Method: Column: ChiralPak AS-H 30×250 mm, 5 μM; Detector Settings: UV-Vis-1; 271 nM; Eluent: 70% CO$_2$ and 30% (EtOH, 0.1% DEA); Flow: 160.00 ml/min; BPR: 100 bar; Temperature: 40° C. Injection volume: 1000 μl.
12.1 mg of the racemate are separated by the method described above to give:
5.3 mg of the S-enantiomer Example 4a and 5.5 mg of the R-enantiomer.

Example 5: rac-2-Cyclohexyl-1-(2-methyl-imidazo[5,1-b]thiazol-3-yl)-ethanol

Step 1: Preparation of ethyl 2-amino-3-oxobutanoate hydrochloride

According to the procedure described for the preparation of Example 1/Step 1 but using acetyl chloride as starting material, 4.84 g of ethyl 2-amino-3-oxobutanoate hydrochloride are obtained. LC-MS (basic): t$_R$=0.41; [M+H]$^+$=146.15.

Step 2: Preparation of ethyl 2-(2-((tert-butoxycarbonyl)amino)acetamido)-3-oxobutanoate According to the procedure described for the preparation of Example 1/Step 2 but using ethyl 2-amino-3-oxobutanoate hydrochloride as starting material, 2.77 g of ethyl 2-(2-((tert-butoxycarbonyl)amino)acetamido)-3-oxobutanoate are obtained. LC-MS (basic): t$_R$=0.61; [M+H]$^+$=303.2.

Step 3: Preparation of ethyl 2-(((tert-butoxycarbonyl)amino)methyl)-5-methylthiazole-4-carboxylate According to the procedure described for the preparation of Example 1/Step 3 but using ethyl 2-(2-((tert-butoxycarbonyl)amino)acetamido)-3-oxobutanoate as starting material, 2.28 g of ethyl 2-(((tert-butoxycarbonyl)amino)methyl)-5-methylthiazole-4-carboxylate are obtained. LC-MS (basic): t$_R$=0.94; [M+H]$^+$=301.15.

Step 4: Preparation of ethyl 2-(formamidomethyl)-5-methylthiazole-4-carboxylate According to the procedure described for the preparation of Example 1/Step 4 but using ethyl 2-(((tert-butoxycarbonyl)amino)methyl)-5-methylthiazole-4-carboxylate as starting material, 1.727 g of ethyl 2-(formamidomethyl)-5-methylthiazole-4-carboxylate are obtained. LC-MS (basic): t$_R$=0.60; [M+H]$^+$=229.13.

Step 5: Preparation of ethyl 2-methylimidazo[5,1-b]thiazole-3-carboxylate

According to the procedure described for the preparation of Example 1/Step 5 but using ethyl 2-(formamidomethyl)-5-methylthiazole-4-carboxylate as starting material, 1.044 g of ethyl 2-methylimidazo[5,1-b]thiazole-3-carboxylate are obtained. LC-MS (basic): t$_R$=0.81; [M+H]$^+$=211.15.

Step 6: Preparation of N-methoxy-N,2-dimethylimidazo[5,1-b]thiazole-3-carboxamide According to the procedure described for the preparation of Example 1/Step 6 but using ethyl 2-methylimidazo[5,1-b]thiazole-3-carboxylate as starting material, 0.895 g of N-methoxy-N,2-dimethylimidazo[5,1-b]thiazole-3-carboxamide are obtained. LC-MS (basic): t$_R$=0.61; [M+H]$^+$=226.14.

Step 7: Preparation of 2-Methylimidazo[5,1-b]thiazole-3-carbaldehyde

According to the procedure described for the preparation of Example 3/Step 7 but using N-methoxy-N,2-dimethylimidazo[5,1-b]thiazole-3-carboxamide as starting material, 1.0 g of 2-methylimidazo[5,1-b]thiazole-3-carbaldehyde are obtained. LC-MS (basic): t$_R$=0.54; [M+H]$^+$=166.99.

Step 8: Preparation of rac-2-Cyclohexyl-1-(2-methylimidazo[5,1-b]thiazol-3-yl)ethan-1-ol According to the procedure described for the preparation of Example 3/Step 8 but using 2-methylimidazo[5,1-b]thiazole-3-carbaldehyde as starting material, 16.4 mg of rac-2-cyclohexyl-1-(2-methylimidazo[5,1-b]thiazol-3-yl)ethan-1-ol are obtained. LC-MS (basic): t$_R$=1.00; [M+H]$^+$=265.23.

Example 5a: (S)-2-Cyclohexyl-1-(2-methyl-imidazo[5,1-b]thiazol-3-yl)-ethanol Separation of the enantiomers on chiral stationary phase: Method: Column: ChiralPak AS-H 30×250 mm, 5 µM; Detector Settings: UV-Vis-1; 271 nM; Eluent: 80% $CO_2$ and 20% (EtOH, 0.1% DEA); Flow: 160.00 ml/min; BPR: 100 bar; Temperature: 40° C. Injection volume: 1000 µl.

16.4 mg of the racemate are separated by the method described above to give:

6.5 mg of the S-enantiomer Example 5a and 7.3 mg of the R-enantiomer.

Example 6: rac-Cyclohexyl-(2-methyl-imidazo[5,1-b]thiazol-3-yl)-methanol

Step 1: Preparation of rac-cyclohexyl(2-methylimidazo[5,1-b]thiazol-3-yl)methanol 2-Methylimidazo[5,1-b]thiazole-3-carbaldehyde is prepared according to the procedure described in Example 5/Step 7. According to the procedure described for the preparation of Example 5/Step 8, 11.6 mg of rac-cyclohexyl(2-methylimidazo[5,1-b]thiazol-3-yl)methanol are obtained. LC-MS (basic): $t_R$=0.93; [M+H]$^+$=251.19.

Example 6a: (S)-Cyclohexyl-(2-methyl-imidazo[5,1-b]thiazol-3-yl)-methanol

Separation of the enantiomers on chiral stationary phase: Method: Column: ChiralPak AS-H 30×250 mm, 5 µM; Detector Settings: UV-Vis-1; 271 nM; Eluent: 80% $CO_2$ and 20% (EtOH, 0.1% DEA); Flow: 160.00 ml/min; BPR: 100 bar; Temperature: 40° C. Injection volume: 1000 µl.

11.6 mg of the racemate are separated by the method described above to give:

4.3 mg of the S-enantiomer Example 6a and 4.1 mg of the R-enantiomer.

Examples 7 to 12 are prepared according to the methods described for the preparation of Example 1 to 6a by using the respective different starting materials.

Example 7: rac-(2-Cyclobutylimidazo[5,1-b]thiazol-3-yl)(cyclohexyl)methanol

LC-MS (basic): $t_R$=1.09; [M+H]$^+$=291.18.

Example 7a: (S)-(2-Cyclobutylimidazo[5,1-b]thiazol-3-yl)(cyclohexyl)methanol LC-MS (basic): $t_R$=1.09; [M+H]$^+$=291.18.

Example 8: rac-1-(2-Cyclobutylimidazo[5,1-b]thiazol-3-yl)-2-cyclohexylethan-1-ol LC-MS (basic): $t_R$=1.16; [M+H]$^+$=305.16.

Example 8a: (S)-1-(2-Cyclobutylimidazo[5,1-b]thiazol-3-yl)-2-cyclohexylethan-1-ol LC-MS (basic): $t_R$=1.16; [M+H]$^+$=305.16.

Example 9: rac-Cyclohexyl(2-cyclopentylimidazo[5,1-b]thiazol-3-yl)methanol

LC-MS (basic): $t_R$=1.15; [M+H]$^+$=305.15.

Example 9a: (S)-Cyclohexyl(2-cyclopentylimidazo[5,1-b]thiazol-3-yl)methanol

LC-MS (basic): $t_R$=1.15; [M+H]$^+$=305.15.

Example 10: rac-2-Cyclohexyl-1-(2-cyclopentylimidazo[5,1-b]thiazol-3-yl)ethan-1-ol LC-MS (basic): $t_R$=1.21; [M+H]$^+$=319.17.

Example 10a: (S)-2-Cyclohexyl-1-(2-cyclopentylimidazo[5,1-b]thiazol-3-yl)ethan-1-ol LC-MS (basic): $t_R$=1.21; [M+H]$^+$=319.17.

Example 11: rac-(2-(tert-Butyl)imidazo[5,1-b]thiazol-3-yl)(cyclohexyl)methanol LC-MS (basic): $t_R$=1.10; [M+H]$^+$=293.30.

Example 12: rac-1-(2-(tert-Butyl)imidazo[5,1-b]thiazol-3-yl)-2-cyclohexylethan-1-ol LC-MS (basic): $t_R$=1.20; [M+H]$^+$=307.23.

Example 13: rac-(2-Chloroimidazo[5,1-b]thiazol-3-yl)(cyclohexyl)methanol

Step 1: Preparation of ethyl 5-chloro-2-methylthiazole-4-carboxylate

Tricholoroisocyanuric acid (3165 mg; 13.6 mmol) is added to a solution of ethyl 2-methylthiazole-4-carboxylate (2120 mg; 12.4 mmol) in DMF (60 ml). The reaction mixture is stirred at RT for 72 hours and then poured into an ice cooled aq. 1M sodium hydroxide solution. The product is extracted twice with EtOAc. The combined organic layers are washed with brine, dried over $MgSO_4$, filtered and the solvent is evaporated under reduced pressure. The residue is purified by FC (Silicagel; heptane/EtOAc) to give 843 mg of ethyl 5-chloro-2-methylthiazole-4-carboxylate as an oily liquid. LC-MS (acidic): $t_R$=0.82; [M+H]$^+$=206.20.

Step 2: Preparation of ethyl 2-(bromomethyl)-5-chlorothiazole-4-carboxylate NBS (1459 mg; 8.2 mmol) and AIBN (673 mg; 4.1 mmol) are subsequently added to a solution of ethyl 5-chloro-2-methylthiazole-4-carboxylate (843 mg; 4.1 mmol) in (trifluoromethyl)benzene (30 ml). The reaction mixture is stirred for 6 hours at 110° C. Then Isolute® (HM-N—R of Biotage) is directly added to the reaction mixture, the solvents are evaporated under reduced pressure and the product is isolated by FC (Silicagel; heptane/EtOAc) to give 853 mg of ethyl 2-(bromomethyl)-5-chlorothiazole-4-carboxylate as a white foam. LC-MS (acidic): $t_R$=0.93; [M+H]$^+$=286.08.

Step 3: Preparation of ethyl 5-chloro-2-(formamidomethyl)thiazole-4-carboxylate Sodium diformylamide (294 mg; 3.09 mmol) is added to a solution of ethyl 2-(bromomethyl)-5-chlorothiazole-4-carboxylate (923 mg; 2.826 mmol) in DMF (15 ml) and stirring is continued at RT for 90 minutes. The reaction mixture is poured onto a saturated aq. solution of $NaHCO_3$ and stirring is continued for 30 minutes, followed by extraction of the product with EtOAc (2×). The combined organic layers are washed with brine, dried over MgSO$_4$, filtered and the solvents are evaporated under reduced pressure to give 655 mg of ethyl 5-chloro-2-(formamidomethyl)thiazole-4-carboxylate which is used without further purification in the next step. LC-MS (acidic): t$_R$=0.68; [M+H]$^+$=249.11.

Step 4: Preparation of Ethyl 2-chloroimidazo[5,1-b]thiazole-3-carboxylate

Phosphorous(V) oxychloride (POCl$_3$) (0.437 ml; 4.69 mmol) is added at RT to a solution of ethyl 5-chloro-2-(formamidomethyl)thiazole-4-carboxylate (655 mg; 2.34 mmol) in toluene (10 ml) followed by stirring of the reaction mixture for 60 minutes at 60° C. The reaction mixture is poured into a saturated aq. NaHCO$_3$ solution and the product is extracted twice with EtOAc. The combined organic layers are washed with brine, dried over MgSO$_4$, filtered and the solvents are evaporated under reduced pressure to give 438 mg of ethyl 2-chloroimidazo[5,1-b]thiazole-3-carboxylate, which is used in the next step without further purification. LC-MS (acidic): t$_R$=0.62; [M+H]$^+$=231.19.

Step 5: Preparation of (2-chloroimidazo[5,1-b]thiazol-3-yl)methanol

NaBH4 (85.3 mg; 2.25 mmol) is added to a solution of ethyl 2-chloroimidazo[5,1-b]thiazole-3-carboxylate (200 mg; 0.867 mmol) in methanol (10 ml) and stirring is continued at RT for 3 hours followed by the addition of another portion of NaBH4 (85.3 mg; 2.25 mmol). After 16 hours of stirring at RT a third portion of NaBH4 (85.3 mg; 2.25 mmol) is added and stirring continued for 4 hours. To this reaction mixture an excess of acetone is added and stirring continued for 30 minutes. The resulting mixture is poured onto brine and the product is extracted with dichloromethane (3×). The combined organic layers are dried over MgSO$_4$, filtered and the solvent evaporated under reduced pressure to give 125 mg of (2-chloroimidazo[5,1-b]thiazol-3-yl)methanol, which is used in the next step without further purification. LC-MS (acidic): t$_R$=0.95; [M+H]$^+$=does not ionize.

Step 6: Preparation of 2-chloroimidazo[5,1-b]thiazole-3-carbaldehyde

Dess-Martin periodinane (344 mg; 0.811 mmol) is added to a solution of (2-chloroimidazo[5,1-b]thiazol-3-yl)methanol (120 mg; 0.541 mmol) in dichloromethane (5 ml) and stirring is continued for 16 hours at RT followed by the addition of a saturated aq. NaHCO$_3$ solution (10 ml) and a saturated aq. sodium thiosulfate solution (10 ml). The product is extracted with dichloromethane (2×30 ml). The combined organic layers are washed with brine, dried over MgSO$_4$, filtered and the solvents are evaporated under reduced pressure to give 89 mg of 2-chloroimidazo[5,1-b]thiazole-3-carbaldehyde as a foamy material used in the next step without further purification. LC-MS (acidic): t$_R$=0.39; [M+H]$^+$=187.22.

Step 7: rac-(2-chloroimidazo[5,1-b]thiazol-3-yl)(cyclohexyl)methanol

A solution of 2-chloroimidazo[5,1-b]thiazole-3-carbaldehyde (89 mg; 0.386 mmol) in THF (4 ml) is cooled to 0° C. followed by the addition of a 1M solution of cyclohexyl magnesium-bromide in THF (0.579 ml; 0.579 mmol). Stirring is continued at 0° C. for 60 minutes. The reaction is quenched by the addition of saturated aq. ammonium chloride solution and the product is extracted from the mixture with EtOAc (3×). The combined organic layers are dried over MgSO$_4$, filtered and the solvent is evaporated under reduced pressure. The residue is purified by reversed phase preparative HPLC to give 13.4 mg of rac-(2-chloroimidazo[5,1-b]thiazol-3-yl)(cyclohexyl)methanol. LC-MS (basic): t$_R$=1.00; [M+H]$^+$=271.15.

Example 13a: (S)-(2-Chloroimidazo[5,1-b]thiazol-3-yl)(cyclohexyl)methanol

The racemic mixture (9.7 mg) is separated into the enantiomers by HPLC on chiral stationary phase (method as described above) to give 5.6 mg of (S)-(2-chloro-imidazo[5,1-b]thiazol-3-yl)-cyclohexyl-methanol (Example 13a). LC-MS (basic): t$_R$=1.00; [M+H]$^+$=271.15.

Example 14: rac-(2-Bromoimidazo[5,1-b]thiazol-3-yl)(cyclohexyl)methanol

Step 1: Preparation of ethyl 5-bromo-2-(bromomethyl)thiazole-4-carboxylate

NBS (3016 mg; 16.9 mmol) and AIBN (1391 mg; 8.47 mmol) is added to a solution of methyl 5-bromo-2-methyl-1,3-thiazole-4-carboxylate (2000 mg; 8.47 mmol) in (trifluoromethyl)benzene (60 ml) and stirring is continued at 110° C. for 3 hours. Then Isolute® (HM-N—R of Biotage) is directly added to the reaction mixture, the solvents are evaporated under reduced pressure and the product is isolated by FC (Silicagel; heptane/EtOAc) to give 1.442 g of ethyl 5-bromo-2-(bromomethyl)thiazole-4-carboxylate as a white foam. LC-MS (acidic): t$_R$=0.87; [M+H]$^+$=315.99.

Step 2: Preparation of ethyl 5-bromo-2-(formamidomethyl)thiazole-4-carboxylate Sodium diformylamide (166 mg; 1.75 mmol) is added to a solution of ethyl 5-bromo-2-(bromomethyl)thiazole-4-carboxylate (500 mg; 1.59 mmol) in DMF (10 ml) and stirring is continued at RT for 3 hours. The reaction mixture is poured onto a saturated aq. solution of NaHCO$_3$ and stirring is continued for 30 minutes, followed by extraction of the product with EtOAc (2×). The combined organic layers are washed with brine, dried over MgSO$_4$, filtered and the solvents are evaporated under reduced pressure to give 294 mg of ethyl 5-bromo-2-(formamidomethyl)thiazole-4-carboxylate which is used without further purification in the next step. LC-MS (acidic): t$_R$=0.62; [M+H]$^+$=279.12.

Step 3: Preparation of ethyl 2-bromoimidazo[5,1-b]thiazole-3-carboxylate

Phosphorous(V) oxychloride (POCl$_3$) (0.194 ml; 2.08 mmol) is added at RT to a solution of ethyl 5-bromo-2-(formamidomethyl)thiazole-4-carboxylate (290 mg; 1.04 mmol) in toluene (6 ml) followed by stirring of the reaction mixture for 60 minutes at 60° C. The reaction mixture is poured into a saturated aq. NaHCO$_3$ solution and the product is extracted twice with EtOAc. The combined organic layers are washed with brine, dried over MgSO$_4$, filtered and the solvents are evaporated under reduced pressure to give 254 mg of ethyl 2-bromoimidazo[5,1-b]thiazole-3-carboxylate, which is used in the next step without further purification. LC-MS (acidic): t$_R$=0.54; [M+H]$^+$=261.09.

Step 4: Preparation of (2-bromoimidazo[5,1-b]thiazol-3-yl)methanol

NaBH4 (70.1 mg; 1.85 mmol) is added to a solution of ethyl 2-bromoimidazo[5,1-b]thiazole-3-carboxylate (200 mg; 0.712 mmol) in methanol (5 ml) and stirring is continued at RT for 3 hours followed by the addition of another portion of NaBH4 (70.1 mg; 1.85 mmol). After 16 hours of stirring at RT a third portion of NaBH$_4$ (70.1 mg; 1.85 mmol) is added and stirring continued for 4 hours. To this reaction mixture an excess of acetone is added and stirring continued for 30 minutes. The resulting mixture is poured onto brine and the product is extracted with dichloromethane (3×). The combined organic layers are dried over MgSO$_4$, filtered and the solvent evaporated under reduced pressure to give 138 mg of (2-bromoimidazo[5,1-b]thiazol-3-yl)methanol, which is used in the next step without further purification. LC-MS (acidic): $t_R$=0.38; [M+H]$^+$=233.08.

Step 5: Preparation of 2-bromoimidazo[5,1-b]thiazole-3-carbaldehyde

Dess-Martin periodinane (377 mg; 0.888 mmol) is added to a solution of (2-bromoimidazo[5,1-b]thiazol-3-yl)methanol (138 mg; 0.592 mmol) in dichloromethane (5 ml) and stirring is continued for 1 hour at RT followed by the addition of a saturated aq. NaHCO$_3$ solution (10 ml) and a saturated aq. sodium thiosulfate solution (10 ml). The product is extracted with dichloromethane (2×30 ml). The combined organic layers are washed with brine, dried over MgSO$_4$, filtered and the solvents are evaporated under reduced pressure to give 140 mg of 2-bromoimidazo[5,1-b]thiazole-3-carbaldehyde as a foamy material used in the next step without further purification. LC-MS (acidic): $t_R$=0.42; [M+H]$^+$=233.01.

Step 6: Preparation of rac-(2-bromoimidazo[5,1-b]thiazol-3-yl)(cyclohexyl)methanol 2-Bromoimidazo[5,1-b]thiazole-3-carbaldehyde (89 mg; 0.386 mmol) is dissolved in THF (4 ml) and cooled to 0° C. followed by slow addition of a solution of cyclohexylmagnesium bromide (0.579 ml; 0.579 mmol; 1M in THF solution). Stirring at 0° C. is continued for 60 minutes. The reaction mixture is quenched by the addition of a saturated aq. solution of ammonium chloride (10 ml) and the product is extracted with EtOAc (2×10 ml). The combined organic layers are washed with brine, dried over MgSO$_4$, filtered and the solvent is evaporated under reduced pressure and the residue purified by preparative HPLC to give 5.5 mg of rac-(2-bromoimidazo[5,1-b]thiazol-3-yl)(cyclohexyl)methanol. LC-MS (acidic): $t_R$=0.74; [M+H]$^+$=315.19.

Example 15 to 19 are prepared in analogy to the description of the preparation of example 13:

Example 15: rac-(2-Chloro-imidazo[5,1-b]thiazol-3-yl)-thiophen-2-yl-methanol LC-MS (acidic): $t_R$=0.59; [M+H]$^+$=270.91.

Example 16: rac-1-(2-Chloro-imidazo[5,1-b]thiazol-3-yl)-2-cyclohexyl-ethanol LC-MS (acidic): $t_R$=0.76; [M+H]$^+$=285.01.

Example 16a: (S)-1-(2-Chloro-imidazo[5,1-b]thiazol-3-yl)-2-cyclohexyl-ethanol LC-MS (acidic): $t_R$=0.76; [M+H]$^+$=285.01.

Example 17: rac-(2-Chloro-imidazo[5,1-b]thiazol-3-yl)-cycloheptyl-methanol

LC-MS (acidic): $t_R$=0.75; [M+H]$^+$=285.01.

Example 18: rac-(2-Chloro-imidazo[5,1-b]thiazol-3-yl)-cyclopentyl-methanol

LC-MS (acidic): $t_R$=0.64; [M+H]$^+$=257.83.

Example 19: rac-(2-Chloro-imidazo[5,1-b]thiazol-3-yl)-cyclopropyl-methanol

LC-MS (acidic): $t_R$=0.50; [M+H]$^+$=229.01.

Example 20 to example 65 are prepared in analogy to the description of the preparation of example 1 and example 3:

Example 20: rac-(1R*,2R*,4S*)-Bicyclo[2.2.1]hept-2-yl-(2-cyclopropyl-imidazo[5,1-b]thiazol-3-yl)-methanol LC-MS (acidic): $t_R$=0.76; [M+H]$^+$=289.31.

Example 21: rac-1-(2-Cyclopropyl-imidazo[5,1-b]thiazol-3-yl)-2-(3,3-difluoro-cyclobutyl)-ethanol LC-MS (QC): $t_R$=0.6; [M+H]$^+$=299.1.

Example 22: rac-2-Bicyclo[2.2.1]hept-1-yl-1-(2-cyclopropyl-imidazo[5,1-b]thiazol-3-yl)-ethanol LC-MS (QC): $t_R$=0.8; [M+H]$^+$=303.1.

Example 23: rac-1-(2-Cyclopropyl-imidazo[5,1-b]thiazol-3-yl)-2-(1-methyl-cyclohexyl)-ethanol LC-MS (QC): $t_R$=0.8; [M+H]$^+$=305.2.

Example 24: rac-2-Cyclopentyl-1-(2-cyclopropyl-imidazo[5,1-b]thiazol-3-yl)-ethanol LC-MS (QC): $t_R$=0.7; [M+H]$^+$=277.1.

Example 24a: (S)-2-Cyclopentyl-1-(2-cyclopropyl-imidazo[5,1-b]thiazol-3-yl)-ethanol LC-MS (QC): $t_R$=0.7; [M+H]$^+$=277.1.

Example 25: rac-1-(2-Cyclopropyl-imidazo[5,1-b]thiazol-3-yl)-2-(4,4-dimethyl-cyclohexyl)-ethanol LC-MS (QC): $t_R$=0.9; [M+H]$^+$=319.1.

Example 26: rac-(2-Cyclopropyl-imidazo[5,1-b]thiazol-3-yl)-(4,4-dimethyl-cyclohexyl)-methanol LC-MS (QC): $t_R$=0.8; [M+H]$^+$=305.2.

Example 27: (2-Cyclopropyl-imidazo[5,1-b]thiazol-3-yl)-(3-methyl-cyclohexyl)-methanol LC-MS (QC): $t_R$=0.7; [M+H]$^+$=291.1.

Example 28: rac-2-Cycloheptyl-1-(2-cyclopropyl-imidazo[5,1-b]thiazol-3-yl)-ethanol LC-MS (QC): $t_R$=0.8; [M+H]$^+$=305.1.

Example 28a: (S)-2-Cycloheptyl-1-(2-cyclopropyl-imidazo[5,1-b]thiazol-3-yl)-ethanol LC-MS (QC): $t_R$=0.8; [M+H]$^+$=305.1.

Example 29: 1-(2-Cyclopropyl-imidazo[5,1-b]thiazol-3-yl)-2-(3-methyl-cyclohexyl)-ethanol LC-MS (QC): $t_R$=0.8; [M+H]$^+$=305.2.

Example 30: (2-Cyclopropyl-imidazo[5,1-b]thiazol-3-yl)-(3-methyl-cyclopentyl)-methanol LC-MS (QC): $t_R$=0.7; [M+H]$^+$=277.1.

Example 31: 1-(2-Cyclopropyl-imidazo[5,1-b]thiazol-3-yl)-2-(2-methyl-cyclohexyl)-ethanol LC-MS (QC): $t_R$=0.8; [M+H]$^+$=305.2.

Example 32: rac-(2-Bromo-imidazo[5,1-b]thiazol-3-yl)-thiophen-2-yl-methanol

LC-MS (QC): $t_R$=0.6; [M+H]$^+$=315.0.

Example 33: rac-1-(2-Bromo-imidazo[5,1-b]thiazol-3-yl)-2-cyclohexyl-ethanol

LC-MS (QC): $t_R$=0.9; [M+H]$^+$=329.1.

Example 34: 1-(2-Cyclopropyl-imidazo[5,1-b]thiazol-3-yl)-2-(3,3-dimethyl-cyclopentyl)-ethanol LC-MS (QC): $t_R$=0.8; [M+H]$^+$=305.2.

Example 34a: (S)-1-(2-Cyclopropyl-imidazo[5,1-b]thiazol-3-yl)-2-(3,3-dimethyl-cyclopentyl)-ethanol LC-MS (QC): $t_R$=0.8; [M+H]$^+$=305.2.

Example 35: 1-(2-Cyclopropyl-imidazo[5,1-b]thiazol-3-yl)-2-(3-phenyl-cyclopentyl)-ethanol LC-MS (QC): $t_R$=0.8; [M+H]$^+$=353.2.

Example 36: rac-(2-Cyclopropyl-imidazo[5,1-b]thiazol-3-yl)-(3,3-dimethyl-cyclobutyl)-methanol LC-MS (QC): $t_R$=0.7; [M+H]$^+$=277.2.

Example 36a: (S)-(2-Cyclopropyl-imidazo[5,1-b]thiazol-3-yl)-(3,3-dimethyl-cyclobutyl)-methanol LC-MS (QC): $t_R$=0.7; [M+H]$^+$=277.2.

Example 37: rac-1-(2-Cyclopropyl-imidazo[5,1-b]thiazol-3-yl)-2-(4-phenyl-cyclohexyl)-ethanol LC-MS (QC): $t_R$=0.9; [M+H]$^+$=367.4.

Example 38: 2-Bicyclo[2.2.1]hept-5-en-2-yl-1-(2-cyclopropyl-imidazo[5,1-b]thiazol-3-yl)-ethanol LC-MS (QC): $t_R$=0.7; [M+H]$^+$=301.2.

Example 39: rac-1-(2-Cyclopropyl-imidazo[5,1-b]thiazol-3-yl)-2-(1-methyl-cyclobutyl)-ethanol LC-MS (QC): $t_R$=0.7; [M+H]$^+$=277.2.

Example 40: rac-2-Cyclobutyl-1-(2-cyclopropyl-imidazo[5,1-b]thiazol-3-yl)-ethanol LC-MS (QC): $t_R$=0.6; [M+H]$^+$=263.2.

Example 41: 1-(2-Cyclopropyl-imidazo[5,1-b]thiazol-3-yl)-2-(7-oxa-bicyclo[2.2.1]hept-2-yl)-ethanol LC-MS (QC): $t_R$=0.5; [M+H]$^+$=305.2.

Example 42: rac-1-(2-Cyclopropyl-imidazo[5,1-b]thiazol-3-yl)-2-(4-trifluoromethyl-cyclohexyl)-ethanol LC-MS (QC): $t_R$=0.8; [M+H]$^+$=359.2.

Example 43: rac-Cyclobutyl-(2-cyclopropyl-imidazo[5,1-b]thiazol-3-yl)-methanol

LC-MS (QC): $t_R$=0.5; [M+H]$^+$=249.2.

Example 44: rac-(2-Cyclopropyl-imidazo[5,1-b]thiazol-3-yl)-(4-methyl-cyclohexyl)-methanol LC-MS (QC): $t_R$=0.7; [M+H]$^+$=291.2.

Example 45: rac-(2-Cyclopropyl-imidazo[5,1-b]thiazol-3-yl)-(4-ethyl-cyclohexyl)-methanol LC-MS (QC): $t_R$=0.8; [M+H]$^+$=305.2.

Example 46: rac-Cyclopentyl-(2-cyclopropyl-imidazo[5,1-b]thiazol-3-yl)-methanol

LC-MS (QC): $t_R$=0.6; [M+H]$^+$=263.2.

Example 47: (2-Cyclopropyl-imidazo[5,1-b]thiazol-3-yl)-(3,3-dimethyl-cyclopentyl)-methanol LC-MS (QC): $t_R$=0.7; [M+H]$^+$=291.2.

Example 48: (2-Cyclopropyl-imidazo[5,1-b]thiazol-3-yl)-(2-methyl-cyclopentyl)-methanol LC-MS (QC): $t_R$=0.7; [M+H]$^+$=277.1.

Example 49: rac-1-(2-Cyclopropyl-imidazo[5,1-b]thiazol-3-yl)-2-(4-methyl-cyclohexyl)-ethanol LC-MS (QC): $t_R$=0.8; [M+H]$^+$=305.2.

Example 50: rac-(2-Cyclopropyl-imidazo[5,1-b]thiazol-3-yl)-phenyl-methanol

LC-MS (QC): $t_R$=0.6; [M+H]$^+$=271.2.

Example 51: rac-(2-Cyclopropyl-imidazo[5,1-b]
thiazol-3-yl)-p-tolyl-methanol

LC-MS (QC): $t_R$=0.6; [M+H]$^+$=285.2.

Example 52: rac-(2-Cyclopropyl-imidazo[5,1-b]
thiazol-3-yl)-m-tolyl-methanol

LC-MS (QC): $t_R$=0.6; [M+H]$^+$=285.1.

Example 53: rac-(2-Cyclopropyl-imidazo[5,1-b]
thiazol-3-yl)-(4-ethyl-phenyl)-methanol LC-MS (QC): $t_R$=0.7; [M+H]$^+$=299.2.

Example 54: rac-(2-Cyclopropyl-imidazo[5,1-b]
thiazol-3-yl)-(3-ethyl-phenyl)-methanol LC-MS (QC): $t_R$=0.7; [M+H]$^+$=299.2.

Example 55: rac-(2-Cyclopropyl-imidazo[5,1-b]
thiazol-3-yl)-(4-methoxy-phenyl)-methanol LC-MS (QC): $t_R$=0.6; [M+H]$^+$=300.9.

Example 56: rac-(2-Cyclopropyl-imidazo[5,1-b]
thiazol-3-yl)-(3-methoxy-phenyl)-methanol LC-MS (QC): $t_R$=0.6; [M+H]$^+$=301.1.

Example 57: rac-(2-Methyl-imidazo[5,1-b]thiazol-3-
yl)-thiophen-2-yl-methanol

LC-MS (QC): $t_R$=0.4; [M+H]$^+$=251.1.

Example 58: rac-(4-Dimethylamino-phenyl)-(2-
methyl-imidazo[5,1-b]thiazol-3-yl)-methanol LC-MS (QC): $t_R$=0.4; [M+H]$^+$=288.5.

Example 59: rac-1-(2-Cyclopropyl-imidazo[5,1-b]
thiazol-3-yl)-2-phenyl-ethanol

LC-MS (QC): $t_R$=0.6; [M+H]$^+$=285.3.

Example 60: rac-1-(2-Cyclopropyl-imidazo[5,1-b]
thiazol-3-yl)-2-(2,6-dichloro-phenyl)-ethanol LC-MS (QC): $t_R$=0.7; [M+H]$^+$=353.3.

Example 61: rac-1-(2-Cyclopropyl-imidazo[5,1-b]
thiazol-3-yl)-2-o-tolyl-ethanol

LC-MS (QC): $t_R$=0.7; [M+H]$^+$=299.2.

Example 62: rac-2-(3-Methoxy-phenyl)-1-(2-
methyl-imidazo[5,1-b]thiazol-3-yl)-ethanol LC-MS (QC): $t_R$=0.5; [M+H]$^+$=289.3.

Example 63: rac-Cyclohexyl-(2-trifluoromethyl-
imidazo[5,1-b]thiazol-3-yl)-methanol LC-MS (QC): $t_R$=1.1; [M+H]$^+$=305.2.

Example 64: rac-2-Cyclohexyl-1-(2-trifluoromethyl-
imidazo[5,1-b]thiazol-3-yl)-ethanol LC-MS (QC): $t_R$=1.2; [M+H]$^+$=319.3.

Example 65: 3-Cyclohexyl-1-(2-cyclopropyl-imi-
dazo[5,1-b]thiazol-3-yl)-butan-1-ol LC-MS (QC): $t_R$=0.9; [M+H]$^+$=319.3.

Examples 47a/47b: (S)-(2-Cyclopropyl-imidazo[5,1-
b]thiazol-3-yl)-((R)-3,3-dimethyl-cyclopentyl)-
methanol and (S)-(2-Cyclopropyl-imidazo[5,1-b]
thiazol-3-yl)-((S)-3,3-dimethyl-cyclopentyl)-
methanol Separation of the diastereoisomers on chiral stationary
phase:
Method: Column: ChiralPak IG 30×250 mm, 5 µM;
Detector Settings: UV-Vis-1; 212 nM; Eluent: 75% $CO_2$ and
25% (MeOH, 0.1% DEA); Flow: 160.00 ml/min; BPR: 100
bar; Temperature: 40° C. Injection volume: 2000 µl.
20 mg of the mixture of diastereoisomers are separated by
the method described above. Two elution peaks were col-
lected at $t_R$=2.45 and 2.85, furnishing 3 to 4 mg of each of
the following isomers: (S)-(2-cyclopropylimidazo[5,1-b]thi-
azol-3-yl)((R)-3,3-dimethylcyclopentyl)-methanol and (S)-
(2-cyclopropylimidazo[5,1-b]thiazol-3-yl)((S)-3,3-dimeth-
ylcyclopentyl)-methanol (LC-MS (QC): $t_R$=0.734 and
0.740; [M+H]$^+$=291.2).

Example 48a: (S)-(2-Cyclopropyl-imidazo[5,1-b]
thiazol-3-yl)-(1-methyl-cyclopentyl)-methanol Separation of the enantiomers on chiral stationary phase:
Method: Column: ChiralCel OZ—H 30×250 mm, 5 µM;
Detector Settings: UV-Vis-1; 275 nM; Eluent: 70% $CO_2$ and
30% (EtOH, 0.1% DEA); Flow: 160.00 ml/min; BPR: 100
bar; Temperature: 40° C. Injection volume: 2000 µl.
20.4 mg of the racemate are separated by the method
described above to give 6.5 mg of (S)-(2-cyclopropyl-
imidazo[5,1-b]thiazol-3-yl)-(1-methyl-cyclopentyl)-metha-
nol and 6.3 mg of its enantiomer. LC-MS (QC): $t_R$=0.657;
[M+H]$^+$=277.2.

Example 50a: (S)-(2-Cyclopropyl-imidazo[5,1-b]
thiazol-3-yl)-phenyl-methanol

Separation of the enantiomers on chiral stationary phase:
Method: Column: ChiralPak IC 30×250 mm, 5 µM;
Detector Settings: UV-Vis-1; 210 nM; Eluent: 75% $CO_2$ and
25% (EtOH, 0.1% DEA); Flow: 160.00 ml/min; BPR: 100
bar; Temperature: 40° C. Injection volume: 1900 µl.
19.8 mg of the racemate are separated by the method
described above to give 8.7 mg of (S)-(2-cyclopropyl-
imidazo[5,1-b]thiazol-3-yl)-phenyl-methanol and 8.8 mg of
its enantiomer. LC-MS (QC): $t_R$=0.560; [M+H]$^+$=271.1.

Example 63a: (S)-Cyclohexyl-(2-trifluoromethyl-
imidazo[5,1-b]thiazol-3-yl)-methanol Separation of the enantiomers on chiral stationary phase:
Method: Column: ChiralPak IC 30×250 mm, 5 µM;
Detector Settings: UV-Vis-1; 210 nM; Eluent: 80% $CO_2$ and
20% (EtOH, 0.1% DEA); Flow: 160.00 ml/min; BPR: 100
bar; Temperature: 40° C. Injection volume: 1200 µl.

13.7 mg of the racemate are separated by the method described above to give 5 mg of (S)-cyclohexyl-(2-trifluoromethyl-imidazo[5,1-b]thiazol-3-yl)-methanol and 5 mg of its enantiomer. LC-MS (QC): $t_R$=1.076; [M+H]$^+$=305.2.

Example 66: 2-Cyclohexyl-1-(2-cyclopropyl-imidazo[5,1-b]thiazol-3-yl)-butan-1-ol

Step 1: Preparation of 2-cyclopropylimidazo[5,1-b]thiazole-3-carbaldehyde

To an ice-cold solution of the product from Example 1, Step 6.2, 2-cyclopropyl-N-methoxy-N-methylimidazo[5,1-b]thiazole-3-carboxamide (2.875 g; 10.9 mmol) in THF (40 ml) is added a solution of DIBALH (1 M in toluene, 10.9 ml, 10.9 mmol). The reaction mixture is stirred at 0° C. for 30 min, treated with more DIBALH (1 M in toluene, 10.9 ml, 10.9 mmol), and further stirred at 0° C. for 30 min. A sat. aq. NH$_4$Cl solution is added followed by a 1.2 M aq. solution of Rochelle's salts and the product is extracted with EtOAc (3×). The combined org. extracts are dried over MgSO$_4$, filtered and concentrated under reduced pressure to give 2.657 g of 2-cyclopropylimidazo[5,1-b]thiazole-3-carbaldehyde. The crude product can be used without further purification. FC (Silicagel; Hept/EtOAc) gives the pure product. LC-MS (acidic): $t_R$=0.44; [M+H]$^+$=193.03. $^1$H NMR (500 MHz, d$_6$-DMSO) δ: 10.14 (s, 1H), 8.52 (d, J=0.5 Hz, 1H), 7.15 (d, J=0.6 Hz, 1H), 2.92 (m, 1H), 1.30-1.34 (m, 2H), 0.98 (m, 2H).

Step 2: Preparation of 2-cyclohexyl-1-(2-cyclopropyl-imidazo[5,1-b]thiazol-3-yl)-butan-1-ol (Example 66)

Prepared following the procedure described in Example 3, Step 8 but using 2-cyclopropylimidazo[5,1-b]thiazole-3-carbaldehyde as starting material. Purification by reversed phase preparative HPLC gives 2-cyclohexyl-1-(2-cyclopropyl-imidazo[5,1-b]thiazol-3-yl)butan-1-ol. LC-MS (QC): $t_R$=0.881; [M+H]$^+$=319.3.

Examples 67, 69-91, 101-106, 114, 120, 123, 131, 133-136, 138-139, 142-152, 159-160, 163-166, 171 and 173 are prepared in analogy to the description of the preparation of example 66:

Example 67: rac-1-(2-Cyclopropyl-imidazo[5,1-b]thiazol-3-yl)-2-naphthalen-1-yl-ethanol LC-MS (QC): $t_R$=0.733; [M+H]$^+$=335.2.

Example 69: (2-Cyclopropyl-imidazo[5,1-b]thiazol-3-yl)-(3,3-dimethyl-cyclohexyl)-methanol LC-MS (QC): $t_R$=0.796; [M+H]$^+$=305.2.

Example 70: rac-(2-Cyclopropyl-imidazo[5,1-b]thiazol-3-yl)-spiro[4.5]dec-8-yl-methanol LC-MS (QC): $t_R$=0.891; [M+H]$^+$=331.2.

Example 71: rac-1-(2-Cyclopropyl-imidazo[5,1-b]thiazol-3-yl)-2-(4,4-difluoro-cyclohexyl)-ethanol LC-MS (QC): $t_R$=0.670; [M+H]$^+$=327.2.

Example 72: rac-(2-Cyclopropyl-imidazo[5,1-b]thiazol-3-yl)-(4-isopropyl-cyclohexyl)-methanol LC-MS (QC): $t_R$=0.885; [M+H]$^+$=319.2.

Example 73: rac-(2-Cyclopropyl-imidazo[5,1-b]thiazol-3-yl)-(4-phenyl-cyclohexyl)-methanol LC-MS (QC): $t_R$=0.852; [M+H]$^+$=353.2.

Example 73a: (S)-(2-Cyclopropyl-imidazo[5,1-b]thiazol-3-yl)-(trans-4-phenyl-cyclohexyl)-methanol Separation of the enantiomers on chiral stationary phase: Method: Column: ChiralPak IG 30×250 mm, 5 µM; Detector Settings: UV-Vis-1; 210 nM; Eluent: 55% CO$_2$ and 45% MeOH; Flow: 160.00 ml/min; BPR: 100 bar; Temperature: 40° C. Injection volume: 1000 µl.

19 mg of the mixture of diastereoisomers are separated by the method described above to give 6 mg of (S)-(2-cyclopropyl-imidazo[5,1-b]thiazol-3-yl)-(trans-4-phenyl-cyclohexyl)-methanol. LC-MS (QC): $t_R$=0.852; [M+H]$^+$=353.2.

Example 74: rac-2-(4-tert-Butyl-cyclohexyl)-1-(2-cyclopropyl-imidazo[5,1-b]thiazol-3-yl)-ethanol LC-MS (QC): $t_R$=1.001; [M+H]$^+$=347.3.

Example 75: 1-(2-Cyclopropyl-imidazo[5,1-b]thiazol-3-yl)-2-(2-phenyl-cyclohexyl)-ethanol LC-MS (QC): $t_R$=0.906; [M+H]$^+$=367.3.

Example 76: 1-(2-Cycclopropyl-imidazo[5,1-b]thiazol-3-yl)-2-(2,2-dimethyl-cyclohexyl)-ethanol LC-MS (QC): $t_R$=0.840; [M+H]$^+$=319.2.

Example 77: (3-Benzyl-cyclopentyl)-(2-cyclopropyl-imidazo[5,1-b]thiazol-3-yl)-methanol LC-MS (QC): $t_R$=0.862; [M+H]$^+$=353.3.

Example 78: (2-Cyclopropyl-imidazo[5,1-b]thiazol-3-yl)-(3-isobutyl-cyclopentyl)-methanol LC-MS (QC): $t_R$=0.899; [M+H]$^+$=319.3.

Example 79: (2-Cyclopropyl-imidazo[5,1-b]thiazol-3-yl)-(3-methoxy-cyclohexyl)-methanol LC-MS (QC): $t_R$=0.559; [M+H]$^+$=307.2.

Example 80: (2-Cyclopropyl-imidazo[5,1-b]thiazol-3-yl)-(1,2,3,4-tetrahydro-naphthalen-2-yl)-methanol LC-MS (QC): $t_R$=0.741; [M+H]$^+$=325.2.

Example 81: rac-(2-Cyclopropyl-imidazo[5,1-b]thiazol-3-yl)-(4-trifluoromethyl-cyclohexyl)-methanol LC-MS (QC): $t_R$=0.742; [M+H]$^+$=345.2.

Example 82: 2-Cyclohexyl-1-(2-cyclopropyl-imidazo[5,1-b]thiazol-3-yl)-propan-1-ol LC-MS (QC): $t_R$=0.820; [M+H]$^+$=305.2.

Example 83: (2-Cyclopropyl-imidazo[5,1-b]thiazol-3-yl)-(2-phenyl-cyclopentyl)-methanol LC-MS (QC): $t_R$=0.765; [M+H]$^+$=339.2.

Example 84: (2-Cyclopropyl-imidazo[5,1-b]thiazol-3-yl)-(2,2-dimethyl-cyclopentyl)-methanol LC-MS (QC): $t_R$=0.724; [M+H]$^+$=291.2.

Example 85: rac-1-(2-Cyclopropyl-imidazo[5,1-b]thiazol-3-yl)-2-(4-isopropyl-cyclohexyl)-ethanol LC-MS (QC): $t_R$=0.945; [M+H]$^+$=333.2.

Example 86: rac-(4-tert-Butyl-cyclohexyl)-(2-cyclopropyl-imidazo[5,1-b]thiazol-3-yl)-methanol LC-MS (QC): $t_R$=0.930; [M+H]$^+$=333.3.

Example 87: rac-2-(4-Cyclobutyl-cyclohexyl)-1-(2-cyclopropyl-imidazo[5,1-b]thiazol-3-yl)-ethanol LC-MS (QC): $t_R$=1.002; [M+H]$^+$=345.3.

Example 88: (2-Cyclopropyl-imidazo[5,1-b]thiazol-3-yl)-(3-methyl-3-phenyl-cyclopentyl)-methanol LC-MS (QC): $t_R$=0.842; [M+H]$^+$=353.2.

Example 89: 1-(2-Cyclopropyl-imidazo[5,1-b]thiazol-3-yl)-2-(decahydro-naphthalen-1-yl)-ethanol LC-MS (QC): $t_R$=0.952; [M+H]$^+$=345.3.

Example 90: (2-Cyclopropyl-imidazo[5,1-b]thiazol-3-yl)-(decahydro-naphthalen-2-yl)-methanol LC-MS (QC): $t_R$=0.885; [M+H]$^+$=331.3.

Example 91: (2-Benzyl-cyclopentyl)-(2-cyclopropyl-imidazo[5,1-b]thiazol-3-yl)-methanol LC-MS (QC): $t_R$=0.866; [M+H]$^+$=353.3.

Example 101: 1-(2-Cyclopropyl-imidazo[5,1-b]thiazol-3-yl)-2-(decahydro-naphthalen-2-yl)-ethanol LC-MS (QC): $t_R$=0.964; [M+H]$^+$=345.3.

Example 102: 1-(2-Cyclopropyl-imidazo[5,1-b]thiazol-3-yl)-2-(3-trifluoromethyl-cyclohexyl)-ethanol LC-MS (QC): $t_R$=0.805; [M+H]$^+$=359.2.

Example 103: rac-(4-Cyclobutyl-cyclohexyl)-(2-cyclopropyl-imidazo[5,1-b]thiazol-3-yl)-methanol LC-MS (QC): $t_R$=0.925; [M+H]$^+$=331.2.

Example 104: (2-Cyclopropyl-imidazo[5,1-b]thiazol-3-yl)-(3-trifluoromethyl-cyclohexyl)-methanol LC-MS (QC): $t_R$=0.734; [M+H]$^+$=345.2.

Example 105: rac-(2-Cyclopropyl-imidazo[5,1-b]thiazol-3-yl)-(1-methyl-cyclohexyl)-methanol LC-MS (QC): $t_R$=0.721; [M+H]$^+$=290.9.

Example 106: 1-(2-Cyclopropyl-imidazo[5,1-b]thiazol-3-yl)-2-(3,3-dimethyl-cyclohexyl)-ethanol LC-MS (QC): $t_R$=0.865; [M+H]$^+$=319.2.

Example 114: 1-(2-Cyclopropyl-imidazo[5,1-b]thiazol-3-yl)-2-(3-methoxy-cyclohexyl)-ethanol LC-MS (QC): $t_R$=0.599; [M+H]$^+$=321.3.

Example 120: (2-Cyclopropyl-imidazo[5,1-b]thiazol-3-yl)-(2,4,4-trimethyl-cyclopentyl)-methanol LC-MS (QC): $t_R$=0.804; [M+H]$^+$=305.2.

Example 123: (2-Cyclopropyl-imidazo[5,1-b]thiazol-3-yl)-(2-ethyl-cyclopentyl)-methanol LC-MS (QC): $t_R$=0.755; [M+H]$^+$=291.1.

Example 131: rac-1-(2-Cyclopropyl-imidazo[5,1-b]thiazol-3-yl)-2-(4-methoxy-cyclohexyl)-ethanol LC-MS (QC): $t_R$=0.590; [M+H]$^+$=321.2.

Example 133: (2-Cyclopropyl-imidazo[5,1-b]thiazol-3-yl)-(octahydro-pentalen-2-yl)-methanol LC-MS (QC): $t_R$=0.765; [M+H]$^+$=303.2.

Example 134: rac-2-(4-Cyclopentyl-cyclohexyl)-1-(2-cyclopropyl-imidazo[5,1-b]thiazol-3-yl)-ethanol LC-MS (QC): $t_R$=1.063; [M+H]$^+$=359.3.

Example 135: 1-(2-Cyclopropyl-imidazo[5,1-b]thiazol-3-yl)-2-(2-phenyl-cyclopentyl)-ethanol LC-MS (QC): $t_R$=0.810; [M+H]$^+$=353.3.

Example 136: (2-Cyclopropyl-imidazo[5,1-b]thiazol-3-yl)-(3-isopropyl-3-methyl-cyclopentyl)-methanol LC-MS (QC): $t_R$=0.861, [M+H]$^+$=319.2.

Example 138: rac-1-(2-Cyclopropyl-imidazo[5,1-b]thiazol-3-yl)-2-(4-difluoromethyl-cyclohexyl)-ethanol LC-MS (QC): $t_R$=0.729, [M+H]$^+$=341.2.

Example 139: (2-Cyclopropyl-imidazo[5,1-b]thiazol-3-yl)-(1,3,3-trimethyl-cyclopentyl)-methanol LC-MS (QC): $t_R$=0.793, [M+H]$^+$=305.2.

Example 142: rac-1-(2-Cyclopropyl-imidazo[5,1-b]thiazol-3-yl)-2-(4-ethyl-cyclohexyl)-ethanol LC-MS (QC): $t_R$=0.901, [M+H]$^+$=319.2.

Example 143: rac-(2-Cyclopropyl-imidazo[5,1-b]
thiazol-3-yl)-(3-trifluoromethyl-phenyl)-methanol LC-MS (QC): $t_R$=0.720, [M+H]$^+$=339.2.

Example 144: rac-(2-Cyclopropyl-imidazo[5,1-b]
thiazol-3-yl)-(4-fluoro-phenyl)-methanol LC-MS (QC): $t_R$=0.588, [M+H]$^+$=289.1.

Example 145: rac-(2-Cyclopropyl-imidazo[5,1-b]
thiazol-3-yl)-(3-fluoro-phenyl)-methanol LC-MS (QC): $t_R$=0.589, [M+H]$^+$=289.2.

Example 146: rac-(4-Chloro-phenyl)-(2-cyclopro-
pyl-imidazo[5,1-b]thiazol-3-yl)-methanol LC-MS (QC): $t_R$=0.666, [M+H]$^+$=305.1.

Example 147: rac-(2-Cyclopropyl-imidazo[5,1-b]
thiazol-3-yl)-(2-methoxy-phenyl)-methanol LC-MS (QC): $t_R$=0.581, [M+H]$^+$=301.2.

Example 148: rac-(2-Cyclopropyl-imidazo[5,1-b]
thiazol-3-yl)-o-tolyl-methanol

LC-MS (QC): $t_R$=0.610, [M+H]$^+$=285.2.

Example 149: rac-(3-Chloro-phenyl)-(2-cyclopro-
pyl-imidazo[5,1-b]thiazol-3-yl)-methanol LC-MS (QC): $t_R$=0.657, [M+H]$^+$=304.9.

Example 150: rac-1-(2-Cyclopropyl-imidazo[5,1-b]
thiazol-3-yl)-2-(4-propyl-cyclohexy-etethanol LC-MS (QC): $t_R$=0.977, [M+H]$^+$=333.3.

Example 151: rac-4-[(2-Cyclopropyl-imidazo[5,1-b]
thiazol-3-yl)-hydroxy-methyl]-cyclohexanol LC-MS (QC): $t_R$=0.399, [M+H]$^+$=293.0.

Example 152: rac-4-[2-(2-Cyclopropyl-imidazo[5,1-
b]thiazol-3-yl)-2-hydroxy-ethyl]-cyclohexanol LC-MS (QC): $t_R$=0.452, [M+H]$^+$=307.2.

Example 159: rac-(2-Cyclopropyl-imidazo[5,1-b]
thiazol-3-yl)-(4-trifluoromethyl-phenyl)-methanol LC-MS (QC): $t_R$=0.734, [M+H]$^+$=339.1.

Example 160: rac-1-(2-Cyclopropyl-imidazo[5,1-b]
thiazol-3-yl)-2-(4-ethylamino-cyclohexyl)-ethanol LC-MS (QC): $t_R$=0.314, [M+H]$^+$=334.2.

Example 163: rac-(2-Cyclopropyl-imidazo[5,1-b]
thiazol-3-yl)-(2-fluoro-phenyl)-methanol LC-MS (QC): $t_R$=0.586, [M+H]$^+$=289.2.

Example 164: rac-(2-Chloro-phenyl)-(2-cyclopro-
pyl-imidazo[5,1-b]thiazol-3-yl)-methanol LC-MS (QC): $t_R$=0.636, [M+H]$^+$=305.1.

Example 165: rac-Cycloheptyl-(2-cyclopropyl-imi-
dazo[5,1-b]thiazol-3-yl)-methanol LC-MS (QC): $t_R$=0.735, [M+H]$^+$=291.2.

Example 166: rac-(2-Cyclopropyl-imidazo[5,1-b]
thiazol-3-yl)-(1-methyl-cycloheptyl)-methanol LC-MS (QC): $t_R$=0.786, [M+H]$^+$=305.3.

Example 171: rac-(2-Cyclopropyl-imidazo[5,1-b]
thiazol-3-yl)-thiophen-2-yl-methanol LC-MS (QC): $t_R$=0.537, [M+H]$^+$=277.1.

Example 173: rac-(2-Cyclopropyl-imidazo[5,1-b]
thiazol-3-yl)-thiophen-3-yl-methanol LC-MS (QC): $t_R$=0.525, [M+H]$^+$=277.1.

Example 188: rac-(2-Cyclopropyl-imidazo[5,1-b]
thiazol-3-yl)-(1-isopropyl-1H-pyrazol-4-yl)-metha-
nol Step 1: Preparation of
2,4-dibromo-5-cyclopropylthiazole To a solution of 4-bromo-5-cyclopropyl-thiazole (6.10 g; 28.1 mmol) in CH$_3$CN (200 ml) is added HBr (10.3 ml; 91.3 mmol) and bromine (4.69 ml; 91.3 mmol). The resulting orange solution is stirred at 95° C. for 7 h. The mixture is cooled down to RT, treated with aq. Na$_2$S$_2$O$_3$ and extracted with EtOAc (2×). The combined organic extracts are washed with brine, dried (MgSO$_4$), filtered and concentrated dunder reduced pressure. Purification by FC (silicagel, Hept/EtOAc) gives 2.91 g of 2,4-dibromo-5-cyclopropylthiazole as a light yellow oil. LC-MS (acidic): $t_R$=0.97; [M+H]$^+$=283.75. $^1$H NMR (400 MHz, d$_6$-DMSO) δ: 2.03 (m, 1H), 1.14 (m, 2H), 0.72 (m, 2 H).

Step 2: Preparation of
4-bromo-5-cyclopropylthiazole-2-carbaldehyde

To a solution of the product of step 1, 2,4-dibromo-5-cyclopropylthiazole (2.91 g; 10.2 mmol) in THF (60 ml) is added n-BuLi (2.5 M in hexanes; 4.28 ml, 10.7 mmol) at −78° C. The mixture is stirred at this temperature for 10 min then DMF (2.05 ml; 26.5 mmol) is added and the stirring continued for 1 h. The mixture is allowed to warm up to RT, treated with 1M HCl (50 ml) and extracted with EtOAc (2×). The combined organic extracts are washed with brine, dried (MgSO$_4$), filtered and concentrated under reduced pressure to give 2.48 g of 4-bromo-5-cyclopropylthiazole-2-carbaldehyde as a brown oil, which is used without further purification in the next step. LC-MS (acidic): $t_R$=0.88; [M+H]$^+$=231.91.

Step 3: Preparation of
(4-bromo-5-cyclopropylthiazol-2-yl)methanol

To a solution of 4-bromo-5-cyclopropylthiazole-2-carbaldehyde (3.50 g; 12.4 mmol) in EtOH (100 ml) is added NaBH$_4$ (1000 mg; 26.4 mmol) and the resulting mixture is stirred at RT for 45 min. Water is added and the resulting aqueous phase is extracted twice with DCM. The combined organic layers are washed with saturated aqueous NaHCO$_3$ solution and brine then dried over MgSO$_4$, filtered and concentrated under reduced pressure to give (4-bromo-5-cyclopropylthiazol-2-yl)methanol (3.06 g) as an amber oil which is used in the next step without purification. LC-MS (acidic): $t_R$=0.72; [M+H]$^+$=233.91.

Step 4: Preparation of 4-bromo-2-(chloromethyl)-5-cyclopropylthiazole

To a solution of (4-bromo-5-cyclopropylthiazol-2-yl)methanol (3.06 g; 11.5 mmol) in DCM (60 ml) is added thionyl chloride (2.46 g) and the resulting mixture is stirred at RT for 45 min. The mixture is poured onto saturated aqueous NaHCO$_3$ solution and the aqueous phase is extracted thrice with DCM. The combined organic layers are washed with brine then dried over MgSO$_4$, filtered and concentrated under reduced pressure to give 4-bromo-2-(chloromethyl)-5-cyclopropylthiazole (2929 mg) as a brown oil which is used in the next step without purification. LC-MS (acidic): $t_R$=0.94; [M+H]$^+$=253.84.

Step 5: Preparation of N-((4-bromo-5-cyclopropylthiazol-2-yl)methyl)formamide

To a solution of 4-bromo-2-(chloromethyl)-5-cyclopropylthiazole (2.93 g; 10.8 mmol) in DMF (50 ml) is added sodium difomylamide (1.54 g; 16.2 mmol). The resulting brown solution is stirred at RT for 4 h. The mixture is poured onto saturated aqueous NaHCO$_3$ solution and stirred for 1 h at RT before being extracted twice with ethyl acetate. The combined organic layers are washed with brine then dried over MgSO$_4$, filtered and concentrated under reduced pressure to give N-((4-bromo-5-cyclopropylthiazol-2-yl)methyl)formamide (3.01 g) as a brown oil which is used in the next step without purification. LC-MS (acidic): $t_R$=0.70; [M+H]$^+$= 262.89. $^1$H NMR (400 MHz, d$_6$-DMSO) δ: 8.84 (m, 1H), 8.16 (s, 1H), 4.49 (d, J=6.2 Hz, 2H), 2.01 (m, 1H), 1.10-1.14 (m, 2H), 0.63-0.68 (m, 2H).

Step 6: Preparation of 3-bromo-2-cyclopropylimidazo[5,1-b]thiazole

To a solution of N-((4-bromo-5-cyclopropylthiazol-2-yl)methyl)formamide (3010 mg, 10.3 mmol) in toluene (60 ml) is added POCl$_3$ (1740 mg, 11.3 mmol) and the resulting mixture is stirred at 70° C. for 1 h. After cooling, the mixture is poured slowly onto saturated aqueous NaHCO$_3$ solution and extracted twice with ethyle acetate. The combined organic extracts are washed with brine, dried over MgSO$_4$, filtered and concentrated under reduced pressure. Purification by FC (silicagel, Hept/EtOAc) gives 1980 mg of 3-bromo-2-cyclopropylimidazo[5,1-b]thiazole as a brown oil. LC-MS (acidic): $t_R$=0.54; [M+H]$^+$=242.77. $^1$H NMR (400 MHz, d$_6$-DMSO) δ: 8.13 (s, 1H), 7.14 (s, 1H), 2.06 (m, 1H), 1.07-1.12 (m, 2H), 0.75 (m, 2H).

Step 7: Preparation of rac-(2-cyclopropyl-imidazo [5,1-b]thiazol-3-yl)-(1-isopropyl-1H-pyrazol-4-yl)-methanol (Example 188)

To a solution of 3-bromo-2-cyclopropylimidazo[5,1-b]thiazole (50 mg; 0.21 mmol) in THF (2 ml) is added n-BuLi (2.5M in hexanes; 23 ml; 0.59 mmol). After 30 min, 1-isopropyl-1H-pyrazole-4-carbaldehyde (81 mg, 0.59 mmol) in THF (1 ml) is added dropwise and the mixture is stirred for 1 h while gradually warming up to RT. Water and sat. aq. NH$_4$Cl are added, and the mixture extracted with CH$_2$Cl$_2$ (2×). The combined organic extracts are washed with brine, dried (MgSO$_4$), filtered and concentrated under reduced pressure. The crude residue is purified by prepHPLC to give 17 mg of rac-(2-cyclopropyl-imidazo[5,1-b]thiazol-3-yl)-(1-isopropyl-1H-pyrazol-4-yl)-methanol. LC-MS (QC): $t_R$=0.485, [M+H]$^+$=303.2.

Example 189: rac-(1-Cyclopentyl-1H-pyrazol-4-yl)-(2-cyclopropyl-imidazo[5,1-b]thiazol-3-yl)-methanol Example 189 is prepared in analogy to the description of the preparation of example 188. LC-MS (QC): $t_R$=0.576, [M+H]$^+$=329.2.

Example 190: rac-(2-Cyclopropyl-imidazo[5,1-b]thiazol-3-yl)-(4-phenyl-bicyclo[2.1.1]hex-1-yl)-methanol Example 190 is prepared in analogy to the description of the preparation of example 188 using 4-phenylbicyclo[2.1.1]hexane-1-carbaldehyde (made from 4-phenylbicyclo[2.1.1]hexane-1-carboxylic acid via reduction with LAH in Et$_2$O followed by oxidation using Dess-Martin periodinane in CH$_2$Cl$_2$). LC-MS (QC): $t_R$=0.809; [M+H]$^+$=351.1.

Example 191: rac-(2-Cycclopropyl-imidazo[5,1-b]thiazol-3-yl)-(3-phenyl-bicyclo[1.1.1]pent-1-yl)-methanol Example 191 is prepared in analogy to the description of the preparation of example 188 using 3-phenylbicyclo[1.1.1]pentane-1-carbaldehyde (made from 3-phenylbicyclo[1.1.1]pentane-1-carboxylic acid via reduction with LAH in Et$_2$O followed by oxidation using Dess-Martin periodinane in CH$_2$Cl$_2$). LC-MS (QC): $t_R$=0.774; [M+H]$^+$=337.2.

Example 96: rac-Cyclohexyl-(2-ethyl-imidazo[5,1-b]thiazol-3-yl)-methanol

Step 1: Preparation of ethyl 2-amino-3-oxopentanoate hydrochloride

To a solution of ethyl isocyanoacetate (2.8 ml, 25.1 mmol) in DMF (25 ml) is added DBU (5.75 ml, 37.7 mmol) followed by propionic anhydride (4.3 ml, 32.5 mmol). The resulting dark brown solution is stirred at 80° C. for 4 h. The mixture is cooled down to RT, poured into water (150 ml) and extracted with EtOAc (3×). The combined organic extracts are washed with water, dried over MgSO$_4$, filtered and concentrated under reduced pressure. The crude residue is purified by FC (siliga gel, Hept/EtOAc) to give 3.767 g of ethyl 5-ethyloxazole-4-carboxylate as a pale yellow oil. LC-MS (acidic): $t_R$=0.72, [M+H]$^+$=170.08. $^1$H NMR (500 MHz, CDCl$_3$) δ: 7.77 (s, 1H), 4.39 (q, J=7.1 Hz, 2H), 3.09 (q, J=7.6 Hz, 2H), 1.41 (t, J=7.1 Hz, 3H), 1.29 (t, J=7.6 Hz, 3H). To a solution of ethyl 5-ethyloxazole-4-carboxylate (1.960 g, 11.6 mmol) in MeOH (33.6 ml) is added 6 N HCl (5.8 ml) and the reaction mixture is stirred at 50° C. until completion of the reaction. MeOH is removed under reduced pressure. To the residue is added water (11.6 ml) and the acidic solution is washed with Et$_2$O (11.6 ml). The aq layer is treated with activated charcoal and then concentrated under reduced pressure. The residue is redissolved in MeOH, the mixture concentrated under reduced pressure, and the process is repeated 5 times in order to give 2.500 g of ethyl 2-amino-3-oxopentanoate hydrochloride as a pale yellow solid. LC-MS (acidic): $t_R$=0.32, [M+H]$^+$=160.12.

Step 2: Preparation of ethyl 2-(2-((tert-butoxycarbonyl)amino)acetamido)-3-oxopentanoate According to the procedure described for the preparation of Example 1/Step 2 but using ethyl 2-amino-3-oxopentanoate hydrochloride as starting material, 2.71 g of ethyl 2-(2-((tert-butoxycarbonyl)amino)acetamido)-3-oxopentanoate are obtained. LC-MS (acidic): $t_R$=0.77; [M+H]$^+$=317.13.

Step 3: Preparation of ethyl 2-(((tert-butoxycarbonyl)amino)methyl)-5-ethylthiazole-4-carboxylate According to the procedure described for the preparation of Example 1/Step 3 but using ethyl 2-(2-((tert-butoxycarbonyl)amino)acetamido)-3-oxopentanoate as starting material, 2.60 g of ethyl 2-(((tert-butoxycarbonyl)amino)methyl)-5-ethylthiazole-4-carboxylate. LC-MS (acidic): $t_R$=0.90; [M+H]$^+$=315.11.

Step 4: Preparation of ethyl 5-ethyl-2-(formamidomethyl)thiazole-4-carboxylate

According to the procedure described for the preparation of Example 1/Step 4 but using ethyl 2-(((tert-butoxycarbonyl)amino)methyl)-5-ethylthiazole-4-carboxylate as starting material, 2.060 g of ethyl 5-ethyl-2-(formamidomethyl)thiazole-4-carboxylate are obtained. LC-MS (acidic): $t_R$=0.64; [M+H]$^+$=243.04.

Step 5: Preparation of ethyl 2-ethylimidazo[5,1-b]thiazole-3-carboxylate

According to the procedure described for the preparation of Example 1/Step 5 but using ethyl 5-ethyl-2-(formamidomethyl)thiazole-4-carboxylate as starting material, 1.140 g of ethyl 2-ethylimidazo[5,1-b]thiazole-3-carboxylate are obtained. LC-MS (acidic): $t_R$=0.57; [M+H]$^+$=225.01.

Step 6: Preparation of 2-ethyl-N-methoxy-N-methylimidazo[5,1-b]thiazole-3-carboxamide Step 6.1: Ester hydrolysis: The product form step 5, ethyl 2-ethylimidazo[5,1-b]thiazole-3-carboxylate (1.114 g; 5.08 mmol) is dissolved in THF (11.1 ml) and water (5.5 ml). LiOH monohydrate (259 mg; 6.10 mmol) is added and the mixture stirred at RT for 1 hour. The mixture is evaporated to dryness under reduced pressure.
Step 6.2: The residue from step 6.1 is dissolved in DMF (16.5 ml). DIPEA (2.61 ml; 15.20 mmol), HATU (2.319 g; 6.10 mmol) and N,O-dimethylhydroxylamine hydrochloride (607 mg; 6.10 mmol) are added and the mixture is stirred at RT for 3 h. The reaction mixture is concentrated under reduced pressure and the residue is purified by preparative HPLC (basic conditions) to give 969 mg of 2-ethyl-N-methoxy-N-methylimidazo[5,1-b]thiazole-3-carboxamide. LC-MS (acidic): $t_R$=0.48; [M+H]$^+$=240.08.

Step 7: Preparation of 2-ethylimidazo[5,1-b]thiazole-3-carbaldehyde

To an ice-cold solution of the product from Step 6.2, 2-ethyl-N-methoxy-N-methylimidazo[5,1-b]thiazole-3-carboxamide (407 mg; 1.70 mmol) in THF (10 ml) is added a solution of DIBALH (1 M in toluene, 1.7 ml, 1.70 mmol). The reaction mixture is stirred at 0° C. for 1 h, treated with more DIBALH (1 M in toluene, 0.85 ml, 0.85 mmol), and further stirred at 0° C. for 1 h. A sat. aq. NH$_4$Cl solution is added and the product is extracted with EtOAc (3×). The combined org. extracts are dried over MgSO$_4$, filtered and concentrated under reduced pressure to give 300 mg of 2-ethylimidazo[5,1-b]thiazole-3-carbaldehyde as a yellow solid. LC-MS (acidic): $t_R$=0.41; [M+H]$^+$=181.19.

Step 8: Preparation of rac-cyclohexyl-(2-ethyl-imidazo[5,1-b]thiazol-3-yl)-methanol (Example 96)

According to the procedure described for preparation of example 3/step 8 but using product from step 7, 2-ethylimidazo[5,1-b]thiazole-3-carbaldehyde and cyclohexylmagnesium bromide as starting materials, 30 mg of rac-cyclohexyl-(2-ethyl-imidazo[5,1-b]thiazol-3-yl)-methanol are obtained. LC-MS (QC): $t_R$=0.640; [M+H]$^+$=265.2.

Example 96a: (S)-Cyclohexyl-(2-ethyl-imidazo[5,1-b]thiazol-3-yl)-methanol

Separation of the enantiomers on chiral stationary phase:
Method: Column: ChiralPak IC 30×250 mm, 5 μM; Detector Settings: UV-Vis-1; 273 nM; Eluent: 65% CO$_2$ and 35% EtOH; Flow: 160 ml/min, BPR: 100 bar; Temperature: 40° C. Injection volume: 1500 μl. 24 mg of the racemate are separated by the method described above to give 9.1 mg of (R)-Cyclohexyl-(2-ethyl-imidazo[5,1-b]thiazol-3-yl)-methanol and 8.5 mg of (S)-Cyclohexyl-(2-ethyl-imidazo[5,1-b]thiazol-3-yl)-methanol. LC-MS (QC): $t_R$=0.640; [M+H]$^+$=265.2.

Example 100: rac-2-Cyclohexyl-1-(2-ethyl-imidazo[5,1-b]thiazol-3-yl)-ethanol

Example 100 is prepared in analogy to the description of the preparation of example 96. LC-MS (QC): $t_R$=0.728; [M+H]$^+$=279.2.

Example 100a: (S)-2-Cyclohexyl-1-(2-ethyl-imidazo[5,1-b]thiazol-3-yl)-ethanol

Separation of the enantiomers on chiral stationary phase:
Method: Column: ChiralCel OD-H, 30×250 mm, 5 μM; Detector Settings: UV-Vis-1; 211 nM; Eluent: 80% CO$_2$ and 20% (EtOH, 0.1% DEA); Flow: 160 ml/min, BPR: 100 bar; Temperature: 40° C. Injection volume: 2000 μl. 30 mg of the racemate are separated by the method described above to give 11 mg of (S)-2-Cyclohexyl-1-(2-ethyl-imidazo[5,1-b]thiazol-3-yl)-ethanol. LC-MS (QC): $t_R$=0.727; [M+H]$^+$=279.2.

Example 100b: (R)-2-Cyclohexyl-1-(2-ethyl-imidazo[5,1-b]thiazol-3-yl)-ethanol

According to the method described above (Example 100a), 13 mg of (R)-2-Cyclohexyl-1-(2-ethyl-imidazo[5,1-b]thiazol-3-yl)-ethanol are obtained. LC-MS (QC): $t_R$=0.728; [M+H]$^+$=279.2.

Examples 172, 175-176, 178-180 are prepared in analogy to the description of the preparation of example 96:

Example 172: rac-(2-Ethyl-imidazo[5,1-b]thiazol-3-yl)-(1-methyl-cyclopentyl)-methanol LC-MS (QC): $t_R$=0.631; [M+H]$^+$=265.2.

Example 175: rac-(2-Ethyl-imidazo[5,1-b]thiazol-3-yl)-(1-methyl-cyclohexyl)-methanol LC-MS (QC): $t_R$=0.697; [M+H]$^+$=279.2.

Example 176: rac-(2-Ethyl-imidazo[5,1-b]thiazol-3-yl)-phenyl-methanol

LC-MS (QC): $t_R$=0.529; [M+H]$^+$=259.1.

Example 178: rac-2-(4,4-Dimethyl-cyclohexyl)-1-(2-ethyl-imidazo[5,1-b]thiazol-3-yl)-ethanol LC-MS (QC): $t_R$=0.851; [M+H]$^+$=307.3.

Example 179: rac-2-Cyclopentyl-1-(2-ethyl-imidazo[5,1-b]thiazol-3-yl)-ethanol LC-MS (QC): $t_R$=0.655; [M+H]$^+$=265.2.

Example 180: rac-(3,3-Dimethyl-cyclobutyl)-(2-ethyl-imidazo[5,1-b]thiazol-3-yl)-methanol LC-MS (QC): $t_R$=0.654; [M+H]$^+$=265.2.

Example 107: 1-(2-Methyl-imidazo[5,1-b]thiazol-3-yl)-2-(3-phenyl-cyclopentyl)-ethanol Example 107 is prepared in analogy to the description of the preparation of example 5. LC-MS (QC): $t_R$=0.770; [M+H]$^+$=327.2.

Example 109: rac-(3,3-Dimethyl-cyclobutyl)-(2-methyl-imidazo[5,1-b]thiazol-3-yl)-methanol Example 109 is prepared in analogy to the description of the preparation of example 5. LC-MS (QC): $t_R$=0.578; [M+H]$^+$=251.2.

Example 113: rac-Cyclopentyl-(2-methyl-imidazo[5,1-b]thiazol-3-yl)-methanol

Example 113 is prepared in analogy to the description of the preparation of example 5. LC-MS (QC): $t_R$=0.493; [M+H]$^+$=237.1.

Example 140: rac-(1-Methyl-cyclopentyl)-(2-methyl-imidazo[5,1-b]thiazol-3-yl)-methanol Example 140 is prepared in analogy to the description of the preparation of example 5. LC-MS (QC): $t_R$=0.557; [M+H]$^+$=251.1.

Example 140a: (S)-(1-Methyl-cyclopentyl)-(2-methyl-imidazo[5,1-b]thiazol-3-yl)-methanol Separation of the enantiomers on chiral stationary phase:
Method: Column: ChiralCel OD-H 30×250 mm, 5 µM; Detector Settings: UV-Vis-1; 273 nM; Eluent: 75% CO$_2$ and 25% EtOH; Flow: 160.00 ml/min; BPR: 100 bar; Temperature: 40° C. Injection volume: 3000 µl.

19 mg of the racemate are separated by the method described above to give 8 mg of (S)-(1-Methyl-cyclopentyl)-(2-methyl-imidazo[5,1-b]thiazol-3-yl)-methanol and 7 mg of its enantiomer. LC-MS (QC): $t_R$=0.558; [M+H]$^+$=251.2.

Example 141: (3,3-Dimethyl-cyclopentyl)-(2-methyl-imidazo[5,1-b]thiazol-3-yl)-methanol Example 141 is prepared in analogy to the description of the preparation of example 5. LC-MS (QC): $t_R$=0.636; [M+H]$^+$=265.0.

Example 158: rac-1-(2-Methyl-imidazo[5,1-b]thiazol-3-yl)-3-phenyl-prop-2-yn-1-ol To a solution of phenylacetylene (62.5 mg; 0.6 mmol) in THF (1 ml) at −78° C. is added n-BuLi (2 M in hexanes; 0.25 ml; 0.5 mmol). The reaction mixture is stirred at this temperature for 45 min. A suspension of the product of example 5/step 7, 2-methylimidazo[5,1-b]thiazole-3-carbaldehyde (83.1 mg; 0.5 mmol), in THF (3 ml) is then added and the mixture gradually warmed up to ca. RT and stirred until completion of the reaction. Saturated aqueous NH4Cl solution is added, followed by water, and the mixture is extracted with EtOAc (3×). The combined organic extracts are dried (MgSO$_4$), filtered and concentrated under reduced pressure. Purification by prepHPLC to give 62 mg of rac-1-(2-Methyl-imidazo[5,1-b]thiazol-3-yl)-3-phenyl-prop-2-yn-1-ol. LC-MS (QC): $t_R$=0.570; [M+H]$^+$=269.1.

Example 162: rac-(2-Methyl-imidazo[5,1-b]thiazol-3-yl)-phenyl-methanol

Example 162 is prepared in analogy to the description of the preparation of example 5. LC-MS (QC): $t_R$=0.450; [M+H]$^+$=245.1.

Examples 167 and 168: rac-(S*)-(2-Methyl-imidazo[5,1-b]thiazol-3-yl)-((1S*,2S*)-2-phenyl-cyclopropyl)-methanol and rac-(R*)-(2-Methyl-imidazo[5,1-b]thiazol-3-yl)-((1S*,2S*)-2-phenyl-cyclopropyl)-methanol

Step 1: Preparation of (4-bromo-5-methylthiazol-2-yl)methanol

To a solution of 4-bromo-5-methylthiazole-2-carbaldehyde (7.74 g; 36.1 mmol) in EtOH (100 ml) is added NaBH$_4$ (1.00 g; 26.4 mmol) and the resulting mixture is stirred at RT for 1 h. Water is added and the resulting aqueous phase is extracted twice with DCM. The combined organic layers are washed with saturated aqueous NaHCO$_3$ solution and brine then dried over MgSO$_4$, filtered and concentrated under reduced pressure to give (4-bromo-5-methylthiazol-2-yl)methanol (7.06 g) as a yellow oil which is used in the next step without purification. LC-MS (acidic): $t_R$=0.60; [M+H]$^+$= 207.92.

Step 2: Preparation of 4-bromo-2-(chloromethyl)-5-methylthiazole

To a solution of (4-bromo-5-methylthiazol-2-yl)methanol (7.06 g; 26.8 mmol) in DCM (100 ml) is added thionyl chloride (6.38 g; 53.6 mmol) and the resulting mixture is stirred at RT for 1 h. The mixture is poured onto saturated aqueous NaHCO$_3$ solution and the aqueous phase is extracted thrice with DCM. The combined organic layers are washed with brine then dried over MgSO$_4$, filtered and concentrated under reduced pressure to give 6850 mg of 4-bromo-2-(chloromethyl)-5-methylthiazole as a brown oil which is used in the next step without further purification. LC-MS (acidic): $t_R$=0.85; [M+H]$^+$=225.87.

Step 3: Preparation of N-((4-bromo-5-methylthiazol-2-yl)methyl)formamide

To a solution of 4-bromo-2-(chloromethyl)-5-methylthiazole (6850 mg; 25.1 mmol) in DMF (100 ml) is added sodium difomylamide (2.62 g; 27.6 mmol). The resulting brown solution is stirred at RT for 3 h. The mixture is poured onto saturated aqueous NaHCO$_3$ solution and stirred for 0.5 h at RT before being extracted twice with ethyl acetate. The combined organic layers are washed with brine then dried over MgSO$_4$, filtered and concentrated under reduced pressure to give 6.05 g of N-((4-bromo-5-methylthiazol-2-yl)methyl)formamide as a brown solid which is used without purification in the next step. LC-MS (acidic): $t_R$=0.59; [M+H]$^+$=234.81. $^1$H NMR (400 MHz, d$_6$-DMSO) δ8.87 (s, 1H), 8.17 (s, 1H), 4.51 (d, J=6.2 Hz, 2H), 2.51 (s, 3H).

Step 4: Preparation of 3-bromo-2-methylimidazo[5,1-b]thiazole

To a solution of N-((4-bromo-5-methylthiazol-2-yl)methyl)formamide (6.05 g; 22.1 mmol) in toluene (120 ml) is added POCl$_3$ (3.73 g; 11.3 mmol) and the resulting mixture is stirred at 70° C. for 3 h. After cooling, the mixture is poured slowly onto saturated aqueous NaHCO$_3$ solution and extracted twice with ethyle acetate. The combined organic extracts are washed with brine, dried over MgSO$_4$, filtered and concentrated under reduced pressure. The crude residue is triturated in Et2O to give 3.68 g of 3-bromo-2-methylimidazo[5,1-b]thiazole as a light brown solid. LC-MS (acidic): $t_R$=0.44; [M+H]$^+$=216.92. $^1$H NMR (400 MHz, d$_6$-DMSO) δ 9.54 (s, 1H), 7.76 (d, J=0.9 Hz, 1H), 2.41 (s, 3H).

Step 5: Preparation of rac-(S*)-(2-methyl-imidazo[5,1-b]thiazol-3-yl)-((1S*,2S*)-2-phenyl-cyclopropyl)-methanol and rac-(R*)-(2-methyl-imidazo[5,1-b]thiazol-3-yl)-((1S*,2S*)-2-phenyl-cyclopropyl)-methanol (Examples 167 and 168)

To a solution of 3-bromo-2-methylimidazo[5,1-b]thiazole (50 mg; 0.23 mmol) in THF (3 ml) is added n-BuLi (1.6M in hexanes; 0.719 ml; 1.15 mmol). After 30 min, 2-phenyl-cyclopropane-1-carbaldehyde (168 mg, 1.15 mmol) in THF (1 ml) is added dropwise and the mixture is stirred for 1 h while gradually warming up to RT. Water is added, and the mixture extracted with CH$_2$CO$_2$ (2×). The combined organc extracts are washed with brine, dried (MgSO$_4$), filtered and concentrated under reduced pressure. The crude residue is purified by prepHPLC to give 9.8 mg and 1 mg of each diastereoisomer.

Example 167

LC-MS (QC): $t_R$=0.574; [M+H]$^+$=285.2.

Example 168

LC-MS (QC): $t_R$=0.594; [M+H]$^+$=285.2.

Example 169: rac-(2-Methyl-imidazo[5,1-b]thiazol-3-yl)-(1-phenyl-piperidin-4-yl)-methanol Example 169 is prepared in analogy to the description of the preparation of example 167. LC-MS (QC): $t_R$=0.398; [M+H]$^+$=328.0.

Example 174: rac-(1-Methyl-cyclohexyl)-(2-methyl-imidazo[5,1-b]thiazol-3-yl)-methanol Example 174 is prepared in analogy to the description of the preparation of example 5. LC-MS (QC): $t_R$=0.620; [M+H]$^+$=265.2.

Example 177: rac-2-(4,4-Dimethyl-cyclohexyl)-1-(2-methyl-imidazo[5,1-b]thiazol-3-yl)-ethanol Example 177 is prepared in analogy to the description of the preparation of example 5. LC-MS (QC): $t_R$=0.785; [M+H]$^+$=293.2.

Example 183: rac-2-Cyclopentyl-1-(2-methyl-imidazo[5,1-b]thiazol-3-yl)-ethanol Example 183 is prepared in analogy to the description of the preparation of example 5. LC-MS (QC): $t_R$=0.578; [M+H]$^+$=251.1.

Example 129: rac-2-Cyclohexyl-1-(2-propyl-imidazo[5,1-b]thiazol-3-yl)-ethanol

Step 1: Preparation of ethyl-2-amino-3-oxohexanoate hydrochloride

According to the procedure described for the preparation of example 96/step 1 but using butyric anhydride as starting material, 3.73 g of ethyl-2-amino-3-oxohexanoate hydrochloride are obtained. LC-MS (acidic): $t_R$=0.42; [M+H]$^+$=174.2.

Step 2: Preparation of ethyl-2-(2-((tert-butoxycarbonyl)amino)acetamido)-3-oxohexanoate According to the procedure described for the preparation of example 1/step 2 but using ethyl-2-amino-3-oxohexanoate hydrochloride as starting material, 5.63 g of ethyl-2-(2-((tert-butoxycarbonyl)amino)acetamido)-3-oxohexanoate are obtained. LC-MS (acidic): $t_R$=0.84; [M+H]$^+$=331.14. $^1$H NMR (500 MHz, DMSO) δ: 8.50-8.55 (m, 1H), 7.02-7.14 (m, 1H), 5.17-5.26 (m, 1H), 4.12-4.23 (m, 2H), 3.63 (m, 2H), 2.58-2.66 (m, 2H), 1.49 (m, 2H), 1.38 (m, 9H), 1.21 (t, J=7.1 Hz, 3H), 0.84 (m, 3H)

Step 3: Preparation of ethyl 2-(((tert-butoxycarbonyl)amino)methyl)-5-propylthiazole-4-carboxylate According to the procedure described for the preparation of example 1/step 3 but using ethyl-2-(2-((tert-butoxycarbonyl)amino)acetamido)-3-oxohexanoate as starting material, 4.59 g of ethyl 2-(((tert-butoxycarbonyl)amino)methyl)-5-propylthiazole-4-carboxylate are obtained. LC-MS (acidic): $t_R$=0.95; [M+H]$^+$=329.07. $^1$H NMR (500 MHz, DMSO) δ: 4.31-4.39 (m, 2H), 4.24-4.29 (m, 2H), 3.12 (t, J=7.5 Hz, 2H), 1.55-1.68 (m, 2H), 1.37-1.46 (m, 9H), 1.26-1.31 (m, 3H), 0.90-0.97 (m, 3H).

Step 4: Preparation of ethyl 2-(formamidomethyl)-5-propylthiazole-4-carboxylate According to the procedure described for the preparation of example 1/step 4 but using ethyl 2-(((tert-butoxycarbonyl)amino)methyl)-5-propylthiazole-4-carboxylate as starting material, 3.06 g of ethyl 2-(formamidomethyl)-5-propylthiazole-4-carboxylate are obtained. LC-MS (acidic): $t_R$=0.71; [M+H]$^+$=257.09. $^1$H NMR (500 MHz, DMSO) δ: 8.90 (t, J=5.7 Hz, 1H), 8.18 (d, J=1.3 Hz, 1H), 4.52 (m, 2H), 4.25-4.30 (m, 2H), 3.07-3.18 (m, 2H), 1.55-1.67 (m, 2H), 1.26-1.31 (m, 3H), 0.85-1.00 (m, 3H).

Step 5: Preparation of ethyl 2-propylimidazo[5,1-b]thiazole-3-carboxylate

According to the procedure described for the preparation of example 1/step 5 but using ethyl 2-(formamidomethyl)-5-propylthiazole-4-carboxylate as starting material, 1.29 g of ethyl 2-propylimidazo[5,1-b]thiazole-3-carboxylate are obtained. LC-MS (acidic): $t_R$=0.64; [M+H]$^+$=239.09.

Step 6: Preparation of N-methoxy-N-methyl-2-propylimidazo[5,1-b]thiazole-3-carboxamide According to the procedure described for the preparation of example 96/step 6.1 and 6.2 but using ethyl 2-propylimidazo[5,1-b]thiazole-3-carboxylate as starting material, 654 mg of N-methoxy-N-methyl-2-propylimidazo[5,1-b]thiazole-3-carboxamide are obtained. LC-MS (acidic): $t_R$=0.54; [M+H]$^+$=254.11.

Step 7: Preparation of 2-propylimidazo[5,1-b]thiazole-3-carbaldehyde

According to the procedure described for the preparation of example 96/step 7 but using N-methoxy-N-methyl-2-propylimidazo[5,1-b]thiazole-3-carboxamide as starting material, 453 mg of 2-propylimidazo[5,1-b]thiazole-3-carbaldehyde are obtained. LC-MS (acidic): $t_R$=0.46; [M+H]$^+$=195.13. $^1$H NMR (500 MHz, DMSO) δ: 10.04 (s, 1H), 8.59 (s, 1H), 7.19 (s, 1H), 3.19 (t, J=7.4 Hz, 2H), 1.74 (d, J=7.4 Hz, 2H), 0.99 (t, J=7.3 Hz, 3H).

Step 8: Preparation of rac-2-Cyclohexyl-1-(2-propyl-imidazo[5,1-b]thiazol-3-yl)-ethanol (Example 129)

According to the procedure described for preparation of example 3/step 8 but using product from step 7, 2-propylimidazo[5,1-b]thiazole-3-carbaldehyde and (cyclohexylmethyl)magnesium bromide as starting materials, 29 mg of rac-2-Cyclohexyl-1-(2-propyl-imidazo[5,1-b]thiazol-3-yl)-ethanol are obtained. LC-MS (QC): $t_R$=0.800; [M+H]$^+$=293.2.

Example 130: rac-Cyclohexyl-(2-propyl-imidazo[5,1-b]thiazol-3-yl)-methanol

Example 130 is prepared in analogy to the description of the preparation of example 129. LC-MS (QC): $t_R$=0.721; [M+H]$^+$=279.2.

Example 181: rac-Cyclohexyl-[2-(3-fluoro-phenyl)-imidazo[5,1-b]thiazol-3-yl]-methanol

Step 1: Preparation of methyl 5-bromo-2-(bromomethyl)thiazole-4-carboxylate

To a solution of methyl 5-bromo-2-methyl-1,3-thiazole-4-carboxylate (19.97 g; 84.6 mmol) in trifluorotoluene (400 ml) is added at rt under argon NBS (7.529 g; 42.3 mmol) and AIBN (4.168 g; 25.4 mmol). The reaction mixture is stirred at 85° C. for 3 h. More NBS and AIBN are added until the conversion is complete. The mixture is cooled to RT, filtered, washed with toluene and concentrated under reduced pressure. Purification by FC (Silicagel; Hept/EtOAc) gives 6.78 g of methyl 5-bromo-2-(bromomethyl)thiazole-4-carboxylate. LC-MS (acidic): $t_R$=0.91; [M+H]$^+$=313.87.

Step 2: Preparation of methyl 5-bromo-2-(formamidomethyl)thiazole-4-carboxylate To a solution of the product from step 1, 5-bromo-2-(bromomethyl)thiazole-4-carboxylate (6.78 g; 21.5 mmol) in DMF (50 ml) is added sodium diformylamide (2.25 g; 23.7 mmol). The reaction mixture is stirred at RT for 2 h. A sat. aq. NaHCO$_3$ solution is then added to the reaction mixture and is stirred overnight at rt. The mixture is extracted with EtOAc (3×) and the combined organic extracts are washed with brine, dried over MgSO$_4$, filtered and concentrated under reduced pressure to give 5.74 g of methyl 5-bromo-2-(formamidomethyl)thiazole-4-carboxylate LC-MS (acidic): $t_R$=0.57; [M+H]$^+$=278.84.

Step 3: Preparation of methyl 2-bromoimidazo[5,1-b]thiazole-3-carboxylate

To a solution of the product from step 2, methyl 5-bromo-2-(formamidomethyl)thiazole-4-carboxylate (5.74 g; 20.6 mmol) is added POCl$_3$ (1.94 ml, 20.6 mmol). The reaction mixture is stirred at 60° C. for 1 h. A sat. aq. NaHCO$_3$ solution is added to the reaction mixture until pH 8 is obtained. The mixture is then extracted with DCM (3×) and the combined organic extracts are washed with brine, dried over MgSO$_4$, filtered and concentrated under reduced pressure. Purification by FC (Silicagel; Hept/EtOAc) gives 1.779 g of methyl 2-bromoimidazo[5,1-b]thiazole-3-carboxylate. LC-MS (acidic): $t_R$=0.51; [M+H]$^+$=260.77. $^1$H NMR (400 MHz, d$_6$-DMSO) δ: 8.48 (d, J=0.6 Hz, 1H), 7.14 (d, J=0.6 Hz, 1H), 3.96 (s, 3H).

Step 4: Preparation of (2-bromoimidazo[5,1-b]thiazol-3-yl)methanol

To a solution of the product from step 3, methyl 2-bromoimidazo[5,1-b]thiazole-3-carboxylate (1.779 g; 6.81 mmol) in EtOH (80 ml) is added NaBH$_4$ (1 g; 26.4 mmol) at rt under argon. The reaction mixture is stirred 24 h at RT. The reaction mixture is concentrated under reduced pressure, diluted with DCM and quenched carefully with H$_2$O and sat. aq. NH$_4$Cl. When the gas evolution ceases the mixture is extracted with DCM (3×) and the combined organic extracts are dried over MgSO$_4$, filtered and concentrated under reduced pressure to give 896 mg of (2-bromoimidazo[5,1-b]thiazol-3-yl)methanol. LC-MS (acidic): $t_R$=0.37; [M+H]$^+$=232.85.

Step 5: Preparation of 2-bromo-3-(((tert-butyldimethylsilyl)oxy)methyl)imidazo[5,1-b]thiazole To a cooled solution of the product from step 4, (2-bromoimidazo[5,1-b]thiazol-3-yl)methanol (896 mg; 3.84 mmol) in dry DCM (20 ml) is added tert-butyl(chloro)dimethylsilane (0.798 ml; 4.61 mmol) and imidazole (314 mg; 4.61 mmol). The reaction mixture is stirred at RT for 2 h. The reaction mixture is diluted with water and extracted with DCM (3×) and the combined organic extracts are washed with brine, dried over MgSO$_4$, filtered and concentrated under reduced pressure. Purification by FC (Silicagel; Hept/EtOAc) gives 380 mg of 2-bromo-3-(((tert-butyldimethylsilyl)oxy)methyl)imidazo[5,1-b]thiazole. LC-MS (acidic): t$_R$=0.89; [M+H]$^+$=346.87. $^1$H NMR (400 MHz, d$_6$-DMSO) δ: 8.13 (s, 1H), 7.08 (s, 1H), 4.88 (s, 2H), 0.85 (s, 9H), 0.08 (s, 6H).

Step 6: Preparation of 3-((((tert-butyldimethylsilyl)oxy)methyl)-2-(3-fluorophenyl)imidazo[5,1-b]thiazole To a solution of the product from step 5, 2-bromo-3-(((tert-butyldimethylsilyl)oxy)methyl)imidazo[5,1-b]thiazole (150 mg; 0.432 mmol) in dioxane (5 ml) are added aq. 1.6 M Na$_2$CO$_3$ (3 ml), 3-fluorobenzeneboronic acid (125 mg; 0.864 mmol) and Pd(PPh$_3$)$_4$ (18 mg; 3.5 mol %). The reaction mixture is stirred at 90° C. for 2 h. The mixture is poured into water and extracted with DCM (2×). The combined organic extracts are dried (MgSO$_4$), filtered and concentrated under reduced pressure. Purification by FC (Silicagel; Hept/EtOAc) gives 146 mg of 3-(((tert-butyldimethylsilyl)oxy)methyl)-2-(3-fluorophenyl)imidazo[5,1-b]thiazole. LC-MS (acidic): t$_R$=0.95; [M+H]$^+$=362.97. $^1$H NMR (400 MHz, d$_6$-DMSO) δ: 8.21 (s, 1H), 7.60 (m, 1H), 7.35-7.43 (m, 3H), 7.15 (s, 1H), 4.90 (s, 2H), 0.81 (s, 9H), −0.02 (s, 6H).

Step 7: Preparation of (2-(3-fluorophenyl)imidazo[5,1-b]thiazol-3-yl)methanol

To a solution of the product from step 5, 3-(((tert-butyldimethylsilyl)oxy)methyl)-2-(3-fluorophenyl)imidazo[5,1-b]thiazole (146 mg; 0.403 mmol) in THF (2 ml) is added TBAF (1 M in THF, 0.604 ml, 0.604 mmol). The reaction mixture is stirred at RT for 20 min. The mixture is poured into saturated aq. NaHCO$_3$ and extracted with DCM (3×). The combined organic extracts are washed with brine, dried (MgSO$_4$), filtered and concentrated under reduced pressure to give 91 mg of (2-(3-fluorophenyl)imidazo[5,1-b]thiazol-3-yl)methanol. LC-MS (acidic): t$_R$=0.57; [M+H]$^+$= 248.97.

Step 8: Preparation of 2-(3-fluorophenyl)imidazo[5,1-b]thiazole-3-carbaldehyde

To an ice-cold solution of the product from Step 7, (2-(3-fluorophenyl)imidazo[5,1-b]thiazol-3-yl)methanol (45 mg; 0.181 mmol) in DCM (3 ml) is added Dess-Martin periodinane (119 mg; 0.281 mmol). The reaction mixture is stirred at RT for 2 hours. A sat. aq. NaHCO$_3$ solution (5 ml) is added followed by a sat. aq. Na$_2$S$_2$O$_3$ (5 ml) and the mixture stirred for 20 min. The mixture is then extracted with DCM (2×). The combined org. extracts are washed with brine, dried over MgSO$_4$, filtered and concentrated under reduced pressure to give 2-(3-fluorophenyl)imidazo[5,1-b]thiazole-3-carbaldehyde. LC-MS (acidic): t$_R$=0.60; [M+H]$^+$= 246.96. $^1$H NMR (400 MHz, d$_6$-DMSO) δ: 9.73 (s, 1H), 8.70 (s, 1H), 7.76-7.79 (m, 1H), 7.64-7.69 (m, 2H), 7.48-7.53 (m, 1H), 7.28 (s, 1H).

Step 9: Preparation of rac-cyclohexyl-[2-(3-fluorophenyl)-imidazo[5,1-b]thiazol-3-yl]-methanol (Example 181)

According to the procedure described for preparation of example 3/step 8 but using product from step 8, 2-(3-fluorophenyl)imidazo[5,1-b]thiazole-3-carbaldehyde and cyclohexylmagnesium bromide as starting materials, 11 mg of rac-cyclohexyl-[2-(3-fluoro-phenyl)-imidazo[5,1-b]thiazol-3-yl]-methanol are obtained. LC-MS (QC): t$_R$=0.869; [M+H]$^+$=331.2.

Example 128: rac-Cyclohexyl-[2-(4-methyl-thiophen-3-yl)-imidazo[5,1-b]thiazol-3-yl]-methanol Step 1: Preparation of 2-bromoimidazo[5,1-b]thiazole-3-carboxylic acid To a solution of the product from example 181/step 3, methyl 2-bromoimidazo[5,1-b]thiazole-3-carboxylate (4.09 g; 15.5 mmol) in THF (40 ml), is added LiOH 1 M (18.6 ml, 18.6 mmol). The suspension is stirred at RT for 2 hours. The mixture is acidified with aqueous HCl 1 M until pH 4, evaporated, and dried under high vacuum to give 4.9 g of 2-bromoimidazo[5,1-b]thiazole-3-carboxylic acid. LC-MS (acidic): t$_R$=0.34; [M+H]$^+$=246.80.

Step 2: Preparation of 2-bromo-N-methoxy-N-methylimidazo[5,1-b]thiazole-3-carboxamide To a solution of the product from step 1, 2-bromoimidazo[5,1-b]thiazole-3-carboxylic acid (4.9 g, 16.9 mmol) in CH$_2$Cl$_2$ (50 ml) and DMF (10 ml) are added at RT HATU (7.724 g, 20.3 mmol), DIPEA (3.48 ml, 20.3 mmol) and N,O-dimethylhydroxylamine hydrochloride (1.734 g, 17.8 mmol). The mixture is stirred at RT for 2 hours. The mixture is poured into a saturated aqueous NaHCO$_3$ solution and extracted with CH$_2$Cl$_2$ (3×). The combined organic layers are washed with brine, dried over MgSO$_4$, filtered and concentrated under reduced pressure. Purification by FC (Silicagel; Hept/EtOAc) gives 5.25 g of 2-bromo-N-methoxy-N-methylimidazo[5,1-b]thiazole-3-carboxamide. LC-MS (acidic): t$_R$=0.48; [M+H]$^+$=291.81.

Step 3: Preparation of N-methoxy-N-methyl-2-(5-methylthiophen-3-yl)imidazo[5,1-b]thiazole-3-carboxamide To a degassed solution of the product from step 2, 2-bromo-N-methoxy-N-methylimidazo[5,1-b]thiazole-3-carboxamide (225 mg, 0.582 mmol) in Na$_2$CO$_3$ 1.6 M (2.5 ml) and dioxane (7.5 ml) are added under argon (5-methylthiophen-3-yl)boronic acid (165 mg, 1.16 mol) and Pd(Ph$_3$)$_4$ (23.5 mg, 0.02 mmol). The mixture is stirred at 90° C. for 1 hour, then cooled to RT, poured into H$_2$O and extracted with CH$_2$Cl$_2$ (2×). The combined organic layers are washed with brine, dried over MgSO$_4$, filtered and concentrated under reduced pressure. Purification by FC (Silicagel; Hept/EtOAc) gives 93 mg of N-methoxy-N-methyl-2-(5-methylthiophen-3-yl)imidazo[5,1-b]thiazole-3-carboxamide. LC-MS (acidic): t$_R$=0.64; [M+H]$^+$=307.87.

Step 4: Preparation of 2-(4-methylthiophen-3-yl)imidazo[5,1-b]thiazole-3-carbaldehyde To a solution of the product from step 3, N-methoxy-N-methyl-2-(5-methylthiophen-3-yl)imidazo[5,1-b]thiazole-3-carboxamide (90 mg, 0.278 mmol) in THF (4 ml) is added dropwise at 0° C. diisobutylaluminium hydride solution 1 M in toluene (0.556 ml, 0.556 mmol). The mixture is allowed to warm up to RT and stirred for 1 hour. The mixture is quenched with a saturated aqueous NH$_4$Cl solution and extracted with CH$_2$Cl$_2$ (3×). The combined organic layers are dried over MgSO$_4$, filtered and concentrated under reduced pressure to give 41 mg of 2-(4-methylthiophen-3-yl)imidazo[5,1-b]thiazole-3-carbaldehyde. LC-MS (acidic): t$_R$=0.62; [M+H]$^+$=248.93.

Step 5: Preparation of rac-cyclohexyl-[2-(4-methyl-thiophen-3-yl)-imidazo[5,1-b]thiazol-3-yl]-methanol (Example 128)

According to the procedure described for preparation of example 3/step 8 but using product from step 4, 2-(4-methylthiophen-3-yl)imidazo[5,1-b]thiazole-3-carbaldehyde and cyclohexylmagnesium bromide as starting materials, 2 mg of rac-cyclohexyl-[2-(4-methyl-thiophen-3-yl)-imidazo[5,1-b]thiazol-3-yl]-methanol are obtained. LC-MS (QC): t$_R$=0.854; [M+H]$^+$=333.2.

Example 68: rac-Cyclohexyl-(2-vinyl-imidazo[5,1-b]thiazol-3-yl)-methanol

Step 1: Preparation of N-methoxy-N-methyl-2-vinylimidazo[5,1-b]thiazole-3-carboxamide According to the procedure described for the preparation of example 128/step 3 but using vinylboronic anhydride pyridine complex as starting material, 675 mg of N-methoxy-N-methyl-2-vinylimidazo[5,1-b]thiazole-3-carboxamide are obtained. LC-MS (acidic): t$_R$=0.49; [M+H]$^+$=238.30. $^1$H NMR (400 MHz, DMSO) δ: 8.12 (s, 1H), 7.09 (s, 1H), 6.84 (dd, J$_1$=10.9 Hz, J$_2$=17.1 Hz, 1H), 5.63 (d, J=17.2 Hz, 1H), 5.53 (d, J=10.9 Hz, 1 H), 3.60 (s, 3H), 3.37 (s, 3H).

Step 2: Preparation of 2-vinylimidazo[5,1-b]thiazole-3-carbaldehyde

According to the procedure described for the preparation of example 128/step 4 but using N-methoxy-N-methyl-2-vinylimidazo[5,1-b]thiazole-3-carboxamide as starting material, 126 mg of 2-vinylimidazo[5,1-b]thiazole-3-carbaldehyde are obtained. LC-MS (acidic): t$_R$=0.41; [M+H]$^+$=179.05.

Step 3: Preparation of rac-cyclohexyl-(2-vinyl-imidazo[5,1-b]thiazol-3-yl)-methanol (Example 68)

According to the procedure described for preparation of example 3/step 8 but using product from step 2, 2-vinylimidazo[5,1-b]thiazole-3-carbaldehyde and cyclohexylmagnesium bromide as starting materials, 2 mg of rac-cyclohexyl-(2-vinyl-imidazo[5,1-b]thiazol-3-yl)-methanol are obtained. LC-MS (QC): t$_R$=0.687; [M+H]$^+$=263.2.

Example 68a: (S)-Cyclohexyl-(2-vinyl-imidazo[5,1-b]thiazol-3-yl)-methanol

Separation of the enantiomers on chiral stationary phase:
Method: Column: ChiralPak IC 30×250 mm, 5 μM; Detector Settings: UV-Vis-1; 255 nM; Eluent: 60% CO$_2$ and 40% (EtOH, 0.1% DEA); Flow: 160.00 ml/min; BPR: 100 bar; Temperature: 40° C. Injection volume: 1800 μl.

16.2 mg of the racemate are separated by the method described above to give 3.8 mg of (R)-cyclohexyl-(2-vinyl-imidazo[5,1-b]thiazol-3-yl)-methanol and 4.1 mg of (S)-cyclohexyl-(2-vinyl-imidazo[5,1-b]thiazol-3-yl)-methanol LC-MS (QC): t$_R$=0.688; [M+H]$^+$=263.2.

Example 97: 2-Cyclohexyl-1-(2-vinyl-imidazo[5,1-b]thiazol-3-yl)-ethanol

Example 97 is prepared in analogy to the description of the preparation of example 68. LC-MS (QC): t$_R$=0.788; [M+H]$^+$=277.0.

Example 92: rac-Cyclohexyl-(2-phenyl-imidazo[5,1-b]thiazol-3-yl)-methanol

Step 1: Preparation of N-methoxy-N-methyl-2-phenylimidazo[5,1-b]thiazole-3-carboxamide According to the procedure described for the preparation of example 128/step 3 but using phenylboronic acid as starting material, 222 mg of N-methoxy-N-methyl-2-phenylimidazo[5,1-b]thiazole-3-carboxamide are obtained. LC-MS (acidic): t$_R$=0.62; [M+H]$^+$=288.03.

Step 2: Preparation of 2-phenylimidazo[5,1-b]thiazole-3-carbaldehyde

According to the procedure described for the preparation of example 128/step 4 but using N-methoxy-N-methyl-2-phenylimidazo[5,1-b]thiazole-3-carboxamide as starting material, 158 mg of 2-phenylimidazo[5,1-b]thiazole-3-carbaldehyde are obtained. LC-MS (acidic): t$_R$=0.58; [M+H]$^+$=229.00. $^1$H NMR (400 MHz, DMSO) δ: 9.72 (s, 1H), 8.69 (s, 1H), 7.80-7.82 (m, 2H), 7.63 (m, 3H), 7.27 (s, 1H).

Step 3: Preparation of rac-cyclohexyl-(2-phenyl-imidazo[5,1-b]thiazol-3-yl)-methanol (Example 92)

According to the procedure described for preparation of example 3/step 8 but using product from step 2, 2-phenylimidazo[5,1-b]thiazole-3-carbaldehyde and cyclohexylmagnesium bromide as starting materials, 12 mg of rac-cyclohexyl-(2-phenyl-imidazo[5,1-b]thiazol-3-yl)-methanol are obtained. LC-MS (QC): t$_R$=0.822; [M+H]$^+$=313.2.

Example 93: rac-2-Cyclohexyl-1-(2-phenyl-imidazo[5,1-b]thiazol-3-yl)-ethanol

Example 93 is prepared in analogy to the description of the preparation of example 92. LC-MS (QC): t$_R$=0.900; [M+H]$^+$=327.2.

Example 92a: (S)-Cyclohexyl-(2-phenyl-imidazo[5,1-b]thiazol-3-yl)-methanol
Separation of the enantiomers on chiral stationary phase:
Method: Column: ChiralPak IC 30×250 mm, 5 μM; Detector Settings: UV-Vis-1; 235 nM; Eluent: 60% CO$_2$ and 40% EtOH; Flow: 160.00 ml/min; BPR: 100 bar; Temperature: 40° C. Injection volume: 1500 μl.

8.3 mg of the racemate are separated by the method described above to give 3.4 mg of (R)-Cyclohexyl-(2-phenyl-imidazo[5,1-b]thiazol-3-yl)-methanol and 3.8 mg of (S)-cyclohexyl-(2-phenyl-imidazo[5,1-b]thiazol-3-yl)-methanol. LC-MS (QC): t$_R$=0.821; [M+H]$^+$=313.3.

Example 98: rac-Cyclohexyl-(2-isobutyl-imidazo[5,1-b]thiazol-3-yl)-methanol

Step 1: Preparation of ethyl 2-amino-5-methyl-3-oxohexanoate hydrochloride

According to the procedure described for the preparation of example 96/step 1 but using isovaleric anhydride as starting material, 2.08 g of ethyl 2-amino-5-methyl-3-oxohexanoate hydrochloride are obtained. LC-MS (acidic): $t_R$=0.50; [M+H]$^+$=188.22.

Step 2: Preparation of ethyl 2-(2-((tert-butoxycarbonyl)amino)acetamido)-5-methyl-3-oxohexanoate According to the procedure described for the preparation of example 1/step 2 but using ethyl 2-amino-5-methyl-3-oxohexanoate hydrochloride as starting material, 910 mg of ethyl 2-(2-((tert-butoxycarbonyl)amino)acetamido)-5-methyl-3-oxohexanoate are obtained. LC-MS (acidic): $t_R$=0.90; [M+H]$^+$=345.13.

Step 3: Preparation of ethyl 2-(((tert-butoxycarbonyl)amino)methyl)-5-isobutylthiazole-4-carboxylate According to the procedure described for the preparation of example 1/step 3 but using ethyl 2-(2-((tert-butoxycarbonyl)amino)acetamido)-5-methyl-3-oxohexanoate as starting material, 797 mg of ethyl 2-(((tert-butoxycarbonyl)amino)methyl)-5-isobutylthiazole-4-carboxylate are obtained. LC-MS (acidic): $t_R$=0.99; [M+H]$^+$=343.11.

Step 4: Preparation of ethyl 2-(formamidomethyl)-5-isobutylthiazole-4-carboxylate According to the procedure described for the preparation of example 1/step 4 but using ethyl 2-(((tert-butoxycarbonyl)amino)methyl)-5-isobutylthiazole-4-carboxylate as starting material, 768 mg of ethyl 2-(formamidomethyl)-5-isobutylthiazole-4-carboxylate are obtained. LC-MS (acidic): $t_R$=0.79; [M+H]$^+$=270.10.

Step 5: Preparation of ethyl 2-isobutylimidazo[5,1-b]thiazole-3-carboxylate

According to the procedure described for the preparation of example 1/step 5 but using ethyl 2-(formamidomethyl)-5-isobutylthiazole-4-carboxylate as starting material, 447 mg of ethyl 2-isobutylimidazo[5,1-b]thiazole-3-carboxylate are obtained. LC-MS (acidic): $t_R$=0.71; [M+H]$^+$=253.09.

Step 6: Preparation of 2-isobutyl-N-methoxy-N-methylimidazo[5,1-b]thiazole-3-carboxamide According to the procedure described for the preparation of example 96/step 6.1 and 6.2 but using ethyl 2-isobutyl-imidazo[5,1-b]thiazole-3-carboxylate as starting material, 201 mg of 2-isobutyl-N-methoxy-N-methylimidazo[5,1-b]thiazole-3-carboxamide are obtained. LC-MS (acidic): $t_R$=0.62; [M+H]$^+$=268.11. $^1$H NMR (500 MHz, CDCl$_3$) δ: 8.77 (s, 1H), 7.54 (s, 1H), 3.65 (s, 3H), 3.50 (s, 3H), 2.87 (d, J=7.4 Hz, 2H), 1.90-2.13 (m, 1H), 1.06 (d, J=6.6 Hz, 6H).

Step 7: Preparation of 2-isobutylimidazo[5,1-b]thiazole-3-carbaldehyde

According to the procedure described for the preparation of example 96/step 7 but using 2-isobutyl-N-methoxy-N-methylimidazo[5,1-b]thiazole-3-carboxamide as starting material, 156 mg of 2-isobutylimidazo[5,1-b]thiazole-3-carbaldehyde are obtained. LC-MS (acidic): $t_R$=0.54; [M+H]$^+$=209.01. $^1$H NMR (500 MHz, CDCl$_3$) δ: 9.96 (s, 1H), 8.76 (s, 1H), 7.17 (s, 1H), 2.99 (d, J=7.2 Hz, 2H), 1.91-2.13 (m, 1H), 1.09 (d, J=6.6 Hz, 6H).

Step 8: Preparation of rac-cyclohexyl-(2-isobutyl-imidazo[5,1-b]thiazol-3-yl)-methanol (Example 98)

According to the procedure described for preparation of example 3/step 8 but using product from step 7, 2-isobutyl-imidazo[5,1-b]thiazole-3-carbaldehyde and cyclohexymagnesium bromide as starting materials, 36 mg of rac-cyclohexyl-(2-isobutyl-imidazo[5,1-b]thiazol-3-yl)-methanol are obtained. LC-MS (QC): $t_R$=0.786; [M+H]$^+$=293.2.

Example 99: rac-2-Cyclohexyl-1-(2-isobutyl-imidazo[5,1-b]thiazol-3-yl)-ethanol

Example 99 is prepared in analogy to the description of the preparation of example 98. LC-MS (QC): $t_R$=0.864; [M+H]$^+$=307.1.

Example 157: rac-Cyclohexyl-(2-methoxymethyl-imidazo[5,1-b]thiazol-3-yl)-methanol Step 1: Preparation of methyl 2-diazo-4-methoxy-3-oxobutanoate Methyl 4-methoxyacetoacetate (0.709 ml, 5.31 mmol) is dissolved in dry toluene (10 ml) before triethylamine (0.795 ml, 5.71 mmol) is added. Under argon atmosphere, a solution of p-toluenesulfonyl azide 11-15% in toluene (7.5 ml) is added to the mixture dropwise at 0° C. The mixture is stirred at RT for 24 h. Heptane/CH$_2$Cl$_2$ 9:1 is added to the mixture to precipitate the salts. It is then filtered and washed with heptane. The filtrate is concentrated under reduced pressure. The crude is purified by FC (siliga gel, Hept/EtOAc) to get 607 mg of methyl 2-diazo-4-methoxy-3-oxobutanoate as a colorless oil. LC-MS (acidic): $t_R$=0.51, [M+H]$^+$=172.95. $^1$H NMR (400 MHz, CDCl$_3$) δ: 4.55 (s, 2H), 3.86 (s, 3H), 3.49 (s, 3H).

Step 2: Preparation of methyl 2-(2-((tert-butoxycarbonyl)amino)acetamido)-4-methoxy-3-oxobutanoate To a solution of product from step 1, methyl 2-diazo-4-methoxy-3-oxobutanoate (600 mg, 3.49 mmol) and Boc-Gly-NH$_2$ (664 mg, 3.66 mmol) in CH$_2$Cl$_2$ (11.5 ml) is added dirhodium tetraacetate (16.6 mg, 0.035 mmol). The mixture is then stirred 24 h at 40° C. under argon atmosphere. The mixture is diluted with water and extracted with CH$_2$Cl$_2$ (3×). The combined organic layers are dried over MgSO$_4$, filtered and concentrated under reduced pressure. The crude is purified by FC (siliga gel, Hept/EtOAc) to get 376 mg of methyl 2-(2-((tert-butoxycarbonyl)amino)acetamido)-4-methoxy-3-oxobutanoate as a purple sticky gum.

Step 3: Preparation of methyl 2-(formamidomethyl)-5-(methoxymethyl)thiazole-4-carboxylate To a solution of product from step 2, methyl 2-(2-((tert-butoxycarbonyl)amino)acetamido)-4-methoxy-3-oxobutanoate (376 mg, 1.18 mmol) in THF (5 ml) is added under argon atmosphere Lawesson's reagent (564 mg, 1.5 mmol). The mixture is stirred at 50° C. until completion of the reaction. The mixture is concentrated under reduced pressure and the crude residue is dissolved in ethyl formate (15 ml) and refluxed for 24 h. The mixture is then concentrated under reduced pressure. The crude residue is diluted with water and saturated aqueous solution of NaHCO$_3$. It is then extracted with CH$_2$Cl$_2$ (3×). The combined organic layers are washed with brine, dried over MgSO$_4$, filtered and concentrated under reduced pressure. The crude residue is purified by FC (siliga gel, Hept/EtOAc) to get 142 mg of methyl 2-(formamidomethyl)-5-(methoxymethyl)thiazole-4-carboxylate as a yellow powder. LC-MS (acidic): $t_R$=0.53, [M+H]$^+$=244.97. $^1$H NMR (400 MHz, DMSO) δ: 8.86-8.97 (m, 1H), 8.18 (d, J=1.0 Hz, 1H), 4.91 (m, 2H), 4.54 (d, J=6.2 Hz, 2H), 3.82 (s, 3H), 3.40 (m, 3 H).

Step 4: Preparation of methyl 2-(methoxymethyl) imidazo[5,1-b]thiazole-3-carboxylate A solution of product from step 3, methyl 2-(formamidomethyl)-5-(methoxymethyl)thiazole-4-carboxylate (142 mg, 0.581 mmol) in CH$_2$Cl$_2$ (5 ml) is cooled to −20° C. before POCl$_3$ (0.109 ml, 1.16 mmol) is added. The mixture is then refluxed for 6 h. The mixture is diluted with water and a saturated aqueous solution of NaHCO$_3$. The two layers are separated and the aqueous phase is extracted with CH$_2$Cl$_2$ (2×). The combined organic layers are washed with brine, dried over MgSO$_4$, filtered and concentrated under reduced pressure to give 162 mg of methyl 2-(methoxymethyl)imidazo[5,1-b]thiazole-3-carboxylate as a brown powder. LC-MS (acidic): $t_R$=0.49, [M+H]$^+$=226.97.

Step 5: Preparation of N-methoxy-2-(methoxymethyl)-N-methylimidazo[5,1-b]thiazole-3-carboxamide To a solution of product from step 4, methyl 2-(methoxymethyl)imidazo[5,1-b]thiazole-3-carboxylate (162 mg, 0.716 mmol) in THF (10 ml) is added an aqueous solution of NaOH 1 M (1 ml). The mixture is stirred at RT for 1 h. The mixture is concentrated under reduced pressure. The residue is dissolved in THF (10 ml) before N,O-dimethylhydroxylamine hydrochloride (93.1 mg, 0.931 mmol), HATU (354 mg, 0.931 mmol) and DIPEA (0.49 ml, 2.6 mmol) are added at RT. The mixture is stirred at RT overnight. The mixture is diluted with water and a saturated aqueous NaHCO$_3$. It is then extracted with CH$_2$Cl$_2$ (3×). The combined organic layers are dried over MgSO$_4$, filtered and concentrated under reduced pressure. The crude is purified by FC (siliga gel, CH$_2$Cl$_2$/MeOH) to get 72 mg of N-methoxy-2-(methoxymethyl)-N-methylimidazo[5,1-b]thiazole-3-carboxamide as a yellow sticky gum. LC-MS (acidic): $t_R$=0.47, [M+H]$^+$=255.94.

Step 6: Preparation of cyclohexyl(2-(methoxymethyl)imidazo[5,1-b]thiazol-3-yl)methanone To a solution of product from step 5, N-methoxy-2-(methoxymethyl)-N-methylimidazo[5,1-b]thiazole-3-carboxamide (72 mg, 0.282 mmol) in THF (5 ml) at RT under argon atmosphere, is added dropwise cyclohexylmagnesium bromide (1.1 ml, 0.55 mmol). The mixture is stirred at RT for 24 h. The mixture is then quenched with saturated aqueous NH$_4$Cl solution and extracted with CH$_2$Cl$_2$ (3×). The combined organic layers are washed with brine, dried over MgSO$_4$, filtered and concentrated under reduced pressure to give 68 mg of cyclohexyl(2-(methoxymethyl)imidazo[5,1-b]thiazol-3-yl)methanone as a yellow sticky gum.

Step 7: Preparation of rac-cyclohexyl-(2-methoxymethyl-imidazo[5,1-b]thiazol-3-yl)-methanol (Example 157)

To a solution of the product from step 6, cyclohexyl(2-(methoxymethyl)imidazo[5,1-b]thiazol-3-yl)methanone (68 mg, 0.244 mmol) in dry EtOH (4 ml) is added at RT under argon atmosphere NaBH$_4$ (18.5 mg, 0.489 mmol). The mixture is stirred at RT for 3 h. The mixture is quenched carefully by adding water. When the gas evolution is finished, it is concentrated under reduced pressure and the residue is purified by preparative HPLC (basic conditions) to give 8.5 mg of rac-cyclohexyl-(2-methoxymethyl-imidazo[5,1-b]thiazol-3-yl)-methanol. LC-MS (QC): $t_R$=0.594; [M+H]$^+$=281.4.

Example 170: rac-Cyclohexyl-[2-(1-methyl-cyclopropyl)-imidazo[5,1-b]thiazol-3-yl]-methanol Step 1: Preparation of ethyl 2-diazo-3-(1-methylcyclopropyl)-3-oxopropanoate In a reaction vessel, a solution of 1-methylcyclopropane-1-carboxylic acid (1890 mg; 17.9 mmol) and 1,1'-carbonyldiimidazole (3938 mg; 24.3 mmol) in anhydrous THF (30 ml) is stirred at RT for 4 hours (solution A). In a second reaction vessel, a solution of ethyl potassium malonate (8093 mg; 46.6 mmol), anhydrous magnesium chloride (5241 mg; 53.9 mmol) and 4-dimethylaminopyridine (219 mg; 1.79 mmol) in a mixture of THF (60 ml) and acetonitrile (30 ml) is stirred at RT for 6 hours (solution B). The two solutions are cooled to 0° C. and solution A is added together with Et$_3$N (10 ml; 71.7 mmol) to solution B. The reaction mixture is then stirred at RT for 18 hours. After completion of the reaction, the solvent is removed under reduced pressure and the residue is suspended in water and extracted with DCM (3×). The combined org. extracts are dried over sodium sulfate, filtered and concentrated under reduced pressure to give ethyl 3-(1-methylcyclopropyl)-3-oxopropanoate as a yellow oil which is used without purification. LC-MS (acidic): $t_R$=0.71; [M+H]$^+$=171.05.

Ethyl 3-(1-methylcyclopropyl)-3-oxopropanoate is redissolved in acetonitrile (100 ml) and successively treated with 4-acetamidobenzenesulfonyl azide (5544 mg; 2.4 mmol) and Et$_3$N (3.12 ml; 22.4 mmol). The reaction mixture is stirred at RT for 18 hours. A mixture of heptane/DCM (95:5) is added to precipitate the salts, and the mixture is filtered. The filter cake is washed with heptane and the filtrate concentrated under reduced pressure. A mixture of heptane/DCM (95:5) is added again, and the mixture filtered. The filter cake is washed with heptane and the filtrate concentrated under reduced pressure. The crude oil is purified by FC (Silicagel; Heptane/EtOAc) to give ethyl 2-diazo-3-(1-methylcyclopropyl)-3-oxopropanoate as a yellow oil. LC-MS (acidic): $t_R$=0.80; [M+H]$^+$ 197.07.

Step 2: Preparation of rac-ethyl-2-(2-((tert-butoxycarbonyl)amino)acetamido)-3-(1-methylcyclopropyl)-3-oxopropanoate Ethyl 2-diazo-3-(1-methylcyclopropyl)-3-oxopropanoate (2560 mg; 13.0 mmol) is dissolved in DCM (50 ml) and tert-butyl (2-amino-2-oxoethyl)carbamate (2486 mg; 13.7 mmol) is added followed by dirhodium tetraacetate (62 mg, 0.13 mmol). The reaction mixture is stirred at 45° C. for 3 days. Water is added, the layers separated and the aq. layer extracted with DCM (2×). The combined org. extracts are dried over magnesium sulfate, filtered and concentrated under reduced pressure. Purification by FC (Silicagel; Heptane/EtOAc) gives 3654 mg of rac-ethyl-2-(2-((tert-butoxycarbonyl)amino)acetamido)-3-(1-methylcyclopropyl)-3-oxopropanoate as a pink solid. LC-MS (acidic): $t_R$=0.84; [M+H]$^+$=342.99.

Step 3: Preparation of ethyl 2-(((tert-butoxycarbonyl)amino)methyl)-5-(1-methylcyclopropyl)thiazole-4-carboxylate The product from step 2, rac-ethyl-2-(2-((tert-butoxycarbonyl)amino)acetamido)-3-(1-methylcyclopropyl)-3-oxopropanoate (3654 mg; 10.7 mmol) and Lawesson's reagent (5000 mg; 12.0 mmol) are suspended in THF (50 ml) and heated to reflux for 24 hours. THF is evaporated under reduced pressure and the residue is purified by FC (Silicagel; EtOAc/heptane) to give 4601 mg of ethyl 2-(((tert-butoxycarbonyl)amino)methyl)-5-(1-methylcyclopropyl)thiazole-4-carboxylate. LC-MS (acidic): $t_R$=0.96; [M+H]$^+$=340.98.

Step 4: Preparation of ethyl 2-(formamidomethyl)-5-(1-methylcyclopropyl)thiazole-4-carboxylate Step 4.1: Boc-cleavage: The product from step 3, ethyl 2-(((tert-butoxycarbonyl)amino)methyl)-5-(1-methylcyclopropyl)thiazole-4-carboxylate (4601 mg; 13.5 mmol) is dissolved in dioxane (50 ml) followed by careful addition of 4N HCl in dioxane (10 ml; 40.0 mmol). The mixture is stirred at RT for 15 hours. The reaction mixture is evaporated to dryness under reduced pressure.

Step 4.2: The residue from step 4.1 is dissolved in ethyl formate (30 ml) and Et$_3$N (4.48 ml; 32.2 mmol) is added. The mixture is stirred at reflux for 4 hours. A sat. aq. NaHCO$_3$ solution is added and the mixture extracted with DCM (2×). The combined org. extracts are dried over MgSO$_4$, filtered and concentrated under reduced pressure to give 3691 mg of ethyl 2-(formamidomethyl)-5-(1-methylcyclopropyl)thiazole-4-carboxylate which is used without further purification in Step 5. LC-MS (acidic): $t_R$=0.73; [M+H]$^+$=269.00.

Step 5: Preparation of ethyl 2-(1-methylcyclopropyl)imidazo[5,1-b]thiazole-3-carboxylate The product from step 4.2, ethyl 2-(formamidomethyl)-5-(1-methylcyclopropyl)thiazole-4-carboxylate (3691 mg; 13.8 mmol) is dissolved in DCM (100 ml) and cooled to −20° C. followed by the addition of phosphorus oxychloride (2.6 ml; 27.6 mmol). The reaction mixture is stirred at RT for 48 h. More phosphorus oxychloride (1 ml; 10.6 mmol) is added and the mixture stirred at reflux for 6 hours. Water was added followed by sat. aq. NaHCO$_3$. The layers are separated and the aq. layer extracted with DCM (2×). The combined organic layers are dried over MgSO$_4$, filtered and concentrated under reduced pressure to give 3066 mg of ethyl 2-(1-methylcyclopropyl)imidazo[5,1-b]thiazole-3-carboxylate as a beige foam. LC-MS (acidic): $t_R$=0.67; [M+H]$^+$= 251.01.

Step 6: Preparation of (2-(1-methylcyclopropyl)imidazo[5,1-b]thiazol-3-yl)methanol The product from step 5, ethyl 2-(1-methylcyclopropyl)imidazo[5,1-b]thiazole-3-carboxylate (3062 mg; 12.2 mmol) is dissolved in EtOH (150 ml) and sodium borohydride (1000 mg; 26.4 mmol) is added. The reaction mixture is stirred at RT for 4 hours. The mixture is concentrated under reduced pressure. The residue is redissolved in DCM and water is carefully added followed by sat. aq. NH$_4$Cl. The layers are separated and the aq. layer extracted with DCM (2×). The combined org. extracts are dried over MgSO$_4$, filtered and concentrated under reduced pressure to give 2059 mg of (2-(1-methylcyclopropyl)imidazo[5,1-b]thiazol-3-yl)methanol. LC-MS (basic): $t_R$=0.69; [M+H]$^+$=209.15.

Step 7: Preparation of 2-(1-methylcyclopropyl)imidazo[5,1-b]thiazole-3-carbaldehyde To an ice-cold solution of the product from Step 6, (2-(1-methylcyclopropyl)imidazo[5,1-b]thiazol-3-yl)methanol (2059 mg; 9.89 mmol) in DCM (150 ml) is added Dess-Martin periodinane (4612 mg; 10.9 mmol). The reaction mixture is stirred at RT for 18 hours. A sat. aq. NaHCO$_3$ solution is added and the mixture stirred for 30 min.

The white precipitate is then filtered and the filtrate extracted with DCM (3×). The combined org. extracts are washed with brine, dried over MgSO$_4$, filtered and concentrated under reduced pressure. Purification by FC (Silicagel; Hept/EtOAc) gives 2-(1-methylcyclopropyl)imidazo[5,1-b]thiazole-3-carbaldehyde. LC-MS (acidic): $t_R$=0.50; [M+H]$^+$= 207.35. $^1$H NMR (500 MHz, d$_6$-DMSO) δ: 10.16 (s, 1H), 8.54 (s, 1H), 7.17 (s, 1H), 1.55 (s, 3H), 1.16-1.18 (m, 2H), 1.04 (m, 2H).

Step 8: Preparation of rac-cyclohexyl-[2-(1-methyl-cyclopropyl)-imidazo[5,1-b]thiazol-3-yl]-methanol (Example 170)

According to the procedure described for preparation of example 3/step 8 but using product from step 7, 2-(1-methylcyclopropyl)imidazo[5,1-b]thiazole-3-carbaldehyde and cyclohexylmagnesium bromide as starting materials, 6 mg of rac-cyclohexyl-[2-(1-methyl-cyclopropyl)-imidazo[5,1-b]thiazol-3-yl]-methanol are obtained. LC-MS (QC): $t_R$=0.748; [M+H]$^+$=291.1.

Example 185: [2-((S)-sec-Butyl)-imidazo[5,1-b]thiazol-3-yl]-cyclohexyl-methanol

Step 1: Preparation of ethyl (4S)-2-amino-4-methyl-3-oxohexanoate hydrochloride According to the procedure described for the preparation of example 96/step 1 but using (S)-(+)-2-methylbutyric anhydride as starting material, 391 mg of ethyl ethyl (4S)-2-amino-4-methyl-3-oxohexanoate hydrochloride are obtained. LC-MS (acidic): $t_R$=0.50; [M+H]$^+$=188.24.

Step 2: Preparation of ethyl (4S)-2-(2-((tert-butoxycarbonyl)amino)acetamido)-4-methyl-3-oxohexanoate According to the procedure described for the preparation of example 1/step 2 but using ethyl (4S)-2-amino-4-methyl-3-oxohexanoate hydrochloride as starting material, 641 mg of ethyl (4S)-2-(2-((tert-butoxycarbonyl)amino)acetamido)-4-methyl-3-oxohexanoate are obtained. LC-MS (acidic): $t_R$=0.89; [M+H]$^+$=345.28.

Step 3: Preparation of ethyl (S)-2-(((tert-butoxycarbonyl)amino)methyl)-5-(sec-butyl)thiazole-4-carboxylate According to the procedure described for the preparation of example 1/step 3 but using ethyl (4S)-2-(2-((tert-butoxycarbonyl)amino)acetamido)-4-methyl-3-oxohexanoate as starting material, 141 mg of ethyl (S)-2-(((tert-butoxycarbonyl)amino)methyl)-5-(sec-butyl)thiazole-4-carboxylate are obtained. LC-MS (acidic): $t_R$=0.99; [M+H]$^+$=343.27.

Step 4: Preparation of ethyl (S)-5-(sec-butyl)-2-(formamidomethyl)thiazole-4-carboxylate According to the procedure described for the preparation of example 1/step 4 but using ethyl (S)-2-(((tert-butoxycarbonyl)amino)methyl)-5-(sec-butyl)thiazole-4-carboxylate as starting material, 110 mg of ethyl (S)-5-(sec-butyl)-2-(formamidomethyl)thiazole-4-carboxylate are obtained. LC-MS (acidic): $t_R$=0.78; [M+H]$^+$=271.17.

Step 5: Preparation of ethyl (S)-2-(sec-butyl)imidazo[5,1-b]thiazole-3-carboxylate According to the procedure described for the preparation of example 1/step 5 but using ethyl (S)-5-(sec-butyl)-2-(formamidomethyl)thiazole-4-carboxylate as starting material, 108 mg of ethyl (S)-2-(sec-butyl)imidazo[5,1-b]thiazole-3-carboxylate are obtained. LC-MS (acidic): $t_R$=0.70; [M+H]$^+$=253.13.

Step 6: Preparation of (S)-2-(sec-butyl)-N-methoxy-N-methylimidazo[5,1-b]thiazole-3-carboxamide According to the procedure described for the preparation of example 96/step 6.1 and 6.2 but using ethyl (S)-2-(sec-butyl)imidazo[5,1-b]thiazole-3-carboxylate as starting material, 100 mg of (S)-2-(sec-butyl)-N-methoxy-N-methylimidazo[5,1-b]thiazole-3-carboxamide are obtained. LC-MS (basic): $t_R$=0.80; [M+H]$^+$=268.21.

Step 7: Preparation of (S)-2-(sec-butyl)imidazo[5,1-b]thiazole-3-carbaldehyde According to the procedure described for the preparation of example 96/step 7 but using (S)-2-(sec-butyl)-N-methoxy-N-methylimidazo[5,1-b]thiazole-3-carboxamide as starting material, 55 mg of (S)-2-(sec-butyl)imidazo[5,1-b]thiazole-3-carbaldehyde are obtained. LC-MS (basic): $t_R$=0.78; [M+H]$^+$=208.94.

Step 8: Preparation of [2-((S)-sec-butyl)-imidazo[5,1-b]thiazol-3-yl]-cyclohexyl-methanol (Example 185)

According to the procedure described for preparation of example 3/step 8 but using product from step 7, (S)-2-(sec-butyl)imidazo[5,1-b]thiazole-3-carbaldehyde and cyclohexylmagnesium chloride as starting materials, 7 mg of [2-((S)-sec-butyl)-imidazo[5,1-b]thiazol-3-yl]-cyclohexyl-methanol are obtained. LC-MS (QC): $t_R$=0.776; [M+H]$^+$=293.2.

Example 186: Cyclohexyl-[2-(cis-2-fluoro-cyclopropyl)-imidazo[5,1-b]thiazol-3-yl]-methanol

Step 1: Preparation of rac-ethyl 2-diazo-3-((1R,2R)-2-fluoro-cyclopropyl)-3-oxo-propanoate According to the procedure described for the preparation of example 170/Step 1 and using rac-ethyl 3-((1R,2R)-2-fluorocyclopropyl)-3-oxopropanoate (2000 mg; 10.9 mmol) as starting material, 2400 mg of rac-ethyl-2-diazo-3-((1R,2R)-2-fluoro-cyclopropyl)-3-oxo-propanoate are obtained as a yellow oil and used without any further purification. LC-MS (acidic): $t_R$=0.75; [M+H]$^+$=201.01.

Step 2: Preparation of cis-ethyl 2-(2-((tert-butoxycarbonyl)amino)acetamido)-3-(2-fluorocyclopropyl)-3-oxopropanoate According to the procedure described for the preparation of example 170/Step 2 and using rac-ethyl 2-diazo-3-((1R,2R)-2-fluoro-cyclopropyl)-3-oxo-propionic acid (2400 mg; 12 mmol) as starting material. In this case, the reaction mixture is stirred at 45° C. for 2 days and 4075 mg of cis-ethyl 2-(2-((tert-butoxycarbonyl)amino)acetamido)-3-(2-fluorocyclopropyl)-3-oxopropanoate are obtained as a brown oil and used without further purification. LC-MS (acidic): $t_R$=0.77; [M+H]$^+$=347.04.

Step 3: Preparation of rac-ethyl 2-(((tert-butoxycarbonyl)amino)methyl)-5-((1R,2S)-2-fluorocyclopropyl)thiazole-4-carboxylate According to the procedure described for the preparation of example 170/Step 3 and using cis-ethyl 2-(2-((tert-butoxycarbonyl)amino)acetamido)-3-(2-fluorocyclopropyl)-3-oxopropanoate (4075 mg, 11.8 mmol) as starting material, 5326 mg of rac-ethyl 2-(((tert-butoxycarbonyl)amino)methyl)-5-((1R,2S)-2-fluorocyclopropyl)thiazole-4-carboxylate are obtained as a white solid after FC (silicagel, Hept/EtOAc). LC-MS (acidic): $t_R$=0.89; [M+H]$^+$=344.99.

Step 4: Preparation of rac-ethyl 5-((1R,2S)-2-fluorocyclopropyl)-2-(formamidomethyl)thiazole-4-carboxylate According to the procedure described for the preparation of example 170/Step 4 and using rac-ethyl 2-(((tert-butoxycarbonyl)amino)methyl)-5-((1R,2S)-2-fluorocyclopropyl)thiazole-4-carboxylate (5326 mg) as starting material, 1965 mg of rac-ethyl 5-((1R,2S)-2-fluorocyclopropyl)-2-(formamidomethyl)thiazole-4-carboxylate are obtained as a white solid after FC (silicagel, Hept/EtOAc). LC-MS (acidic): $t_R$=0.64; [M+H]$^+$=272.99.

Step 5: Preparation of rac-ethyl 2-((1R,2S)-2-fluorocyclopropyl)imidazo[5,1-b]thiazole-3-carboxylate According to the procedure described for the preparation of example 170/Step 5 and using rac-ethyl 5-((1R,2S)-2-fluorocyclopropyl)-2-(formamidomethyl)thiazole-4-carboxylate (1965 mg) as starting material, 1810 mg of rac-ethyl 2-((1R,2S)-2-fluorocyclopropyl)imidazo[5,1-b]thiazole-3-carboxylate are obtained as an orange powder. LC-MS (acidic): $t_R$=0.58; [M+H]$^+$=255.28.

Step 6: Preparation of rac-(2-((1R,2S)-2-fluorocyclopropyl)imidazo[5,1-b]thiazol-3-yl)methanol According to the procedure described for the preparation of example 170/Step 6 and using rac-ethyl 2-((1R,2S)-2-fluorocyclopropyl)imidazo[5,1-b]thiazole-3-carboxylate (1810 mg, 7.12 mmol) as starting material, 940 mg of rac-(2-((1R,2S)-2-fluorocyclopropyl)imidazo[5,1-b]thiazol-3-yl)methanol are obtained as a white powder and used in the next step without purification. LC-MS (basic): $t_R$=0.42; [M+H]$^+$=213.00.

Step 7: Preparation of rac-2-((1R,2S)-2-fluorocyclopropyl)imidazo[5,1-b]thiazole-3-carbaldehyde According to the procedure described for the preparation of example 170/Step 7 and using rac-(2-((1R,2S)-2-fluorocyclopropyl)imidazo[5,1-b]thiazol-3-yl)methanol (940 mg) as starting material, 1655 mg of rac-2-((1R,2S)-2-fluorocyclopropyl)imidazo[5,1-b]thiazole-3-carbaldehyde are obtained as a yellow gum. LC-MS (acidic): $t_R$=0.44; $[M+H]^+$=211.01. $^1$H NMR (400 MHz, $d_6$-DMSO) δ: 10.08 (s, 1H), 8.57 (s, 1H), 7.17 (s, 1H), 5.25 (m, 1 H), 2.95-3.02 (m, 1H), 1.61-1.71 (m, 1H), 1.48 (dtd, $J_1$=3.2 Hz, $J_2$=7.6 Hz, $J_3$=23.9 Hz, 1H).

Step 8: Preparation of cyclohexyl-[2-(cis-2-fluoro-cyclopropyl)-imidazo[5,1-b]thiazol-3-yl]-methanol (Example 186)

According to the procedure described for preparation of example 3/step 8 but using product from step 7, rac-2-((1R,2S)-2-fluorocyclopropyl)imidazo[5,1-b]thiazole-3-carbaldehyde and cyclohexylmagnesium bromide as starting materials, 4 mg of cyclohexyl-[2-(cis-2-fluoro-cyclopropyl)-imidazo[5,1-b]thiazol-3-yl]-methanol are obtained. LC-MS (QC): $t_R$=0.620; $[M+H]^+$=295.2.

Example 187: Cyclohexyl-[2-(trans-2-fluoro-cyclopropyl)-imidazo[5,1-b]thiazol-3-yl]-methanol Step 1: Preparation of rac-ethyl 2-diazo-3-((1 S,2R)-2-fluoro-cyclopropyl)-3-oxo-propanoate According to the procedure described for the preparation of example 170/Step 1 and using rac-ethyl-3-((1 S,2R)-2-fluorocyclopropyl)-3-oxopropanoate (2000 mg; 10.9 mmol) as starting material, 2190 mg of rac-ethyl-2-diazo-3-((1 S,2R)-2-fluoro-cyclopropyl)-3-oxo-propanoate are obtained as a yellow oil and used without any further purification. LC-MS (acidic): $t_R$=0.81; $[M+H]^+$=not observed.

Step 2: Preparation of trans-ethyl 2-(2-((tert-butoxycarbonyl)amino)acetamido)-3-(2-fluorocyclopropyl)-3-oxopropanoate According to the procedure described for the preparation of example 170/Step 2 and using rac-ethyl 2-diazo-3-((1 S,2R)-2-fluoro-cyclopropyl)-3-oxo-propionic acid (2195 mg; 11 mmol) as starting material. In this case, the reaction mixture is stirred at 45° C. for 2 days and 3816 mg of trans-ethyl 2-(2-((tert-butoxycarbonyl)amino)acetamido)-3-(2-fluorocyclopropyl)-3-oxopropanoate are obtained as a brown oil and used without further purification. LC-MS (acidic): $t_R$=0.81; $[M+H]^+$=347.05.

Step 3: Preparation of rac-ethyl 2-(((tert-butoxycarbonyl)amino)methyl)-5-((1R,2R)-2-fluorocyclopropyl)thiazole-4-carboxylate According to the procedure described for the preparation of example 170/Step 3 and using trans-ethyl 2-(2-((tert-butoxycarbonyl)amino)acetamido)-3-(2-fluorocyclopropyl)-3-oxopropanoate (3816 mg, 11 mmol) as starting material, 3956 mg of rac-ethyl 2-(((tert-butoxycarbonyl)amino)methyl)-5-((1R,2R)-2-fluorocyclopropyl)thiazole-4-carboxylate are obtained as a brown sticky oil and used without purification in the next step. LC-MS (acidic): $t_R$=0.91; $[M+H]^+$=345.07.

Step 4: Preparation of rac-ethyl 5-((1R,2R)-2-fluorocyclopropyl)-2-(formamidomethyl)thiazole-4-carboxylate According to the procedure described for the preparation of example 170/Step 4 and using rac-ethyl 2-(((tert-butoxycarbonyl)amino)methyl)-5-((1R,2R)-2-fluorocyclopropyl)thiazole-4-carboxylate (3956 mg) as starting material, 1210 mg of rac-ethyl 5-((1R,2R)-2-fluorocyclopropyl)-2-(formamidomethyl)thiazole-4-carboxylate are obtained as a brown sticky gum after flash chromatography (silicagel, Hept/EtOAc). LC-MS (acidic): $t_R$=0.67; $[M+H]^+$=273.04.

Step 5: Preparation of rac-ethyl 2-((1R,2R)-2-fluorocyclopropyl)imidazo[5,1-b]thiazole-3-carboxylate According to the procedure described for the preparation of example 170/Step 5 and using rac-ethyl 5-((1R,2R)-2-fluorocyclopropyl)-2-(formamidomethyl)thiazole-4-carboxylate (1210 mg) as starting material, 950 mg of rac-ethyl 2-((1R,2R)-2-fluorocyclopropyl)imidazo[5,1-b]thiazole-3-carboxylate are obtained as a yellow powder. LC-MS (acidic): $t_R$=0.60; $[M+H]^+$=254.98.

Step 6: Preparation of rac-(2-((1R,2R)-2-fluorocyclopropyl)imidazo[5,1-b]thiazol-3-yl)methanol According to the procedure described for the preparation of example 170/Step 6 and using rac-ethyl 2-((1R,2R)-2-fluorocyclopropyl)imidazo[5,1-b]thiazole-3-carboxylate (950 mg, 3.74 mmol) as starting material, 810 mg of rac-(2-((1R,2R)-2-fluorocyclopropyl)imidazo[5,1-b]thiazol-3-yl)methanol are obtained as a yellow powder and used in the next step without purification. LC-MS (basic): $t_R$=0.42; $[M+H]^+$=213.02.

Step 7: Preparation of rac-2-((1R,2R)-2-fluorocyclopropyl)imidazo[5,1-b]thiazol-3-carbaldehyde According to the procedure described for the preparation of example 170/Step 7 and using rac-(2-((1R,2R)-2-fluorocyclopropyl)imidazo[5,1-b]thiazol-3-yl)methanol (810 mg) as starting material, 1210 mg of rac-2-((1R,2R)-2-fluorocyclopropyl)imidazo[5,1-b]thiazole-3-carbaldehyde are obtained as a yellow powder. LC-MS (acidic): $t_R$=0.42; $[M+H]^+$=211.02. $^1$H NMR (400 MHz, $d_6$-DMSO) δ: 10.13 (s, 1H), 8.55 (s, 1H), 7.17 (s, 1H), 5.11-5.29 (m), 3.43-3.44 (m, 1H), 1.92 (m, 1H), 1.40 (dd, J1=6.8 Hz, J2=11.6 Hz, 1H).

Step 8: Preparation of cyclohexyl(2-(trans-2-fluorocyclopropyl)imidazo[5,1-b]thiazol-3-yl)methanol (Example 187)

According to the procedure described for preparation of example 3/step 8 but using product from step 7, rac-2-((1R,2R)-2-fluorocyclopropyl)imidazo[5,1-b]thiazole-3-carbaldehyde and cyclohexylmagnesium bromide as starting materials, 20 mg of cyclohexyl-[2-(trans-2-fluoro-cyclopropyl)-imidazo[5,1-b]thiazol-3-yl]-methanol are obtained. LC-MS (QC): $t_R$=0.671; $[M+H]^+$=295.2.

Example 184: rac-Cyclohexyl-[2-(1-fluoro-cyclopropyl)-imidazo[5,1-b]thiazol-3-yl]-methanol Step 1: Preparation of ethyl 2-diazo-3-(1-fluorocyclopropyl)-3-oxopropanoate According to the procedure described for the preparation of example 170/Step 1 and using 1-fluorocyclopropane-1- carboxylic acid (2014 mg; 18.8 mmol) as starting material, 3092 mg of ethyl 3-(1-fluorocyclopropyl)-3-oxopropanoate are obtained and used without further purification. LC-MS (acidic): $t_R$=0.71; [M+H]$^+$=not observed. Ethyl 2-diazo-3-(1-fluorocyclopropyl)-3-oxopropanoate is then obtained as a brown oil and used without any further purification. LC-MS (acidic): $t_R$=0.75; [M+H]$^+$=201.03.

Step 2: Preparation of rac-ethyl 2-(2-((tert-butoxycarbonyl)amino)acetamido)-3-(1-fluorocyclopropyl)-3-oxopropanoate According to the procedure described for the preparation of example 170/Step 2 and using ethyl 2-diazo-3-(1-fluorocyclopropyl)-3-oxopropanoate (2124 mg; 10.6 mmol) as starting material. In this case, the reaction mixture is stirred at 45° C. for 5 days and 3223 mg of rac-ethyl 2-(2-((tert-butoxycarbonyl)amino)acetamido)-3-(1-fluorocyclopropyl)-3-oxopropanoate are obtained as a brown solid and used without further purification. LC-MS (acidic): $t_R$=0.81; [M+H]$^+$=347.01.

Step 3: Preparation of rac-ethyl 2-(((tert-butoxycarbonyl)amino)methyl)-5-((1R,2R)-2-fluorocyclopropyl)thiazole-4-carboxylate According to the procedure described for the preparation of example 170/Step 3 and using rac-ethyl-2-(2-((tert-butoxycarbonyl)amino)acetamido)-3-(1-fluorocyclopropyl)-3-oxopropanoate (3223 mg, 9.31 mmol) as starting material, 2727 mg of ethyl 2-(((tert-butoxycarbonyl)amino)methyl)-5-(1-fluorocyclopropyl)thiazole-4-carboxylate are obtained as a light yellow sticky oil. LC-MS (acidic): $t_R$=0.92; [M+H]$^+$=344.99.

Step 4: Preparation of ethyl 2-(formamidomethyl)-5-(1-fluorocyclopropyl)thiazole-4-carboxylate According to the procedure described for the preparation of example 170/Step 4 and using ethyl 2-(((tert-butoxycarbonyl)amino)methyl)-5-(1-fluorocyclopropyl)thiazole-4-carboxylate (2727 mg) as starting material, 2129 mg of ethyl 2-(formamidomethyl)-5-(1-fluorocyclopropyl)thiazole-4-carboxylate are obtained as a reddish oil which is used without further purification. LC-MS (acidic): $t_R$=0.66; [M+H]$^+$=272.99.

Step 5: Preparation of ethyl 2-(1-fluorocyclopropyl)imidazo[5,1-b]thiazole-3-carboxylate According to the procedure described for the preparation of Example 170/Step 5 and using 2-(formamidomethyl)-5-(1-fluorocyclopropyl)thiazole-4-carboxylate (2129 mg) as starting material, 1790 mg of ethyl 2-(1-fluorocyclopropyl)imidazo[5,1-b]thiazole-3-carboxylate are obtained as a yellow powder. LC-MS (acidic): $t_R$=0.63; [M+H]$^+$=255.00.

Step 6: Preparation of (2-(1-fluorocyclopropyl)imidazo[5,1-b]thiazol-3-yl)methanol According to the procedure described for the preparation of example 170/Step 6 and using ethyl 2-(1-fluorocyclopropyl)imidazo[5,1-b]thiazole-3-carboxylate (1582 mg, 6.22 mmol) as starting material, 782 mg of (2-(1-fluorocyclopropyl)imidazo[5,1-b]thiazol-3-yl)methanol are obtained as a yellow powder and used in the next step without purification. LC-MS (basic): $t_R$=0.45; [M+H]$^+$=213.04.

Step 7: Preparation of 2-(1-fluorocyclopropyl)imidazo[5,1-b]thiazole-3-carbaldehyde According to the procedure described for the preparation of example 170/Step 7 and using (2-(1-fluorocyclopropyl)imidazo[5,1-b]thiazol-3-yl)methanol (782 mg) as starting material, 687 mg of 2-(1-fluorocyclopropyl)imidazo[5,1-b]thiazole-3-carbaldehyde are obtained as a yellow powder. LC-MS (acidic): $t_R$=0.47; [M+H]$^+$=211.00. $^1$H NMR (500 MHz, d$_6$-DMSO) δ: 10.16 (s, 1H), 8.64 (s, 1H), 7.25 (s, 1H), 1.75 (m, 2 H), 1.46 (m, 2H).

rac-cyclohexyl-[2-(1-fluoro-cyclopropyl)-imidazo[5,1-b]thiazol-3-yl]-methanol (Example 184) According to the procedure described for preparation of example 3/step 8 but using product from step 7, 2-(1-fluorocyclopropyl)imidazo[5,1-b]thiazole-3-carbaldehyde and cyclohexylmagnesium bromide as starting materials, 18 mg of rac-cyclohexyl-[2-(1-fluoro-cyclopropyl)-imidazo[5,1-b]thiazol-3-yl]-methanol are obtained. LC-MS (QC): $t_R$=0.791; [M+H]$^+$=295.2.

Example 94: rac-Cyclohexyl-(2-thiophen-3-yl-imidazo[5,1-b]thiazol-3-yl)-methanol Step 1: Preparation of N-methoxy-N-methyl-2-(thiophen-3-yl)imidazo[5,1-b]thiazole-3-carboxamide According to the procedure described for the preparation of example 128/step 3 but using 3-thiopheneboronic acid as starting material, 137 mg of N-methoxy-N-methyl-2-(thiophen-3-yl)imidazo[5,1-b]thiazole-3-carboxamide are obtained. LC-MS (acidic): $t_R$=0.59; [M+H]$^+$=294.16. $^1$H NMR (400 MHz, DMSO) δ: 8.18 (s, 1 H), 7.84 (d, J=1.6 Hz, 1H), 7.75 (dd, J$_1$=2.9 Hz, J$_2$=5.0 Hz, 1H), 7.24-7.26 (m, 1H), 7.13 (s, 1H), 3.53 (s, 3 H), 3.29 (s, 3H).

Step 2: Preparation of 2-(thiophen-3-yl)imidazo[5,1-b]thiazole-3-carbaldehyde

According to the procedure described for the preparation of example 128/step 4 but using N-methoxy-N-methyl-2-(thiophen-3-yl)imidazo[5,1-b]thiazole-3-carboxamide as starting material, 100 mg of 2-(thiophen-3-yl)imidazo[5,1-b]thiazole-3-carbaldehyde are obtained. LC-MS (acidic): $t_R$=0.54; [M+H]$^+$=234.85. $^1$H NMR (400 MHz, DMSO) δ: 9.87 (s, 1H), 8.68 (s, 1H), 8.32-8.32 (m, 1H), 7.88 (dd, J$_1$=2.9 Hz, J$_2$=5.0 Hz, 1H), 7.58-7.60 (m, 1H), 7.25 (s, 1H).

Step 3: Preparation of rac-cyclohexyl-(2-thiophen-3-yl-imidazo[5,1-b]thiazol-3-yl)-methanol (Example 94)

According to the procedure described for preparation of example 3/step 8 but using product from step 2, 2-(thiophen-3-yl)imidazo[5,1-b]thiazole-3-carbaldehyde and cyclohexylmagnesium bromide as starting materials, 32 mg of rac-cyclohexyl-(2-thiophen-3-yl-imidazo[5,1-b]thiazol-3-yl)-methanol are obtained. LC-MS (QC): $t_R$=0.792; [M+H]$^+$=319.1.

Example 95: rac-2-Cyclohexyl-1-(2-thiophen-3-yl-imidazo[5,1-b]thiazol-3-yl)-ethanol Example 95 is prepared in analogy to the description of the preparation of example 94. LC-MS (QC): $t_R$=0.868; [M+H]$^+$=333.2.

Example 153: rac-Cyclohexyl-[2-(5-methyl-thiophen-3-yl)-imidazo[5,1-b]thiazol-3-yl]-methanol

Step 1: Preparation of N-methoxy-N-methyl-2-(5-methylthiophen-3-yl)imidazo[5,1-b]thiazole-3-carboxamide According to the procedure described for the preparation of example 128/step 3 but using (5-methylthiophen-0.3-yl) boronic acid as starting material, 93 mg of N-methoxy-N-methyl-2-(5-methylthiophen-3-yl)imidazo[5,1-b]thiazole-3-carboxamide are obtained. LC-MS (acidic): $t_R$=0.64; [M+H]$^+$=307.87. $^1$H NMR (400 MHz, DMSO) δ: 8.16 (d, J=0.3 Hz, 1H), 7.57 (d, J=1.5 Hz, 1H), 7.12 (d, J=0.4 Hz, 1H), 6.95 (t, J=1.2 Hz, 1H), 3.54-3.59 (m, 3H), 3.30 (s, 3H), 2.48 (d, J=0.9 Hz, 3H)

Step 2: Preparation of 2-(5-methylthiophen-3-yl)imidazo[5,1-b]thiazole-3-carbaldehyde According to the procedure described for the preparation of example 128/step 4 but using N-methoxy-N-methyl-2-(5-methylthiophen-3-yl)imidazo[5,1-b]thiazole-3-carboxamide as starting material, 41 mg of 2-(5-methylthiophen-3-yl)imidazo[5,1-b]thiazole-3-carbaldehyde are obtained. LC-MS (acidic): $t_R$=0.62; [M+H]$^+$=248.93. $^1$H NMR (400 MHz, DMSO) δ: 9.88 (s, 1H), 8.66 (s, 1H), 8.06 (d, J=1.5 Hz, 1H), 7.28 (m, 1H), 7.23 (d, J=0.5 Hz, 1H), 2.53 (d, J=0.9 Hz, 3H).

Step 3: Preparation of rac-cyclohexyl-[2-(5-methyl-thiophen-3-yl)-imidazo[5,1-b]thiazol-3-yl]-methanol (Example 153)

According to the procedure described for preparation of example 3/step 8 but using product from step 2, 2-(5-methylthiophen-3-yl)imidazo[5,1-b]thiazole-3-carbaldehyde and cyclohexylmagnesium bromide as starting materials, 27 mg of rac-cyclohexyl-[2-(5-methyl-thiophen-3-yl)-imidazo[5,1-b]thiazol-3-yl]-methanol are obtained. LC-MS (QC): $t_R$=0.872; [M+H]$^+$=333.2.

Example 155: rac-2-Cyclohexyl-1-[2-(3,3-difluorocyclobutyl)-imidazo[5,1-b]thiazol-3-yl]-ethanol

Step 1: Preparation of methyl 2-diazo-3-(3,3-difluorocyclobutyl)-3-oxopropanoate A solution of methyl 3-(3,3-difluorocyclobutyl)-3-oxopropanoate (2.67 g, 13.9 mmol) and 4-acetamidobenzenesulfonyl azide (4.123 g, 16.6 mmol) in CH$_3$CN (60 ml) is stirred under argon atmosphere and cooled to 0° C. with an ice-water bath. Triethylamine is then added dropwise to the mixture which is stirred for 2 h at 0° C. and at RT overnight. Heptane/CH$_2$Cl$_2$ 9:1 is added to the mixture to precipitate the salts. It is then filtered and washed with heptane. The filtrate is concentrated under reduced pressure. The crude is purified by FC (siliga gel, Hept/EtOAc) to get 2.75 g of methyl 2-diazo-3-(3,3-difluorocyclobutyl)-3-oxopropanoate as a yellow oil. $^1$H NMR (400 MHz, CDCl$_3$) δ: 3.87-3.89 (m, 3H), 3.75-3.85 (m, 1H), 2.74-2.98 (m, 4H).

Step 2: Preparation of methyl 2-(2-((tert-butoxycarbonyl)amino)acetamido)-3-(3,3-difluorocyclobutyl)-3-oxopropanoate According to the procedure for the preparation of example 157/step 2 but using methyl 2-diazo-3-(3,3-difluorocyclobutyl)-3-oxopropanoate as starting material, 4.10 g of methyl 2-(2-((tert-butoxycarbonyl)amino)acetamido)-3-(3,3-difluorocyclobutyl)-3-oxopropanoate are obtained. LC-MS (acidic): $t_R$=0.63; [M+H]$^+$=364.93. $^1$H NMR (400 MHz, DMSO) δ: 5.30-5.42 (m, 1H), 8.64-8.70 (m, 1H), 7.05-7.15 (m, 1 H), 3.71 (s, 3H), 3.64 (d, J=6.1 Hz, 2H), 3.40-3.49 (m, 1H), 2.63-2.85 (m, 4H), 1.29-1.44 (m, 9H).

Step 3: Preparation of methyl 2-(((tert-butoxycarbonyl)amino)methyl)-5-(3,3-difluorocyclobutyl)thiazole-4-carboxylate According to the procedure for the preparation of example 170/step 3 but using methyl 2-(2-((tert-butoxycarbonyl)amino)acetamido)-3-(3,3-difluorocyclobutyl)-3-oxopropanoate as starting material, 4.90 g of methyl 2-(((tert-butoxycarbonyl)amino)methyl)-5-(3,3-difluorocyclobutyl)thiazole-4-carboxylate are obtained. LC-MS (acidic): $t_R$=0.92; [M+H]$^+$=362.92.

Step 4: Preparation of methyl 5-(3,3-difluorocyclobutyl)-2-(formamidomethyl)thiazole-4-carboxylate According to the procedure for the preparation of example 170/step 4 but using methyl 2-(((tert-butoxycarbonyl)amino)methyl)-5-(3,3-difluorocyclobutyl)thiazole-4-carboxylate as starting material, 2.55 g of methyl 5-(3,3-difluorocyclobutyl)-2-(formamidomethyl)thiazole-4-carboxylate are obtained. LC-MS (acidic): $t_R$=0.68; [M+H]$^+$=290.78. $^1$H NMR (400 MHz, DMSO) δ: 8.88-8.98 (m, 1H), 8.19 (s, 1H), 4.54 (d, J=6.2 Hz, 2 H), 4.10-4.22 (m, 1H), 3.82 (s, 3H), 3.09-3.27 (m, 2H), 2.62-2.76 (m, 2H).

Step 5: Preparation of methyl 2-(3,3-difluorocyclobutyl)imidazo[5,1-b]thiazole-3-carboxylate According to the procedure for the preparation of example 170/step 5 but using methyl 5-(3,3-difluorocyclobutyl)-2-(formamidomethyl)thiazole-4-carboxylate as starting material, 2.33 g of methyl 2-(3,3-difluorocyclobutyl)imidazo[5,1-b]thiazole-3-carboxylate are obtained. LC-MS (acidic): $t_R$=0.60; [M+H]$^+$=272.99. $^1$H NMR (400 MHz, DMSO) δ: 8.45 (s, 1H), 7.20 (s, 1H), 4.12-4.27 (m, 1H), 3.95 (s, 3H), 3.06-3.26 (m, 2H), 2.69-2.89 (m, 2H).

Step 6: Preparation of (2-(3,3-difluorocyclobutyl)imidazo[5,1-b]thiazol-3-yl)methanol According to the procedure for the preparation of example 170/step 6 but using methyl 2-(3,3-difluorocyclobutyl)imidazo[5,1-b]thiazole-3-carboxylate as starting material, 879 mg of (2-(3,3-difluorocyclobutyl)imidazo[5,1-b]thiazol-3-yl)methanol are obtained. LC-MS (acidic): $t_R$=0.50; [M+H]$^+$= 244.97.

$^1$H NMR (400 MHz, DMSO) δ: 8.13 (s, 1H), 7.07 (s, 1H), 5.53 (t, J=5.8 Hz, 1H), 4.63 (d, J=5.9 Hz, 2H), 3.83 (quint d, J$_1$=2.1 Hz, J$_2$=8.7 Hz, 1H), 3.03-3.20 (m, 2H), 2.63-2.81 (m, 2H).

Step 7: Preparation of 2-(3,3-difluorocyclobutyl)imidazo[5,1-b]thiazole-3-carbaldehyde According to the procedure for the preparation of example 170/step 7 but using (2-(3,3-difluorocyclobutyl)imidazo[5,1-b]thiazol-3-yl)methanol as starting material, 362 mg of 2-(3,3-difluorocyclobutyl)imidazo[5,1-b]thiazole-3-carbaldehyde are obtained. LC-MS (acidic): $t_R$=0.50; [M+H]$^+$=242.79. $^1$H NMR (400 MHz, DMSO) δ: 4.32-4.50 (m, 1H), 10.00 (s, 1H), 8.56 (s, 1H), 7.23 (s, 1H), 3.20-3.30 (m, 2H), 2.83-3.01 (m, 2H).

Step 8: Preparation of rac-2-cyclohexyl-1-[2-(3,3-difluoro-cyclobutyl)-imidazo[5,1-b]thiazol-3-yl]-ethanol (Example 155)

According to the procedure described for preparation of example 3/step 8 but using product from step 7, 2-(3,3-difluorocyclobutyl)imidazo[5,1-b]thiazole-3-carbaldehyde and (cyclohexylmethyl)magnesium bromide as starting materials, 6 mg of rac-2-cyclohexyl-1-[2-(3,3-difluoro-cyclobutyl)-imidazo[5,1-b]thiazol-3-yl]-ethanol are obtained. LC-MS (QC): $t_R$=0.838; [M+H]$^+$=341.2.

Example 156: rac-Cyclohexyl-[2-(3,3-difluoro-cyclobutyl)-imidazo[5,1-b]thiazol-3-yl]-methanol Example 156 is prepared in analogy to the description of the preparation of example 155. LC-MS (QC): $t_R$=0.754; [M+H]$^+$=327.2.

Example 124: rac-Cyclohexyl-(2-pyridin-3-yl-imidazo[5,1-b]thiazol-3-yl)-methanol Step 1: Preparation of N-methoxy-N-methyl-2-(pyridin-3-yl)imidazo[5,1-b]thiazole-3-carboxamide According to the procedure described for the preparation of example 128/step 3 but using 3-pyridinboronic acid as starting material, 20 mg of N-methoxy-N-methyl-2-(pyridin-3-yl)imidazo[5,1-b]thiazole-3-carboxamide are obtained. LC-MS (acidic): $t_R$=0.48; [M+H]$^+$=288.94. $^1$H NMR (400 MHz, DMSO) δ: 8.68-8.71 (m, 2H), 8.24 (s, 1H), 7.94 (dd, $J_1$=0.9 Hz, $J_2$=7.5 Hz, 1H), 7.55-7.58 (m, 1H), 7.19 (s, 1H), 3.50 (s, 3H), 3.24 (s, 3H).

Step 2: Preparation of 2-(pyridin-3-yl)imidazo[5,1-b]thiazole-3-carbaldehyde

According to the procedure described for the preparation of example 128/step 4 but using N-methoxy-N-methyl-2-(pyridin-3-yl)imidazo[5,1-b]thiazole-3-carboxamide as starting material, 15 mg of 2-(pyridin-3-yl)imidazo[5,1-b]thiazole-3-carbaldehyde are obtained. LC-MS (acidic): $t_R$=0.44; [M+H]$^+$=229.95. $^1$H NMR (400 MHz, DMSO) δ: 9.70 (s, 1H), 8.99 (m, 1H), 8.81 (dd, $J_1$=1.5 Hz, $J_2$=4.9 Hz, 1H), 8.72 (s, 1H), 8.25 (m, 1H), 7.60-7.67 (m, 1H), 7.30 (s, 1H).

Step 3: Preparation of rac-cyclohexyl-(2-pyridin-3-yl-imidazo[5,1-b]thiazol-3-yl)-methanol (Example 124)

According to the procedure described for preparation of example 3/step 8 but using product from step 2, 2-(pyridin-3-yl)imidazo[5,1-b]thiazole-3-carbaldehyde and cyclohexylmagnesium bromide as starting material, 3 mg of rac-cyclohexyl-(2-pyridin-3-yl-imidazo[5,1-b]thiazol-3-yl)-methanol are obtained. LC-MS (QC): $t_R$=0.615; [M+H]$^+$=314.0.

Example 125: rac-Cyclohexyl-[2-(1-methyl-1H-pyrazol-4-yl)-imidazo[5,1-b]thiazol-3-yl]-methanol Step 1: Preparation of N-methoxy-N-methyl-2-(1-methyl-1H-pyrazol-4-yl)imidazo[5,1-b]thiazole-3-carboxamide According to the procedure described for the preparation of example 128/step 3 but using 1-methylpyrazole-4-boronic acid pinacol ester as starting material, 71 mg of N-methoxy-N-methyl-2-(1-methyl-1H-pyrazol-4-yl)imidazo[5,1-b]thiazole-3-carboxamide are obtained. LC-MS (acidic): $t_R$=0.49; [M+H]$^+$=291.94. $^1$H NMR (400 MHz, DMSO) δ: 8.12 (s, 1H), 8.08 (s, 1H), 7.65 (s, 1H), 7.09 (s, 1H), 3.89 (s, 3H), 3.54 (s, 3H), 3.32 (s, 3H).

Step 2: Preparation of 2-(1-methyl-1H-pyrazol-4-yl)imidazo[5,1-b]thiazole-3-carbaldehyde According to the procedure described for the preparation of example 128/step 4 but using N-methoxy-N-methyl-2-(1-methyl-1H-pyrazol-4-yl)imidazo[5,1-b]thiazole-3-carboxamide as starting material, 45 mg of 2-(1-methyl-1H-pyrazol-4-yl)imidazo[5,1-b]thiazole-3-carbaldehyde are obtained. LC-MS (acidic): $t_R$=0.46; [M+H]$^+$=232.96. $^1$H NMR (400 MHz, DMSO) δ: 9.93 (s, 1H), 8.63 (s, 1H), 8.49 (s, 1H), 8.05 (s, 1H), 7.21 (d, J=0.4 Hz, 1H), 3.94 (s, 3H).

Step 3: Preparation of rac-cyclohexyl-[2-(1-methyl-1H-pyrazol-4-yl)-imidazo[5,1-b]thiazol-3-yl]-methanol (Example 125)

According to the procedure described for preparation of example 3/step 8 but using product from step 2, 2-(1-methyl-1H-pyrazol-4-yl)imidazo[5,1-b]thiazole-3-carbaldehyde and cyclohexylmagnesium bromide as starting materials, 39 mg of rac-cyclohexyl-[2-(1-methyl-1H-pyrazol-4-yl)-imidazo[5,1-b]thiazol-3-yl]-methanol are obtained. LC-MS (QC): $t_R$=0.582; [M+H]$^+$=317.2.

Example 182: rac-Cyclohexyl-[2-(2-fluoro-phenyl)-imidazo[5,1-b]thiazol-3-yl]-methanol Step 1: Preparation of 3-(((tert-butyldimethylsilyl)oxy)methyl)-2-(2-fluorophenyl)imidazo[5,1-b]thiazole According to the procedure described for the preparation of example 181/step 6 but using 2-fluorophenylborane diol as starting material, 17.5 mg of 3-(((tert-butyldimethylsilyl)oxy)methyl)-2-(2-fluorophenyl)imidazo[5,1-b]thiazole are obtained. LC-MS (acidic): $t_R$=0.93; [M+H]$^+$=362.98.

Step 2: Preparation of (2-(2-fluorophenyl)imidazo[5,1-b]thiazol-3-yl)methanol

According to the procedure described for the preparation of example 181/Step 7 but using 3-(((tert-butyldimethylsilyl)oxy)methyl)-2-(2-fluorophenyl)imidazo[5,1-b]thiazole as starting material, 11.4 mg of (2-(2-fluorophenyl)imidazo[5,1-b]thiazol-3-yl)methanol are obtained. LC-MS (acidic): $t_R$=0.56; [M+H]$^+$=248.99.

Step 3: Preparation of 2-(2-fluorophenyl)imidazo[5,1-b]thiazole-3-carbaldehyde

According to the procedure described for the preparation of example 181/step 8 but using (2-(2-fluorophenyl)imidazo

[5,1-b]thiazol-3-yl)methanol as starting material, 9.1 mg of 2-(2-fluorophenyl)imidazo[5,1-b]thiazole-3-carbaldehyde are obtained. LC-MS (acidic): $t_R$=0.60; [M+H]$^+$=246.95.

Step 3: Preparation of rac-cyclohexyl-[2-(2-fluoro-phenyl)-imidazo[5,1-b]thiazol-3-yl]-methanol (Example 182)

According to the procedure described for preparation of example 3/step 8 but using product from step 3, 2-(2-fluorophenyl)imidazo[5,1-b]thiazole-3-carbaldehyde and cyclohexylmagnesium bromide as starting materials, 23 mg of rac-cyclohexyl-[2-(2-fluoro-phenyl)-imidazo[5,1-b]thiazol-3-yl]-methanol are obtained. LC-MS (QC): $t_R$=0.835; [M+H]$^+$=331.2.

Example 154: rac-(2-Benzyl-imidazo[5,1-b]thiazol-3-yl)-cyclohexyl-methanol

Step 1: Preparation of 2-phenylacetic anhydride

To a solution of phenylacetic acid (3.86 ml, 30 mmol) in toluene (200 ml) is added DCC (6.252 g, 30 mmol) portionwise. The resulting suspension is stirred at RT for 20 min, then filtered off. The filtrate is concentrated under reduced pressure to give 7.32 g of 2-phenylacetic anhydride as a white solid. LC-MS (acidic): $t_R$=0.99; [M+H]$^+$=no mass detected. $^1$H NMR (500 MHz, CDCl$_3$) δ: 7.32-7.43 (m, 6H), 7.23-7.27 (m, 4H), 3.76 (s, 4H).

Step 2: Preparation of ethyl 2-amino-3-oxo-4-phenylbutanoate hydrochloride

According to the procedure described for the preparation of example 96/step 1 but using product from step 1, 2-phenylacetic anhydride as starting material, 276 mg of ethyl 2-amino-3-oxo-4-phenylbutanoate hydrochloride are obtained. LC-MS (acidic): $t_R$=0.55; [M+H]$^+$=222.23. $^1$H NMR (500 MHz, DMSO) δ: 8.92 (d, J=0.5 Hz, 2 H), 7.34-7.37 (m, 2H), 7.28-7.30 (m, 1H), 7.19-7.22 (m, 2H), 5.44 (s, 1H), 4.30 (q, J=7.0 Hz, 2H), 4.17 (s, 2 H), 1.29 (t, J=7.1 Hz, 3H).

Step 3: Preparation of ethyl 2-(2-((tert-butoxycarbonyl)amino)acetamido)-3-oxo-4-phenylbutanoate According to the procedure described for the preparation of example 1/step 2 but using ethyl 2-amino-3-oxo-4-phenylbutanoate hydrochloride as starting material, 426 mg of ethyl 2-(2-((tert-butoxycarbonyl)amino)acetamido)-3-oxo-4-phenylbutanoate are obtained. LC-MS (acidic): $t_R$=0.91; [M+H]$^+$=379.16.

Step 4: Preparation of ethyl 5-benzyl-2-(((tert-butoxycarbonyl)amino)methyl)thiazole-4-carboxylate According to the procedure described for the preparation of example 1/step 3 but using ethyl 2-(2-((tert-butoxycarbonyl)amino)acetamido)-3-oxo-4-phenylbutanoate as starting material, 255 mg of ethyl 5-benzyl-2-(((tert-butoxycarbonyl)amino)methyl)thiazole-4-carboxylate are obtained. LC-MS (acidic): $t_R$=0.99; [M+H]$^+$=377.10.

Step 5: Preparation of ethyl 5-benzyl-2-(formamidomethyl)thiazole-4-carboxylate

To a solution of product from step 4, ethyl 5-benzyl-2-(((tert-butoxycarbonyl)amino)methyl)thiazole-4-carboxy-late (250 mg, 0.664 mmol) in CH$_2$Cl$_2$ (2.5 ml) is added HCl 4N in dioxane (0.65 ml, 2.6 mmol). The mixture is stirred at RT for 24 h. More HCl 4N (0.65 ml, 2.6 mmol) is added and the mixture is stirred at RT until completion of the reaction. The mixture is then concentrated under reduced pressure. To the residue is added ethyl formate (1.63 ml, 19.9 mmol) and DIPEA (0.455 ml, 2.66 mmol). The mixture is stirred at 70° C. for 3 h. Ethyl formate (0.545 ml, 6.64 mmol) and DIPEA (0.227 ml, 1.33 mmol) are added to the mixture and stirred at 70° C. for 1 h. The mixture is then concentrated under reduced pressure. The residue is diluted with an aqueous saturated NaHCO$_3$ solution and CH$_2$Cl$_2$. The layers are separated and the aqueous phase is extracted with CH$_2$Cl$_2$ (3×). The combined organic layers are dried over MgSO$_4$, filtered and concentrated under reduced pressure to give 170 mg of ethyl 5-benzyl-2-(formamidomethyl)thiazole-4-carboxylate as a beige solid. LC-MS (acidic): $t_R$=0.78; [M+H]$^+$= 305.03.

Step 6: Preparation of ethyl 2-benzylimidazo[5,1-b]thiazole-3-carboxylate

According to the procedure described for the preparation of example 1/step 5 but using ethyl 5-benzyl-2-(formamidomethyl)thiazole-4-carboxylate as starting material, 113 mg of ethyl 2-benzylimidazo[5,1-b]thiazole-3-carboxylate are obtained. LC-MS (acidic): $t_R$=0.71; [M+H]$^+$=287.08. $^1$H NMR (500 MHz, DMSO) δ: 8.42 (d, J=0.7 Hz, 1H), 7.34-7.43 (m, 4H), 7.09 (d, J=0.7 Hz, 1H), 4.50 (s, 2H), 4.44 (q, J=7.1 Hz, 2H), 1.37 (t, J=7.1 Hz, 3H).

Step 7: Preparation of 2-benzyl-N-methoxy-N-methylimidazo[5,1-b]thiazole-3-carboxamide According to the procedure described for the preparation of example 96/step 6.1 and 6.2 but using ethyl 2benzylimidazo[5,1-b]thiazole-3-carboxylate as starting material, 117 mg of 2-benzyl-N-methoxy-N-methylimidazo[5,1-b]thiazole-3-carboxamide are obtained. LC-MS (acidic): $t_R$=0.64; [M+H]$^+$=302.09.

Step 8: Preparation of 2-benzylimidazo[5,1-b]thiazole-3-carbaldehyde

According to the procedure described for the preparation of example 96/step 7 but using 2-benzyl-N-methoxy-N-methylimidazo[5,1-b]thiazole-3-carboxamide as starting material, 68 mg of 2-benzylimidazo[5,1-b]thiazole-3-carbaldehyde are obtained. LC-MS (acidic): $t_R$=0.60; [M+H]$^+$= 243.01.

Step 9: Preparation of rac-(2-benzyl-imidazo[5,1-b]thiazol-3-yl)-cyclohexyl-methanol (Example 154)

According to the procedure described for preparation of example 3/step 8 but using product from step 8, 2-benzylimidazo[5,1-b]thiazole-3-carbaldehyde and cyclohexylmagnesium chloride as starting materials, 11 mg of rac-(2-benzyl-imidazo[5,1-b]thiazol-3-yl)-cyclohexyl-methanol are obtained. LC-MS (QC): $t_R$=0.811; [M+H]$^+$=327.0.

Example 126: rac-Cyclohexyl-(2-p-tolyl-imidazo[5,1-b]thiazol-3-yl)-methanol

Step 1: Preparation of N-methoxy-N-methyl-2-(p-tolyl)imidazo[5,1-b]thiazole-3-carboxamide According to the procedure described for the preparation of example 128/step 3 but using 4-methylphenylboronic acid as starting material, 141 mg of N-methoxy-N-methyl-2-(p-tolyl)imidazo[5,1-b]thiazole-3-carboxamide are obtained. LC-MS (acidic): $t_R$=0.65; [M+H]$^+$=301.91. $^1$H NMR (400 MHz, DMSO) δ: 8.17 (s, 1H), 7.39 (m, 2H), 7.33 (m, 2H), 7.14 (s, 1H), 3.49 (s, 3H), 3.15-3.27 (m, 3H), 3.21 (s), 2.36 (s, 3H).

Step 2: Preparation of 2-(p-tolyl)imidazo[5,1-b]thiazole-3-carbaldehyde

According to the procedure described for the preparation of example 128/step 4 but using N-methoxy-N-methyl-2-(p-tolyl)imidazo[5,1-b]thiazole-3-carboxamide as starting material, 71 mg of 2-(p-tolyl)imidazo[5,1-b]thiazole-3-carbaldehyde are obtained. LC-MS (acidic): $t_R$=0.65; [M+H]$^+$= 242.85. $^1$H NMR (400 MHz, DMSO) δ: 9.71 (s, 1H), 8.68 (d, 1H), 7.70 (d, J=8.1 Hz, 2H), 7.43 (d, J=7.9 Hz, 2H), 7.26 (d, J=0.6 Hz, 1 H), 2.42 (s, 3H).

Step 3: Preparation of rac-cyclohexyl-(2-p-tolyl-imidazo[5,1-b]thiazol-3-yl)-methanol (Example 126)

According to the procedure described for preparation of example 3/step 8 but using product from step 2, 2-(p-tolyl)imidazo[5,1-b]thiazole-3-carbaldehyde and cyclohexylmagnesium bromide as starting materials, 28 mg of rac-cyclohexyl-(2-p-tolyl-imidazo[5,1-b]thiazol-3-yl)-methanol are obtained. LC-MS (QC): $t_R$=0.892; [M+H]$^+$=327.0.

Example 127: rac-Cyclohexyl-[2-(4-methoxy-phenyl)-imidazo[5,1-b]thiazol-3-yl]-methanol Step 1: Preparation of N-methoxy-2-(4-methoxyphenyl)-N-methylimidazo[5,1-b]thiazole-3-carboxamide According to the procedure described for the preparation of example 128/step 3 but using 4-methoxyphenylboronic acid as starting material, 104 mg of N-methoxy-2-(4-methoxyphenyl)-N-methylimidazo[5,1-b]thiazole-3-carboxamide are obtained. LC-MS (acidic): $t_R$=0.62; [M+H]$^+$= 317.94. $^1$H NMR (400 MHz, DMSO) δ: 8.15 (s, 1H), 7.44 (d, J=8.3 Hz, 2H), 7.07-7.13 (m, 3H), 3.82 (s, 3H), 3.50 (s, 3H), 3.18-3.20 (m, 3H).

Step 2: Preparation of 2-(4-methoxyphenyl)imidazo[5,1-b]thiazole-3-carbaldehyde

According to the procedure described for the preparation of example 128/step 4 but using N-methoxy-2-(4-methoxyphenyl)-N-methylimidazo[5,1-b]thiazole-3-carboxamide as starting material, 82 mg of 2-(4-methoxyphenyl)imidazo[5,1-b]thiazole-3-carbaldehyde are obtained. LC-MS (acidic): $t_R$=0.62; [M+H]$^+$=268.83. $^1$H NMR (400 MHz, DMSO) δ: 9.70 (s, 1H), 8.67 (d, J=0.3 Hz, 1H), 7.76 (d, J=8.8 Hz, 2H), 7.25 (d, J=0.4 Hz, 1H), 7.16 (m, 2H), 3.86 (s, 3H).

Step 3: Preparation of rac-cyclohexyl-[2-(4-methoxy-phenyl)-imidazo[5,1-b]thiazol-3-yl]-methanol (Example 127)

According to the procedure described for preparation of example 3/step 8 but using product from step 2, 2-(4-methoxyphenyl)imidazo[5,1-b]thiazole-3-carbaldehyde and cyclohexylmagnesium bromide as starting materials, 39 mg of rac-cyclohexyl-[2-(4-methoxy-phenyl)-imidazo[5,1-b]thiazol-3-yl]-methanol are obtained. LC-MS (QC): $t_R$=0.818; [M+H]$^+$=343.2.

Example 108: (3,3-Dimethyl-cyclopentyl)-(2-trifluoromethyl-imidazo[5,1-b]thiazol-3-yl)-methanol Step 1: Preparation of ethyl 4,4,4-trifluoro-2-(hydroxyimino)-3-oxobutanoate To an aqueous solution of sodium nitrite (40 ml; 312 mmol) is added a solution of ethyl 4,4,4-trifluoro-3-oxobutanoate (50.0 g; 272 mmol) in glacial acetic acid (90 ml) while maintaining the temperature at 0-5° C. The reaction mixture is stirred in an ice-water bath for 30 min, and at RT for another 5 h. The solution is concentrated under reduced pressure to give 54 g of ethyl 4,4,4-trifluoro-2-(hydroxyimino)-3-oxobutanoate. $^1$H NMR (400 MHz, CDCl$_3$) δ: 8.40-9.55 (br s, 1H), 4.42 (q, J=7.0 Hz, 2H), 1.45 (t, J=7.0 Hz, 3H).

Step 2: Preparation of ethyl 2-amino-4,4,4-trifluoro-3-oxobutanoate hydrochloride A suspension of ethyl 4,4,4-trifluoro-2-(hydroxyimino)-3-oxobutanoate (54.0 g; 253 mmol) and palladium on activated carbon in a mixture of ethanol (150 ml) and 4N HCl (100 ml) is stirred under 0.3-0.5 MPa of hydrogen at RT for 2.5 h. The reaction mixture is then filtered, and the filtrate concentrated under reduced pressure to give 42.0 g of ethyl 2-amino-4,4,4-trifluoro-3-oxobutanoate hydrochloride as a yellow solid. $^1$H NMR (400 MHz, CDCl$_3$) δ: 8.40-9.55 (br s, 1H), 4.31 (q, J=7.0 Hz, 2H), 4.10 (s, 1H), 1.22 (t, J=7.0 Hz, 3H).

Step 3: Preparation of ethyl 2-(2-((tert-butoxycarbonyl)amino)acetamido)-4,4,4-trifluoro-3-oxobutanoate Boc-Gly-OH (24.98 g; 143 mmol) is dissolved in THF (250 ml) and cooled to −20° C. Et$_3$N (19.8 ml; 143 mmol) is added, followed by isobutyl chloroformate (19.48 g; 143 mmol). The reaction mixture is stirred for 30 minutes at −20° C. followed by slow addition of a solution of ethyl 2-amino-4,4,4-trifluoro-3-oxobutanoate hydrochloride (42.0 g; 178.7 mmol) in THF (250 ml). Then a second portion of Et$_3$N (19.8 ml; 143 mmol) is slowly added to the reaction mixture and the reaction mixture is warmed to RT and stirring is continued for 2 h. Water and EtOAc are added, the layers separated and the organic layer washed with saturated aqueous NaHCO$_3$ solution, dried over MgSO$_4$, filtered and concentrated under reduced pressure. The residue is purified by FC (Silicagel; Hexanes/EtOAc) to give 46.5 g of ethyl 2-(2-((tert-butoxycarbonyl)amino)acetamido)-4,4,4-trifluoro-3-oxobutanoate as a yellow thick oil (mixture of keto- and enol tautomers). $^1$H NMR (400 MHz, CDCl$_3$) δ: 7.05-7.47 (m, 1.5 H), 4.92-5.00 (m, 1H), 4.33-4.45 (m, 2H), 4.10 (s, 0.5 H), 3.77-3.89 (m, 2H), 1.45 (s, 9H), 1.25-1.33 (m, 3H).

Step 4: Preparation of ethyl 2-(((tert-butoxycarbonyl)amino)methyl)-5-(trifluoromethyl)thiazole-4-carboxylate Ethyl 2-(2-((tert-butoxycarbonyl)amino)acetamido)-4,4,4-trifluoro-3-oxobutanoate (46.5 g; 131 mmol) is dissolved in THF (800 ml) followed by the addition of Lawesson's reagent (79.0 g; 195 mmol). The mixture is stirred at reflux for 8 hours. THF is then removed under reduced pressure. The residue is dissolved in EtOAc, washed twice with saturated aq. NaHCO$_3$ solution and with brine, dried over MgSO$_4$, filtered and the solvent is evaporated under reduced pressure to give 24.8 g of ethyl 2-(((tert-butoxycarbonyl)amino)methyl)-5-(trifluoromethyl)thiazole-4-carboxylate.

Step 5: Preparation of ethyl 2-(formamidomethyl)-5-(trifluoromethyl)thiazole-4-carboxylate Step 5.1: Boc-cleavage: The product from step 4, ethyl 2-(((tert-butoxycarbonyl)amino)methyl)-5-(trifluoromethyl)thiazole-4-carboxylate (24.8 g; 70 mmol) is dissolved in TFA (96 g; 840 mmol). The mixture is stirred at RT for 1 h. The reaction mixture is evaporated to dryness under reduced pressure.

Step 5.2: The residue from step 5.1 is dissolved in ethyl formate (150 ml) and the mixture stirred at reflux for 5 h. The solution is then concentrated under reduced pressure to give 14.1 g of ethyl 2-(formamidomethyl)-5-(trifluoromethyl)thiazole-4-carboxylate. $^1$H NMR (400 MHz, CDCl$_3$) δ: 8.22-8.33 (m, 1H), 4.20-4.48 (m, 2H), 3.95-4.05 (m, 2H), 1.15-1.44 (m, 3H).

Step 6: Preparation of ethyl 2-(trifluoromethyl)imidazo[5,1-b]thiazole-3-carboxylate Phosphorous(V) oxychloride (POCl$_3$) (7 ml; 74.9 mmol) is added at RT to a solution of ethyl 2-(formamidomethyl)-5-(trifluoromethyl)thiazole-4-carboxylate (14.1 g; 50.0 mmol) in toluene (150 ml). The reaction mixture is stirred at reflux for 2 h. Toluene and POCl$_3$ are removed under reduced pressure, water is added to the residue and the pH adjusted to pH 8 by adding solid NaHCO$_3$. The aq layer is extracted with CH$_2$Cl$_2$ (2×), dried (MgSO$_4$), filtered and concentrated under reduced pressure to give 10.5 g of ethyl 2-(trifluoromethyl)imidazo[5,1-b]thiazole-3-carboxylate as a yellow solid.

Step 7: Preparation of (2-(trifluoromethyl)imidazo[5,1-b]thiazol-3-yl)methanol

NaBH$_4$ (4.76 g; 119 mmol) is added to a solution of ethyl 2-(trifluoromethyl)imidazo[5,1-b]thiazole-3-carboxylate (10.5 g; 39.7 mmol) in methanol (50 ml) and stirring is continued at 50° C. for 5 h. The solvent is removed under reduced pressure, water is added and the mixture extracted with EtOAc (5×). The combined organic layers are dried over MgSO$_4$, filtered and concentrated under reduced pressure to give 7.0 g of (2-(trifluoromethyl)imidazo[5,1-b]thiazol-3-yl)methanol as a yellow solid. $^1$H NMR (400 MHz, CDCl$_3$) δ: 8.22 (s, 1 H), 7.04 (s, 1H), 4.98 (s, 2H).

Step 8: Preparation of 2-(trifluoromethyl)imidazo[5,1-b]thiazole-3-carbaldehyde

Dess-Martin periodinane (14.7 g; 34.7 mmol) is added to a solution of (2-(trifluoromethyl)imidazo[5,1-b]thiazol-3-yl)methanol (7.0 g; 0.541 mmol) in dichloromethane (250 ml) and stirring is continued for 2 hours at RT. The reaction mixture is then concentrated under reduced pressure, diluted with 1N NaOH, and extracted with EtOAc (3×). The combined organic extracts are dried over MgSO$_4$, filtered and concentrated under reduced pressure to give 3.0 g of 2-(trifluoromethyl)imidazo[5,1-b]thiazole-3-carbaldehyde. $^1$H NMR (400 MHz, CDCl$_3$) δ: 10.06 (s, 1H), 8.86 (s, 1H), 7.12 (s, 1H).

Step 9: Preparation of (3,3-dimethyl-cyclopentyl)-(2-trifluoromethyl-imidazo[5,1-b]thiazol-3-yl)-methanol (Example 108)

According to the procedure described for preparation of example 3/step 8 but using product from step 8, 2-(trifluoromethyl)imidazo[5,1-b]thiazole-3-carbaldehyde and (3,3-dimethylcyclopentyl)magnesium chloride as starting materials. LC-MS (QC): $t_R$=1.142; [M+H]$^+$=319.2.

Examples 110-112, 115-119, 121-122, 132, 137 and 161 are prepared in analogy to the description of the preparation of example 108:

Example 110: rac-(3,3-Dimethyl-cyclobutyl)-(2-trifluoromethyl-imidazo[5,1-b]thiazol-3-yl)-methanol LC-MS (QC): $t_R$=1.078; [M+H]$^+$=305.2.

Example 111: rac-2-Cyclopentyl-1-(2-trifluoromethyl-imidazo[5,1-b]thiazol-3-yl)-ethanol LC-MS (QC): $t_R$=1.100; [M+H]$^+$=305.3.

Example 112: 2-(3-Phenyl-cyclopentyl)-1-(2-trifluoromethyl-imidazo[5,1-b]thiazol-3-yl)-ethanol LC-MS (QC): $t_R$=1.264; [M+H]$^+$=381.4.

Example 115: rac-(4-Methyl-cyclohexyl)-(2-trifluoromethyl-imidazo[5,1-b]thiazol-3-yl)-methanol LC-MS (QC): $t_R$=1.174; [M+H]$^+$=319.2.

Example 116: (3-Methyl-cyclopentyl)-(2-trifluoromethyl-imidazo[5,1-b]thiazol-3-yl)-methanol LC-MS (QC): $t_R$=1.082; [M+H]$^+$=305.2.

Example 117: 2-(2-Methyl-cyclohexyl)-1-(2-trifluoromethyl-imidazo[5,1-b]thiazol-3-yl)-ethanol LC-MS (QC): $t_R$=1.246; [M+H]$^+$=333.2.

Example 118: rac-2-(4,4-Dimethyl-cyclohexyl)-1-(2-trifluoromethyl-imidazo[5,1-b]thiazol-3-yl)-ethanol LC-MS (QC): $t_R$=1.324; [M+H]$^+$=347.2.

Example 119: (2-Methyl-cyclopentyl)-(2-trifluoromethyl-imidazo[5,1-b]thiazol-3-yl)-methanol LC-MS (QC): $t_R$=1.080; [M+H]$^+$=305.2.

Example 121: 2-(3,3-Dimethyl-cyclopentyl)-1-(2-trifluoromethyl-imidazo[5,1-b]thiazol-3-yl)-ethanol LC-MS (QC): $t_R$=1.249; [M+H]$^+$=333.2.

Example 122: 2-(3-Methyl-cyclohexyl)-1-(2-trifluoromethyl-imidazo[5,1-b]thiazol-3-yl)-ethanol LC-MS (QC): $t_R$=1.256; [M+H]$^+$=333.2.

Example 132: rac-Cyclopentyl-(2-trifluoromethyl-imidazo[5,1-b]thiazol-3-yl)-methanol LC-MS (QC): $t_R$=0.985; [M+H]$^+$=291.1.

Example 137: rac-(1-Methyl-cyclopentyl)-(2-trifluoromethyl-imidazo[5,1-b]thiazol-3-yl)-methanol LC-MS (QC): $t_R$=1.064; [M+H]$^+$=305.2.

Example 161: rac-(4,4-Dimethyl-cyclohexyl)-(2-trifluoromethyl-imidazo[5,1-b]thiazol-3-yl)-methanol LC-MS (QC): $t_R$=1.223; [M+H]$^+$=333.2.

Example 192: rac-(2-Cyclopropyl-imidazo[5,1-b]thiazol-3-yl)-(1-methyl-1H-[1,2,3]triazol-4-yl)-methanol

Step 1: Preparation of rac-1-(2-cyclopropylimidazo[5,1-b]thiazol-3-yl)prop-2-yn-1-ol To an ice-cold solution of the product from Example 66/Step 1, 2-cyclopropylimidazo[5,1-b]thiazole-3-carbaldehyde (1000 mg; 5.20 mmol) in THF (20 ml) is added a solution of ethynylmagnesium bromide (0.5 M in THF, 31.2 ml, 15.6 mmol) in a dropwise manner. The reaction mixture is stirred at 0° C. for 1 h. The reaction is quenched by careful addition of aq. ammonium chloride solution. The product is extracted with EtOAc (3×20 ml) and the combined organic extracts are dried over MgSO$_4$, filtered and concentrated under reduced pressure. The residue is purified by preparative HPLC (basic conditions) to give 689 mg of rac-1-(2-cyclopropylimidazo[5,1-b]thiazol-3-yl)prop-2-yn-1-ol. LC-MS (basic): $t_R$=0.66; [M+H]$^+$=219.01. $^1$H NMR (500 MHz, d$_6$-DMSO) δ: 8.14 (d, J=0.6 Hz, 1H), 7.02 (d, J=0.6 Hz, 1H), 6.54 (d, J=4.5 Hz, 1H), 5.91 (dd, J$_1$=2.3 Hz, J$_2$=4.5 Hz, 1H), 3.64 (d, J=2.3 Hz, 1H), 2.25 (m, 1H), 1.05 (m, 2H), 0.65-0.74 (m, 2H).

Step 2: Preparation of rac-(2-cyclopropyl-imidazo[5,1-b]thiazol-3-yl)-(1-methyl-1H-[1,2,3]triazol-4-yl)-methanol (Example 192)

In a vial under argon, the product from Step 1, rac-1-(2-cyclopropylimidazo[5,1-b]thiazol-3-yl)prop-2-yn-1-ol (22 mg; 0.10 mmol), azidomethane (prepared by reacting iodomethane (28 mg; 0.20 mmol) with sodium azide (13.1 mg; 0.20 mmol) in DMF (0.6 ml) followed by filtration), copper (II) sulfate (1.25 mg, 0.005 mmol) and L-(+)-ascorbic acid sodium salt (2 mg, 0.01 mmol) are stirred at RT for 16 h. The mixture is filtered through a Whatman 0.45 μM glass microfiber filter, concentrated under reduced pressure and purified by prepHPLC (basic conditions) to give 20 mg of rac-(2-cyclopropyl-imidazo[5,1-b]thiazol-3-yl)-(1-methyl-1H-[1,2,3]triazol-4-yl)-methanol. LC-MS (QC): $t_R$=0.314; [M+H]$^+$=276.1.

Example 193: rac-(2-Cyclopropyl-imidazo[5,1-b]thiazol-3-yl)-(1-ethyl-1H-[1,2,3]triazol-4-yl)-methanol Example 193 is prepared in analogy to the description of the preparation of example 192. LC-MS (QC): $t_R$=0.364; [M+H]$^+$=290.1.

Example 194: rac-(2-Cyclopropyl-imidazo[5,1-b]thiazol-3-yl)-(1-isopropyl-1H-[1,2,3]triazol-4-yl)-methanol Example 194 is prepared in analogy to the description of the preparation of example 192. LC-MS (QC): $t_R$=0.416; [M+H]$^+$=304.1.

Example 195: rac-(1-Cyclopentyl-1H-[1,2,3]triazol-4-yl)-(2-cyclopropyl-imidazo[5,1-b]thiazol-3-yl)-methanol Example 195 is prepared in analogy to the description of the preparation of example 192. LC-MS (QC): $t_R$=0.509; [M+H]$^+$=330.2.

Example 196: rac-(1-Cyclobutyl-1H-[1,2,3]triazol-4-yl)-(2-cyclopropyl-imidazo[5,1-b]thiazol-3-yl)-methanol Example 196 is prepared in analogy to the description of the preparation of example 192. LC-MS (QC): $t_R$=0.463; [M+H]$^+$=316.2.

Example 197: rac-(1-Cyclohexyl-1H-[1,2,3]triazol-4-yl)-(2-cyclopropyl-imidazo[5,1-b]thiazol-3-yl)-methanol Example 197 is prepared in analogy to the description of the preparation of example 192. LC-MS (basic): $t_R$=0.567; [M+H]$^+$=344.2.

Example 200: rac-(2-Cyclopropyl-imidazo[5,1-b]thiazol-3-yl)-(1H-[1,2,3]triazol-4-yl)-methanol Example 200 is prepared in analogy to the description of the preparation of example 192 (using sodium azide as the azide source in the Step 2). LC-MS (QC): $t_R$=0.314; [M+H]$^+$=262.2.

Example 198: rac-(1-Cyclopentyl-1H-[1,2,3]triazol-4-yl)-(2-ethyl-imidazo[5,1-b]thiazol-3-yl)-methanol

Step 1: Preparation of rac-1-(2-ethylimidazo[5,1-b]thiazol-3-yl)prop-2-yn-1-ol To an ice-cold solution of the product from Example 96/Step 7, 2-ethylimidazo[5,1-b]thiazole-3-carbaldehyde (324 mg; 1.80 mmol) in THF (7.2 ml) is added a solution of ethynylmagnesium bromide (0.5 M in THF, 10.8 ml, 5.40 mmol) in a dropwise manner. The reaction mixture is stirred at 0° C. for 1 h. The reaction is quenched by careful addition of aq. ammonium chloride solution. The product is extracted with EtOAc (3×20 ml) and the combined organic extracts are dried over MgSO$_4$, filtered and concentrated under reduced pressure to give 375 mg of rac-1-(2-ethylimidazo[5,1-b]thiazol-3-yl)prop-2-yn-1-ol. LC-MS (acidic): $t_R$=0.47; [M+H]$^+$=207.26. $^1$H NMR (500 MHz, d$_6$-DMSO) δ: 8.17 (s, 1H), 7.04 (s, 1H), 6.47 (d, J=4.5 Hz, 1H), 5.82 (dd, J$_1$=2.3 Hz, J$_2$=4.5 Hz, 1H), 3.63 (d, J=2.3 Hz, 1H), 2.79 (m, 2H), 1.19 (t, J=7.5 Hz, 4H).

Step 2: Preparation of rac-(1-cyclopentyl-1H-[1,2,3]triazol-4-yl)-(2-ethyl-imidazo[5,1-b]thiazol-3-yl)-methanol (Example 198)

In a vial under argon, the product from Step 1, rac-1-(2-ethylimidazo[5,1-b]thiazol-3-yl)prop-2-yn-1-ol (30.9 mg;

0.15 mmol), azidocyclopentane (prepared by reacting bromocyclopentane (34.2 mg; 0.225 mmol) with sodium azide (14.7 mg; 0.225 mmol) in DMF (0.6 ml) followed by filtration), copper (II) sulfate (1.87 mg, 0.0075 mmol) and L-(+)-ascorbic acid sodium salt (3 mg, 0.015 mmol) are stirred at RT for 16 h. The mixture is filtered through a Whatman 0.45 µM glass microfiber filter, concentrated under reduced pressure and purified by prepHPLC (basic conditions) to give 27 mg of rac-(1-cyclopentyl-1H-[1,2,3]triazol-4-yl)-(2-ethyl-imidazo[5,1-b]thiazol-3-yl)-methanol. LC-MS (QC): $t_R$=0.486; $[M+H]^+$=318.2.

Example 199: rac-(1-Cyclopentyl-1H-[1,2,3]triazol-4-yl)-(2-methyl-imidazo[5,1-b]thiazol-3-yl)-methanol Step 1: Preparation of rac-1-(2-methylimidazo[5,1-b]thiazol-3-yl)prop-2-yn-1-ol To an ice-cold solution of the product from Example 5/Step 7, 2-methylimidazo[5,1-b]thiazole-3-carbaldehyde (249 mg; 1.50 mmol) in THF (6 ml) is added a solution of ethynylmagnesium bromide (0.5 M in THF, 9.0 ml, 4.50 mmol) in a dropwise manner. The reaction mixture is stirred at 0° C. for 1.5 h. The reaction is quenched by careful addition of aq. ammonium chloride solution. The product is extracted with EtOAc (3×20 ml) and the combined organic extracts are dried over MgSO$_4$, filtered and concentrated under reduced pressure. The residue is triturated with CH$_2$Cl$_2$/Et$_2$O then filtered to give 233 mg of rac-1-(2-methylimidazo[5,1-b]thiazol-3-yl)prop-2-yn-1-ol. LC-MS (acidic): $t_R$=0.41; $[M+H]^+$=193.16. $^1$H NMR (500 MHz, d$_6$-DMSO) δ: 8.16 (d, J=0.2 Hz, 1H), 7.02 (d, J=0.2 Hz, 1H), 6.46 (d, J=4.5 Hz, 1H), 5.81 (dd, J$_1$=2.3 Hz, J$_2$=4.5 Hz, 1H), 3.63 (d, J=2.3 Hz, 1H), 2.37 (s, 3H).

Step 2: Preparation of rac-(1-cyclopentyl-1H-[1,2,3]triazol-4-yl)-(2-methyl-imidazo[5,1-b]thiazol-3-yl)-methanol (Example 199)

In a vial under argon, the product from Step 1, rac-1-(2-methylimidazo[5,1-b]thiazol-3-yl)prop-2-yn-1-ol (28.8 mg; 0.15 mmol), azidocyclopentane (prepared by reacting bromocyclopentane (34.2 mg; 0.225 mmol) with sodium azide (14.7 mg; 0.225 mmol) in DMF (0.6 ml) followed by filtration), copper (II) sulfate (1.87 mg, 0.0075 mmol) and L-(+)-ascorbic acid sodium salt (3 mg, 0.015 mmol) are stirred at RT for 16 h. The mixture is filtered through a Whatman 0.45 µM glass microfiber filter, concentrated under reduced pressure and purified by prepHPLC (basic conditions) to give 24 mg of rac-(1-cyclopentyl-1H-[1,2,3]triazol-4-yl)-(2-methyl-imidazo[5,1-b]thiazol-3-yl)-methanol. LC-MS (QC): $t_R$=0.414; $[M+H]^+$=304.1.

The absolute chirality and the binding mode of the compound of Example 9a was determined by an X-ray diffraction analysis of the corresponding compound-enzyme co-crystals using the following experimental procedure:

1. Protein Purification and Co-Crystallization:

IDO1 protein was expressed and purified following a procedure described in the literature (Biochem et Biophysica Acta 1814 (2011) 1947-1954). IDO1 protein was concentrated to 29 mg/ml in a buffer containing 10 mM MES (2-(N-morpholino)ethanesulfonic acid) pH 6.50, 100 mM NaCl and 2 mM TCEP (Tris(2-carboxyethyl)phosphine hydrochloride). The protein solution was incubated with the compound of Example 9a at a final concentration of 2 mM for 3 hours at 277 K. The solution was then centrifuged for 5 minutes at 15,000 rpm at 277 K using an Eppendorf 5424R benchtop centrifuge. The centrifuged solution was mixed with a reservoir solution containing 100 mM arginine hydrochloride, 100 mM threonine, 100 mM histidine monohydrochloride monohydrate, 100 mM 5-hydroxylysine hydrochloride, 100 mM trans-4-hydroxy-L-proline, 100 mM BES (N,N-Bis(2-hydroxyethyl)-2-aminoethanesulfonic acid, N,N-Bis(2-hydroxyethyl)taurine)-triethanolamine pH 7.5, 2% (w/v) 3-(N-Phenylmethyl-N,N-dimethylammonio)propanesulfonate, 10% (w/v) PEG 8000 and 20% (w/v) 1,5-Pentanediol. Co-crystals of IDO1 and the compound of Example 9a were finally obtained by vapour diffusion from sitting drops at 293 K.

2. X-Ray Data Collection and Structure Determination:

The above-mentioned co-crystals were harvested using nylon loops and placed directly in liquid nitrogen. Synchrotron data were collected at beamline X06DA of the Swiss Light Source at the Paul Scherrer Institute, Villigen, Switzerland using a Pilatus 2M-F detector. Diffraction images were processed using the program XDS (Acta Cryst. (2010) D66, 125-132). The preliminary structure was solved using the program Phaser (J. Appl. Cryst. (2007) 40, 658-674). Refinement and rebuilding of the structure were carried out using the programs Refmac5 (Acta Cryst. (2004) D60, 2284-2295) and Coot (Acta Cryst. (2010) D66, 486-501), respectively. R-free was calculated using a randomly selected 5% of total data from the observed reflections. Based on the measured electron density, it was unambiguously established that the compound of Example 9a is the (S)-enantiomer.

Data Collection and Refinement Statistics

| | |
|---|---|
| Final resolution (Å) | 1.95 |
| Space group | P 21 21 21 |
| Unit cell dimensions (Å) | a = 84.6, b = 92.0, c = 132.3 |
| Wavelength (Å) | 1.0000 |
| observed/unique reflections | 692692/102271 |
| Resolution range (Å)[a] | 46.00-1.76 (1.87-1.76) |
| Completeness (%) | 99.2 (97.2) |
| Rmerge (%)[b] | 10.0 (449.0) |
| I/σ(I) | 10.8 (0.33) |
| Refinement | |
| Rwork (%) | 20.5 |
| Rfree (%) | 24.3 |
| RMSD | |
| bond length (Å) | 0.018 |
| bond angle (°) | 2.0 |
| Ramachandran outliers | 0 |

[a] values shown in parentheses correspond to the highest resolution shell

[b] $$R = \frac{\sum_{hkl} \sum_j |I_{hkl,j} - \langle I_{hkl} \rangle|}{\sum_{hkl} \sum_j I_{hkl,j}}$$

(S)-configuration is assigned to the compounds of Examples 1a, 2a, 3a, 4a, 5a, 6a, 7a, 8a, 10a, 13a, 16a, 24a, 28a, 34a, 36a, 47a, 47b, 48a, 50a, 63a, 68a, 73a, 92a, 96a, 100a, 140a, based on the assumption that the binding mode of the more active enantiomer is the same as the one for the compound of Example 9a.

BIOLOGICAL TESTS

1) Testing Compounds for IDO Inhibitory Activity in an IDO1 Enzymatic Assay:

Recombinant full-length human IDO1 with a N-terminal hexahistidine tag expressed in *E. coli* and purified to homogeneity is incubated at a final concentration of 2 nM in assay buffer consisting of 37.5 mM phosphate buffer at pH6.5 supplemented with 10 mM sodium L-ascorbate, 0.45 µM methylene blue, 50 U/ml catalase, 0.01% BSA, and 0.01% Tween 20 (protocol modified from Seegers et al, JBS 2014). Example compounds are serially diluted in DMSO, further diluted in phosphate buffer, and added to the enzyme at final concentrations ranging from 10 µM to 0.5 nM. The final DMSO concentration is 0.6%. Following a pre-incubation of 30 minutes at RT, the reaction is started by the addition of L-tryptophan at a final concentration of 5 µM in assay buffer. After 30 minutes of incubation at RT, 3 µL of the reaction mixture are transferred to a 384 deep well plate containing 25 µL of deionized water. 100 µl of 200 nM L-Tryptophan-(indole-d5) in cold 100% methanol are added followed by a 10 minutes centrifugation at 4,000 rpm at 4° C. An additional 75 µL of deionized water are then added and followed by a 10 minutes centrifugation at 4,000 rpm at 4° C. The product of the reaction N'-Formylkynurenine (NFK) is quantified by LCMS and normalized to the L-Tryptophan-(indole-d5) signal. Samples with 0.6% DMSO (0% effect) and a TDO/IDO inhibitor (100% effect) are used as control samples to set the parameters for the non-linear regression necessary for the determination of the half-maximal inhibitory concentration (IC50) for each compound. For each compound concentration the percentage of activity compared to 0% and 100% effect is calculated as average ±STDEV (each concentration measured in duplicate). IC50 values and curves are generated with XLfit software (IDBS) using Dose-Response One Site model 203 (four parameter logistic curve model). When compounds are measured multiple times, mean values are given.

2) Testing Compounds for TDO Inhibitory Activity in a TDO2 Enzymatic Assay:

Recombinant human TDO comprising amino acids 19-407 with a N-terminal hexahistidine tag expressed in *E. coli* and purified to homogeneity is incubated at a final concentration of 15 nM in assay buffer consisting of 75 mM phosphate buffer at pH7 supplemented with 100 µM ascorbic acid, 50 U/ml Catalase, 0.01% BSA, and 0.01% Tween 20 (protocol modified from Seegers et al, JBS 2014). Example compounds are serially diluted in DMSO, further diluted in phosphate buffer, and added to the reaction mixture at final concentrations ranging from 10 µM to 0.5 nM. The final DMSO concentration is 0.6%. Following a pre-incubation of 30 minutes at RT, the reaction is started by the addition of L-tryptophan at a final concentration of 200 µM in assay buffer. After 30 minutes of incubation at RT, 3 µL of the reaction mixture are transferred to a 384 deep well plate containing 25 µL of deionized water. 100 µl of 200 nM L-Tryptophan-(indole-d5) in cold 100% methanol are added followed by a 10 minutes centrifugation at 4,000 rpm at 4° C. An additional 75 µL of deionized water are then added and followed by a 10 minutes centrifugation at 4,000 rpm at 4° C. The product of the reaction N'-Formylkynurenine (NFK) is quantified by LCMS and normalized to the L-Tryptophan-(indole-d5) signal. Samples with 0.6% DMSO (0% effect) and a TDO/IDO inhibitor (100% effect) are used as control samples to set the parameters for the non-linear regression necessary for the determination of the half-maximal inhibitory concentration (IC50) for each compound. For each compound concentration the percentage of activity compared to 0% and 100% effect is calculated as average±STDEV (each concentration measured in duplicate). IC50 values and curves are generated with XLfit software (IDBS) using Dose-Response One Site model 203 (four parameter logistic curve model). When compounds are measured multiple times, mean values are given.

The results of biological tests 1 and 2 obtained for the compounds of Examples 1 to 200 are summarized in Table 1 below:

| Example Number | hIDO activity ($IC_{50}$ in nM) | hTDO activity ($IC_{50}$ in nM) |
|---|---|---|
| 1 | 15.1 | 288.2 |
| 1a | 7.5 | 115 |
| 2 | 22.4 | 585 |
| 2a | 10.3 | 268 |
| 3a | 11.7 | 603 |
| 4a | 15.5 | 386 |
| 5a | 16.5 | 375 |
| 6 | 134 | 143 |
| 6a | 37.3 | 60.4 |
| 7 | 94.2 | 324 |
| 7a | 39.7 | 138 |
| 8 | 122 | 256 |
| 8a | 72.3 | 129 |
| 9 | 237 | 193 |
| 9a | 131 | 131 |
| 10 | 384 | 277 |
| 10a | 190 | 164 |
| 11 | 895 | 2050 |
| 12 | 895 | 2130 |
| 13 | 110 | 172 |
| 13a | 93 | 162 |
| 14 | 28 | 218 |
| 15 | 333 | 690 |
| 16 | 159 | 1210 |
| 16a | 35.6 | 658 |
| 17 | 170 | 301 |
| 18 | 168 | 228 |
| 19 | 1040 | 2660 |
| 20 | 16.1 | 190 |
| 21 | 113 | 470 |
| 22 | 33.7 | 177 |
| 23 | 40.5 | 204 |
| 24 | 25.6 | 394 |
| 24a | 20.5 | 356 |
| 25 | 75.2 | 775 |
| 26 | 25.2 | 387 |
| 27 | 17.2 | 384 |
| 28 | 24.3 | 470 |
| 28a | 22.2 | 358 |
| 29 | 21.4 | 509 |
| 30 | 12.1 | 454 |
| 31 | 45.2 | 411 |
| 32 | 63.4 | 643 |
| 33 | 55.7 | 1410 |
| 34 | 39.4 | 321 |
| 34a | 19.5 | 262 |
| 35 | 114 | 1570 |
| 36 | 5.38 | 269 |
| 36a | 5.03 | 246 |
| 37 | 353 | 2460 |
| 38 | 22.6 | 191 |
| 39 | 41.7 | 300 |
| 40 | 44.9 | 697 |
| 41 | 93.4 | 2340 |
| 42 | 92.2 | 520 |
| 43 | 25.1 | 907 |
| 44 | 15.8 | 383 |
| 45 | 35.7 | 583 |
| 46 | 11.4 | 473 |
| 47 | 18.8 | 287 |
| 48 | 8.4 | 70.6 |
| 49 | 50.3 | 638 |
| 50 | 50.5 | 989 |
| 51 | 48.4 | 1460 |
| 52 | 64.8 | 22.30 |
| 53 | 60.1 | 1530 |
| 54 | 120 | 1850 |
| 55 | 86.9 | 2270 |
| 56 | 251 | 3310 |
| 57 | 433 | 829 |
| 58 | 1430 | >10200 |
| 59 | 249 | 881 |
| 60 | 287 | 455 |

| Example Number | hIDO activity (IC$_{50}$ in nM) | hTDO activity (IC$_{50}$ in nM) |
| --- | --- | --- |
| 61 | 431 | 578 |
| 62 | 3150 | 7160 |
| 63 | 27.0 | 564 |
| 64 | 69.0 | 3180 |
| 65 | 124 | 931 |
| 47a | 15.0 | 328 |
| 47b | 5.99 | 190 |
| 48a | 4.37 | 42.5 |
| 50a | 20.0 | 494 |
| 63a | 20.9 | 341 |
| 66 | 1570 | >10200 |
| 67 | 325 | 3510 |
| 68 | 14.4 | 29.3 |
| 68a | 4.63 | 11.6 |
| 69 | 40.0 | 255 |
| 70 | 72.1 | 746 |
| 71 | 28.5 | 263 |
| 72 | 102 | 1470 |
| 73 | 43.7 | 3110 |
| 73a | 6.45 | 2300 |
| 74 | 950 | 4330 |
| 75 | 1040 | 9460 |
| 76 | 147 | 295 |
| 77 | 91.2 | 3900 |
| 78 | 72.3 | 2010 |
| 79 | 109 | 1850 |
| 80 | 34.2 | 1810 |
| 81 | 43.3 | 772 |
| 82 | 87.3 | 822 |
| 83 | 296 | 5200 |
| 84 | 74.0 | 133 |
| 85 | 511 | 2830 |
| 86 | 511 | 2780 |
| 87 | 820 | 3100 |
| 88 | 76.7 | 1280 |
| 89 | 528 | 2130 |
| 90 | 133 | 1080 |
| 91 | 288 | 1640 |
| 92 | 382 | 246 |
| 92a | 242 | 171 |
| 93 | 296 | 496 |
| 94 | 144 | 181 |
| 95 | 313 | 386 |
| 96 | 10.5 | 39.9 |
| 96a | 5.32 | 20.0 |
| 97 | 10.5 | 62.6 |
| 98 | 435 | 583 |
| 99 | 837 | 1070 |
| 100 | 6.63 | 299 |
| 100a | 7.82 | 202 |
| 100b | 1190 | 9950 |
| 101 | 485 | 1790 |
| 102 | 87.6 | 818 |
| 103 | 70.1 | 1780 |
| 104 | 75.7 | 1080 |
| 105 | 10.6 | 104 |
| 106 | 85.1 | 546 |
| 107 | 167 | 1890 |
| 108 | 56.7 | 922 |
| 109 | 13.6 | 190 |
| 110 | 9.81 | 912 |
| 111 | 101 | 2430 |
| 112 | 666 | >10200 |
| 113 | 149 | 206 |
| 114 | 40.5 | 1830 |
| 115 | 84.1 | 1960 |
| 116 | 45.5 | 701 |
| 117 | 165 | 2680 |
| 118 | 447 | 7280 |
| 119 | 191 | 187 |
| 120 | 172 | 247 |
| 121 | 313 | 8490 |
| 122 | 205 | 3810 |
| 123 | 29.4 | 228 |
| 124 | 341.5 | 880.5 |
| 125 | 209 | >10200 |
| 126 | 3100 | 1010 |
| 127 | 3090 | 1990 |
| 128 | 537 | 420 |
| 129 | 36.8 | 595 |
| 130 | 49.5 | 153 |
| 131 | 11.3 | 1330 |
| 132 | 44.3 | 591 |
| 133 | 7.07 | 259 |
| 134 | 757 | 2800 |
| 135 | 139 | 3770 |
| 136 | 33.2 | 579 |
| 137 | 16.3 | 54.7 |
| 138 | 24.3 | 467 |
| 139 | 18.7 | 151 |
| 140 | 30.0 | 19.9 |
| 140a | 23.9 | 15.8 |
| 141 | 81.2 | 412 |
| 142 | 85.8 | 2000 |
| 143 | 587 | 765 |
| 144 | 32.8 | 475 |
| 145 | 33.1 | 449 |
| 146 | 63.9 | 1090 |
| 147 | 1110 | 6800 |
| 148 | 1160 | 2530 |
| 149 | 65.1 | 1820 |
| 150 | 687 | 3230 |
| 151 | 102 | 2640 |
| 152 | 18.4 | 1130 |
| 153 | 766 | 854 |
| 154 | 7110 | 4270 |
| 155 | 485 | 1910 |
| 156 | 1070 | 1780 |
| 157 | 744 | 327 |
| 158 | 459 | >10200 |
| 159 | 305 | 2700 |
| 160 | 2370 | >10200 |
| 161 | 58.3 | 2770 |
| 162 | 561 | 1000 |
| 163 | 56.7 | 1290 |
| 164 | 1120 | 3020 |
| 165 | 14.2 | 382 |
| 166 | 32.1 | 310 |
| 167 | 338 | >10200 |
| 168 | 123 | 2710 |
| 169 | 537 | 3960 |
| 170 | 415 | 2260 |
| 171 | 90.3 | 1580 |
| 172 | 4.97 | 28.7 |
| 173 | 77.3 | 1770 |
| 174 | 32.4 | 37.9 |
| 175 | 7.04 | 66.8 |
| 176 | 59.3 | 195 |
| 177 | 199 | 1950 |
| 178 | 118 | 1290 |
| 179 | 28.9 | 203 |
| 180 | 6.65 | 72.9 |
| 181 | 965 | 885 |
| 182 | 441 | 239 |
| 183 | 190 | 573 |
| 184 | 115 | 1760 |
| 185 | 172 | 962 |
| 186 | 21.8 | 491 |
| 187 | 18.5 | 2260 |
| 188 | 111 | >10200 |
| 189 | 112 | >10200 |
| 190 | 61.2 | 891 |
| 191 | 28.6 | 1270 |
| 192 | 590 | >10200 |
| 193 | 498 | >10200 |
| 194 | 304 | >10200 |
| 195 | 96.1 | >10200 |
| 196 | 183 | >10200 |
| 197 | 287 | >10200 |
| 198 | 116.5 | >10200 |

-continued

| Example Number | hIDO activity ($IC_{50}$ in nM) | hTDO activity ($IC_{50}$ in nM) |
|---|---|---|
| 199 | 835 | >10200 |
| 200 | 1950 | >10200 |

The invention claimed is:
1. A compound of Formula (I)

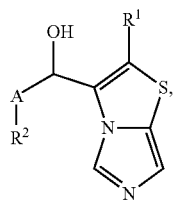

Formula (I)

wherein
A represents a direct bond wherein $R^2$ is directly attached to the carbon atom bearing the OH group; $C_{1-3}$-alkylene; $C_{2-3}$-alkenylene; or $C_{2-3}$-alkynylene;
$R^1$ represents:
   $C_{2-3}$-alkenyl;
   $C_{1-4}$-alkyl;
   $C_{1-3}$-fluoroalkyl;
   halogen;
   $C_{3-6}$-cycloalkyl which independently is unsubstituted, or mono-, or di-substituted, wherein the substituents are independently selected from $C_{1-4}$-alkyl and fluorine;
   phenyl which independently is unsubstituted, or mono-, or di-substituted, wherein the substituents are independently selected from $C_{1-4}$-alkyl, halogen, $C_{1-3}$-alkoxy, $C_{1-3}$-fluoroalkyl and $C_{1-3}$-fluoroalkoxy;
   5- to 6-membered heteroaryl which contains one or two ring heteroatoms independently selected from nitrogen, oxygen and sulphur, wherein said 5- to 6-membered heteroaryl independently is unsubstituted or mono-substituted with $C_{1-4}$-alkyl;
   $C_{1-3}$-alkoxy-methyl; or
   benzyl;
$R^2$ represents:
   aryl or 5- to 6-membered heteroaryl, wherein said aryl or 5- to 6-membered heteroaryl independently is unsubstituted, or mono-, di- or tri-substituted, wherein the substituents are independently selected from $C_{1-4}$-alkyl, $C_{3-6}$-cycloalkyl, halogen, $C_{1-3}$-fluoroalkyl, $C_{1-3}$-alkoxy, $C_{1-3}$-fluoroalkoxy, and $-NR^{N1}R^{N2}$, wherein $R^{N1}$ and $R^{N2}$ independently represent hydrogen or $C_{1-4}$-alkyl;
   5- to 6-membered heterocycloalkyl which independently is unsubstituted, or mono-substituted with phenyl;
   $C_{3-7}$-cycloalkyl, wherein said $C_{3-7}$-cycloalkyl independently is unsubstituted, or mono-, di- or tri-substituted, wherein the substituents are independently selected from $C_{1-4}$-alkyl; hydroxy; halogen; $C_{1-3}$-alkoxy; $C_{1-3}$-fluoroalkoxy; $C_{1-3}$-fluoroalkyl; $C_{3-6}$-cycloalkyl; $NR^{N3}R^{N4}$, wherein $R^{N3}$ and $R^{N4}$ independently represent hydrogen or $C_{1-4}$-alkyl; and phenyl-$(CH_2)_{0-1}$-, wherein the phenyl is independently unsubstituted, or mono- or di-substituted, wherein the substituents are independently selected from $C_{1-4}$-alkyl, halogen, $C_{1-3}$-fluoroalkyl, $C_{1-3}$-alkoxy and $C_{1-3}$-fluoroalkoxy;
   a saturated 5- to 11-membered bridged, fused, or spiro-bicyclic hydrocarbon ring system; wherein said ring system independently is unsubstituted or mono-substituted with phenyl; wherein said ring system optionally contains one carbon-carbon double bond; or wherein in said ring system optionally one ring carbon atom is replaced by a ring oxygen atom;
   $C_{5-6}$-cycloalkyl which is fused to a phenyl ring, wherein said $C_{5-6}$-cycloalkyl is independently unsubstituted, or mono-, or di-substituted, wherein the substituents are independently selected from $C_{1-4}$-alkyl; and wherein said fused phenyl ring is independently unsubstituted, or mono- or di-substituted, wherein the substituents are independently selected from $C_{1-4}$-alkyl, halogen, $C_{1-3}$-fluoroalkyl, $C_{1-3}$-alkoxy and $C_{1-3}$-fluoroalkoxy; or
   branched $C_{3-6}$-alkyl;
or a pharmaceutically acceptable salt thereof.
2. The compound according to claim 1, wherein $R^2$ represents:
   phenyl, thiophenyl, triazolyl or pyrazolyl, wherein said phenyl, thiophenyl, triazolyl or pyrazolyl independently are unsubstituted, or mono-, or di-substituted, wherein the substituents are independently selected from $C_{1-4}$-alkyl, cyclopentyl, trifluoromethyl, halogen, methoxy and dimethylamino;
   $C_{3-7}$-cycloalkyl, wherein said $C_{3-7}$-cycloalkyl independently is unsubstituted, or mono-, di- or tri-substituted, wherein the substituents are independently selected from $C_{1-4}$-alkyl, $C_{3-6}$-cycloalkyl, hydroxy, fluorine, difluoromethyl, trifluoromethyl, methoxy, ethylamino, phenyl and benzyl;
   bicyclo[1.1.1]pent-1-yl, bicyclo[2.1.1]hex-1-yl, bicyclo[2.2.1]hept-2-yl, bicyclo[2.2.1]hept-1-yl, 4-phenyl-bicyclo[2.1.1]hex-1-yl, 3-phenyl-bicyclo[1.1.1]pent-1-yl, bicyclo[2.2.1]hept-5-en-2-yl, or 7-oxa-bicyclo[2.2.1]hept-2-yl;
   bicyclo[3.3.0]oct-3-yl or bicyclo[4.4.0]dec-3-yl;
   1,2,3,4-tetrahydronaphthalen-2-yl; or
   spiro[4.5]dec-8-yl;
or a pharmaceutically acceptable salt thereof.
3. The compound according to claim 1, wherein $R^2$ represents any one chemical group selected from group I) or group II):

I)

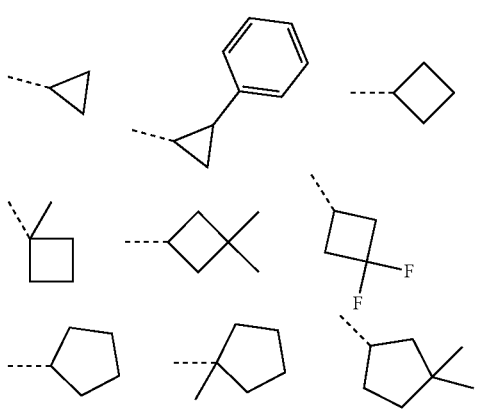

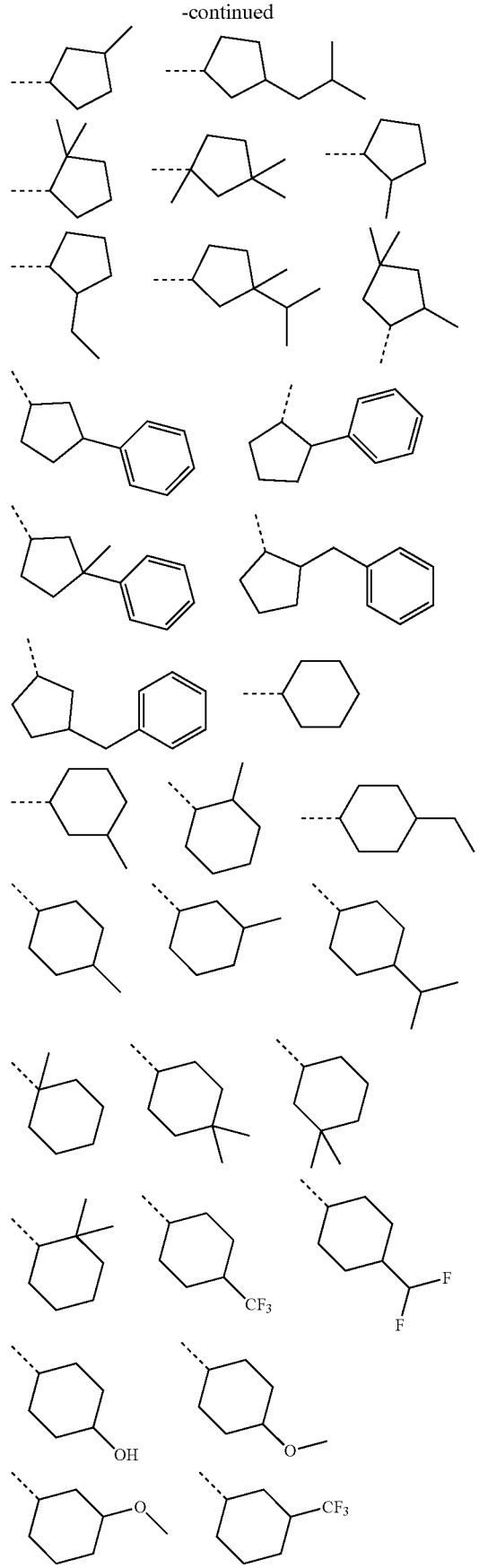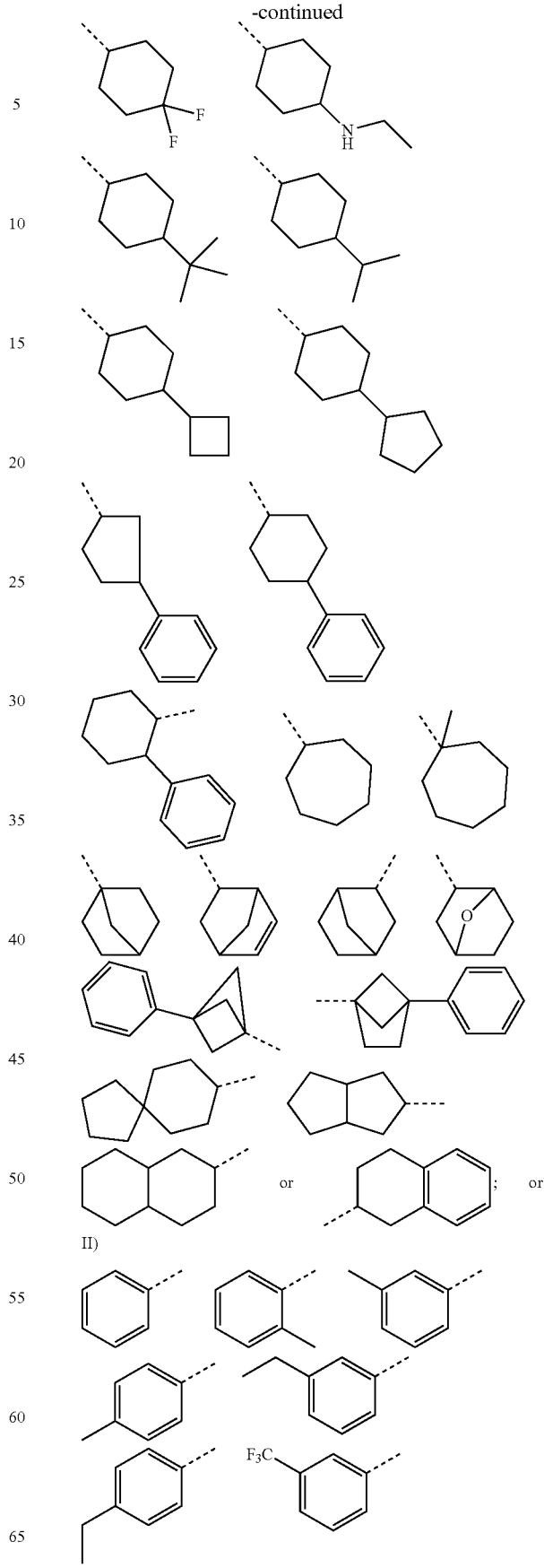

-continued

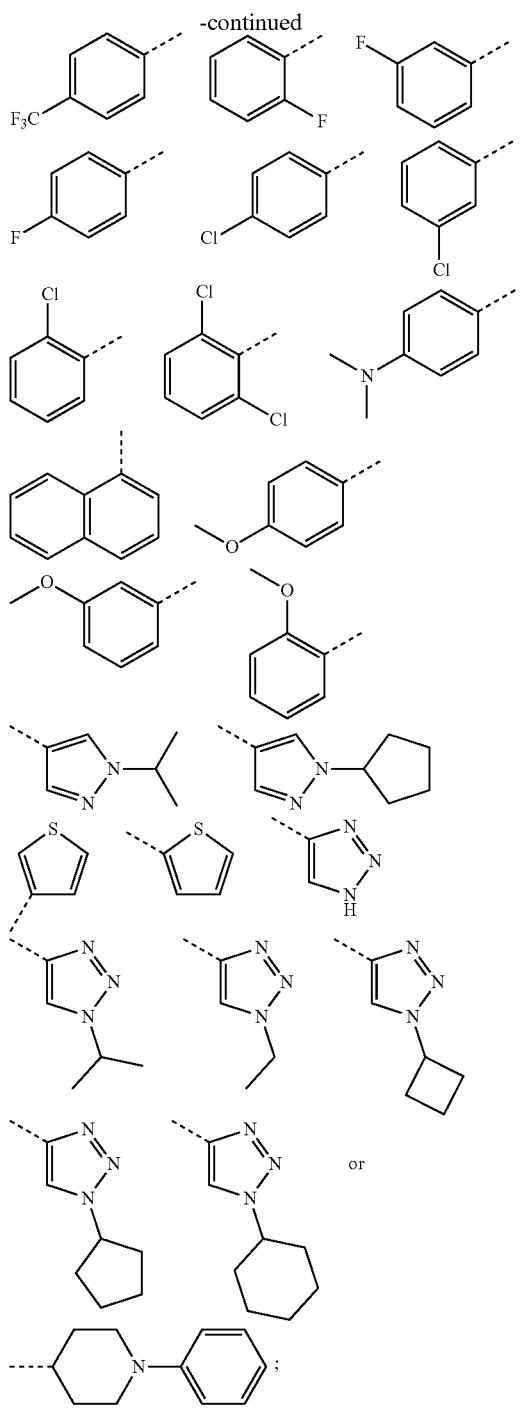

or a pharmaceutically acceptable salt thereof.

4. The compound according to claim 1, wherein A represents a direct bond; or a pharmaceutically acceptable salt thereof.

5. The compound according to claim 1, wherein A represents —CH$_2$—; or a pharmaceutically acceptable salt thereof.

6. The compound according to claim 1, wherein R$^1$ represents C$_{1-4}$-alkyl, chloro, bromo, C$_1$-fluoroalkyl, C$_{3-6}$-cycloalkyl or C$_{2-3}$-alkenyl; or a pharmaceutically acceptable salt thereof.

7. The compound according to claim 1, wherein the asymmetric carbon atom to which the fragment R$^2$-A- is attached has the absolute configuration depicted in Formula (II):

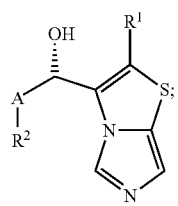

Formula (II)

or a pharmaceutically acceptable salt thereof.

8. The compound according to claim 1, selected from the group consisting of:
(S)-cyclohexyl(2-cyclopropylimidazo[5,1-b]thiazol-3-yl)methanol;
(S)-2-cyclohexyl-1-(2-cyclopropylimidazo[5,1-b]thiazol-3-yl)ethan-1-ol;
(S)-cyclohexyl-(2-isopropyl-imidazo[5,1-b]thiazol-3-yl)-methanol;
(S)-2-cyclohexyl-1-(2-isopropyl-imidazo[5,1-b]thiazol-3-yl)-ethanol;
(S)-2-cyclohexyl-1-(2-methyl-imidazo[5,1-b]thiazol-3-yl)-ethanol;
(S)-cyclohexyl-(2-methyl-imidazo[5,1-b]thiazol-3-yl)-methanol;
(S)-(2-cyclobutylimidazo[5,1-b]thiazol-3-yl)(cyclohexyl)methanol;
(S)-1-(2-cyclobutylimidazo[5,1-b]thiazol-3-yl)-2-cyclohexylethan-1-ol;
(S)-cyclohexyl(2-cyclopentylimidazo[5,1-b]thiazol-3-yl)methanol;
(S)-2-cyclohexyl-1-(2-cyclopentylimidazo[5,1-b]thiazol-3-yl)ethan-1-ol;
(2-(tert-butyl)imidazo[5,1-b]thiazol-3-yl)(cyclohexyl)methanol;
1-(2-(tert-butyl)imidazo[5,1-b]thiazol-3-yl)-2-cyclohexylethan-1-ol;
(S)-(2-chloroimidazo[5,1-b]thiazol-3-yl)(cyclohexyl)methanol;
(2-bromoimidazo[5,1-b]thiazol-3-yl)(cyclohexyl)methanol;
(2-chloro-imidazo[5,1-b]thiazol-3-yl)-thiophen-2-yl-methanol;
(S)-1-(2-chloro-imidazo[5,1-b]thiazol-3-yl)-2-cyclohexyl-ethanol;
(2-chloro-imidazo[5,1-b]thiazol-3-yl)-cycloheptyl-methanol;
(2-chloro-imidazo[5,1-b]thiazol-3-yl)-cyclopentyl-methanol;
(2-chloro-imidazo[5,1-b]thiazol-3-yl)-cyclopropyl-methanol;
(1R*,2R*,4S*)-bicyclo[2.2.1]hept-2-yl-(2-cyclopropyl-imidazo[5,1-b]thiazol-3-yl)-methanol;
1-(2-cyclopropyl-imidazo[5,1-b]thiazol-3-yl)-2-(3,3-difluoro-cyclobutyl)-ethanol;
2-bicyclo[2.2.1]hept-1-yl-1-(2-cyclopropyl-imidazo[5,1-b]thiazol-3-yl)-ethanol;
1-(2-cyclopropyl-imidazo[5,1-b]thiazol-3-yl)-2-(1-methyl-cyclohexyl)-ethanol;
(S)-2-cyclopentyl-1-(2-cyclopropyl-imidazo[5,1-b]thiazol-3-yl)-ethanol;

1-(2-cyclopropyl-imidazo[5,1-b]thiazol-3-yl)-2-(4,4-dimethyl-cyclohexyl)-ethanol;
(2-cyclopropyl-imidazo[5,1-b]thiazol-3-yl)-(4,4-dimethyl-cyclohexyl)-methanol;
(2-cyclopropyl-imidazo[5,1-b]thiazol-3-yl)-(3-methyl-cyclohexyl)-methanol;
(S)-2-cycloheptyl-1-(2-cyclopropyl-imidazo[5,1-b]thiazol-3-yl)-ethanol;
1-(2-cyclopropyl-imidazo[5,1-b]thiazol-3-yl)-2-(3-methyl-cyclohexyl)-ethanol;
(2-cyclopropyl-imidazo[5,1-b]thiazol-3-yl)-(3-methyl-cyclopentyl)-methanol;
1-(2-cyclopropyl-imidazo[5,1-b]thiazol-3-yl)-2-(2-methyl-cyclohexyl)-ethanol;
(2-bromo-imidazo[5,1-b]thiazol-3-yl)-thiophen-2-yl-methanol;
1-(2-bromo-imidazo[5,1-b]thiazol-3-yl)-2-cyclohexyl-ethanol;
(S)-1-(2-cyclopropyl-imidazo[5,1-b]thiazol-3-yl)-2-(3,3-dimethyl-cyclopentyl)-ethanol;
1-(2-cyclopropyl-imidazo[5,1-b]thiazol-3-yl)-2-(3-phenyl-cyclopentyl)-ethanol;
(S)-(2-cyclopropyl-imidazo[5,1-b]thiazol-3-yl)-(3,3-dimethyl-cyclobutyl)-methanol;
1-(2-cyclopropyl-imidazo[5,1-b]thiazol-3-yl)-2-(4-phenyl-cyclohexyl)-ethanol;
2-bicyclo[2.2.1]hept-5-en-2-yl-1-(2-cyclopropyl-imidazo[5,1-b]thiazol-3-yl)-ethanol;
1-(2-cyclopropyl-imidazo[5,1-b]thiazol-3-yl)-2-(1-methyl-cyclobutyl)-ethanol;
2-cyclobutyl-1-(2-cyclopropyl-imidazo[5,1-b]thiazol-3-yl)-ethanol;
1-(2-cyclopropyl-imidazo[5,1-b]thiazol-3-yl)-2-(7-oxabicyclo[2.2.1]hept-2-yl)-ethanol;
1-(2-cyclopropyl-imidazo[5,1-b]thiazol-3-yl)-2-(4-trifluoromethyl-cyclohexyl)-ethanol;
cyclobutyl-(2-cyclopropyl-imidazo[5,1-b]thiazol-3-yl)-methanol;
(2-cyclopropyl-imidazo[5,1-b]thiazol-3-yl)-(4-methyl-cyclohexyl)-methanol;
(2-cyclopropyl-imidazo[5,1-b]thiazol-3-yl)-(4-ethyl-cyclohexyl)-methanol;
cyclopentyl-(2-cyclopropyl-imidazo[5,1-b]thiazol-3-yl)-methanol;
(2-cyclopropyl-imidazo[5,1-b]thiazol-3-yl)-(3,3-dimethyl-cyclopentyl)-methanol;
(S)-(2-cyclopropyl-imidazo[5,1-b]thiazol-3-yl)-((R)-3,3-dimethyl-cyclopentyl)-methanol;
(S)-(2-cyclopropyl-imidazo[5,1-b]thiazol-3-yl)-((S)-3,3-dimethyl-cyclopentyl)-methanol;
(S)-(2-cyclopropyl-imidazo[5,1-b]thiazol-3-yl)-(1-methyl-cyclopentyl)-methanol;
1-(2-cyclopropyl-imidazo[5,1-b]thiazol-3-yl)-2-(4-methyl-cyclohexyl)-ethanol;
(S)-(2-cyclopropyl-imidazo[5,1-b]thiazol-3-yl)-phenyl-methanol;
(2-cyclopropyl-imidazo[5,1-b]thiazol-3-yl)-p-tolyl-methanol;
(2-cyclopropyl-imidazo[5,1-b]thiazol-3-yl)-m-tolyl-methanol;
(2-cyclopropyl-imidazo[5,1-b]thiazol-3-yl)-(4-ethyl-phenyl)-methanol;
(2-cyclopropyl-imidazo[5,1-b]thiazol-3-yl)-(3-ethyl-phenyl)-methanol;
(2-cyclopropyl-imidazo[5,1-b]thiazol-3-yl)-(4-methoxy-phenyl)-methanol;
(2-cyclopropyl-imidazo[5,1-b]thiazol-3-yl)-(3-methoxy-phenyl)-methanol;
(2-methyl-imidazo[5,1-b]thiazol-3-yl)-thiophen-2-yl-methanol;
(4-dimethylamino-phenyl)-(2-methyl-imidazo[5,1-b]thiazol-3-yl)-methanol;
1-(2-cyclopropyl-imidazo[5,1-b]thiazol-3-yl)-2-phenyl-ethanol;
1-(2-cyclopropyl-imidazo[5,1-b]thiazol-3-yl)-2-(2,6-dichloro-phenyl)-ethanol;
1-(2-cyclopropyl-imidazo[5,1-b]thiazol-3-yl)-2-o-tolyl-ethanol;
2-(3-methoxy-phenyl)-1-(2-methyl-imidazo[5,1-b]thiazol-3-yl)-ethanol;
(S)-cyclohexyl-(2-trifluoromethyl-imidazo[5,1-b]thiazol-3-yl)-methanol;
2-cyclohexyl-1-(2-trifluoromethyl-imidazo[5,1-b]thiazol-3-yl)-ethanol;
3-cyclohexyl-1-(2-cyclopropyl-imidazo[5,1-b]thiazol-3-yl)-butan-1-ol;
2-cyclohexyl-1-(2-cyclopropyl-imidazo[5,1-b]thiazol-3-yl)-butan-1-ol;
1-(2-cyclopropyl-imidazo[5,1-b]thiazol-3-yl)-2-naphthalen-1-yl-ethanol;
(S)-cyclohexyl-(2-vinyl-imidazo[5,1-b]thiazol-3-yl)-methanol;
(2-cyclopropyl-imidazo[5,1-b]thiazol-3-yl)-(3,3-dimethyl-cyclohexyl)-methanol;
(2-cyclopropyl-imidazo[5,1-b]thiazol-3-yl)-spiro[4.5]dec-8-yl-methanol;
1-(2-cyclopropyl-imidazo[5,1-b]thiazol-3-yl)-2-(4,4-difluoro-cyclohexyl)-ethanol;
(2-cyclopropyl-imidazo[5,1-b]thiazol-3-yl)-(4-isopropyl-cyclohexyl)-methanol;
(2-cyclopropyl-imidazo[5,1-b]thiazol-3-yl)-(4-phenyl-cyclohexyl)-methanol;
(S)-(2-cyclopropyl-imidazo[5,1-b]thiazol-3-yl)-(trans-4-phenyl-cyclohexyl)-methanol;
trans-2-(4-tert-butyl-cyclohexyl)-1-(2-cyclopropyl-imidazo[5,1-b]thiazol-3-yl)-ethanol;
1-(2-cyclopropyl-imidazo[5,1-b]thiazol-3-yl)-2-(2-phenyl-cyclohexyl)-ethanol;
1-(2-cyclopropyl-imidazo[5,1-b]thiazol-3-yl)-2-(2,2-dimethyl-cyclohexyl)-ethanol;
(3-benzyl-cyclopentyl)-(2-cyclopropyl-imidazo[5,1-b]thiazol-3-yl)-methanol;
(2-cyclopropyl-imidazo[5,1-b]thiazol-3-yl)-(3-isobutyl-cyclopentyl)-methanol;
(2-cyclopropyl-imidazo[5,1-b]thiazol-3-yl)-(3-methoxy-cyclohexyl)-methanol;
(2-cyclopropyl-imidazo[5,1-b]thiazol-3-yl)-(1,2,3,4-tetrahydro-naphthalen-2-yl)-methanol;
(2-cyclopropyl-imidazo[5,1-b]thiazol-3-yl)-(4-trifluoromethyl-cyclohexyl)-methanol;
2-cyclohexyl-1-(2-cyclopropyl-imidazo[5,1-b]thiazol-3-yl)-propan-1-ol;
(2-cyclopropyl-imidazo[5,1-b]thiazol-3-yl)-(2-phenyl-cyclopentyl)-methanol;
(2-cyclopropyl-imidazo[5,1-b]thiazol-3-yl)-(2,2-dimethyl-cyclopentyl)-methanol;
1-(2-cyclopropyl-imidazo[5,1-b]thiazol-3-yl)-2-(4-isopropyl-cyclohexyl)-ethanol;
(4-tert-butyl-cyclohexyl)-(2-cyclopropyl-imidazo[5,1-b]thiazol-3-yl)-methanol;
2-(4-cyclobutyl-cyclohexyl)-1-(2-cyclopropyl-imidazo[5,1-b]thiazol-3-yl)-ethanol;

(2-cyclopropyl-imidazo[5,1-b]thiazol-3-yl)-(3-methyl-3-phenyl-cyclopentyl)-methanol;
1-(2-cyclopropyl-imidazo[5,1-b]thiazol-3-yl)-2-(decahydro-naphthalen-1-yl)-ethanol;
(2-cyclopropyl-imidazo[5,1-b]thiazol-3-yl)-(decahydro-naphthalen-2-yl)-methanol;
(2-benzyl-cyclopentyl)-(2-cyclopropyl-imidazo[5,1-b]thiazol-3-yl)-methanol;
(S)-cyclohexyl-(2-phenyl-imidazo[5,1-b]thiazol-3-yl)-methanol;
2-cyclohexyl-1-(2-phenyl-imidazo[5,1-b]thiazol-3-yl)-ethanol;
cyclohexyl-(2-thiophen-3-yl-imidazo[5,1-b]thiazol-3-yl)-methanol;
2-cyclohexyl-1-(2-thiophen-3-yl-imidazo[5,1-b]thiazol-3-yl)-ethanol;
(S)-cyclohexyl-(2-ethyl-imidazo[5,1-b]thiazol-3-yl)-methanol;
2-cyclohexyl-1-(2-vinyl-imidazo[5,1-b]thiazol-3-yl)-ethanol;
cyclohexyl-(2-isobutyl-imidazo[5,1-b]thiazol-3-yl)-methanol;
2-cyclohexyl-1-(2-isobutyl-imidazo[5,1-b]thiazol-3-yl)-ethanol;
(S)-2-cyclohexyl-1-(2-ethyl-imidazo[5,1-b]thiazol-3-yl)-ethanol;
1-(2-cyclopropyl-imidazo[5,1-b]thiazol-3-yl)-2-(decahydro-naphthalen-2-yl)-ethanol;
1-(2-cyclopropyl-imidazo[5,1-b]thiazol-3-yl)-2-(3-trifluoromethyl-cyclohexyl)-ethanol;
(4-cyclobutyl-cyclohexyl)-(2-cyclopropyl-imidazo[5,1-b]thiazol-3-yl)-methanol;
(2-cyclopropyl-imidazo[5,1-b]thiazol-3-yl)-(3-trifluoromethyl-cyclohexyl)-methanol;
(2-cyclopropyl-imidazo[5,1-b]thiazol-3-yl)-(1-methyl-cyclohexyl)-methanol;
1-(2-cyclopropyl-imidazo[5,1-b]thiazol-3-yl)-2-(3,3-dimethyl-cyclohexyl)-ethanol;
1-(2-Methyl-imidazo[5,1-b]thiazol-3-yl)-2-(3-phenyl-cyclopentyl)-ethanol;
(3,3-Dimethyl-cyclopentyl)-(2-trifluoromethyl-imidazo[5,1-b]thiazol-3-yl)-methanol;
(3,3-Dimethyl-cyclobutyl)-(2-methyl-imidazo[5,1-b]thiazol-3-yl)-methanol;
(3,3-Dimethyl-cyclobutyl)-(2-trifluoromethyl-imidazo[5,1-b]thiazol-3-yl)-methanol;
2-cyclopentyl-1-(2-trifluoromethyl-imidazo[5,1-b]thiazol-3-yl)-ethanol;
2-(3-Phenyl-cyclopentyl)-1-(2-trifluoromethyl-imidazo[5,1-b]thiazol-3-yl)-ethanol;
1-(2-cyclopropyl-imidazo[5,1-b]thiazol-3-yl)-2-(3-methoxy-cyclohexyl)-ethanol;
(4-Methyl-cyclohexyl)-(2-trifluoromethyl-imidazo[5,1-b]thiazol-3-yl)-methanol;
(3-Methyl-cyclopentyl)-(2-trifluoromethyl-imidazo[5,1-b]thiazol-3-yl)-methanol;
2-(2-Methyl-cyclohexyl)-1-(2-trifluoromethyl-imidazo[5,1-b]thiazol-3-yl)-ethanol;
2-(4,4-Dimethyl-cyclohexyl)-1-(2-trifluoromethyl-imidazo[5,1-b]thiazol-3-yl)-ethanol;
(2-Methyl-cyclopentyl)-(2-trifluoromethyl-imidazo[5,1-b]thiazol-3-yl)-methanol;
(2-cyclopropyl-imidazo[5,1-b]thiazol-3-yl)-(2,4,4-trimethyl-cyclopentyl)-methanol;
2-(3,3-Dimethyl-cyclopentyl)-1-(2-trifluoromethyl-imidazo[5,1-b]thiazol-3-yl)-ethanol;
2-(3-Methyl-cyclohexyl)-1-(2-trifluoromethyl-imidazo[5,1-b]thiazol-3-yl)-ethanol;
(2-cyclopropyl-imidazo[5,1-b]thiazol-3-yl)-(2-ethyl-cyclopentyl)-methanol;
cyclohexyl-(2-pyridin-3-yl-imidazo[5,1-b]thiazol-3-yl)-methanol;
cyclohexyl-[2-(1-methyl-1H-pyrazol-4-yl)-imidazo[5,1-b]thiazol-3-yl]-methanol;
cyclohexyl-(2-p-tolyl-imidazo[5,1-b]thiazol-3-yl)-methanol;
cyclohexyl-[2-(4-methoxy-phenyl)-imidazo[5,1-b]thiazol-3-yl]-methanol;
cyclohexyl-[2-(4-methyl-thiophen-3-yl)-imidazo[5,1-b]thiazol-3-yl]-methanol;
2-cyclohexyl-1-(2-propyl-imidazo[5,1-b]thiazol-3-yl)-ethanol;
cyclohexyl-(2-propyl-imidazo[5,1-b]thiazol-3-yl)-methanol;
1-(2-cyclopropyl-imidazo[5,1-b]thiazol-3-yl)-2-(4-methoxy-cyclohexyl)-ethanol;
cyclopentyl-(2-trifluoromethyl-imidazo[5,1-b]thiazol-3-yl)-methanol;
(2-cyclopropyl-imidazo[5,1-b]thiazol-3-yl)-(octahydro-pentalen-2-yl)-methanol;
2-(4-cyclopentyl-cyclohexyl)-1-(2-cyclopropyl-imidazo[5,1-b]thiazol-3-yl)-ethanol;
1-(2-cyclopropyl-imidazo[5,1-b]thiazol-3-yl)-2-(2-phenyl-cyclopentyl)-ethanol;
(2-cyclopropyl-imidazo[5,1-b]thiazol-3-yl)-(3-isopropyl-3-methyl-cyclopentyl)-methanol;
(1-Methyl-cyclopentyl)-(2-trifluoromethyl-imidazo[5,1-b]thiazol-3-yl)-methanol;
1-(2-cyclopropyl-imidazo[5,1-b]thiazol-3-yl)-2-(4-difluoromethyl-cyclohexyl)-ethanol;
(2-cyclopropyl-imidazo[5,1-b]thiazol-3-yl)-(1,3,3-trimethyl-cyclopentyl)-methanol;
(S)-(1-Methyl-cyclopentyl)-(2-methyl-imidazo[5,1-b]thiazol-3-yl)-methanol;
(3,3-Dimethyl-cyclopentyl)-(2-methyl-imidazo[5,1-b]thiazol-3-yl)-methanol;
1-(2-cyclopropyl-imidazo[5,1-b]thiazol-3-yl)-2-(4-ethyl-cyclohexyl)-ethanol;
(2-cyclopropyl-imidazo[5,1-]thiazol-3-yl)-(3-trifluoromethyl-phenyl)-methanol;
(2-cyclopropyl-imidazo[5,1-b]thiazol-3-yl)-(4-fluoro-phenyl)-methanol;
(2-cyclopropyl-imidazo[5,1-b]thiazol-3-yl)-(3-fluoro-phenyl)-methanol;
(4-chloro-phenyl)-(2-cyclopropyl-imidazo[5,1-b]thiazol-3-yl)-methanol;
(2-cyclopropyl-imidazo[5,1-b]thiazol-3-yl)-(2-methoxy-phenyl)-methanol;
(2-cyclopropyl-imidazo[5,1-b]thiazol-3-yl)-o-tolyl-methanol;
(3-chloro-phenyl)-(2-cyclopropyl-imidazo[5,1-b]thiazol-3-yl)-methanol;
1-(2-cyclopropyl-imidazo[5,1-b]thiazol-3-yl)-2-(4-propyl-cyclohexyl)-ethanol;
4-[(2-cyclopropyl-imidazo[5,1-b]thiazol-3-yl)-hydroxy-methyl]-cyclohexanol;
4-[2-(2-cyclopropyl-imidazo[5,1-b]thiazol-3-yl)-2-hydroxy-ethyl]-cyclohexanol;
cyclohexyl-[2-(5-methyl-thiophen-3-yl)-imidazo[5,1-b]thiazol-3-yl]-methanol;
(2-Benzyl-imidazo[5,1-b]thiazol-3-yl)-cyclohexyl-methanol;

2-cyclohexyl-1-[2-(3,3-difluoro-cyclobutyl)-imidazo[5,1-b]thiazol-3-yl]-ethanol;
cyclohexyl-[2-(3,3-difluoro-cyclobutyl)-imidazo[5,1-b]thiazol-3-yl]-methanol;
cyclohexyl-(2-methoxymethyl-imidazo[5,1-b]thiazol-3-yl)-methanol;
1-(2-Methyl-imidazo[5,1-b]thiazol-3-yl)-3-phenyl-prop-2-yn-1-ol;
(2-cyclopropyl-imidazo[5,1-b]thiazol-3-yl)-(4-trifluoromethyl-phenyl)-methanol;
1-(2-cyclopropyl-imidazo[5,1-b]thiazol-3-yl)-2-(4-ethylamino-cyclohexyl)-ethanol;
(4,4-Dimethyl-cyclohexyl)-(2-trifluoromethyl-imidazo[5,1-b]thiazol-3-yl)-methanol;
(2-Methyl-imidazo[5,1-b]thiazol-3-yl)-phenyl-methanol;
(2-cyclopropyl-imidazo[5,1-b]thiazol-3-yl)-(2-fluoro-phenyl)-methanol;
(2-chloro-phenyl)-(2-cyclopropyl-imidazo[5,1-b]thiazol-3-yl)-methanol;
cycloheptyl-(2-cyclopropyl-imidazo[5,1-b]thiazol-3-yl)-methanol;
(2-cyclopropyl-imidazo[5,1-b]thiazol-3-yl)-(1-methyl-cycloheptyl)-methanol;
(S*)-(2-Methyl-imidazo[5,1-b]thiazol-3-yl)-((1S*,2S*)-2-phenyl-cyclopropyl)-methanol;
(R*)-(2-Methyl-imidazo[5,1-b]thiazol-3-yl)-((1S*,2S*)-2-phenyl-cyclopropyl)-methanol;
(2-Methyl-imidazo[5,1-b]thiazol-3-yl)-(1-phenyl-piperidin-4-yl)-methanol;
cyclohexyl-[2-(1-methyl-cyclopropyl)-imidazo[5,1-b]thiazol-3-yl]-methanol;
(2-cyclopropyl-imidazo[5,1-b]thiazol-3-yl)-thiophen-2-yl-methanol;
(2-Ethyl-imidazo[5,1-b]thiazol-3-yl)-(1-methyl-cyclopentyl)-methanol;
(2-cyclopropyl-imidazo[5,1-b]thiazol-3-yl)-thiophen-3-yl-methanol;
(1-Methyl-cyclohexyl)-(2-methyl-imidazo[5,1-b]thiazol-3-yl)-methanol;
(2-Ethyl-imidazo[5,1-b]thiazol-3-yl)-(1-methyl-cyclohexyl)-methanol;
(2-Ethyl-imidazo[5,1-b]thiazol-3-yl)-phenyl-methanol;
2-(4,4-Dimethyl-cyclohexyl)-1-(2-methyl-imidazo[5,1-b]thiazol-3-yl)-ethanol;
2-(4,4-Dimethyl-cyclohexyl)-1-(2-ethyl-imidazo[5,1-b]thiazol-3-yl)-ethanol;
2-cyclopentyl-1-(2-ethyl-imidazo[5,1-b]thiazol-3-yl)-ethanol;
(3,3-Dimethyl-cyclobutyl)-(2-ethyl-imidazo[5,1-b]thiazol-3-yl)-methanol;
cyclohexyl-[2-(3-fluoro-phenyl)-imidazo[5,1-b]thiazol-3-yl]-methanol;
cyclohexyl-[2-(2-fluoro-phenyl)-imidazo[5,1-b]thiazol-3-yl]-methanol;
2-cyclopentyl-1-(2-methyl-imidazo[5,1-b]thiazol-3-yl)-ethanol;
cyclohexyl-[2-(1-fluoro-cyclopropyl)-imidazo[5,1-b]thiazol-3-yl]-methanol;
[2-((S)-sec-Butyl)-imidazo[5,1-b]thiazol-3-yl]-cyclohexyl-methanol;
cyclohexyl-[2-(cis-2-fluoro-cyclopropyl)-imidazo[5,1-b]thiazol-3-yl]-methanol;
cyclohexyl-[2-(trans-2-fluoro-cyclopropyl)-imidazo[5,1-b]thiazol-3-yl]-methanol;
(2-cyclopropyl-imidazo[5,1-b]thiazol-3-yl)-(1-isopropyl-1H-pyrazol-4-yl)-methanol;
(1-cyclopentyl-1H-pyrazol-4-yl)-(2-cyclopropyl-imidazo[5,1-b]thiazol-3-yl)-methanol;
(2-cyclopropyl-imidazo[5,1-b]thiazol-3-yl)-(4-phenyl-bicyclo[2.1.1]hex-1-yl)-methanol;
(2-cyclopropyl-imidazo[5,1-b]thiazol-3-yl)-(3-phenyl-bicyclo[1.1.1]pent-1-yl)-methanol;
(2-cyclopropyl-imidazo[5,1-b]thiazol-3-yl)-(1-methyl-1H-[1,2,3]triazol-4-yl)-methanol;
(2-cyclopropyl-imidazo[5,1-b]thiazol-3-yl)-(1-ethyl-1H-[1,2,3]triazol-4-yl)-methanol;
(2-cyclopropyl-imidazo[5,1-b]thiazol-3-yl)-(1-isopropyl-1H-[1,2,3]triazol-4-yl)-methanol;
(1-cyclopentyl-1H-[1,2,3]triazol-4-yl)-(2-cyclopropyl-imidazo[5,1-b]thiazol-3-yl)-methanol;
(1-cyclobutyl-1H-[1,2,3]triazol-4-yl)-(2-cyclopropyl-imidazo[5,1-b]thiazol-3-yl)-methanol;
(1-cyclohexyl-1H-[1,2,3]triazol-4-yl)-(2-cyclopropyl-imidazo[5,1-b]thiazol-3-yl)-methanol;
(1-cyclopentyl-1H-[1,2,3]triazol-4-yl)-(2-ethyl-imidazo[5,1-b]thiazol-3-yl)-methanol;
cyclopentyl-(2-methyl-imidazo[5,1-b]thiazol-3-yl)-methanol;
(1-cyclopentyl-1H-[1,2,3]triazol-4-yl)-(2-methyl-imidazo[5,1-b]thiazol-3-yl)-methanol;
and
(2-cyclopropyl-imidazo[5,1-b]thiazol-3-yl)-(1H-[1,2,3]triazol-4-yl)-methanol;

or a pharmaceutically acceptable salt thereof.

9. A pharmaceutical composition comprising a compound according to claim 1, and at least one pharmaceutically acceptable carrier.

10. A method for the treatment of cancer, the method comprising administering a pharmaceutically effective compound according to claim 1 to a patient in need thereof.

11. The method according to claim 10, wherein said compound is used in combination with one or more chemotherapeutical agents and/or radiotherapy and/or targeted therapy.

12. A pharmaceutical composition comprising a compound according to claim 8, and at least one pharmaceutically acceptable carrier.

13. A method for the treatment of cancer, the method comprising administering a pharmaceutically effective compound according to claim 8 to a patient in need thereof.

14. The method according to claim 13, wherein said compound is used in combination with one or more chemotherapeutical agents and/or radiotherapy and/or targeted therapy.

* * * * *